United States Patent
Kularatne et al.

(10) Patent No.: US 11,555,821 B2
(45) Date of Patent: *Jan. 17, 2023

(54) CA IX-NIR DYES AND THEIR USES

(71) Applicant: On Target Laboratories, Inc., West Lafayette, IN (US)

(72) Inventors: Sumith A. Kularatne, West Lafayette, IN (US); Mini Thomas, West Lafayette, IN (US)

(73) Assignee: ON TARGET LABORATORIES, INC., West Lafayette, IN (US)

(*) Notice: Subject to any disclaimer, the term of this patent is extended or adjusted under 35 U.S.C. 154(b) by 109 days.

This patent is subject to a terminal disclaimer.

(21) Appl. No.: 17/025,711

(22) Filed: Sep. 18, 2020

(65) Prior Publication Data

US 2021/0063406 A1 Mar. 4, 2021

Related U.S. Application Data

(63) Continuation-in-part of application No. 16/925,033, filed on Jul. 9, 2020, now abandoned, which is a continuation of application No. 16/723,319, filed on Dec. 20, 2019, now Pat. No. 10,746,741, which is a continuation of application No. 15/461,361, filed on Mar. 16, 2017, now Pat. No. 10,557,854.

(60) Provisional application No. 62/309,412, filed on Mar. 16, 2016.

(51) Int. Cl.
| | | |
|---|---|---|
| *G01N 33/53* | (2006.01) | |
| *G01N 33/58* | (2006.01) | |
| *C09B 23/01* | (2006.01) | |
| *G01N 33/574* | (2006.01) | |
| *C07D 311/90* | (2006.01) | |
| *C07D 209/12* | (2006.01) | |
| *A61B 1/00* | (2006.01) | |
| *A61B 1/04* | (2006.01) | |
| *A61B 5/00* | (2006.01) | |
| *C09B 23/16* | (2006.01) | |
| *G01N 33/573* | (2006.01) | |
| *A61K 49/00* | (2006.01) | |
| *A61B 90/30* | (2016.01) | |
| *A61B 90/00* | (2016.01) | |
| *A61B 90/20* | (2016.01) | |
| *A61B 90/50* | (2016.01) | |

(52) U.S. Cl.
CPC ....... *G01N 33/583* (2013.01); *A61B 1/00009* (2013.01); *A61B 1/043* (2013.01); *A61B 5/0071* (2013.01); *A61B 5/0073* (2013.01); *A61B 5/0084* (2013.01); *A61B 5/7282* (2013.01); *C07D 209/12* (2013.01); *C07D 311/90* (2013.01); *C09B 23/0008* (2013.01); *C09B 23/0025* (2013.01); *C09B 23/0066* (2013.01); *C09B 23/166* (2013.01); *C12Y 402/01001* (2013.01); *G01N 33/573* (2013.01); *G01N 33/574* (2013.01); *G01N 33/57484* (2013.01); *G01N 33/582* (2013.01); *A61B 90/20* (2016.02); *A61B 90/30* (2016.02); *A61B 2090/373* (2016.02); *A61B 2090/502* (2016.02); *A61B 2560/0431* (2013.01); *A61K 49/0017* (2013.01); *A61K 49/0032* (2013.01); *G01N 2333/988* (2013.01)

(58) Field of Classification Search
None
See application file for complete search history.

(56) References Cited

U.S. PATENT DOCUMENTS

| | | | |
|---|---|---|---|
| 10,557,854 B2* | 2/2020 | Kularatne | G01N 33/573 |
| 10,746,741 B2* | 8/2020 | Kularatne | C09B 23/0025 |
| 2013/0129619 A1 | 5/2013 | Morse et al. | |
| 2014/0161725 A1 | 6/2014 | Morse et al. | |
| 2014/0271476 A1 | 9/2014 | Kularatne et al. | |
| 2014/0271482 A1 | 9/2014 | Low et al. | |
| 2017/0066719 A1 | 3/2017 | Kularatne et al. | |

FOREIGN PATENT DOCUMENTS

| | | |
|---|---|---|
| CN | 103687854 A | 3/2014 |
| JP | 2019-512500 | 5/2019 |
| WO | 2012-154885 | 11/2012 |
| WO | 2012154885 A2 | 11/2012 |
| WO | 2013184514 A1 | 12/2013 |
| WO | 2014-062044 | 4/2014 |
| WO | 2014-143309 | 9/2014 |

(Continued)

OTHER PUBLICATIONS

Chinese Patent Office, Office Action for Patent Application No. 201780017435.9, dated Sep. 26, 2021, 15 pages.

(Continued)

*Primary Examiner* — Michael G. Hartley
*Assistant Examiner* — Melissa J Perreira
(74) *Attorney, Agent, or Firm* — McAndrews Held & Malloy, Ltd.

(57) ABSTRACT

The present disclosure relates to compounds that are useful as near-infrared fluorescence probes, wherein the compounds include i) a ligand that binds to the active site of carbonic anhydrase, ii) a dye molecule, and iii) a linker molecule that comprises an amino acid, amide, ureido, or polyethylene glycol derivative thereof. The disclosure further describes methods and compositions for making and using the compounds, methods incorporating the compounds, and kits incorporating the compounds.

20 Claims, 78 Drawing Sheets
(55 of 78 Drawing Sheet(s) Filed in Color)

(56) References Cited

FOREIGN PATENT DOCUMENTS

| WO | 2014-149069 | 9/2014 |
| WO | 2015-114171 | 6/2015 |
| WO | 2015114171 A1 | 8/2015 |

OTHER PUBLICATIONS

Japan Patent Office, Office Action regarding Patent Application No. 2018-548414, dated Mar. 30, 2021, 7 pages.
Hou, Tai-Cheng et al., "Near-infrared fluorescence activation proves based on disassembly-induced emission cyanine dye," Chem. Sci. 2015, 6, 4643, dated May 22, 2015, 7 pages.
Groves, Kevin et al., "Synthesis and evaluation of near-infrared fluorescent sulfonamide derivatives for imaging of hypoxia-induced carbonic anhydrase IX expression in tumors," Bioorganic & Medicinal Chemistry Letters 22 (2012), dated Oct. 24, 2011, 5 pages.
Krall, N. et al. "A bivalent small molecule-drug conjugate directed against carbonic anhydrase IX can elicit complete tumour regression in mice," Chem. Sci. 2014, 5, 3640, dated Jun. 19, 2014, 5 pages.
Krall, N. et al. "A Small-Molecule Druge Conjugate for the Treatment of Carbonic Anydrase IX Expressing Tumors," Cancer Therapy, Angew Chem. Int. Ed. 2014, 53, dated Mar. 12, 2014, 5 pages.
Kazokaite, J et al., "Intrinsic binding of 4-substituted-2,3,4,6-tetrafluorobenezenesulfonamides to native and recombinant human carbonic anhydrase VI," FEBS Journal 53, dated Jan. 12, 2015, 12 pages.
Dudutiene, V. et al., "Functionalization of Fluorinated Benzenesulfonamides and Their Inhibitory Properties toward Carbonic Anhydrases," Chem. Med. Chem. 2015, 10, dated Mar. 10, 2015, 26 pages.
Talibov, V. et al., "Kinetically Selective Inhibitors of Human Carbonic Anhydrase Isozymes I, II, VII, IX, X11, and XIII," J. Med. Chem. 2016, dated Jan. 26, 2016, 11 pages.
China National Intellectual Property Administration, Office Action re: Application No. 201780017435.9, 17 pages, dated Feb. 22, 2017.
International Search Report and Written Opinion for PCT/US2017/022824, 14 pages, dated Jun. 1, 2017.
International Preliminary Reporton Patentability for PCT/US2017/022822 and PCT/US2017/022824, 11 pages, dated Sep. 27, 2018.
Groves, Kevin, et al., "Synthesis and evaluation of near-infrared fluorescent sulfonamide derivatives for imaging of hypoxia-induced carbonic anhydrase IX expression in tumors," Bioorganic & Medicinal Chemistry Letters 22 (2012), pp. 653-657, 5 pages.
Krall, Nikolaus, et al., "A Small-Molecule Drug Conjugate for the Treatment of Carbonic Anhydrase IX Expressing Tumors," Wiley Online Library, Angew. Chem. Int. Ed. 2014, 53, 4231-4235, 6 pages.
Hou, Tai-Cheng, et al., "Near-infrared fluorescence activation probes based on disassembly-induced emission cyanine dye," Chemical Science, 2015, 6, pp. 4643-4649, 4 pages.
Lv, Peng-Cheng, et al., "Evaluation of a Carbonic Anhydrase IX_Targeted Near-Infrared Dye for Fluorescence-Guided Surgery of Hypoxic Tumors," American Chemical Society, Apr. 4, 2016, pp. 1618-1625, 8 pages.
International Search Report for PCT/US2017/022822, 2 pages, dated Jun. 5, 2017.

* cited by examiner

CA IX-NIR DYES AND THEIR USES

RELATED APPLICATIONS

The present patent application is a continuation-in-part of U.S. patent application Ser. No. 16/925,033 which is a continuation of U.S. patent application Ser. No. 16/723,319, filed Dec. 20, 2019 which is a continuation of U.S. patent application Ser. No. 15/461,361, filed Mar. 16, 2017 and is related to and claims the priority benefit of U.S. Provisional Patent Application Ser. No. 62/309,412, filed Mar. 16, 2016 the content of which is hereby incorporated by reference in its entirety into this disclosure.

FIELD

The present disclosure relates to carbonic anhydrase nine (CA IX)-targeted near-infra red (NIR) dyes and methods for their therapeutic and diagnostic use. More specifically, this disclosure provides compounds and methods for diagnosing and surgical removal (image-guided surgery) of cells expressing CA IX (a widely accepted marker of hypoxic tissues and hypoxic regions of tumors), such as cancer cells of kidney, endometrial, urinary, colorectal, ovarian, breast, pancreatic, and esophagus, and hypoxic regions of many solid tumors, and related diseases. The disclosure further describes methods and compositions for making and using the compounds, methods incorporating the compounds, and kits incorporating the compounds.

BACKGROUND OF THE INVENTION

Carbonic anhydrase (CA) is a family of zinc metalloenzymes that catalyze the reversible hydration of carbon dioxide to bicarbonate and a proton. Out of fifteen CA isoforms (CA I, II, III, VA, VB, VI, VII, VIII, IX, X, XI, XII, XIII, XIV, and XV) present in human, twelve of them display catalytic activity. Three isoforms CA VIII, X and XI are non-catalytic and are termed as CA related proteins. Apart from the differences in catalytic efficiency, 12 active isoforms also differ in cellular, localization, tissue distribution, and involvement in physiological processes. Furthermore, aberrant expression of the enzymes is commonly associated with a host of diseases. These include: glaucoma (CA II, IV), cancer (CA IX, XII), edema (CA II), sterility (CA XIII), altitude sickness (CA II), obesity (CA VA) and hemolytic anemia (CA I). Out of 15 CA isoforms (alpha-class CAs), CA IV, IX, XII, XIV isoforms are associated with cell membrane. While both CA IX and XII express in solid tumors, CA IX has been shown to express more prevalent in solid tumors and exhibiting low expressions in normal tissues thereby making it an excellent biomarker for targeted-drug deliver for cancers.

The CA9 gene encodes for a 459 amino acid transmembrane glycoprotein that exists as a homodimer. It is comprised of: a proteoglycan-like domain (PG) (59 aa), catalytic domain (CA) (257 aa), a signal peptide domain (which is removed prior to enzyme maturation) (37 aa), transmembrane domain (TM) (20 aa), and a C-terminal intracellular domain (25 aa). Mass spectroscopy and X-ray crystallography have confirmed the presence of an intermolecular disulfide bridge between adjacent Cys137 residues of the mature homodimer that, coupled with a region of hydrophobic residues, are proposed to stabilize the dimer interface. N-linked and O-linked glycosylation sites also exist at Asn 309 and Thr 78, respectively.

The catalytic domain of CA IX is structurally homologous to the alpha-CAs with high amino acid conservation within the active site. The active site is located in a larger conical cavity (15 Å deep), which spans from the surface to the center of the protein. The zinc atom is located at the bottom of the cavity. In CA IX three histidine residues (His 226, 228 and 251, as numbered in the full length aa sequence) coordinate the zinc ion at the base of the active site cleft; in the crystal structure (PDB ID: 3IAI) sulfonamide amine group in the acetazolamide (AZM) displaces a zinc bound water/hydroxide (Zn—OH/$H_2O$) molecule maintaining a tetrahedral coordination about the zinc ion. Variability between the CA isoforms occurs in the hydrophobic and hydrophilic pockets of the active site and surface amino acids. In CA IX, Leu-223, Val-253, Val-263, Leu-267, Leu-273, Leu-330, and Pro-334 define the hydrophobic region, while Asn-194, His-196, Ser-197, Gln-199, Thr-201, and Gln-224 identify the hydrophilic one.

The catalytic efficiency of CA IX is fast and comparable to that of CA II; CA II exhibits a $k_{cat}$ of $1.4 \times 10^6$ while CA IX has a $k_{cat}$ of $3.8 \times 10^5$. The presence of the PG domain in CA IX is unique compared to the other CA isoforms and is thought to be responsible for its cell adhesion capability and maintaining its catalytic activity in the acidic tumor microenvironment.

The most critical role of CA IX is thought to be extracellular pH regulation, especially in the tumor microenvironment. Proliferating cancer cells often produce large amounts of lactate, carbon dioxide and protons during oncogenic metabolism making CA function pivotal in tumor cell survival. These metabolic products accumulate in the extracellular environment and significantly lower the extracellular pH. In order to maintain a near physiological intracellular pH, bicarbonate anions generated by CA IX during the hydrolysis of carbon dioxide are transported into the cell via anion transporters to buffer intracellular pH levels. In addition protons produced from the reaction remain extracellular thus contributing to the acidic nature of the tumor milieu. Disruption of this regulatory pathway would therefore have detrimental effects on overall tumor cell survival.

In a non-disease state CA IX expression is limited to the gut epithelium; specifically, the basolateral surfaces of the cryptic enterocytes of the duodenum, jejunum and ileum. The most prominent levels of CA IX are seen in these proliferating crypt cells suggesting that CA IX may be involved in intestinal stem cell proliferation and regulation of certain metabolic functions. Northern blot and immunohistochemical staining have also confirmed that CA IX expression in the ovarian coelomic epithelium, cells of hair follicles, pancreatic ductal cells and fetal rete testis. In addition high levels of CA IX are observed in developing embryonic tissues of the gut, lung and skeletal muscle and decrease in adult tissues. These observations indicate CA IX expression is primarily associated with areas of low pH and high rates of cell proliferation in normal tissues. Whether or not this makes CA IX a regulatory element in normal tissues has not been confirmed.

CA IX is ectopically expressed in a variety of neoplastic tissues. Expression has been observed in malignancies of the breast, lung, kidney, colon/rectum, cervix uteri, oral cavity, head/neck, gallbladder, liver, brain (high-grade), pancreas, and gastric epithelium. No differences exist between the cDNA of CA IX isolated from normal and tumor tissues, which implies similar physiological function in both tissues. CA IX expression depends on Hypoxia-inducible factor 1 (HIF-1) activation [via the upregulation of HIF-1α or the down regulation of Von Hippel-Linadau (VHL)]. Specifically, the activation of the HIF-1 mediated pathway that induces CA IX expression can be due to a reduction in cellular $O_2$ levels, an activation of signaling pathways via the presents of growth factors and inflammatory response elements, and in some cases due to mutations in the tumor suppressor, VHL as seen in cases of renal cell carcinoma (RCC) where CA IX is homogenously expressed. More recently, CA IX has shown to have significant expression levels in stromal cells that are engaged in a molecular cross-talk circuitry with cancer cells. Specifically, CA IX has been shown to be expressed in cancer-associated fibroblasts (CAFs) via redox-based stabilization of HIF-1. It is postulated that expression of CA IX in CAFs provides the acidic extracellular environment necessary to drive epithelial-mesenchymal transitions (EMTs) in adjacent cancer cells. Summation of these findings indicates CA IX as a diagnostic marker of events of tumor hypoxia in many solid tumors.

CA IX expression levels also serve as prognostic markers for several cancer types. Specifically, patients suffering from brain, breast, cervical, rectal or lung cancer that also display high levels of CA IX typically show a poorer prognosis. In contrast, for clear cell renal cell carcinoma patients low CA IX levels indicate poor clinical outcome. CA IX's contribution to maintaining the hypoxic tumor microenvironment is highly correlated to patient prognosis thus making it both a biomarker and drug target.

Hypoxia is a condition commonly seen in metastatic tumors where cells are deprived of oxygen due to rapid proliferation and a shift in their metabolism. Specifically, hypoxic tumor cells outgrow their blood supply leading to regions of low oxygen concentration (typically ≤1% of overall oxygen content) as well as a decrease in extracellular pH (~pH 6.5) in the tumor microenvironment. This hypoxic stress induces a shift in the tumor cells general metabolism from oxidative phosphorylation in the mitochondria to aerobic glycolysis in the cytosol as the main energy source. Interestingly, this metabolic shift remains present in the tumor cells regardless of the amount of the available $O_2$ in the given environment; a phenomenon often described as the Warburg effect. Since these tumor cells rapidly use glycolysis, increased amounts of lactic acid are exported from the cell, thus lowering the extracellular pH. As a result, there is an upregulation of pH homeostasis factors in tumor cells to establish a regulated intracellular/extracellular pH gradient.

Since the 1930s it has been well established that there is a correlation between tumor hypoxia and a resistance to radiation therapy. In addition, hypoxic tumors have shown to also present a resistance to common chemotherapeutics and a high probability of metastases; hence tumor hypoxia has been associated with a poor patient prognosis. Hypoxia inducible factors (HIF) are key regulators of the hypoxic-induced stress response in both normal and tumor cells. Specifically, increased HIF-1 has been associated with activating hypoxia-inducible genes that express hypoxia-responsive elements (HRE) that upregulate elements associated with metabolism, cell proliferation, drug resistance, pH regulation, angiogenesis, metastasis, and the overall progression of cancer. In order to survive in the acidic microenvironment these tumor cells must be able to maintain an intracellular pH at or near physiological levels (pH 7.4). Therefore CA activity is key in this regulatory process.

CA IX expression directly correlates to an upregulation of HIF elements, and has been shown to play a role in tumor cell survival, proliferation, migration, growth, adhesion, pH regulation, and cell-signaling pathways. The minimal expression of CA IX in normal tissues and its location on the external interface of tumor cells have made it an attractive therapeutic target. As a result, several methods have been employed to try to target CA IX in terms of isoform selective small-molecule inhibition, location specific targeting, knockdown using RNAi technology, and more recently antigenic targeting of CA IX as a means to deliver anti-cancer therapeutics directly to tumor.

CAIs have been extensively studied and their inhibition mechanisms are well established. Sulfonamide-based compounds are the most potent and most utilized among the CAI classes. These compounds bind to the zinc ion via a sulfonamide as the zinc-binding group (ZBG) in a deprotonated form displacing the zinc bound water/hydroxide molecule while still maintaining the tetrahedral coordination about the zinc ion. Though some sulfonamides display inhibition constants in the sub-nanomolar range for CA IX, they also inhibit other isoforms of CA. This is due to the conserved architecture of the active site among the human CAs. For all the catalytic human CAs, the three histidines coordinating the zinc, Thr 199 (CA II numbering; termed the "gatekeeper"), and Glu 106 are conserved. Both T199 and E106 play roles in catalysis. T199 hydrogen bonds to the zinc bound water/hydroxide via its OH group, while E106 hydrogen bonds to T199.

Small molecular weight CA inhibitors (CAIs) that utilize a ZBG tend to bind deep into the active site cavity and do not make extensive interactions with amino acids that vary between the CA isoforms, thus contributing to their indiscriminatory inhibition profiles. As a result, alternative approaches have been developed for better isoform specific CAIs, with the "tail-approach" being one of the most successful. In the "tail approach" a chemical moiety (known as the tail) is appended onto an organic scaffold of a ZBG (for example heterocyclic or aromatic). This tail elongates the inhibitor allowing it to make extensive interactions with amino acids towards the outside of the active site. The addition of these tails can also alter the properties of the CAI, for example making it more soluble by the addition of a tail that is hydrophilic in nature, or manipulating the overall charge of the compound; such as cationic CAIs. The use of structure-based drug design has proven a valuable technique to exploit the subtle differences existing between the active site of the various isoforms. For example, utilizing steroidal based sulfonamides as lead compounds has led to the development of several similar CAIs that are able to exploit CA IX's larger hydrophobic pocket by increasing the number of hydrophobic interactions via van der Waals contacts.

Despite the promise of structural exploitation of the CA IX active site to improve upon current and novel CAIs, the expression and crystallization of wild type CA IX has been an arduous challenge and thus made it difficult to carry out extensive structural analysis. A CA IX-mimic has been engineered, it is a modified CA II (an enzyme that is routinely expressed and crystallized) that contains active site mutations specific to CA IX. This has provided a useful template to rapidly analyze and predict modes of binding of CAIs to CA IX. Structural analysis of several CAIs has made it possible to design drugs that exhibit both location specific targeting and prodrug like properties that have shown to be useful in selectively inhibiting CA IX.

Apart from the development of small-molecule inhibitors, CA IX specific antibodies and their conjugates have also been engineered with some are currently in Phase III clinical trials (RECENARX). M75 and G250 are two such monoclonal antibodies that recognize the enzymes proteoglycan domain. Upon binding to CA IX these antibodies cause a reduction in tumor cell adhesion and motility, and induce natural killer cells to target tumor cells for eradication. The development of monoclonal antibodies with high binding affinity eliminates the problem of off-target effects commonly encountered in CAI drug design.

The extracellular location of the active site of CA IX presents an alternative method of targeting the enzyme in tumor cells. Specifically, CAIs can be designed that have physiochemical properties that allow them to be impermeable to the plasma membrane; hence decreasing the chance of inhibiting off-target cytosolic CAs observed by classic CAIs. This presents a drug design strategy that incorporates location specific targeting of CA IX rather than exploiting differences in inhibition profiles alone. To date several compounds that show limited membrane permeability have been synthesized and designed. Such compounds utilize bulky chemical moieties, such as in albumin-acetazolamide, or exploit charged moieties in the form of fluorescently labeled sulfonamides or cationic sulfonamide derivatives. The design of such CAIs employs essentially two distinct rationales: (1) high molecular weight compounds that are simply too bulky to cross the plasma membrane, or (2) a cationic moiety that is incapable of permeating into the reduced cytosolic environment. Despite both types of compounds showing favorable inhibition and membrane impermeability, the use of cationic sulfonamides has shown to be the more feasible option for drug development since high molecular weight compounds often induces potent allergic reactions and reduced bioavailability in vivo. As a result several cationic sulfonamides have been developed using quaternary ammonium sulfate (QAS) as a lead compound, or fluorescently labeled sulfonamide derivatives.

Glycoconjugated sulfonamides, a more recent class of CAIs, have shown to exhibit both membrane impermeability and isoform selective inhibition of CA IX. These particular CAIs utilize benzene sulfonamides, sulfonamides, or cyclic secondary sulfonamides conjugated to a mono- or disaccharide tail. The design of these CAIs was through the influence of the clinically used Topiramate (anti-epileptic therapeutic). Most likely the reason these compounds do not permeate into the cell is due to their high molecular weights, and the addition of a sugar moiety that is not easily transported. Furthermore, unlike previously used bulky sulfonamide derivatives, the addition of a sugar moiety allows these CAIs to maintain water-solubility, and thus maintain good bioavailability. Another promising aspect is that these CAIs show an impressive inhibition profile, with a >1000-fold selectivity for CA IX over CA II in some cases. Also, the carbohydrate attachment presents an area of manipulation on these CAIs where cleavable ester bonds can be added to the carbonyls of the carbohydrate tail allowing the CAI to be "packaged" in the form of a prodrug. Although these compounds present great promise in terms of developing a drug for CA IX, the use of carbohydrate moieties poses a potential dilemma. That is, the use of a carbohydrate, specifically a monosaccharide, might unintentionally interact with glucose transporters, similar to statins, in which myotoxicity was observed. However, this notion has not been tested. Interestingly, a way to circumvent such an issue would be the development of sucrose-based conjugates that would have no interactions with specific transporters due to the lack of sucrose transporters in human tissue. Interestingly, the current disaccharide-conjugates that have been developed into CAIs utilize a galactose moiety and show stronger inhibition for CA II versus CA IX. Although these compounds will not enter the cytosol, they may not bind to CA IX tightly enough to be considered a valid drug candidate. However, utilization of other disaccharide-based compounds, such as the suggested sucrose-conjugate mentioned previously, might show higher inhibition for CA IX, and thus present a CAI that is selective for CA IX in both location specificity and direct inhibition.

There are many publications containing both CA IX targets and NIR dyes. One work targets CA IX by synthesizing sulfonamide derivatives and testing them both in vitro and in vivo [Kevin Groves, Bagna Bao, Jun Zhang, Emma Handy, Paul Kennedy, Garry Cuneo, Claudiu T. Supuran, Wael Yared, Jeffrey D. Peterson, Milind Rajopadhye, Synthesis and evaluation of near-infrared fluorescent sulfonamide derivatives for imaging of hypoxia-induced carbonic anhydrase IX expression in tumors, Bioorganic & Medicinal Chemistry Letters, Volume 22, Issue 1, 1 Jan. 2012, Pages 653-657, ISSN 0960-894X, http://dx.doi.org/10.1016/j.bmcl.2011.10.058.]. Groves et al. synthesized sulfonamide derivatives and used amide linkage to couple them to succinimidyl esters of one or more of four commercially available hydropobic indocyanine NIR fluorochromes. They show localization of the synthesized sulfonamide derivatives to tumors in HT-29 tumor bearing mice.

A CA IX targeted agent is validated by Bao et al. for in vivo detection of CA IX expressing tumors [Bao B, Groves K, Zhang J, Handy E, Kennedy P, Cuneo G, et al. (2012) In Vivo Imaging and Quantification of Carbonic Anhydrase IX Expression as an Endogenous Biomarker of Tumor Hypoxia. PLoS ONE 7(11): e50860. doi:10.1371/journal.pone.0050860]. Localization was compared using a CA IX antibody.

Groves and Bao are both inventors on U.S. Patent Application Publication 2012/0321563, which discloses imaging agents that target carbonic anhydrase. The '563 claims a carbonic anhydrase targeting agent composed of a sulfonamide carbonic anhydrase binding moiety (CAB) that is linked to a linker L, and then to an optional Q group, and then finally to a NIR chromophore. The claimed NIR chromophore is a genus structure for the closed chain subgroup of the cyanine dye family.

Claudiu Trandafir Supuran is a co-inventor of International Patent Publication No. WO 2014/136076 titled "Assembly comprising an absorber of near infrared (NIR) light covalently linked to an inhibitor of carbonic anhydrase". The absorber of NIR light has an optical absorption cross section not lower than 100 $nm^2$.

Neri and co-workers use small molecule drug conjugates to target CA IX expressed in solid tumors in vivo [Krall, N., Pretto, F., Decurtins, W., Bernardes, G. J. L., Supuran, C. T. and Neri, D. (2014), A Small-Molecule Drug Conjugate for the Treatment of Carbonic Anhydrase IX Expressing Tumors. Angew. Chem. Int. Ed., 53: 4231-4235. doi: 10.1002/anie.201310709]. They prepare CAIX ligand-linker-dye conjugates, and show that it preferentially accumulates in subcutaneous CAIX-expressing SKRC52 tumors in nude mice. Claudiu Supuran is also an inventor in U.S. Pat. No. 8,628,771 B2 which discloses methods for inhibiting growth of cells that express CA IX, methods to screen for CA IX specific inhibitors, methods to visualize and image tissues that selectively bind the activated CA IX, methods to target cells that have expressed CA IX, and methods utilizing CA IX specific inhibitors coupled to gene therapy agents. The '771 uses a CA IX-specific antibody conjugated to a radioisotope to target and detect CA IX.

In another work, Neri and co-workers show that a bivalent ligand against the tumour marker carbonic anhydrase IX leads to an improved tumor targeting performance compared with the corresponding monovalent counterpart in the SKRC52 model of constitutively CAIX-positive renal cell carcinoma [Krall, Nikolaus, Francesca Pretto, and Dario Neri. "A bivalent small molecule-drug conjugate directed against carbonic anhydrase IX can elicit complete tumour regression in mice." Chem. Sci. 5.9 (2014): 3640-3644.]. The acetoazolamide derivatives are linked to monovalent and bivalent dye conjugates utilizing the commercially available dye, IRDye750.

Pomper and co-workers report on the synthesis and in vivo performance of [$^{111}$In]XYIMSR-0, a modified dual motif CAIX inhibitor for nuclear imaging of the clear cell subtype of renal cell carcinoma inspired by the earlier bivalent work by Neri et al. [Yang, X., et al. "Imaging of carbonic anhydrase IX with an 111In-labeled dual-motif inhibitor." Oncotarget 6.32 (2015): 33733-33742.]. Pomper replaced the IRDye750 portion of the molecule with 1,4,7,10-tetraazacyclododecane-1,4,7,10-tetraacetic acid (DOTA), a more hydrophilic species that also enables convenient radiolabeling with metal isotopes for positron emission tomography, single photon emission computed tomography, and radiopharmaceutical therapy. Indium-111 is used as the radionuclide for its relatively long half-life (2.8 day) to enable extended monitoring of pharmacokinetics. A FITC label is used as standard to measure CAIX binding affinities in the radiotracers.

In another work, Neri and co-workers describe the synthesis of an acetazolamide-based carbonic anhydrase ligand with high affinity for the tumor associated isoform CAIX, labeled with 99m Tc, a widely-used gamma-emitting radionuclide for nuclear medicine applications [Nikolaus Krall, Francesca Pretto, Martin Mattarella, Cristina Müller, and Dario Neri, A technetium 99m-labeled ligand of carbonic anhydrase IX selectively targets renal cell carcinoma in vivo, *J Nucl Med jnumed*.115.170514 published ahead of print Feb. 18, 2016 (10.2967/jnumed.115.170514).].

Supuran and co-workers describe the development of a new class of CA IX inhibitors that comprise a sulfamate as the zinc binding group, a variable linker, and a carbohydrate "tail" moiety [Moeker, Janina, et al. "Structural insights into carbonic anhydrase IX isoform specificity of carbohydrate-based sulfamates." *Journal of medicinal chemistry* 57.20 (2014): 8635-8645.]. The crystal structures of two of these compounds in complex with a CA IX-mimic (a variant of CA II, with active site residues that mimic CA IX) and one compound in complex with CA II have been determined to 1.7 Å resolution or better and demonstrate a selective mechanism of binding between the hydrophilic and hydrophobic pockets of CA IX versus CA II. Their structural analysis indicates that there exist two distinct modes of binding between CA IX and CA II of compound 5e of Moeker et al., however, in both cases, this compound interacts with the hydrophilic pocket of the enzyme. As this pocket is generally conserved between CA II and CA IX, it may account for the nanomolar binding affinities between both enzymes. In contrast, compound 5d of Moeker et al., which showed a differential inhibition profile between CA II and CA IX, binds to the CA IX active via interactions with the hydrophobic pocket. This region in the CA active site contains more variability between residues of CA II versus CA IX. As a result, this region has been termed as one of the "selective pockets" in the CA active site.

The X-ray structure of the catalytic domain of CA IX shows a fold that is significantly different from the other CA isoforms in quaternary structure [Alterio, Vincenzo, et al. "Crystal structure of the catalytic domain of the tumor-associated human carbonic anhydrase IX." Proceedings of the National Academy of Sciences 106.38 (2009): 16233-16238.]. They conclude that the region 125-137 differs both in structure and sequence in all these isozymes, and it represents a "hot spot" to be considered in structure-based drug design.

Treating cancer typically requires the use of several therapeutic strategies such as surgery, radiation therapy, and/or chemotherapies. Often therapies must be combined due to efficacy of one preceding the other. For example surgery and radiation therapy, although effective in a vast majority of cases, present limitations in that they can only target confined local regions of neoplastic tissue and are not effective at treating highly metastatic cancer cases. At this stage combinations of multiple chemotherapeutics are usually employed in an attempt to kill cancer cells that have migrated from the primary tumor site. Furthermore, highly aggressive and hypoxic tumors often develop resistance to radiation and certain chemotherapies, or are inoperable; hence alternative or combinations of chemotherapeutics are the only method of treatment available in these particular cases. This feature of hypoxia and its association with resistance to radiation and chemotherapies has been observed in several cancer types. This is most likely due to several factors including a reduction in overall 02 content making the generation of free-radicals needed for radiation therapy extremely difficult, the reduced extracellular pH disrupting functions of alkylating agents, and an upregulation of drug-resistance factors induced by HIFs. CA IX, has been linked to cases of therapeutic resistance for several cancers, and is often used as a biomarker for radiation resistance. As such evidence suggests labeling CA IX via a active site binding moiety linked to a NIR dye allows localization of hypoxic cancer cells, indicating its potential use as a means to assist surgeons in removing cancerous tissue during surgery.

Ferreira and co-workers compared the in vitro cytotoxicity of four NIR Dyes: IR125, IR780, IR813, and IR820 [Conceição, David S., Diana P. Ferreira, and Luis F. Vieira Ferreira. "Photochemistry and Cytotoxicity Evaluation of Heptamethinecyanine Near Infrared (NIR) Dyes." International journal of molecular sciences 14.9 (2013): 18557-18571.]. One source of cytotoxicity is due to after the intersystem crossing to the triplet state, the sensitizer can interact with molecular oxygen via a triplet-triplet annihilation process, generating singlet oxygen, or, alternatively, the sensitizer in its triplet state can participate in electron transfer processes or radical intermediate formation, also leading to the generation of reactive oxygen species. But Ferreira proposed that the main cause for the significant values of cytotoxicity presented by IR125 and IR813 should be related with their instability in solution (during long periods of time), and degradation products and photoproducts that arose during the inoculation of the dyes in the cellular culture. The addition of a cyclohexenyl ring promoted a significant molecular stabilization, and IR820 is the only NIR dye examined that exhibited no major cytotoxic effects, both in the presence and absence of light.

BRIEF SUMMARY OF THE INVENTION

This disclosure provides CA IX-targeted ligands linked to NIR dyes via different linkers to improve clinical properties (e.g. stability, PK properties, solubility, fast tumor accumulation, higher fluorescence, fast skin clearance, and higher tumor-to-background ratios) of the compounds. The disclosure also provides uses of the compounds in image-guided surgery and methods for synthesizing the same. This disclosure provides improvement of binding affinity CA IX ligands by incorporating hydrophobic groups to the ligands (using crystal structure of the CA IX protein) to fit into the extra binding pockets in the hydrophobic region of the active site of the protein. This disclosure also provides novel higher affinity ligands to improve in vivo affinity and PK properties of NIR conjugates. This disclosure further provides variation of the length of the linker between the ligands and NIR dyes to find optimize distance to fit in to the 15 Å cone shape cavity that span from the middle of the protein to the surface, thereby maintaining the binding affinity of the ligand to the active site by eliminate the steric hindrance effect of bulky NIR dye. This disclosure also provide variation of total charge of the Ligand-Linker-NIR dye conjugate by adding positive charges to the linker or reducing number of negative charges in the dye molecules to improve the specificity to the CA IX protein. This disclosure also provides compounds for use in the targeted imaging of tumors expressing CA IX and methods of use, for example, in imaging and surgery involving CA IX positive tissues and tumors.

In certain embodiments, compounds of the present invention have the form: B-W-X-Y-Z
wherein B is a CA IX-targeted molecule;
W is an extended hydrophobic residue
X is a hydrophobic spacer;
Y is an amino acid spacer; and
Z is a NIR dye.

In some embodiments, the CA IX-targeted molecule is chosen from the group consisting of a small molecule, a ligand, an inhibitor, an agonist or a derivative thereof. In some embodiments, the CA IX-targeted compound is a ligand. In other embodiments, the CA IX-targeted compound is a small molecule that binds to CA IX. In some embodiments, the CA IX-targeted compound is a small molecule with an extended hydrophobic moiety. In some embodiments, the CA IX-targeted compound is a small molecule with a fluorinated aromatic moiety.

In some embodiments, W is an extended hydrophobic residue. In some embodiments W is selected from the group consisting of: hydrophobic amino acids or moieties, such as neutral nonpolar (hydrophobic) amino acids, such as alanine, leucine, isoleucine, valine, proline, phenylalanine, tryptophan, and methionine or aromatic group, cyclohexyl group, tyrosine, and derivative thereof; basic (positively charged) amino acids such as arginine, histidine, and lysine and derivative thereof; neutral polar amino acids, such as glycine, serine, threonine, cysteine, tyrosine, asparagine, and glutamine and derivative thereof. In some embodiments, W is an aromatic amino acid and derivative thereof. In some embodiments, W has a positive charge. In other embodiments, W has a negative charge.

In some embodiments, X is a hydrophobic spacer. In some embodiments, X is selected from the group consisting of an six aminohectanoic acid (SAHA), eight aminooctonoic acid (EAOA), polyethylene glycol (PEG), polyethylene amine (PEA) unit, N-amino-dPEG$_2$ acid, a chain of 6 atoms, a spacer 6 atoms in length, a chain from 6 to 20 atoms in length; a peptide comprising aryl or aryl alkyl groups, each of which is optionally substituted, and where one aryl or aryl alkyl group is about 6 to about 10, or about 6 to about 14 atoms, and the other aryl or aryl alkyl group is about 10 to about 14, or about 10 to about 15 atoms. In another embodiment, the spacer comprises about 1 to about 20 atoms. In some embodiments, the spacer is 6 atoms in length. In some embodiments, the spacer comprises EAOA. In some embodiments, the spacer is variably charged. In some embodiments, X is peptide compromising positively charge amino acids (e.g. Arg, Lys, Orn) or quaternary amine containing amino acid. In other embodiments, X has a negative charge.

In some embodiments, Y is an amino acid spacer. In some embodiments, Y is selected from the group consisting of: acidic (negatively charged) amino acids, such as aspartic acid and glutamic acid and derivative thereof; basic (positively charged) amino acids such as arginine, histidine, and lysine and derivative thereof; neutral polar amino acids, such as glycine, serine, threonine, cysteine, tyrosine, asparagine, and glutamine and derivative thereof; neutral nonpolar (hydrophobic) amino acids, such as alanine, leucine, isoleucine, valine, proline, phenylalanine, tryptophan, and methionine; and derivatives thereof. In some embodiments, Y is an aromatic amino acid and derivative thereof. In some embodiments, Y has a positive charge. In other embodiments, Y has a negative charge.

In some embodiments, Z is selected from the group consisting of near-infra red dyes, including but not limited to, LS288, IR800, SP054, S0121, KODAK, S2076, S0456 and/or the dyes selected from group consisting of:

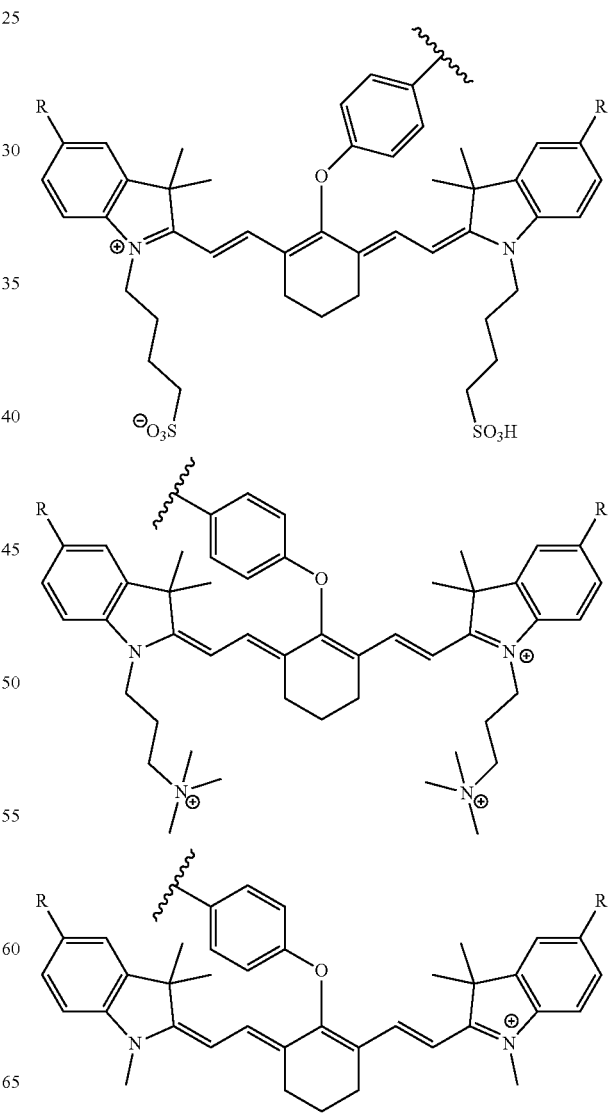

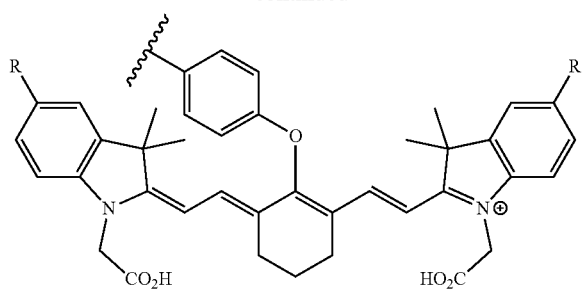

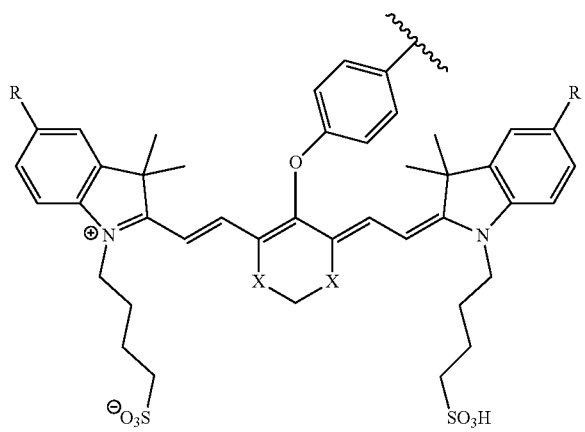

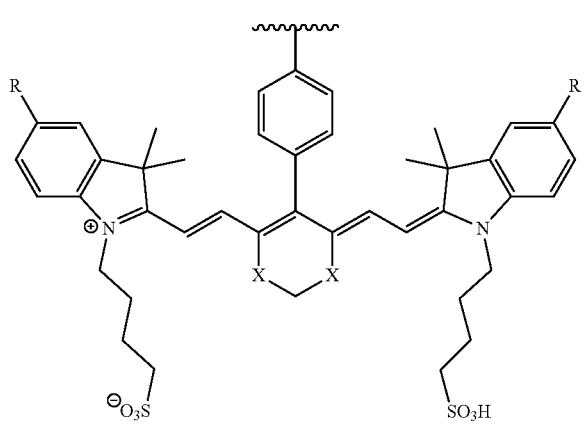

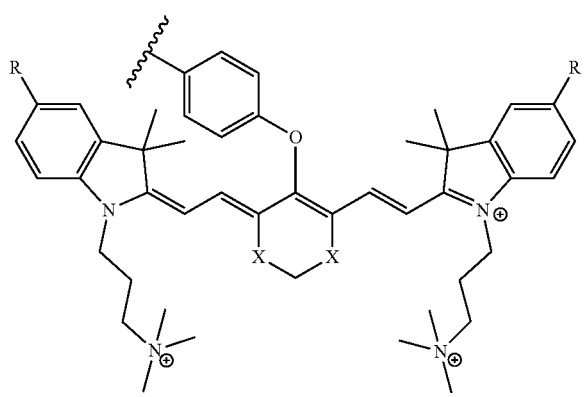

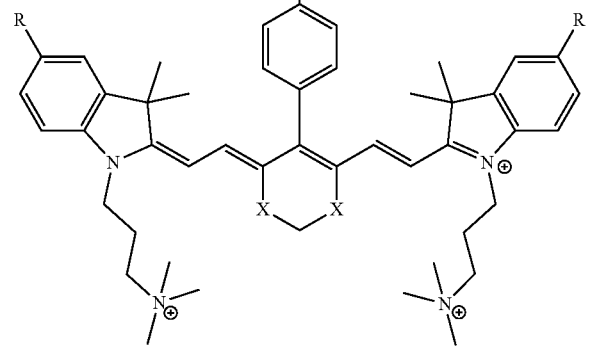

R = H or R = SO₃H; X = O, S, N

In certain embodiments, the Z is variably charged. In some embodiments, Z has a positive charge. In other embodiments, Z has a negative charge.

In some embodiments, compounds of the present invention have the form:

B-W-X-Y-Z wherein B is a CA IX-targeted molecule; W is an extended hydrophobic residue; X is a hydrophobic spacer; Y is an amino acid spacer; and Z is a NIR dye.

In certain embodiments, compounds of the present invention have the formula:

B-W-X-Y-Z wherein B is a CA IX-targeted molecule; W is an extended hydrophobic residue, X is a spacer; Y is an amino acid spacer with a sulfur-containing side chain group; and Z is an NIR dye. In some embodiments, the amino acid spacer with a sulfur-containing side group is cysteine. In some embodiments, the amino acid spacer with a sulfur-containing side group is methionine. In some embodiments, the amino acid spacer with a sulfur-containing side group is molecule containing a thiophenol moiety.

In some embodiments, compounds of the present invention have the form:

B-W-X-Y-Z wherein B is a CA IX-targeted molecule; W is an extended hydrophobic residue, X is a hydrophopic spacer; Y is an amino acid spacer with a chalcogen-containing side chain group; and Z is an NIR dye.

In some embodiments the present invention provides compounds of the form:

B-W-X-Y-Z

Wherein, B is a CA IX-targeted molecule; W is an extended hydrophobic residue, X is a spacer; Y is an amino acid chosen from the group consisting of tyrosine, cysteine, lysine, or a derivative thereof; and Z is an NIR dye. In some embodiments, Y comprises a tyrosine or tyrosine derivative. In some embodiments, Y comprises a tyrosine and a carbon isotope is on the aromatic ring of tyrosine. In some embodiments, Y comprises an amino acid with an aromatic ring with a hydrogen isotope.

The present invention also relates to a compound having the structural formula:

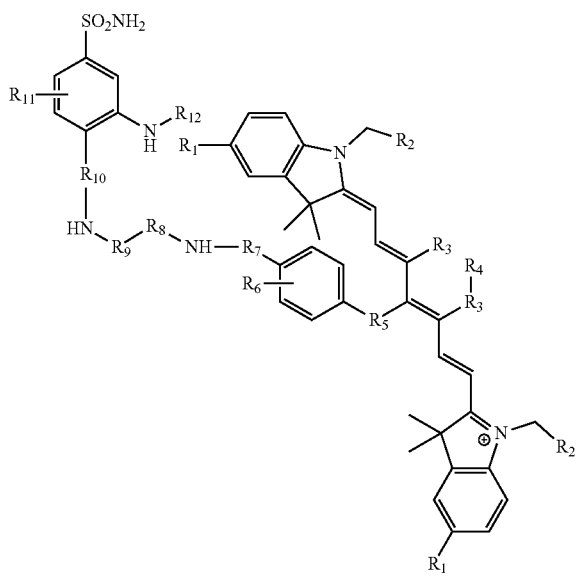

or a pharmaceutically acceptable salt thereof, or isotopes thereof, wherein:

$R_1$ represents a hydrogen or $SO_3H$;

$R_2$ represents a hydrogen, $CH_3$, $C_3H_6SO_3^-$, $C_3H_6SO_3H$ or $C_4H_8SO_3^-$, or $C_4H_8SO_3H$ or $C_3H_6N^+(CH_3)_3$;

$R_3$ represents a carbon, optionally one or more sharing bonds, $R_4$ represents a carbon with optionally one or more sharing bonds;

$R_5$ represents nitrogen, oxygen, or sulfur or no atom (direct C—C bond between aromatic ring and vinyl ring);

$R_6$ is optional and when present represents aromatic substitution group to enhance the spectral properties such as increase brightness and stability of the vinyl ether bridge;

$R_7$ is optional and when present represents linkers with aromatic amino acids such as Phe, Trp, His or derivative thereof, cationic amino acids such Arg, Lys, or derivative thereof, anionic amino acids such as Asp, Glu or derivative of them, unnatural amino acids of aromatic/cationic/anionic acids or derivative thereof;

$R_8$ is optional and when present represents a linear carbon chain, or polyethylene glycol linker, cationic linker, or derivative thereof;

$R_9$ optional and when present represents hydrophobic moiety such as Phe, Val, Leu, Ile, Trp, His, Arg, Lys, Asp, Glu, or derivative thereof;

$R_{10}$ represents hydrophobic linker; and $R_{11}$ is optional and when present represents aromatic substitution group to enhance the binding affinity, stability, hydrophobicity of the molecule such as F, NO2, or thereof, R12 optional and when present represents hydrophobic moiety such as Phe, Val, Leu, Ile, Trp, His, or derivative thereof or cyclic moiety such as cyclohexyl, cyclooctyl, or derivative thereof.

In some embodiments compounds of the present invention have an absorption and emission maxima between about 500 nm and about 900 nm. In some embodiments compounds of the present invention have an absorption and emission maxima between about 600 nm and 800 nm.

In some embodiments compounds of the present invention are made to fluoresce after distribution thereof in the tissue cells. In some embodiments compounds of the present invention are made to fluoresce by subjecting the compounds to excitation light of near infrared wavelength. In some embodiments compounds of the present invention have a binding affinity to CA IX that is similar to the binding affinity of ligand (C-SPA). In some embodiments compounds of the present invention are highly selective for targeting to a tumor cell. In particularly preferred embodiments, the compounds of the present invention are targeted to cancer cells under hypoxia condition or hypoxic tissues.

In certain embodiments compounds of the present invention are administered to a subject in need thereof and in some embodiments the administered composition comprises, in addition to the compound, a pharmaceutically acceptable carrier, excipient or diluent.

Some embodiments of the present invention provide methods of optical imaging of CA IX-expressing biological tissue, said method comprising:
(a) contacting the biological tissue with a composition comprising a CA IX-targeted NIR dye compound,
(b) allowing time for the compound in the composition to distribute within the biological target;
(c) illuminating the tissue with an excitation light of a wavelength absorbable by the compound; and
(d) detecting the optical signal emitted by the compound.

In some embodiments, these methods are used in detection of diseases associated with high CA IX expression. In some embodiments, further comprising the step of constructing an image from the signal emitted in (d). In some embodiments, the invention provides the aforementioned method wherein step (a) includes two or more fluorescent compounds whose signal properties are distinguishable are contacted with the tissue, and optionally the tissue is in a subject. In some embodiments the present invention provides use of an endoscope, catheter, tomographic system, hand-held optical imaging system, surgical goggles, or intraoperative microscope for the illuminating and/or detecting method steps.

In some embodiments, compositions and methods of the present invention are used to treat cancer. In some embodiments, the cancer is selected from the group consisting of lung cancer, bladder cancer, pancreatic cancer, liver cancer, kidney cancer, sarcoma, breast cancer, brain cancer, neuroendocrine carcinoma, colon cancer, prostate cancer, testicular cancer or melanoma. In some embodiments, CA IX-targeted NIR dye compounds of the present invention are used for imaging of CA IX-expressing cells. In certain embodiments those cells are chosen from the group consisting of bladder cancer cells, pancreatic cancer cells, liver cancer cells, lung cancer cells, kidney cancer cells, sarcoma cells, breast cancer cells, brain cancer cells, neuroendocrine carcinoma cells, colon cancer cells, prostate cancer cells, testicular cancer cells or melanoma cells.

The present invention also provides methods of targeting a cell type in a biological sample comprising: (a) contacting the biological sample with a CA IX-targeted NIR dye compound for a time and under conditions that allow for binding of the compound to at least one cell of the target cell type; and (b) optically detecting the presence or absence of the compound of in the biological sample, wherein presence of the compound in detecting step (b) indicates that the target cell type is present in the biological sample. In some embodiments the present invention provides methods for optical detection of CA IX-expressing cells comprising administering CA IX-targeting NIR dye compounds of the present invention and subjecting the compound to an excitation light source and detecting fluorescence from the compound. In some embodiments, the excitation light source is near-infrared wavelength light. In some embodiments the excitation light wavelength is within a range from about 600 to 1000 nanometers. In some embodiments the excitation light wavelength is within a range from about 670 to 850 nanometers.

In certain embodiments the present invention provides methods of performing image guided surgery on a subject comprising:
 a) administering a composition comprising a CA IX-targeting NIR dye compound under conditions and for a time sufficient for the compound to accumulate at a given surgical site;
 b) illuminating the compound to visualize the compound using infrared light; and
 c) performing surgical resection of the areas that fluoresce upon excitation by the infrared light.

In some embodiments methods of the present invention the infrared light wavelength is within a range from about 600 to 1000 nanometers. In some embodiments methods of the present invention use an infrared light wavelength is within a range from about 670 to 850 nanometers.

Some embodiments of the present invention provide a method of diagnosing a disease in a subject comprising:
 a) administering to a subject in need of diagnosis an amount of a CA IX-targeted NIR dye compound for a time and under conditions that allow for binding of the compound to at least one CA IX-expressing cell;
 b) measuring the signal from the compound of present in the biological sample;
 c) comparing the signal measured in b) with at least one control data set, wherein the at least one control data set comprises signals from the compound of claim 1 contacted with a biological sample that does not comprise the target cell type; and
 d) providing a diagnosis of disease wherein the comparison in step c) indicates the presence of the disease.

Some embodiments of the present invention provide a kit comprising a CA IX-targeting NIR dye compound. In some embodiments, the kit is used for the imaging of CA IX-expressing cells. In some embodiments the CA IX-expressing cells are tumor cells. In certain embodiments the CA IX-expressing cells are cancer cells. In certain embodiments the CA IX-expressing area is tumor microenvironment. In some embodiments the present invention is used for detection of metastatic disease. In some embodiments compounds of the present invention are used for improved surgical resection and/or improved prognosis. In some embodiments methods of the present invention provide cleaner surgical margins than non-NIR conjugated fluorescing dyes. In some embodiments CA IX-targeted NIR dye compounds of the present invention have an improved tumor-to-background ratio.

In other embodiments, the cells being detected are more than 5 mm below the skin. In some embodiments, the tissue being detected is more than 5 mm below the skin. In other embodiments, the tumor being detected is more than 5 mm below the skin. In some embodiments, the cells being detected are more than 6 mm, 7 mm, 8 mm, 9 mm, or 10 mm below the subject's skin. In some embodiments of the present invention dye probes that are detectable outside of the visible light spectrum. In some embodiments dye probes greater than the visible light spectrum are used. In some embodiments compounds of the present invention comprise dye probes sensitive to wavelengths between 650 nm and 900 nm.

In some embodiments the CA IX-targeted NIR dye compounds of the present invention have maximum light absorption wavelengths in the near infrared region of between about 650 nm and 1000 nm, for example and in one embodiment, at approximately 800 nm.

In a further embodiment of the methods provided, the CA IX-expressing cancer cells are of a tumor. In still a further embodiment of the methods provided, the CA IX-expressing cancer is a tumor. In some embodiments, the volume of the tumor is at least 1000 mm$^3$. In some embodiments, the volume of the tumor is less than 1000 mm$^3$. In some embodiments, the volume of the tumor is less than 950 mm$^3$. In some embodiments, the volume of the tumor is less than 900 mm$^3$. In some embodiments, the volume of the tumor is less than 850 mm$^3$. In some embodiments, the volume of the tumor is less than 800 mm$^3$. In some embodiments, the volume of the tumor is less than 750 mm$^3$. In some embodiments, the volume of the tumor is less than 700 mm$^3$. In some embodiments, the volume of the tumor is less than 650 mm$^3$. In some embodiments, the volume of the tumor is less than 600 mm$^3$. In some embodiments, the volume of the tumor is less than 550 mm$^3$. In some embodiments, the volume of the tumor is less than 500 mm$^3$. In some embodiments, the volume of the tumor is less than 450 mm$^3$. In some embodiments, the volume of the tumor is less than 400 mm$^3$. In some embodiments, the volume of the tumor is less than 350 mm$^3$. In some embodiments, the volume of the tumor is less than 300 mm$^3$. In some embodiments, the volume of the tumor is less than 250 mm$^3$. In some embodiments, the volume of the tumor is less than 200 mm$^3$. In some embodiments, the volume of the tumor is less than 150 mm$^3$. In some embodiments, the volume of the tumor is less than 100 mm$^3$. In one embodiment, the volume of the tumor is at least 75 mm$^3$. In another embodiment, the volume of the tumor is less than 75 mm$^3$. In another embodiment, the volume of the tumor is less than 70 mm$^3$. In another embodiment, the volume of the tumor is less than 65 mm$^3$. In another embodiment, the volume of the tumor is less than 60 mm$^3$. In another embodiment, the volume of the tumor is less than 55 mm$^3$. In one embodiment, the volume of the tumor is at least 50 mm$^3$. In other embodiments, the tumor is less than 50 mm$^3$. In another embodiment, the volume of the tumor is less than 45 mm$^3$. In other embodiments, the volume of the tumor is less than 40 mm$^3$. In another embodiment, the volume of the tumor is less than 35 mm$^3$. In still another embodiment, the volume of the tumor is less than 30 mm$^3$. In another embodiment, the volume of the tumor is less than 25 mm$^3$. In still another embodiment, the volume of the tumor is less than 20 mm$^3$. In another embodiment, the volume of the tumor is less than 15 mm$^3$. In still another embodiment, the volume of the tumor is less than 10 mm$^3$. In still another embodiment, the volume of the tumor is less than 12 mm$^3$. In still another embodiment, the volume of the tumor is less than 9 mm$^3$. In still another embodiment, the volume of the tumor is less than 8 mm$^3$. In still another embodiment, the volume of the tumor is less than 7 mm$^3$. In still another embodiment, the volume of the tumor is less than 6 mm$^3$. In still another embodiment, the volume of the tumor is less than 5 mm$^3$.

In one embodiment, the tumor has a length of at least 5 mm prior to surgical recession using a CA IX-targeted NIR dye compound of the present invention. In one embodiment, these methods detect tumors less than 5 mm. In other embodiments the methods herein detect tumors less than 4 mm. In some embodiments, the methods herein detect tumors less than 3 mm. In another embodiment, the tumor has a length of at least 6 mm. In still another embodiment, the tumor has a length of at least 7 mm. In yet another embodiment, the tumor has a length of at least 8 mm. In another embodiment, the tumor has a length of at least 9 mm. In still another embodiment, the tumor has a length of at least 10 mm. In yet another embodiment, the tumor has a length of at least 11 mm. In a further embodiment, the tumor has a length of at least 12 mm. In still a further embodiment, the tumor has a length of at least 13 mm. In still a further embodiment, the tumor has a length of at least 14 mm. In another embodiment, the tumor has a length of at least 15 mm. In yet another embodiment, the tumor has a length of at least 16 mm. In still another embodiment, the tumor has a length of at least 17 mm. In a further embodiment, the tumor has a length of at least 18 mm. In yet a further embodiment, the tumor has a length of at least 19 mm. In still a further embodiment, the tumor has a length of at least 20 mm. In another embodiment, the tumor has a length of at least 21 mm. In still another embodiment, the tumor has a length of at least 22 mm. In yet another embodiment, the tumor has a length of at least 23 mm. In a further embodiment, the tumor has a length of at least 24 mm. In still a further embodiment, the tumor has a length of at least 25 mm. In yet a further embodiment, the tumor has a length of at least 30 mm.

In some embodiments the present disclosure relates to CA IX-targeted compounds conjugated to near-infra red (NIR) dyes and methods for their therapeutic and diagnostic use. More specifically, this disclosure provides compounds and methods for diagnosing and treating diseases associated with cells expressing CA IX, such as of kidney, endometrial, urinary, colorectal, ovarian, breast, pancreatic, and esophagus, and hypoxic regions of many solid tumors, and related diseases. The disclosure further describes methods and compositions for making and using the compounds, methods incorporating the compounds, and kits incorporating the compounds. It has been discovered that a CA IX-targeted compound, such as ligands with extended hydrophopic residues (W) to improve the binding affinity and specificity for CA IX conjugated to an NIR dye via a linker (X-Y) may be useful in the imaging, diagnosis, and/or treatment of kidney, endometrial, urinary, colorectal, ovarian, breast, pancreatic, and esophagus, and hypoxic regions of many solid tumors, and related diseases that involve pathogenic cell populations expressing or overexpressing CA IX. CA IX is a cell surface protein that is internalized in a process analogous to endocytosis observed with cell surface receptors, such as vitamin receptors. Accordingly, it has been discovered that certain conjugates that include a linker having a predetermined length, and/or a predetermined diameter, and/or preselected functional groups along its length may be used to treat, image, and/or diagnose such diseases.

In one illustrative embodiment, the linker [either X or spacer between the ligand and NIR dye (W-X-Y)] may be a releasable or non-releasable linker. In one aspect, the linker L is at least about 6 atoms in length. In one variation, the linker [X or W-X-Y] is at least about 8 atoms in length. In one variation, the linker [X or W-X-Y] is at least about 10 atoms in length. In another variation, the linker [X or W-X-Y] is between about 6 and about 14, between about 6 and about 20, or between about 6 and about 18 atoms in length. In another variation, the linker [X or W-X-Y] is between about 10 and about 20, between about 14 and about 12, or between about 10 and about 16 atoms in length.

In an alternative aspect, the linker [X or W-X-Y] is at least about 10 angstroms (Å) in length. In one variation, the linker [X or W-X-Y] is at least about 14 Å in length. In another variation, the linker [X or W-X-Y] is at least about 16 Å in length. In another variation, the linker [X or W-X-Y] is in the range from about 10 Å to about 20 Å in length.

In an alternative aspect, at least a portion of the length of the linker [X or W-X-Y] is about 4 Å in diameter or less at the end connected to the binding ligand B. In one variation, at least a portion of the length of the linker [X or W-X-Y] is about 4 Å or less, or about 3 Å or less in diameter at the end connected to the binding ligand B. It is appreciated that the illustrative embodiments that include a diameter requirement of about 5 Å or less, about 4 Å or less, or about 3 Å or less may include that requirement for a predetermined length of the linker, thereby defining a conical cavity-like portion of the linker. Illustratively, in another variation, the linker includes a conical cavity portion at the end connected to the binding ligand that is at least about 6 Å in length and about 5 Å or less, about 4 Å or less, or about 3 Å or less in diameter.

In another embodiment, the linker [W-X-Y] includes one or more hydrophobic linkers capable of interacting with one or more residues of CA IX, including amino acids that have hydrophobic side chains, such as Val, Leu, Phe, Tyr, His, Trp, Met, and like residues. In another embodiment, the linker [W-X-Y] includes one or more hydrophilic linkers capable of interacting with one or more residues of CA Ix protein, including amino acids that have hydrophilic side chains, such as Ser, Thr, Cys, Arg, Orn, Lys, Asp, Glu, Gln and like residues. It is to be understood that the foregoing embodiments and aspects may be included in the linker X either alone or in combination with each other [W-X-Y or X-Y, or W-Y]. For example, linkers X that are at least about 6 atoms in length and about 5 Å, about 4 Å or less, or about 3 Å or less in diameter or less are contemplated and described herein, and also include one or more hydrophilic linkers capable of interacting with one or more residues of CA IX, including Asn, His, Ser, Glu, Thr, Gln in the hydrophilic pocket or Leu, Val, Val, Leu, Pro in the hydrophobic pocket and like residues are contemplated and described herein.

In another embodiment, one end of the linker is not branched and comprises a chain of carbon, oxygen, nitrogen, and sulfur atoms. In one embodiment, the linear chain of carbon, oxygen, nitrogen, and sulfur atoms is at least 5 atoms in length. In one variation, the linear chain is at least 7 atoms, or at least 10 atoms in length. In another embodiment, the chain of carbon, oxygen, nitrogen, and sulfur atoms are not substituted. In one variation, a portion of the chain of carbon, oxygen, nitrogen, and sulfur atoms is cyclized with a divalent fragment. For example, a linker (Y) comprising the dipeptide Phe-Tyr, or amino acid Tyr, may include a piperazin-1,4-diyl structure by cyclizing two nitrogens with an ethylene fragment, or substituted variation thereof.

In another embodiment, pharmaceutical compositions are described herein, where the pharmaceutical composition includes the conjugates described herein in amounts effective to treat diseases and disease states, diagnose diseases or disease states, and/or image tissues and/or cells that are associated with pathogenic populations of cells expressing or over expressing CA IX. Illustratively, the pharmaceutical compositions also include one or more carriers, diluents, and/or excipients.

In another embodiment, methods for treating diseases and disease states, diagnosing diseases or disease states, and/or imaging tissues and/or cells that are associated with pathogenic populations of cells expressing or over expressing CA IX are described herein. Such methods include the step of administering the conjugates described herein, and/or pharmaceutical compositions containing the conjugates described herein, in amounts effective to treat diseases and disease states, diagnose diseases or disease states, and/or image tissues and/or cells that are associated with pathogenic populations of cells expressing or over expressing CA IX.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The above-mentioned and other features of this disclosure, and the manner of attaining them, will become more apparent and the disclosure itself will be better understood by reference to the following description of embodiments of the disclosure taken in conjunction with the accompanying drawings.

FIG. 51A illustrates Ex vivo fluorescence image of a mouse injected with 1 nmol of OTL410 collected 3 h post injection and after removal of the skin around the tumor. FIG. 51B illustrates a grey scale image of the same mouse with a line drawn across the tumor. FIG. 51D illustrates a rectangle drawn around the tumor. FIG. 51C illustrates a plot profile generated from the a grey scale image of the same mouse showing grey vale versus distance.

FIG. 52A illustrates 3 h, n=5. FIG. 52B illustrates 12 h, n=4. FIG. 52C illustrates 24 h, n=4. Blue bars indicate mean and yellow bars indicate standard deviation. FIG. 52D illustrates a comparison of mean TBR of OTL410 and the untargeted dye PPES0456 with n=5 mice/group. The conjugate in each case was administered in 100 µl of 5% aqueous dextrose by tail vein injection, and the mice were euthanized by $CO_2$ inhalation 3 h post injection or 12 h or 24 h. Whole body fluorescence images were collected ex vivo, and subsequently, indicated tissues and organs were isolated and imaged using an AMI small animal imager (Ex=745 nm, Em=810 nm, FOV=25, binning 2, lamp power=55%).

FIG. 53A illustrates the image acquired after ex vivo whole-body fluorescence imaging and skin around the tumor was removed. FIG. 53B illustrates, guided by the fluorescence image, the image acquired after the tumor was resected. Note complete removal of the tumor with no fluorescent cells left behind (Ex=745 nm, Em=810 nm, FOV=25, binning 2, lamp power=55%).

FIGS. 54A and 54B illustrate KB, a derivative of HeLa cervical cancer cell line. FIGS. 54C and 54D illustrate MDA-MB-231, a triple negative breast cancer cell line. FIGS. 54E and 54F illustrate FaDu, a head & neck cancer cell line; and FIGS. 54G and 54H illustrate HT29, a colorectal cancer cell line. OTL410 was administered at a dose of 2 nmol/mouse in 100 µl of 5% aqueous dextrose, and the images were collected 4 h later using an AMI imager with the mice under anesthesia.

Figure 1:
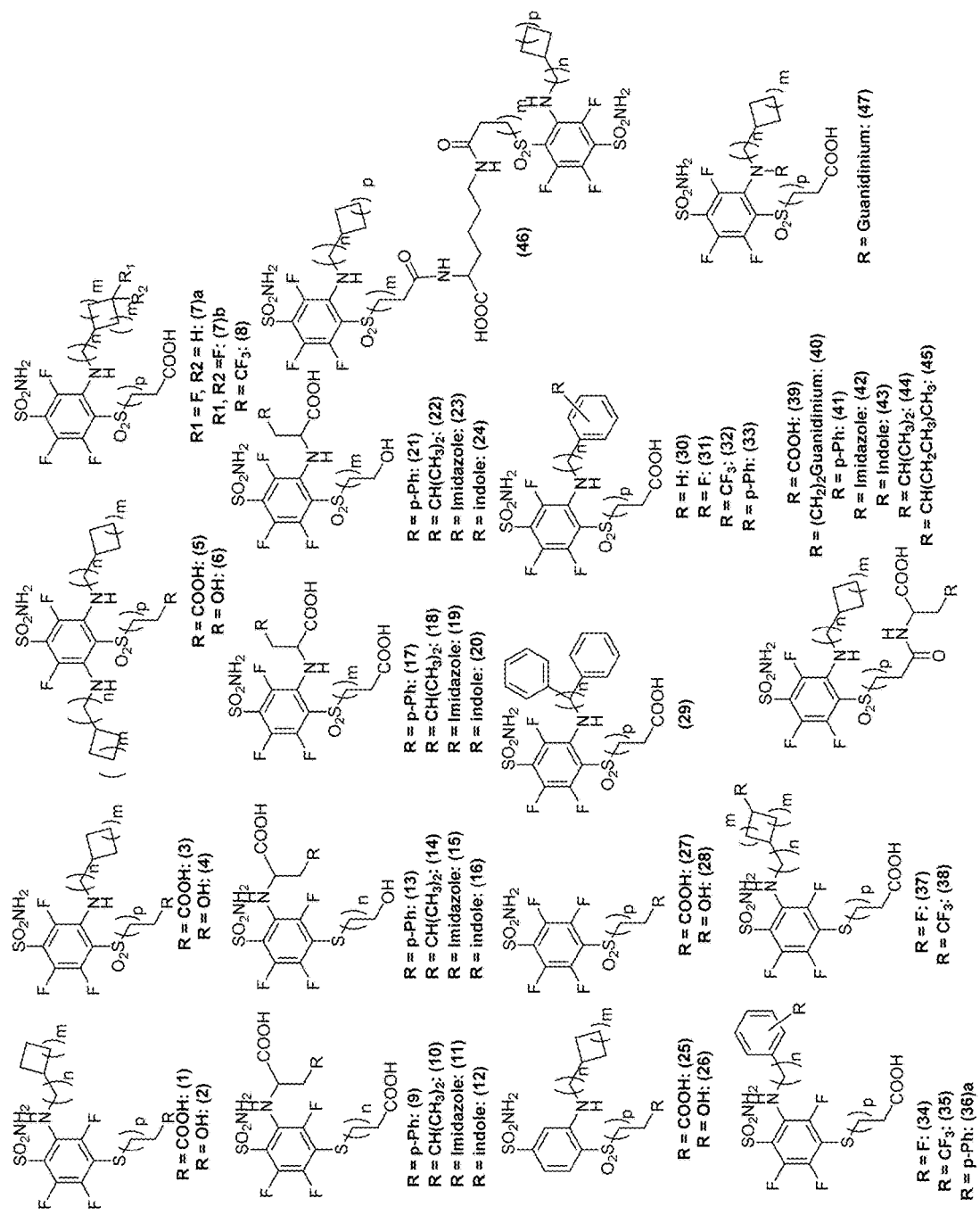
FIG. 1 shows The chemical structure of unconventional CA IX ligands with extended binding residues (n, m, p=0, 1, 2, 3 . . . )

Corresponding reference characters indicate corresponding parts throughout the several views. Although the drawings represent embodiments of the present disclosure, the drawings are not necessarily to scale and certain features may be exaggerated in order to better illustrate and explain the present disclosure.

Definitions

It is to be understood that this invention is not limited to the particular methodology, protocols, cell lines, constructs, and reagents described herein and as such may vary. It is also to be understood that the terminology used herein is for the purpose of describing particular embodiments only, and is not intended to limit the scope of the present invention, which will be limited only by the appended claims.

As used herein and in the appended claims, the singular forms "a," "an," and "the" include plural reference unless the context clearly indicates otherwise. Thus, for example, reference to a "carbonic anhydrase IX ligand" "CA IX ligand" is a reference to one or more such ligands and includes equivalents thereof known to those skilled in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

With respect to CA IX-targeted NIR conjugates of the present invention, the term "antigenically specific" or "specifically binds" refers to CA IX-targeting compounds that bind to one or more epitopes of CA IX protein, but which do not substantially recognize and bind other molecules in a sample containing a mixed population of antigens.

The term "epitope" as used herein refers to a site on CA IX that is recognized by Ligand. An epitope may be a linear or conformationally formed sequence or the shape of amino acids.

As used herein, "CA IX-targeting compound" or "CA IX-targeted compound" shall include those small molecules, ligands, polypeptides and proteins that have at least the biological activity of specific binding to CA IX or an epitope of CA IX. These compounds include ligands, receptors, peptides, or any amino acid sequence that binds to CA IX or to at least one CA IX epitope.

Compounds of the present invention comprise a CA IX-targeting compound, they may bind a portion of CA IX itself, or they may bind a cell surface protein or receptor that is associated with CA IX.

As used herein, "extended hydrophobic residue" shall include hydrophobic amino acids or moieties, such as neutral nonpolar (hydrophobic) amino acids, such as alanine, leucine, isoleucine, valine, proline, phenylalanine, tryptophan, and methionine or aromatic group, cyclohexyl group, tyrosine, and derivative thereof; basic (positively charged) amino acids such as arginine, histidine, and lysine and derivative thereof; neutral polar amino acids, such as glycine, serine, threonine, cysteine, tyrosine, asparagine, and glutamine and derivative thereof.

As used herein "hydrophobic spacer" shall include six aminohectanoic acid (SAHA), eight aminooctonoic acid (EAOA), polyethylene glycol (PEG), polyethylene amine (PEA) unit, N-amino-dPEG$_2$ acid, a chain of 6 atoms, a spacer 6 atoms in length, a chain from 6 to 20 atoms in length; a peptide comprising aryl or aryl alkyl groups, each of which is optionally substituted, and where one aryl or aryl alkyl group is about 6 to about 10, or about 6 to about 14 atoms, and the other aryl or aryl alkyl group is about 10 to about 14, or about 10 to about 15 atoms.

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission.

The present invention addresses, among other things, problems associated with the early diagnosis and surgical treatment of CA IX-expressing cells involved in disease and/or cancer, and in particular CA IX-targeted dye conjugates with improved imaging, diagnostic, biological properties including, as non-limiting examples, higher specificity, decreased background signal and increased tumor fluorescence.

DETAILED DESCRIPTION

Surgery cures 50% of patients with solid tumors in the US, while chemo- and radiotherapy cure less than 5% of all cancer patients. Over 700,000 patients undergo cancer surgery every year in the US and 40% of surgical patients have a recurrence of locoregional disease within 5 years. Despite major advances in the field of oncology there remains a need for early detection, methods to overcome hurdles to complete surgical resection of the primary tumor with negative margins, and removal of metastatic cancer cells and identification of satellite disease. Achieving these three goals not only improves disease clearance but also guides decisions regarding postoperative chemotherapy and radiation. While non-targeted fluorescent dyes have been shown to passively accumulate in some tumors, the resulting tumor-to-background ratios are often poor and the boundaries between malignant and healthy tissues can be difficult to define. Although ligand targeted fluorescence dyes (e.g., EC17: Folate-EDA-FITC) have been used for imaging a tissue, those dyes have been ineffective as they would not penetrate deep tissue and hence only identified the specific cells on the surface of a tissue rather than deeper within the tissue sample. In addition, fluorescein-based dyes have the disadvantages that of low shelf-life stability. Thiourea bridge formed by Fluorescence isothiocynate (FITC) compounds easily decomposes making unstable compound. In addition, as EC17 uses fluorescein which has the drawback of a relatively high level of nonspecific background noise from collagen in the tissues surrounding the imaging site. Moreover, the absorption of visible light by biological chromophores, in particular hemoglobin, further limits the usefulness of dyes that incorporate fluorescein. Therefore, conventional dyes cannot readily detect tumors that may be buried deeper than a few millimeters in the tissue. Furthermore, fluorescence from fluorescein is quenched at low pH (below pH 5).

In order for a dye material to be useful in detecting and guiding surgery or providing detection of early, metastatic, and other tissue imaging it is important to overcome these drawbacks. The present invention provides design and development of CA IX-targeted ligand with extended hydrophobic moiety using crystal structure of CA IX to increase binding affinity and specificity for CA IX. The present invention provides CA IX-targeted conjugates of near infrared dyes that are stable, fluoresce in the infrared range, penetrate deep within targeted tissue to produce a specific and bright identification of areas of tissue that express CA IX, fast clearance from tissues that do not express CA IX to obtain high tumor-to-background ratio, and fast skin clearance. More specifically, the CA IX-targeted conjugates are linked to the near infrared dyes through a linker consisting of one or more atomic spacers, amino acids, amino acid derivatives, and/or hydrophobic residues. Even more specifically, it has been found that where the atomic spacer is hydrophobic 6-atom spacer with neutral, hydrophobic or charged atoms and amino acid spacer is aromatic amino acid or a derivative of aromatic amino acid, or negative or positive charge amino acid and tyrosine or a derivative of tyrosine. Charge of the linker can be varied to obtain fast skin clearance and fast tumor accumulation to obtain higher tumor-to-background ratio. Moreover, the fluorescence intensity of the NIR dye is maintained or even enhanced by having the aromatic amino acid or tyrosine or derivative of tyrosine and charge of the NIR dye can be varied to accomplish fast skin clearance.

This disclosure provides CA IX-targeted ligands linked to NIR dyes and methods for synthesizing the same. This disclosure also provides compounds for use in the targeted imaging of tumors expressing CA IX, including but not limited to kidney, endometrial, urinary, colorectal, ovarian, breast, pancreatic, and esophagus, and hypoxic regions of many solid tumors, and related diseases, and methods of use, for example, in imaging and surgery involving CA IX positive tissues and tumors.

In this manner, the compounds of the present disclosure can be used for the in vivo identification of diseased tissue in a subject in need thereof. The disclosure method includes irradiating an in vivo body part of the subject containing diseased tissue with light having at least one excitation wavelength in the near infrared range from about 600 nm to about 1000 nm. Fluorescence emanating from a compound of the present disclosure administered to the subject and which has specifically bound to and/or been taken up by the diseased tissue in the body part, in response to the at least one excitation wavelength is directly viewed to determine the location and/or surface area of the diseased tissue in the subject.

Light having a wavelength range from 600 nm and 850 nm lies within the near infrared range of the spectrum, in contrast to visible light, which lies within the range from about 400 nm to about 500 nm. Therefore, the excitation light used in practice of the disclosure diagnostic methods will contain at least one wavelength of light to illuminates the tissue at the infrared wavelength to excite the compounds in order that the fluorescence obtained from the area having uptake of the compounds of the present disclosure is clearly visible and distinct from the auto-fluorescence of the surrounding tissue. The excitation light may be monochromatic or polychromatic. In this manner, the compounds of the present disclosure are advantageous as they eliminate the need for use of filtering mechanisms that would be used to obtain a desired diagnostic image if the fluorescent probe is one that fluoresces at wavelengths below about 600 nm. In this manner, the compounds of the present disclosure avoid obscured diagnostic images that are produced as a result of excitation light of wavelengths that would be reflected from healthy tissue and cause loss of resolution of the fluorescent image.

Diagnostic labs, physicians' offices and operating rooms for surgical procedures can be equipped with an overhead light that produces wavelengths of light in the optical emitting spectrum useful in practice of disclosure diagnostic methods, such as lamps that produce light in the appropriate wavelength. Such a light can be utilized in the practice of the disclosure diagnostic methods merely by turning out the other lights in the operating room (to eliminate extraneous light that would be visibly reflected from tissue in the body part under investigation) and shining the excitation light of near infrared wavelength into the body cavity or surgically created opening so that the fluorescent image received directly by the eye of the observer (e.g., the surgeon) is predominantly the fluorescent image emanating from the fluorophore(s) in the field of vision. Light emanating from a source in the 600 nm and 850 nm range, preferably 750 nm-850 nm range would be used in accomplishing the goal of direct visualization by the observer so that light reflecting from the body part, other than that from the fluorescing moiet(ies), is minimized or eliminated.

Accordingly, the diseased tissue (and bound or taken-up targeting construct) is "exposed" to the excitation light (e.g., by surgically created opening or endoscopic delivery of the light to an interior location. The disclosure of these methods of imaging is particularly suited to in vivo detection of diseased tissue located at an interior site in the subject, such as within a natural body cavity or a surgically created opening, where the diseased tissue is "in plain view" (i.e., exposed to the human eye) to facilitate a procedure of biopsy or surgical excision of the area that has been highlighted by uptake of the compounds of the present disclosure. As the precise location and/or surface area of the diseased or inflamed tissue are readily determined by the uptake of the compounds of the present disclosure, the methods employing the compounds of the present disclosure provide a valuable guide to pathologists, immunologists, technicians and surgeons alike, who needs to "see" in real time the exact outlines, size, etc., of the mass of the inflamed areas for diagnosis and imaging, and if necessary, surgery.

Thus, in specific embodiments, the present disclosure entails optical imaging of a biological tissue that expresses a CA IX through administration to a patient having cancer by contacting the tissue with a composition comprising an effective amount of compounds of the present disclosure (e.g., compounds of Examples herein) and allowing time for the compound in the composition to distribute within the tissue and interact with the site of folate receptor. After a sufficient time for such interaction has passed, the tissue is illuminated with an excitation light to cause the compound in the composition to fluoresce. The fluorescence is then detected as and where such fluorescence is observed is an area that contains CA IX.

In like manner, the compounds of the present disclosure are used to identify a target cell type in a biological sample by contacting the biological sample with such compounds for a time and under conditions that allow for binding of the compound to at least one cell of the target cell type. The bound compound is then optically detected such that presence of fluorescence of the near infrared wavelength emanating from the bound, targeted compound of the present disclosure indicated that the target cell type is present in the biological sample. This method thus provides an image of the targeted cell type in the tissue being assessed. Most preferably, the targeted cell type is a cancerous cell, including but not limited to brain, breast, cervical, rectal or lung cancer that also display high levels of CA IX.

The most suitable route for administration of an effective amount of the conjugated compounds disclosed herein will vary depending upon the disease state to be treated, or the location of the suspected condition to be diagnosed. This includes but is not limited to parentally, e.g., intradermally, subcutaneously, intramuscularly, intraperitoneally, or intravenously. In other embodiments, the conjugate may be administered to the patient by other medically useful processes, and any effective dose and suitable therapeutic dosage form, including prolonged release dosage forms, can be used. Illustratively, the method described herein may be used in combination with biological therapies such as other therapies or therapeutic strategies such as surgery, radiation therapy, and/or chemotherapies For example, for treatment of cancerous conditions, local administration, including administration by injection directly into the body part to be irradiated by the excitation light (e.g., intracavitarily) provides the advantage that the targeting construct (e.g., fluorescently tagged antibodies) can be administered in a high concentration without risk of the complications that may accompany systemic administration thereof. However, oral, topical and parenteral applications can also be envisioned.

These methods advantageously provide an improved method of performing image-guided diagnosis and treatment of cancer on a subject as the administration of a composition comprising the compound of the disclosure under conditions and for a time sufficient for said compound to accumulate at a given tissue site will assist a physician in visualizing the tissue to be treated.

If the putative diseased site is a natural body cavity or surgically produced interior site, an endoscopic device can be optionally used to deliver the excitation light to the site, to receive fluorescence emanating from the site within a body cavity, and to aid in formation of a direct image of the fluorescence from the diseased tissue. For example, a lens in the endoscopic device can be used to focus the detected fluorescence as an aid in formation of the image. As used herein, such endoscope-delivered fluorescence is said to be "directly viewed" by the practitioner and the tissue to which the targeting construct binds or in which it is taken up must be "in plain view" to the endoscope since the light used in the disclosure diagnostic procedure will not contain wavelengths of light that penetrate tissue, such as wavelengths in the near infrared range. Alternatively, the excitation light may be directed by any convenient means into a body cavity or surgical opening containing a targeting construct administered as described herein and the fluorescent image so produced can be directly visualized by the eye of the observer without aid from an endoscope. With or without aid from any type of endoscopic device, the fluorescent image produced by the disclosure method is such that it can be viewed without aid of an image processing device, such as a CCD camera, TV monitor, photon collecting device, and the like.

It is contemplated that the diagnostic or imaging methods of the present disclosure allow the surgeon/practitioner to contemporaneously see/view/visualize diseased or abnormal tissue through a surgical opening to facilitate a procedure of biopsy or surgical excision. As the location and/or surface area of the diseased tissue are readily determined by the diagnostic procedure of the disclosure employing the compounds described herein, the disclosure method is a valuable guide to the surgeon, who needs to know the exact outlines, size, etc. of the mass, for example, for resection as the surgery proceeds. In particular, it is noted that the compounds of the disclosure fluorescence in the near infrared range to a greater intensity than those previously described. As such, advantageously, it is contemplated that less of the compound will be needed to achieve diagnostic imaging. In addition, the compounds of the present disclosure penetrate deep into the tissue and hence the disclosure advantageously allows a greater accuracy that the proper course of treatment of the cancer is taken.

In some embodiments, a single type of fluorescent moiety is relied upon for generating fluorescence emanating from the irradiated body part (i.e., from the fluorescent targeting construct that binds to or is taken up by diseased tissue) and subjecting the targeting construct with a source of light from the near infrared spectrum.

In other embodiments, it is contemplated that a plurality of (i.e., two, three, four, or more) targeting constructs are used to obtain a diagnostic image. Such additional targeting constructs may be additional compounds of the present disclosure distinct from the first such compound. Alternatively, the additional targeting constructs may comprise the dyes described herein but with the acetoazolamide derivative being replaced by a ligand for another receptor other than CA IX. In still other embodiments, the additional targeting moieties may be other fluorescing targeting constructs (e.g., antibodies, or biologically active fragments thereof, having attached fluorophores) that bind to other receptors or antigens on the tumor or tissue to be imaged. Any additional targeting moiety that specifically targets the tumor or specific site on the tissue may be used provided that it is specific for the site to be monitored. The purpose of the additional fluorescing targeting construct is to increase the intensity of fluorescence at the site to be monitored thereby aiding in detection of diseased or abnormal tissue in the body part. For example, a given diseased tissue may have numerous markers and in addition to the compounds of the present disclosure a cocktail of fluorescent moieties is provided which are specific for that given site such that the signal emanating from the tissue is generated by more than one compound or fluorescent moiety that has targeted and become localized to the tissue site of interest.

In practice, the skilled person would administer a compound of the present disclosure either alone or as part of a cocktail of targeting detectable moieties and allow these compounds and targeting moieties to bind to and/or be taken up by any targeting tissue that may be present at the site under investigation and then provide a supply of the light source. Typically, the compounds of the present disclosure and any additional targeting moieties will be administered prior to surgery for a time and in compositions that allow the fluorescent compounds of the present disclosure as well as any additional fluorescent constructs to be taken up by the target tissue.

Those of skill in the art will be able to devise combinations of successively administered fluorescing targeting constructs, each of which specifically binds to the target site. It is preferable that all of the fluorescing targeting constructs used in such cocktails to identify the target tissue comprise fluorophores that fluoresce within the same wavelength band or at the same wave length as does the compound of the present disclosure (e.g., a fluorescing sensitive to near infrared wavelength of light in the compounds of the present disclosure) to minimize the number of different light sources that need to be employed to excite simultaneous fluorescence from all of the different targeting constructs used in practice of the disclosure method. However, it is contemplated that the additional targeting moieties other than the compounds of the present disclosure may fluorescence in response to the irradiating light at a different color (i.e., has a different wavelength) than that from the florescent compounds of the present disclosure. The difference in the colors of the fluorescence emanating from the compounds of the present disclosure and those of the additional targeting compounds may aid the observer in determining the location and size of the diseased tissue. In some examples, it may be desirable to include fluorophores in targeting constructs targeted to target normal tissue and the compounds of the present disclosure to target diseased tissue such that the contrast between the diseased tissue and normal tissue is further enhanced to further aid the observer in determining the location and size of the target tissue. The use of such additional fluorophores and targeting agents in addition to the compounds of the present disclosure provides the advantage that any natural fluorescence emanating from normal tissue is obscured by the fluorescence emanating from fluorophore(s) in supplemental targeting constructs targeted to the normal tissue in the body part. The greater the difference in color between the fluorescence emanating from normal and target tissue, the easier it is for the observer to visualize the outlines and size of the target tissue. For instance, targeting a fluorescing targeting construct comprising a fluorophore producing infrared light from the compounds of the present disclosure to the target tissue (i.e., abnormal tissue) and a fluorophore producing green light to healthy tissue aids the observer in distinguishing the target tissue from the normal tissue. Those of skill in the art can readily select a combination of fluorophores that present a distinct visual color contrast.

The spectrum of light used in the practice of the disclosure method is selected to contain at least one wavelength that corresponds to the predominate excitation wavelength of the targeting construct, or of a biologically compatible fluorescing moiety contained within the targeting construct. Generally, the excitation light used in practice of the disclosure method comprises at least one excitation wavelength of light in the near infrared wavelength range from about 600 nm to about 850 nm.

However, when a combination of targeting ligands that fluoresce at different wavelengths is used in practice of the disclosure, the spectrum of the excitation light must be broad enough to provide at least one excitation wavelength for each of the fluorophores used. For example, it is particularly beneficial when fluorophores of different colors are selected to distinguish normal from diseased tissue, that the excitation spectrum of the light(s) include excitation wavelengths for the fluorophores targeted to normal and target tissue.

As noted herein the compounds of the present disclosure are specifically targeted to CA IX by way of acetoazolamide derivative being part of the compounds of the present disclosure. In embodiments where an additional targeting moiety is used, the targeting construct of such an additional targeting moiety is selected to bind to and/or be taken up specifically by the target tissue of interest, for example to an antigen or other surface feature contained on or within a cell that characterizes a disease or abnormal state in the target tissue. As in other diagnostic assays, it is desirable for the targeting construct to bind to or be taken up by the target tissue selectively or to an antigen associated with the disease or abnormal state; however, targeting constructs containing ligand moieties that also bind to or are taken up by healthy tissue or cell structures can be used in the practice of the disclosure method so long as the concentration of the antigen in the target tissue or the affinity of the targeting construct for the target tissue is sufficiently greater than for healthy tissue in the field of vision so that a fluorescent image representing the target tissue can be clearly visualized as distinct from any fluorescence coming from healthy tissue or structures in the field of vision.

The disease or abnormal state detected by the disclosure method can be any type characterized by the presence of a known target tissue for which a specific binding ligand is known. It is contemplated that the target tissue may be characterized by cells that produce either a surface antigen for which a binding ligand is known, or an intracellular marker (i.e., antigen), since many targeting constructs penetrate the cell membrane. Representative disease states that can be identified using the disclosure method include such various conditions as different types of tumors, bacterial, fungal and viral infections, and the like. As used herein "abnormal" tissue includes precancerous conditions, necrotic or ischemic tissue, and tissue associated with precancerous states as well as cancer, and the like. Further, examples of the types of target tissue suitable for diagnosis or examination using the disclosure method include brain, breast, cervical, rectal, lung, and the like, as well as combinations of any two or more thereof.

Simply by way of example, antigens for some common malignancies and the body locations in which they are commonly found are known to those of skill in the art, and targeting ligands, such as antibodies or for these antigens or indeed ligands where the antigens are receptors are known in the art.

The targeting constructs and supplemental targeting constructs used in practice of the disclosure method can be administered by any route known to those of skill in the art, such as topically, intraarticularly, intracisternally, intraocularly, intraventricularly, intrathecally, intravenously, intramuscularly, intraperitoneally, intradermally, intratracheally, intracavitarily, and the like, as well as by any combination of any two or more thereof.

The most suitable route for administration will vary depending upon the disease state to be treated, or the location of the suspected condition or tumor to be diagnosed. For example, for imaging of inflammatory conditions and various tumors, local administration, including administration by injection directly into the body part to be irradiated by the excitation light (e.g., intracavitarily) provides the advantage that the targeting construct (e.g., fluorescently tagged antibodies) can be administered in a high concentration without risk of the complications that may accompany systemic administration thereof.

The compounds of the present disclosure as well as any additional targeting constructs used in diagnostic cocktails comprising the compounds of the present disclosure are administered in an "effective amount" for diagnosis. An effective amount is the quantity of a targeting construct necessary to aid in direct visualization of any target tissue located in the body part under investigation in a subject. A "subject" as the term is used herein is contemplated to include any mammal, such as a domesticated pet, farm animal, or zoo animal, but preferably is a human. Amounts effective for diagnostic use will, of course, depend on the size and location of the body part to be investigated, the affinity of the targeting construct for the target tissue, the type of target tissue, as well as the route of administration. Local administration of the targeting construct will typically require a smaller dosage than any mode of systemic administration, although the local concentration of the targeting construct may, in some cases, be higher following local administration than can be achieved with safety upon systemic administration.

An effective amount of the conjugate compound to be administered will be dependent on the patient's condition including surgical conditions such as blood loss, the disease state being treated, the molecular weight of the conjugate, its route of administration and tissue distribution, and the possibility of co-usage with therapeutic treatments such as radiation therapy, or chemotherapies radiation therapy. The effective amount to be administered to a patient is based on body surface area, patient weight, and physician assessment of patient condition. In various exemplary embodiments, an effective dose amount may be done with or without an excipient/carrier, including but not limited to saline. Since individual subjects may present a wide variation in severity of symptoms and each targeting construct has its unique diagnostic characteristics, including, affinity of the targeting construct for the target, rate of clearance of the targeting construct by bodily processes, the properties of the fluorophore contained therein, and the like, the skilled practitioner will weigh the factors and vary the dosages accordingly.

The compounds of the present disclosure as well as cocktails comprising these compounds can be formulated as a sterile injectable suspension according to known methods using suitable dispersing or wetting agents and suspending agents. The sterile injectable preparation may also be a sterile injectable solution or suspension in a non-toxic parenterally-acceptable diluent or solvent, for example, as a solution in 1-4, butanediol. Sterile, fixed oils are conventionally employed as a solvent or suspending medium. For this purpose any bland fixed oil may be employed, including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate, or the like. Buffers, preservatives, antioxidants, and the like, can be incorporated as required, or, alternatively, can comprise the formulation.

The examples that follow are merely provided for the purpose of illustrating particular embodiments of the disclosure and are not intended to be limiting to the scope of the appended claims. As discussed herein, particular features of the disclosed compounds and methods can be modified in various ways that are not necessary to the operability or advantages they provide. For example, the compounds can incorporate a variety of amino acids and amino acid derivatives as well as targeting ligands depending on the particular use for which the compound will be employed. One of skill in the art will appreciate that such modifications are encompassed within the scope of the appended claims.

In certain embodiments, compounds of the present invention have the form: B-W-X-Y-Z
wherein B is a CA IX-targeted molecule;
W is an extended hydrophobic residue;
X is a hydrophobic spacer;
Y is an amino acid spacer; and
Z is a NIR dye.

In some embodiments, the CA IX-targeted molecule is chosen from the group consisting of a small molecule, a ligand, an inhibitor, an agonist or a derivative thereof. In some embodiments, the CA IX-targeted compound is a ligand. In other embodiments, the CA IX-targeted compound is a small molecule that binds to CA IX. In some embodiments, the CA IX-targeted compound is a small molecule with an extended hydrophobic moiety. In some embodiments, the CA IX-targeted compound is a small molecule with a fluorinated aromatic moiety.

As used herein, "extended hydrophobic residue" shall include in some embodiments, W is selected from the group consisting of: hydrophobic amino acids or moieties, such as neutral nonpolar (hydrophobic) amino acids, such as alanine, leucine, isoleucine, valine, proline, phenylalanine, tryptophan, and methionine or aromatic group, cyclohexyl group, tyrosine, and derivative thereof; basic (positively charged) amino acids such as arginine, histidine, and lysine and derivative thereof; neutral polar amino acids, such as glycine, serine, threonine, cysteine, tyrosine, asparagine, and glutamine and derivative thereof; In some embodiments, W is an aromatic amino acid and derivative thereof. In some embodiments, W has a positive charge. In other embodiments, W has a negative charge.

As used herein, "hydrophobic spacer" shall include in some embodiments, X is a hydrophobic spacer. In some embodiments, X is selected from the group consisting of an six aminohectanoic acid (SAHA), eight aminooctonoic acid (EAOA), polyethylene glycol (PEG), polyethylene amine (PEA) unit, a chain of 6 atoms, a spacer 6 atoms in length, a chain from 6 to 20 atoms in length; a peptide comprising aryl or aryl alkyl groups, each of which is optionally substituted, and where one aryl or aryl alkyl group is about 6 to about 10, or about 6 to about 14 atoms, and the other aryl or aryl alkyl group is about 10 to about 14, or about 10 to about 15 atoms. In another embodiment, the spacer comprises about 1 to about 20 atoms. In some embodiments, the spacer is 6 atoms in length. In some embodiments, the spacer comprises EAOA. In some embodiments, the spacer is variably charged. In some embodiments, X is peptide compromising positively charge amino acids (e.g. Arg, Lys, Orn) or quaternary amine containing amino acid. In other embodiments, X has a negative charge.

In some embodiments, Y is selected from the group consisting of: acidic (negatively charged) amino acids, such as aspartic acid and glutamic acid and derivative thereof; basic (positively charged) amino acids such as arginine, histidine, and lysine and derivative thereof; neutral polar amino acids, such as glycine, serine, threonine, cysteine, tyrosine, asparagine, and glutamine and derivative thereof; neutral nonpolar (hydrophobic) amino acids, such as alanine, leucine, isoleucine, valine, proline, phenylalanine, tryptophan, and methionine; and derivatives thereof. In some embodiments, Y is an aromatic amino acid and derivative thereof. In some embodiments, Y has a positive charge. In other embodiments, Y has a negative charge.

In some embodiments, Z is selected from the group consisting of near-infra red dyes, including but not limited to, LS288, IR800, SP054, S0121, KODAK, S2076, S0456 and/or the dyes selected from group consisting of:

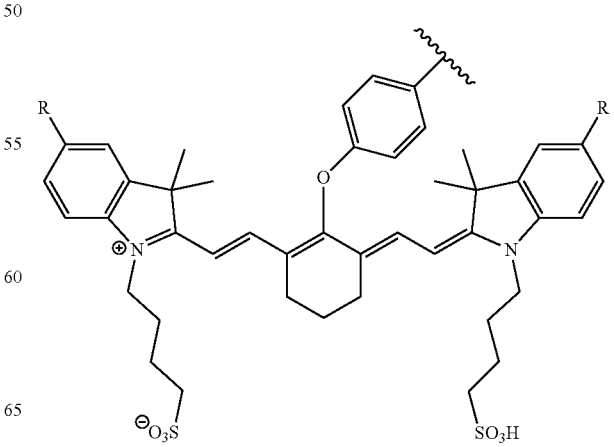

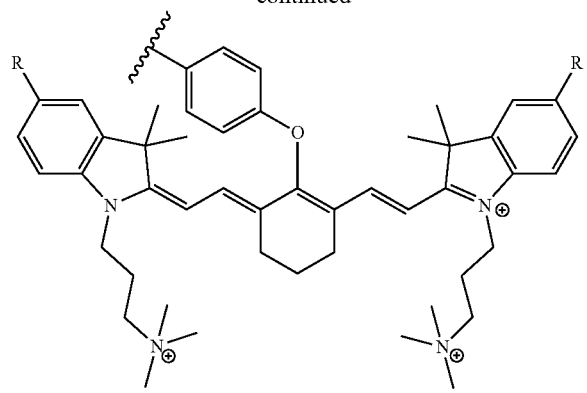

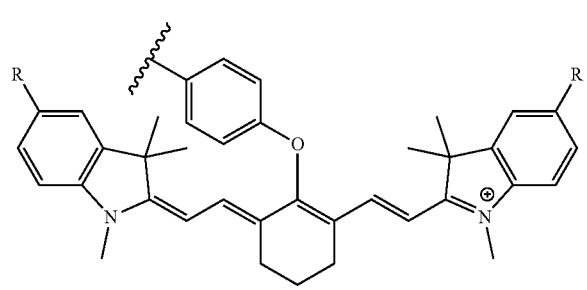

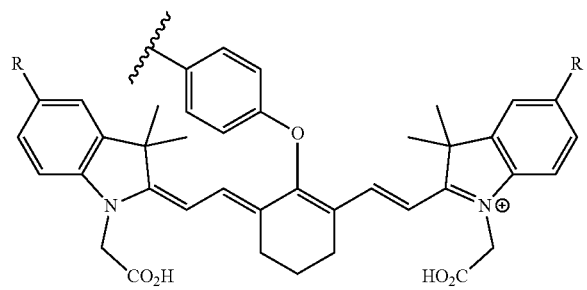

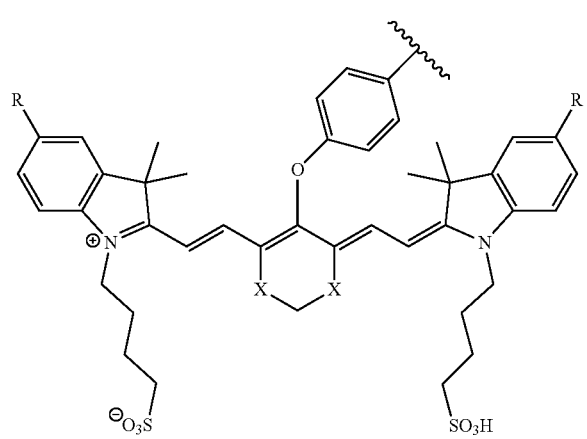

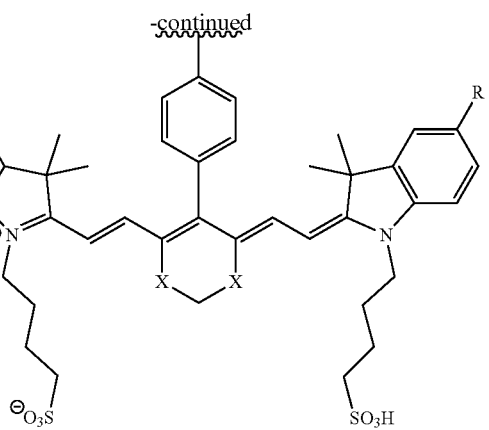

R = H or R = SO₃H; X = O, S, N

In certain embodiments, the Z is variably charged. In some embodiments, Z has a positive charge. In other embodiments, Z has a negative charge.

In certain embodiments, compounds of the present invention have the formula:

B-W-X-Y-Z wherein B is a CA IX-targeted compound; W is an extended hydrophobic residue, X is a hydrophopic spacer; Y is an amino acid spacer with a sulfur-containing side chain group; and Z is an NIR dye. In some embodiments, the amino acid spacer with a sulfur-containing side group is cysteine. In some embodiments, the amino acid spacer with a sulfur-containing side group is methionine. In some embodiments, the amino acid spacer with a sulfur-containing side group is molecule containing thiophenol moiety.

In some embodiments, compounds of the present invention have the form:

B-W-X-Y-Z wherein B is a CA IX-targeted compound; W is an extended hydrophobic residue, X is a hydrophopic spacer; Y is an amino acid spacer with a chalcogen-containing side chain group; and Z is an NIR dye.

In some embodiments the present invention provides compounds of the form:

B-W-X-Y-Z wherein, B is a CA IX-targeted compound; W is an extended hydrophobic residue, X is a hydrophobic spacer; Y is an amino acid chosen from the group consisting of tyrosine, cysteine, lysine, or a derivative thereof; and Z is an NIR dye. In some embodiments, Y comprises a tyrosine or tyrosine derivative. In some embodiments, Y comprises a tyrosine and a carbon isotope is on the aromatic ring of tyrosine. In some embodiments, Y comprises an amino acid with an aromatic ring with a hydrogen isotope.

The present invention also relates to a compound having the structural formula:

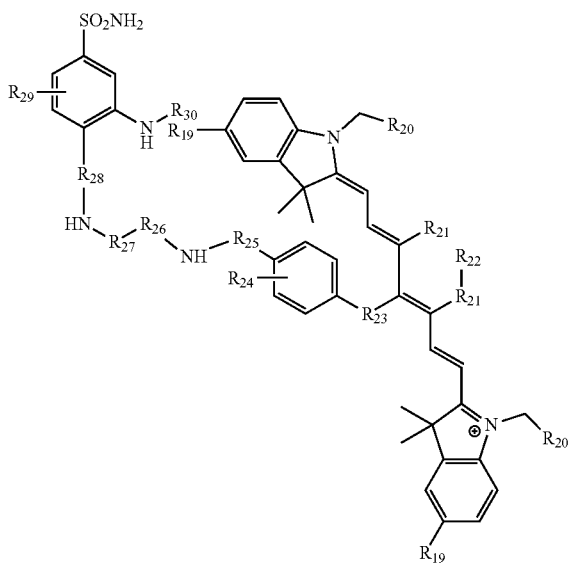

or a pharmaceutically acceptable salt thereof, or isotopes thereof, wherein:

$R_{19}$ represents a hydrogen or $SO_3H$;

$R_{20}$ represents a hydrogen, $CH_3$, $C_3H_6SO_3^-$, $C_3H_6SO_3H$ or $C_4H_8SO_3^-$, or $C_4H_8SO_3H$ or $C_3H_6N^+(CH_3)_3$;

$R_{21}$ represents a carbon, optionally one or more sharing bonds, $R_{22}$ represents a carbon with optionally one or more sharing bonds;

$R_{23}$ represents nitrogen, oxygen, or sulfur or no atom (direct C—C bond between aromatic ring and vinyl ring);

$R_{24}$ is optional and when present represents aromatic substitution group to enhance the spectral properties such as increase brightness and stability of the vinyl ether bridge;

$R_{25}$ is optional and when present represents linkers with aromatic amino acids such as Phe, Trp, His or derivative thereof, cationic amino acids such Arg, Lys, or derivative thereof, anionic amino acids such as Asp, Glu or derivative of them, unnatural amino acids of aromatic/cationic/anionic acids or derivative thereof;

$R_{26}$ is optional and when present represents a linear carbon chain, or polyethylene glycol linker, cationic linker, or derivative thereof;

$R_{27}$ optional and when present represents hydrophobic moiety such as Phe, Val, Leu, Ile, Trp, His, Arg, Lys, Asp, Glu, or derivative thereof;

$R_{28}$ represents hydrophobic linker; and $R_{29}$ is optional and when present represents aromatic substitution group to enhance the binding affinity, stability, hydrophobicity of the molecule such as F, $NO_2$, or thereof, $R_{30}$ optional and when present represents hydrophobic moiety such as Phe, Val, Leu, Ile, Trp, His, or derivative thereof or cyclic moiety such as cyclohexyl, cyclooctyl, or derivative thereof.

In some embodiments the present invention includes a compound that has the structural formula:

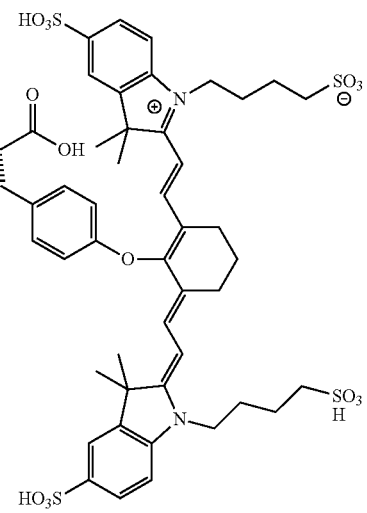

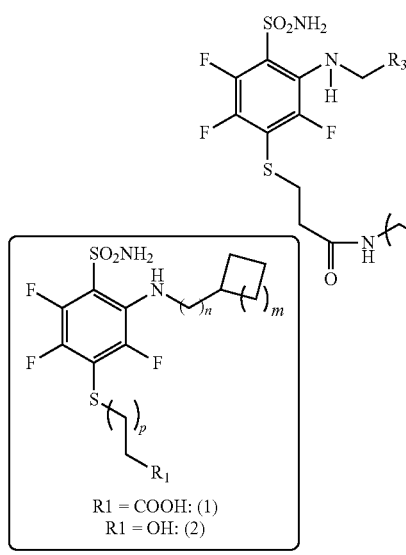

R1 = COOH: (1)
R1 = OH: (2)

R31 = cyclohexyl: (54)
R31 = cyclooctyl: (55)

-continued
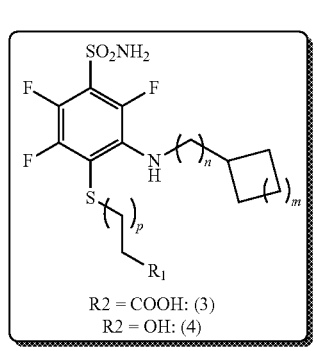
R2 = COOH: (3)
R2 = OH: (4)
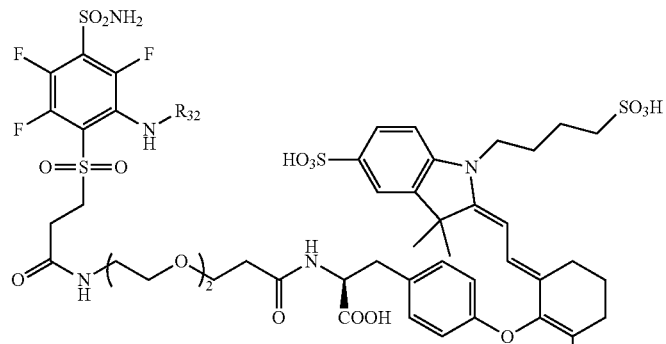
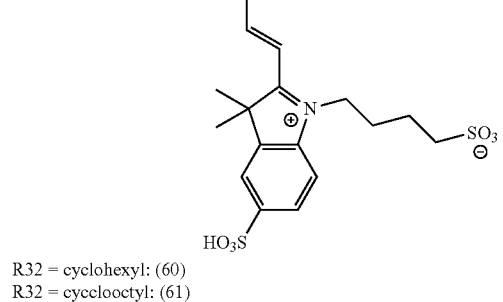
R32 = cyclohexyl: (60)
R32 = cycclooctyl: (61)
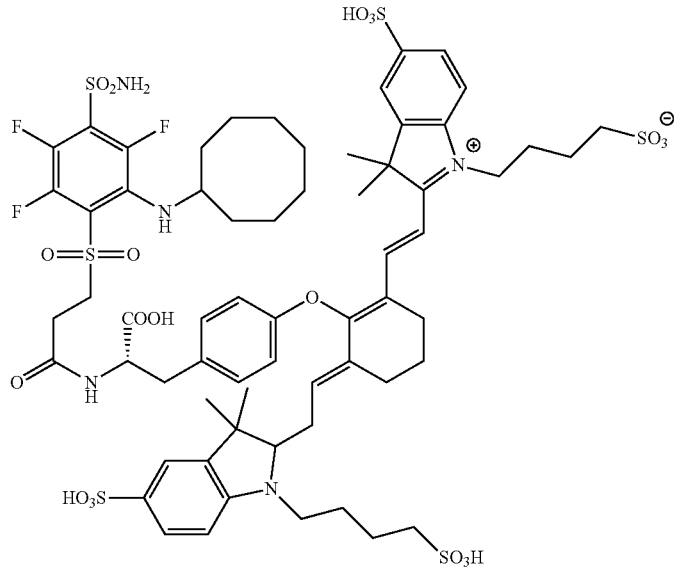
(62)

(63)
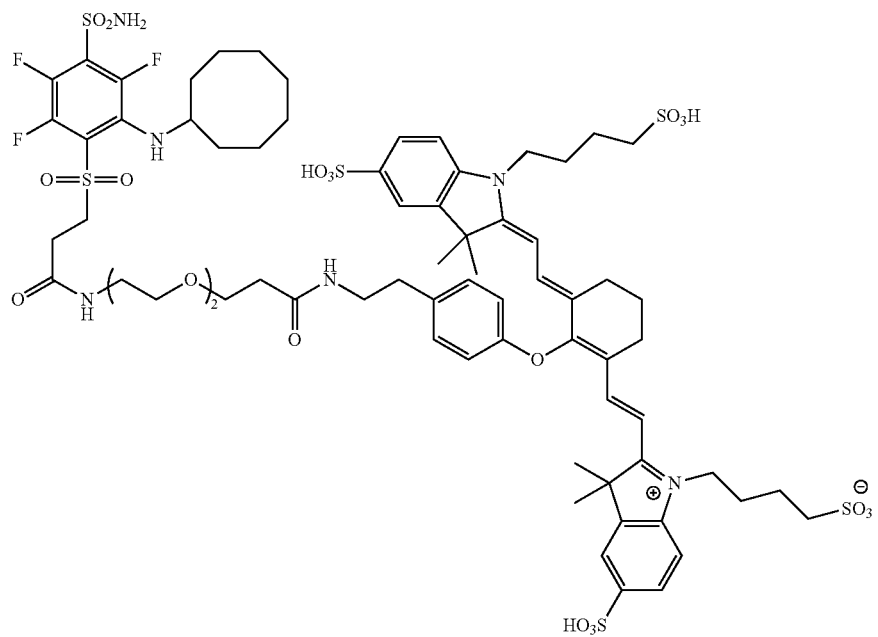
(64)
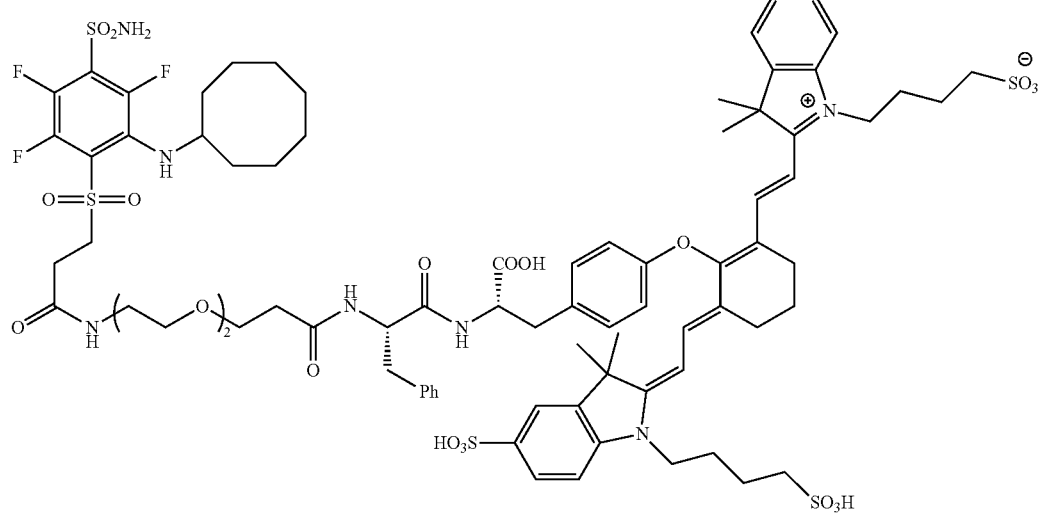

(65)
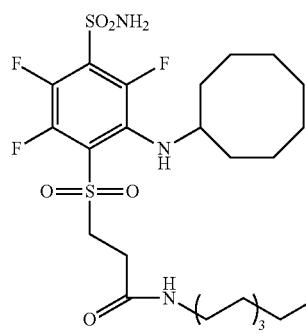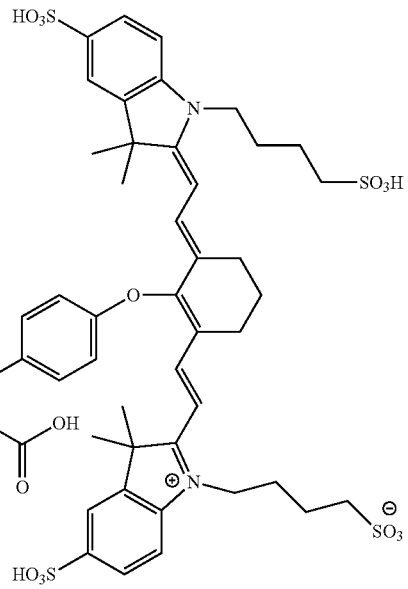
(66)
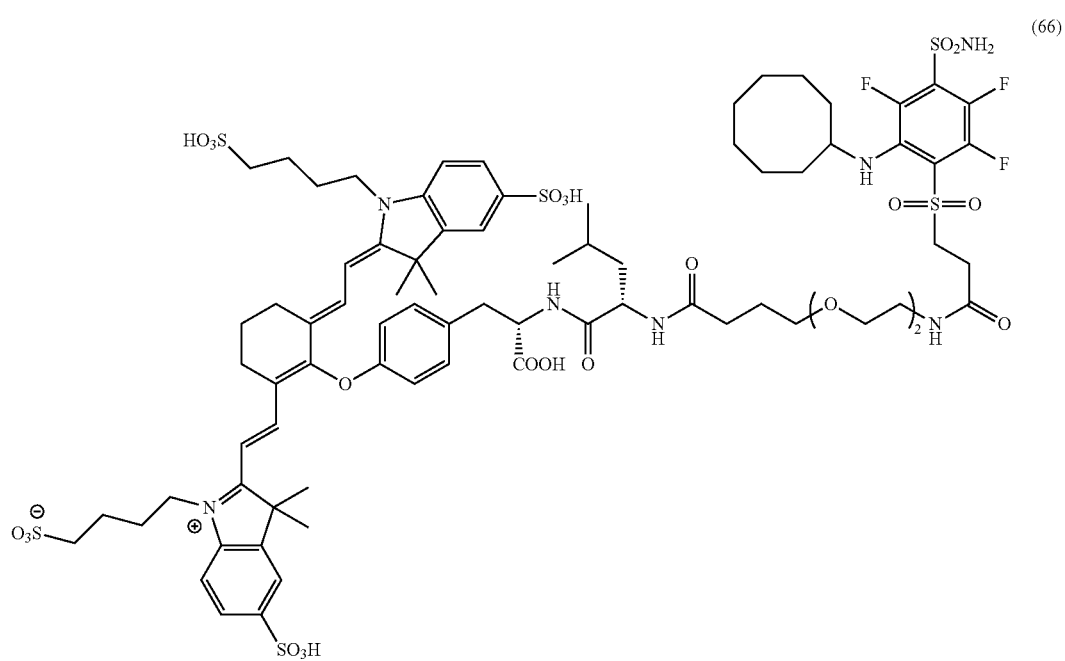

-continued
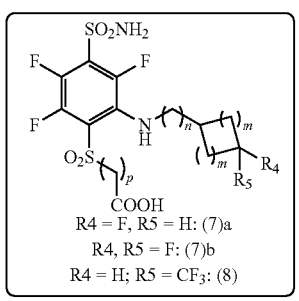
R4 = F, R5 = H: (7)a
R4, R5 = F: (7)b
R4 = H; R5 = CF3: (8)
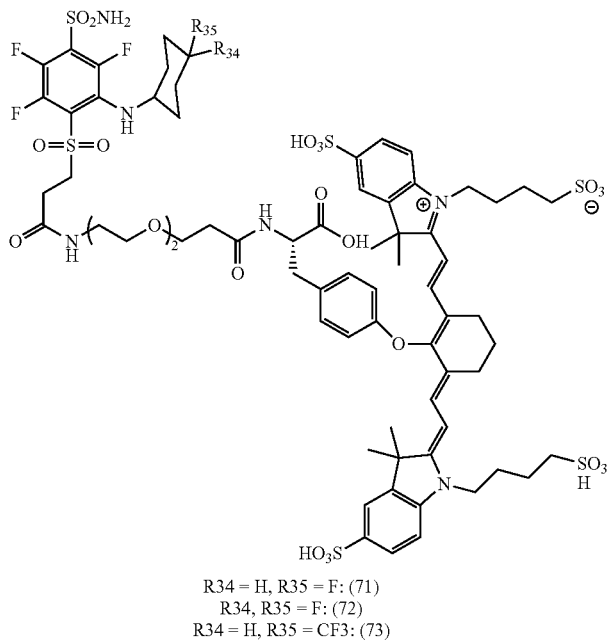
R34 = H, R35 = F: (71)
R34, R35 = F: (72)
R34 = H, R35 = CF3: (73)
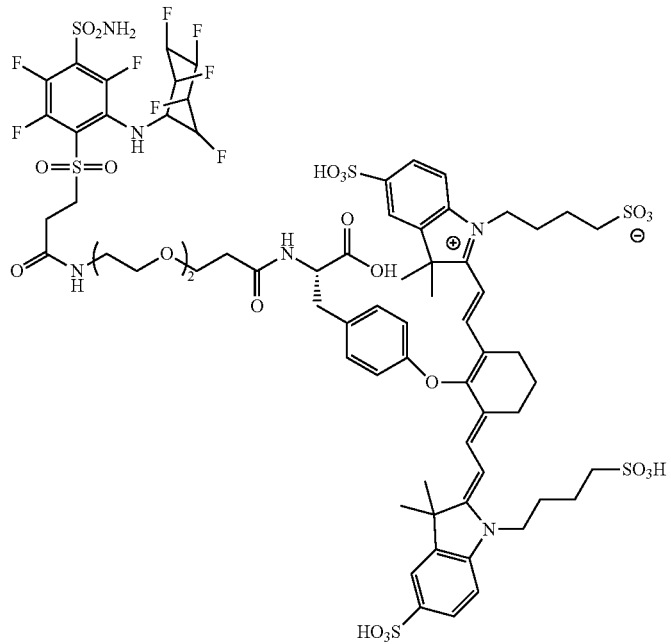
(74)

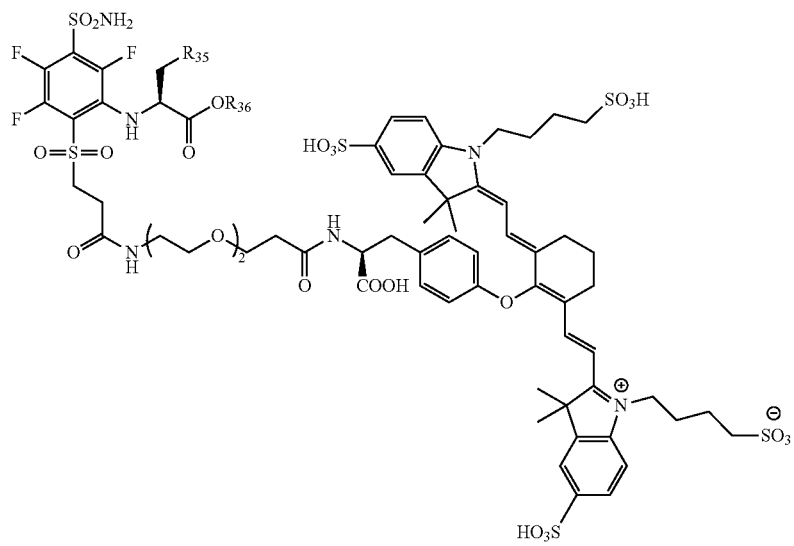
R35 = p-Ph, R36 = Bz: (75)
R35 = CH(CH3)2, R36 = Bz: (76)
R35 = CH(CH3)2, R36 = H: (77)
R35 = Imidazole, R36 = Bz: (78)
R35 = indole, R36 = Bz: (79)
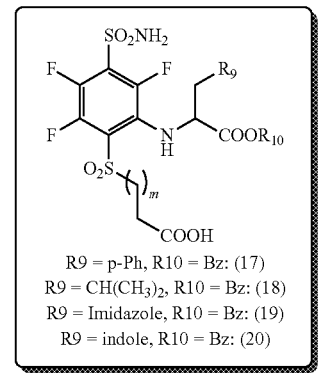
R9 = p-Ph, R10 = Bz: (17)
R9 = CH(CH3)2, R10 = Bz: (18)
R9 = Imidazole, R10 = Bz: (19)
R9 = indole, R10 = Bz: (20)
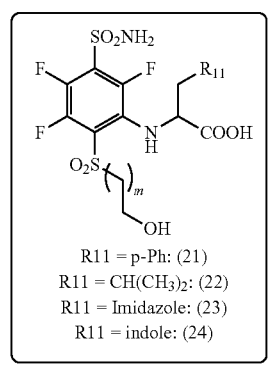
R11 = p-Ph: (21)
R11 = CH(CH3)2: (22)
R11 = Imidazole: (23)
R11 = indole: (24)
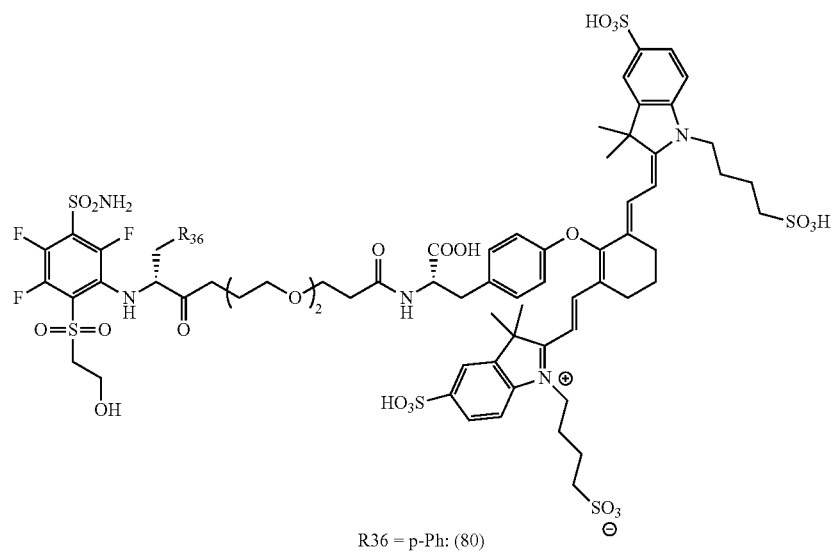
R36 = p-Ph: (80)
R36 = CH(CH3)2: (81)
R36 = Imidazole: (82)
R36 = indole: (83)

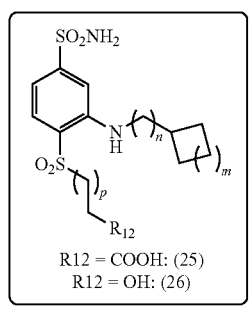
R12 = COOH: (25)
R12 = OH: (26)
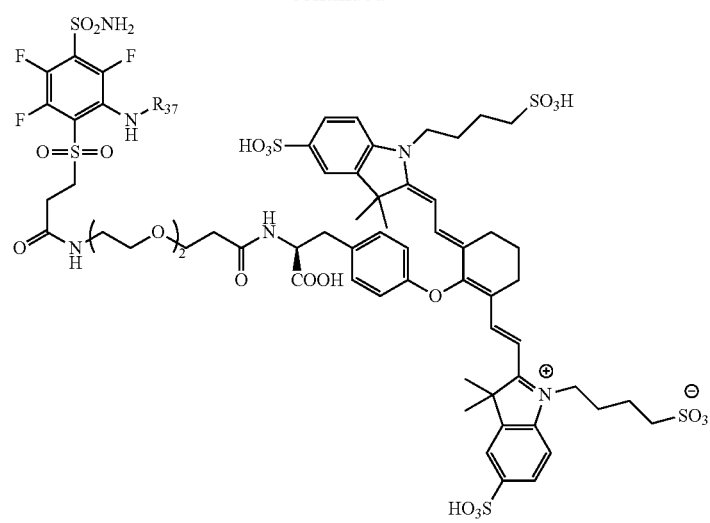
R37 = cyclohexyl: (84)
R37 = cyclooctyl: (85)
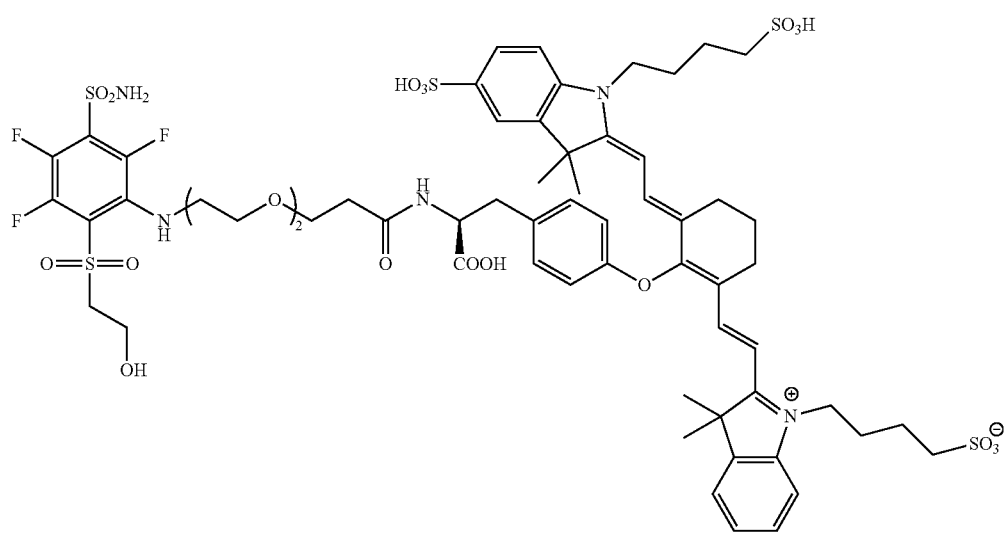
(86)

(87)
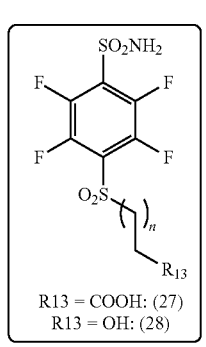
R13 = COOH: (27)
R13 = OH: (28)
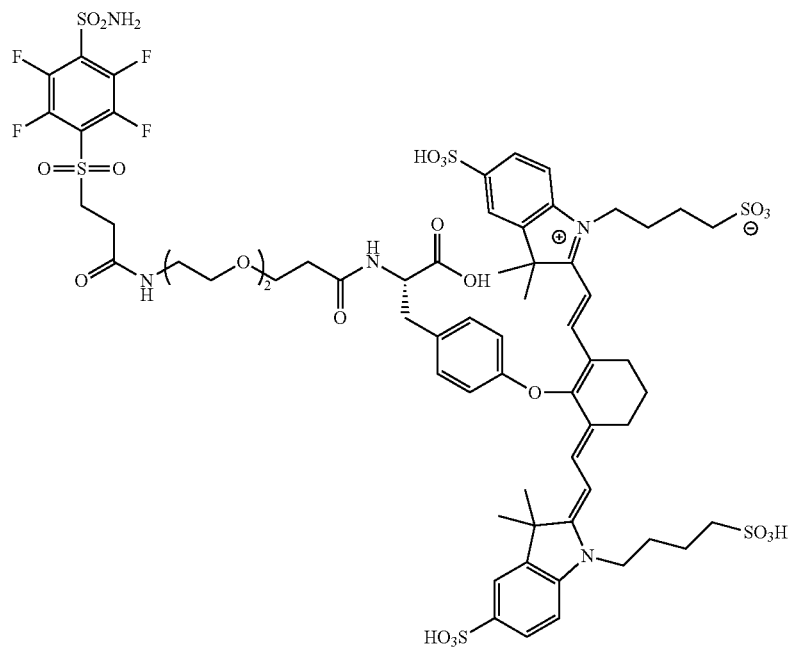
(88)
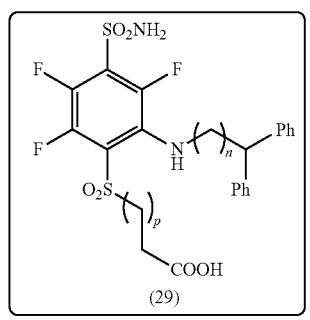
(29)
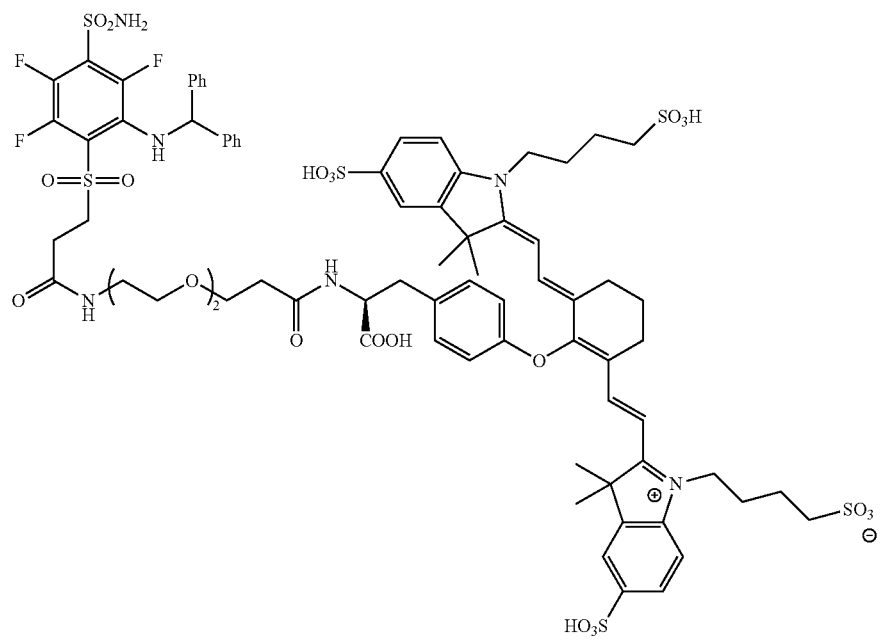

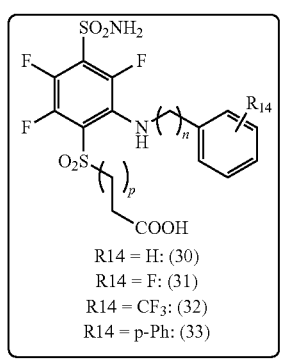
R14 = H: (30)
R14 = F: (31)
R14 = CF₃: (32)
R14 = p-Ph: (33)
-continued
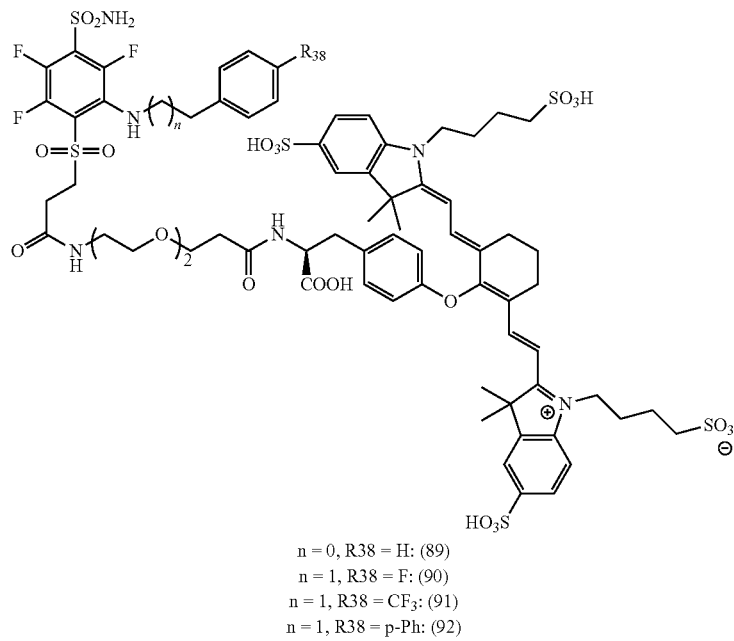
n = 0, R38 = H: (89)
n = 1, R38 = F: (90)
n = 1, R38 = CF₃: (91)
n = 1, R38 = p-Ph: (92)
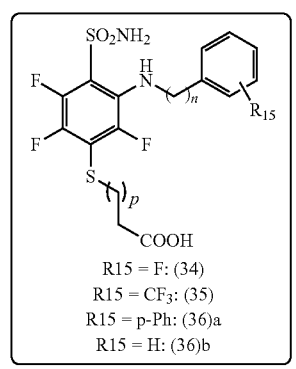
R15 = F: (34)
R15 = CF₃: (35)
R15 = p-Ph: (36)a
R15 = H: (36)b
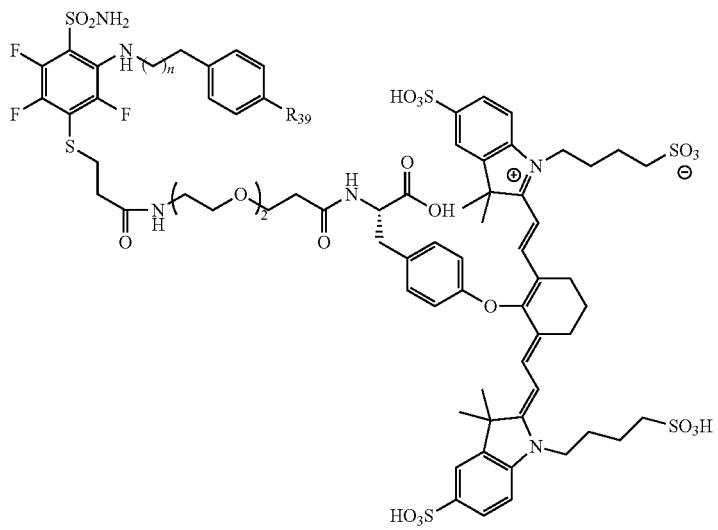
n = 0, R39 = H: (93)
n = 1, R39 = F: (94)
n = 0, R39 = p-Ph: (95)
n = 1, R39 = p-Ph: (96)

-continued
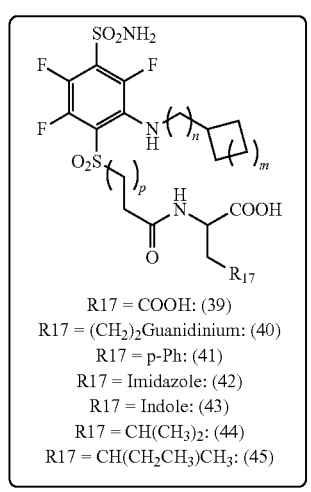
R17 = COOH: (39)
R17 = (CH$_2$)$_2$Guanidinium: (40)
R17 = p-Ph: (41)
R17 = Imidazole: (42)
R17 = Indole: (43)
R17 = CH(CH$_3$)$_2$: (44)
R17 = CH(CH$_2$CH$_3$)CH$_3$: (45)
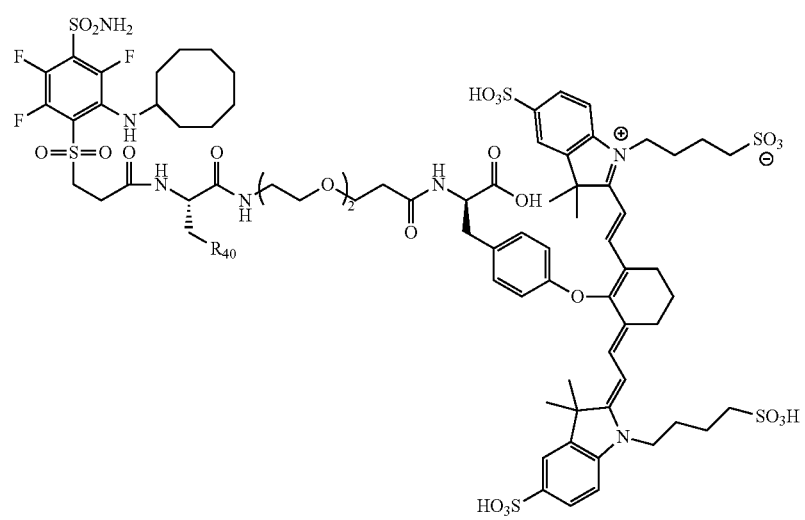
R40 = COOH: (97)
R40 = (CH$_2$)$_2$Guanidinium: (98)
R40 = p-Ph: (99)
R40 = Imidazole: (100)
R40 = Indole: (101)
R40 = CH(CH$_3$)$_2$: (102)
R40 = CH(CH$_2$CH$_3$)CH$_3$: (103)
(104)
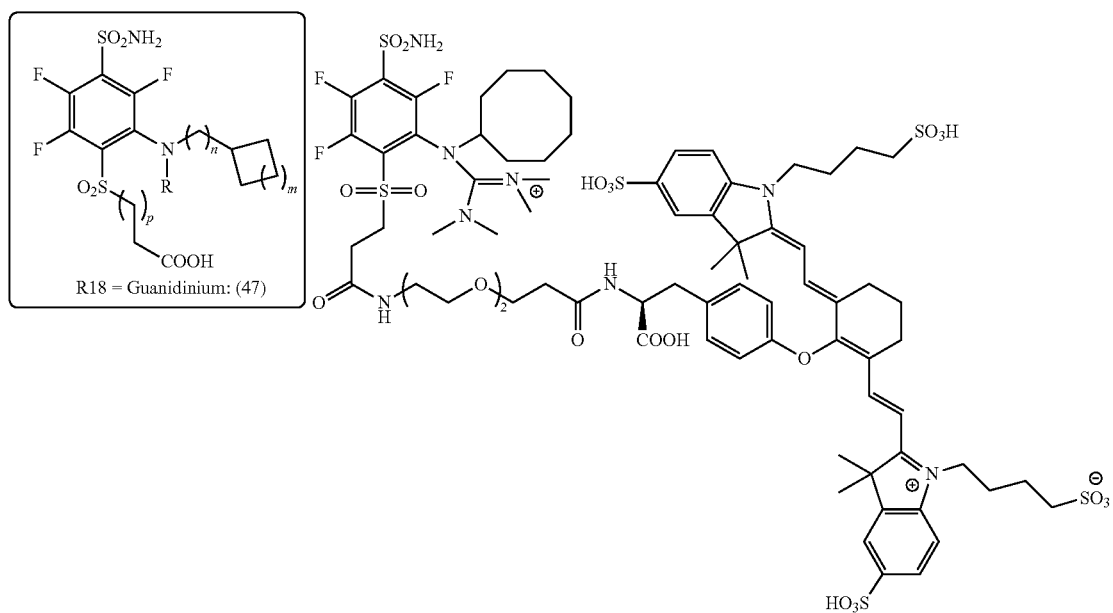
R18 = Guanidinium: (47)

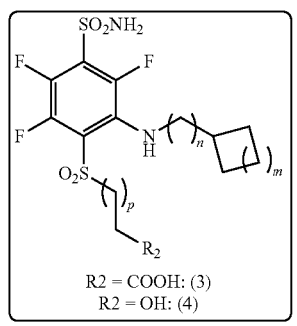

R2 = COOH: (3)
R2 = OH: (4)

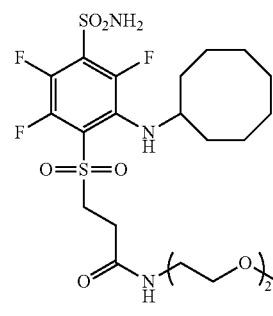

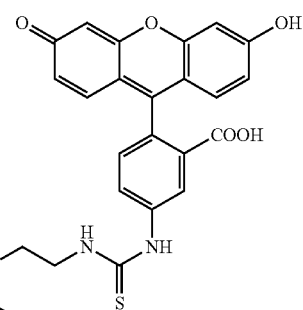

(105)

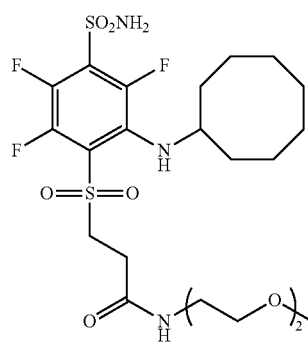

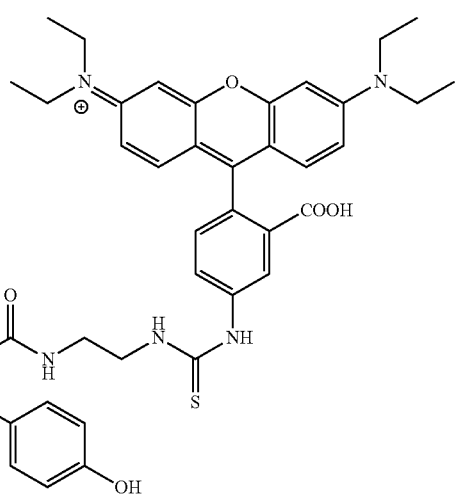

(106)

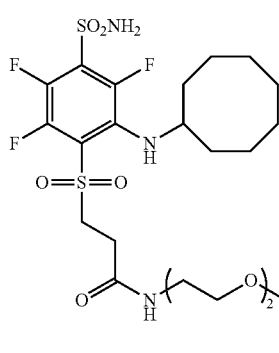

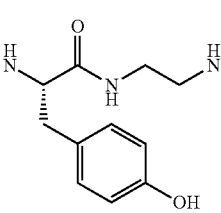

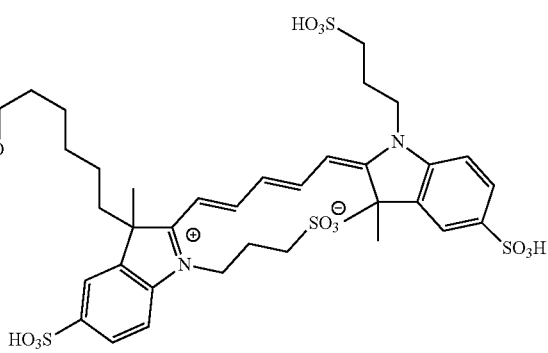

(107)

In some embodiments compounds of the present invention have an absorption and emission maxima between about 500 nm and about 900 nm. In some embodiments compounds of the present invention have an absorption and emission maxima between about 600 nm and 800 nm.

In some embodiments compounds of the present invention are made to fluoresce after distribution thereof in the tissue cells. In some embodiments compounds of the present invention are made to fluoresce by subjecting the compounds to excitation light of near infrared wavelength. In some embodiments compounds of the present invention have a binding affinity to CA IX that is similar to the binding affinity of ligand. In some embodiments compounds of the present invention are highly selective for targeting to a tumor cell. In particularly preferred embodiments, the compounds of the present invention are targeted to cancer cells under hypoxia condition or hypoxic tissues.

In certain embodiments compounds of the present invention are administered to a subject in need thereof and in some embodiments the administered composition comprises, in addition to the compound, a pharmaceutically acceptable carrier, excipient or diluent.

Some embodiments of the present invention provide methods of optical imaging of CA IX-expressing biological tissue, said method comprising:
(a) contacting the biological tissue with a composition comprising a CA IX-targeted NIR dye compound,
(b) allowing time for the compound in the composition to distribute within the biological target;
(c) illuminating the tissue with an excitation light of a wavelength absorbable by the compound; and
(d) detecting the optical signal emitted by the compound.

In some embodiments, these methods are used in detection of diseases associated with high CA IX expression. In some embodiments, further comprising the step of constructing an image from the signal emitted in (d). In some embodiments, the invention provides the aforementioned method wherein step (a) includes two or more fluorescent compounds whose signal properties are distinguishable are contacted with the tissue, and optionally the tissue is in a subject. In some embodiments the present invention provides use of an endoscope, catheter, tomographic system, hand-held optical imaging system, surgical goggles, or intraoperative microscope for the illuminating and/or detecting method steps.

In some embodiments, compositions and methods of the present invention are used to treat cancer. In some embodiments, the cancer is selected from the group consisting of lung cancer, bladder cancer, pancreatic cancer, liver cancer, kidney cancer, sarcoma, breast cancer, brain cancer, neuroendocrine carcinoma, colon cancer, prostate cancer, testicular cancer or melanoma. In some embodiments, CA IX-targeted NIR dye compounds of the present invention are used for imaging of CA IX-expressing cells. In certain embodiments those cells are chosen from the group consisting of bladder cancer cells, pancreatic cancer cells, liver cancer cells, lung cancer cells, kidney cancer cells, sarcoma cells, breast cancer cells, brain cancer cells, neuroendocrine carcinoma cells, colon cancer cells, prostate cancer cells, testicular cancer cells or melanoma cells.

The present invention also provides methods of targeting a cell type in a biological sample comprising: (a) contacting the biological sample with a CA IX-targeted NIR dye compound for a time and under conditions that allow for binding of the compound to at least one cell of the target cell type; and (b) optically detecting the presence or absence of the compound of in the biological sample, wherein presence of the compound in detecting step (b) indicates that the target cell type is present in the biological sample. In some embodiments the present invention provides methods for optical detection of CA IX-expressing cells comprising administering CA IX-targeting NIR dye compounds of the present invention and subjecting the compound to an excitation light source and detecting fluorescence from the compound. In some embodiments, the excitation light source is near-infrared wavelength light. In some embodiments the excitation light wavelength is within a range from about 600 to 1000 nanometers. In some embodiments the excitation light wavelength is within a range from about 670 to 850 nanometers.

In certain embodiments the present invention provides methods of performing image guided surgery on a subject comprising:
a) administering a composition comprising a CA IX-targeting NIR dye compound under conditions and for a time sufficient for the compound to accumulate at a given surgical site;
b) illuminating the compound to visualize the compound using infrared light; and
c) performing surgical resection of the areas that fluoresce upon excitation by the infrared light.

In some embodiments methods of the present invention the infrared light wavelength is within a range from about 600 to 1000 nanometers. In some embodiments methods of the present invention use an infrared light wavelength is within a range from about 670 to 850 nanometers.

Some embodiments of the present invention provide a method of diagnosing a disease in a subject comprising:
a) administering to a subject in need of diagnosis an amount of a CA IX-targeted NIR dye compound for a time and under conditions that allow for binding of the compound to at least one CA IX-expressing cell;
b) measuring the signal from the compound of present in the biological sample;
c) comparing the signal measured in b) with at least one control data set, wherein the at least one control data set comprises signals from the compound of claim 1 contacted with a biological sample that does not comprise the target cell type; and
d) providing a diagnosis of disease wherein the comparison in step c) indicates the presence of the disease.

Some embodiments of the present invention provide a kit comprising a CA IX-targeting NIR dye compound. In some embodiments, the kit is used for the imaging of CA IX-expressing cells. In some embodiments the CA IX-expressing cells are tumor cells. In certain embodiments the CA IX-expressing cells are cancer cells. In certain embodiments the CA IX-expressing area is tumor microenvironment. In some embodiments the present invention is used for detection of metastatic disease. In some embodiments compounds of the present invention are used for improved surgical resection and/or improved prognosis. In some embodiments methods of the present invention provide cleaner surgical margins than non-NIR conjugated fluorescing dyes. In some embodiments CA IX-targeted NIR dye compounds of the present invention have an improved tumor-to-background ratio.

In other embodiments, the cells being detected are more than 5 mm below the skin. In some embodiments, the tissue being detected is more than 5 mm below the skin. In other embodiments, the tumor being detected is more than 5 mm below the skin. In some embodiments, the cells being detected are more than 6 mm, 7 mm, 8 mm, 9 mm, or 10 mm below the subject's skin. In some embodiments of the present invention dye probes that are detectable outside of the visible light spectrum. In some embodiments dye probes greater than the visible light spectrum are used. In some embodiments compounds of the present invention comprise dye probes sensitive to wavelengths between 650 nm and 900 nm.

In some embodiments the CA IX-targeted NIR dye compounds of the present invention have maximum light absorption wavelengths in the near infrared region of between about 650 nm and 1000 nm, for example and in one embodiment, at approximately 800 nm.

In a further embodiment of the methods provided, the CA IX-expressing cancer cells are of a tumor. In still a further embodiment of the methods provided, the CA IX-expressing cancer is a tumor. In some embodiments, the volume of the tumor is at least 1000 mm$^3$. In some embodiments, the volume of the tumor is less than 1000 mm$^3$. In some embodiments, the volume of the tumor is less than 950 mm$^3$. In some embodiments, the volume of the tumor is less than 900 mm$^3$. In some embodiments, the volume of the tumor is less than 850 mm$^3$. In some embodiments, the volume of the tumor is less than 800 mm$^3$. In some embodiments, the volume of the tumor is less than 750 mm$^3$. In some embodiments, the volume of the tumor is less than 700 mm$^3$. In some embodiments, the volume of the tumor is less than 650 mm$^3$. In some embodiments, the volume of the tumor is less than 600 mm$^3$. In some embodiments, the volume of the tumor is less than 550 mm$^3$. In some embodiments, the volume of the tumor is less than 500 mm$^3$. In some embodiments, the volume of the tumor is less than 450 mm$^3$. In some embodiments, the volume of the tumor is less than 400 mm$^3$. In some embodiments, the volume of the tumor is less than 350 mm$^3$. In some embodiments, the volume of the tumor is less than 300 mm$^3$. In some embodiments, the volume of the tumor is less than 250 mm$^3$. In some embodiments, the volume of the tumor is less than 200 mm$^3$. In some embodiments, the volume of the tumor is less than 150 mm$^3$. In some embodiments, the volume of the tumor is less than 100 mm$^3$. In one embodiment, the volume of the tumor is at least 75 mm$^3$. In another embodiment, the volume of the tumor is less than 75 mm$^3$. In another embodiment, the volume of the tumor is less than 70 mm$^3$. In another embodiment, the volume of the tumor is less than 65 mm$^3$. In another embodiment, the volume of the tumor is less than 60 mm$^3$. In another embodiment, the volume of the tumor is less than 55 mm$^3$. In one embodiment, the volume of the tumor is at least 50 mm$^3$. In other embodiments, the tumor is less than 50 mm$^3$. In another embodiment, the volume of the tumor is less than 45 mm$^3$. In other embodiments, the volume of the tumor is less than 40 mm$^3$. In another embodiment, the volume of the tumor is less than 35 mm$^3$. In still another embodiment, the volume of the tumor is less than 30 mm$^3$. In another embodiment, the volume of the tumor is less than 25 mm$^3$. In still another embodiment, the volume of the tumor is less than 20 mm$^3$. In another embodiment, the volume of the tumor is less than 15 mm$^3$. In still another embodiment, the volume of the tumor is less than 10 mm$^3$. In still another embodiment, the volume of the tumor is less than 12 mm$^3$. In still another embodiment, the volume of the tumor is less than 9 mm$^3$. In still another embodiment, the volume of the tumor is less than 8 mm$^3$. In still another embodiment, the volume of the tumor is less than 7 mm$^3$. In still another embodiment, the volume of the tumor is less than 6 mm$^3$. In still another embodiment, the volume of the tumor is less than 5 mm$^3$.

In one embodiment, the tumor has a length of at least 5 mm prior to surgical recession using a CA IX-targeted NIR dye compound of the present invention. In one embodiment, these methods detect tumors less than 5 mm. In other embodiments the methods herein detect tumors less than 4 mm. In some embodiments, the methods herein detect tumors less than 3 mm. In another embodiment, the tumor has a length of at least 6 mm. In still another embodiment, the tumor has a length of at least 7 mm. In yet another embodiment, the tumor has a length of at least 8 mm. In another embodiment, the tumor has a length of at least 9 mm. In still another embodiment, the tumor has a length of at least 10 mm. In yet another embodiment, the tumor has a length of at least 11 mm. In a further embodiment, the tumor has a length of at least 12 mm. In still a further embodiment, the tumor has a length of at least 13 mm. In still a further embodiment, the tumor has a length of at least 14 mm. In another embodiment, the tumor has a length of at least 15 mm. In yet another embodiment, the tumor has a length of at least 16 mm. In still another embodiment, the tumor has a length of at least 17 mm. In a further embodiment, the tumor has a length of at least 18 mm. In yet a further embodiment, the tumor has a length of at least 19 mm. In still a further embodiment, the tumor has a length of at least 20 mm. In another embodiment, the tumor has a length of at least 21 mm. In still another embodiment, the tumor has a length of at least 22 mm. In yet another embodiment, the tumor has a length of at least 23 mm. In a further embodiment, the tumor has a length of at least 24 mm. In still a further embodiment, the tumor has a length of at least 25 mm. In yet a further embodiment, the tumor has a length of at least 30 mm.

In some embodiments the present disclosure relates to CA IX-targeted compounds conjugated to near-infra red (NIR) dyes and methods for their therapeutic and diagnostic use. More specifically, this disclosure provides compounds and methods for diagnosing and treating diseases associated with cells expressing CA IX, such as of kidney, endometrial, urinary, colorectal, ovarian, breast, pancreatic, and esophagus, and hypoxic regions of many solid tumors, and related diseases. The disclosure further describes methods and compositions for making and using the compounds, methods incorporating the compounds, and kits incorporating the compounds. It has been discovered that a CA IX-targeted compound, such as ligands with extended hydrophobic residues (W) to improve the binding affinity and specificity for CA IX conjugated to an NIR dye via a linker (X-Y) may be useful in the imaging, diagnosis, and/or treatment of kidney, endometrial, urinary, colorectal, ovarian, breast, pancreatic, and esophagus, and hypoxic regions of many solid tumors, and related diseases that involve pathogenic cell populations expressing or overexpressing CA IX. CA IX is a cell surface protein that is internalized in a process analogous to endocytosis observed with cell surface receptors, such as vitamin receptors. Accordingly, it has been discovered that certain conjugates that include a linker having a predetermined length, and/or a predetermined diameter, and/or preselected functional groups along its length may be used to treat, image, and/or diagnose such diseases.

In one illustrative embodiment, the linker [either X or spacer between the ligand and NIR dye (W-X-Y)] may be a releasable or non-releasable linker. In one aspect, the linker L is at least about 6 atoms in length. In one variation, the linker [X or W-X-Y] is at least about 8 atoms in length. In one variation, the linker [X or W-X-Y] is at least about 10 atoms in length. In another variation, the linker [X or W-X-Y] is between about 6 and about 14, between about 6 and about 20, or between about 6 and about 18 atoms in length. In another variation, the linker [X or W-X-Y] is between about 10 and about 20, between about 14 and about 12, or between about 10 and about 16 atoms in length.

In an alternative aspect, the linker [X or W-X-Y] is at least about 10 angstroms (Å) in length. In one variation, the linker [X or W-X-Y] is at least about 14 Å in length. In another variation, the linker [X or W-X-Y] is at least about 16 Å in length. In another variation, the linker [X or W-X-Y] is in the range from about 10 Å to about 20 Å in length.

In an alternative aspect, at least a portion of the length of the linker [X or W-X-Y] is about 4 Å in diameter or less at the end connected to the binding ligand B. In one variation, at least a portion of the length of the linker [X or W-X-Y]

is about 4 Å or less, or about 3 Å or less in diameter at the end connected to the binding ligand B. It is appreciated that the illustrative embodiments that include a diameter requirement of about 5 Å or less, about 4 Å or less, or about 3 Å or less may include that requirement for a predetermined length of the linker, thereby defining a conical cavity-like portion of the linker. Illustratively, in another variation, the linker includes a conical cavity portion at the end connected to the binding ligand that is at least about 6 Å in length and about 5 Å or less, about 4 Å or less, or about 3 Å or less in diameter.

In another embodiment, the linker [W-X-Y] includes one or more hydrophobic linkers capable of interacting with one or more residues of CA IX, including amino acids that have hydrophobic side chains, such as Val, Leu, Phe, Tyr, His, Trp, Met, and like residues. In another embodiment, the linker [W-X-Y] includes one or more hydrophilic linkers capable of interacting with one or more residues of CA Ix protein, including amino acids that have hydrophilic side chains, such as Ser, Thr, Cys, Arg, Orn, Lys, Asp, Glu, Gln and like residues. It is to be understood that the foregoing embodiments and aspects may be included in the linker X either alone or in combination with each other [W-X-Y or X-Y, or W-Y]. For example, linkers X that are at least about 6 atoms in length and about 5 Å, about 4 Å or less, or about 3 Å or less in diameter or less are contemplated and described herein, and also include one or more hydrophilic linkers capable of interacting with one or more residues of CA IX, including Asn, His, Ser, Glu, Thr, Gln in the hydrophilic pocket or Leu, Val, Val, Leu, Pro in the hydrophobic pocket and like residues are contemplated and described herein.

In another embodiment, one end of the linker is not branched and comprises a chain of carbon, oxygen, nitrogen, and sulfur atoms. In one embodiment, the linear chain of carbon, oxygen, nitrogen, and sulfur atoms is at least 5 atoms in length. In one variation, the linear chain is at least 7 atoms, or at least 10 atoms in length. In another embodiment, the chain of carbon, oxygen, nitrogen, and sulfur atoms are not substituted. In one variation, a portion of the chain of carbon, oxygen, nitrogen, and sulfur atoms is cyclized with a divalent fragment. For example, a linker (Y) comprising the dipeptide Phe-Tyr, or amino acid Tyr, may include a piperazin-1,4-diyl structure by cyclizing two nitrogens with an ethylene fragment, or substituted variation thereof.

In another embodiment, pharmaceutical compositions are described herein, where the pharmaceutical composition includes the conjugates described herein in amounts effective to treat diseases and disease states, diagnose diseases or disease states, and/or image tissues and/or cells that are associated with pathogenic populations of cells expressing or over expressing CA IX. Illustratively, the pharmaceutical compositions also include one or more carriers, diluents, and/or excipients.

In another embodiment, methods for treating diseases and disease states, diagnosing diseases or disease states, and/or imaging tissues and/or cells that are associated with pathogenic populations of cells expressing or over expressing CA IX are described herein. Such methods include the step of administering the conjugates described herein, and/or pharmaceutical compositions containing the conjugates described herein, in amounts effective to treat diseases and disease states, diagnose diseases or disease states, and/or image tissues and/or cells that are associated with pathogenic populations of cells expressing or over expressing CA IX.

In some embodiments the present disclosure includes any individual or combination of CA 1X-targeted molecules (B) including any one of the following structural formulas:

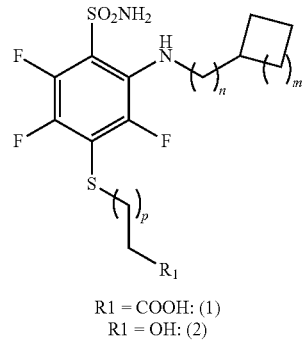

R1 = COOH: (1)
R1 = OH: (2)

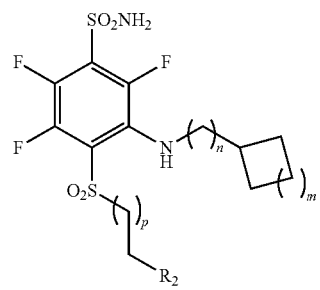

R2 = COOH: (3)
R2 = OH: (4)

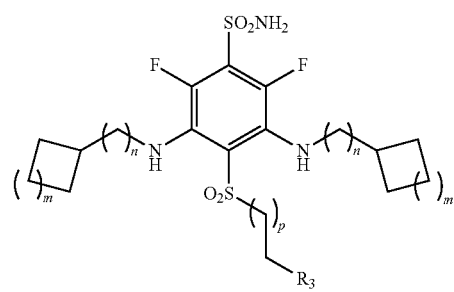

R3 = COOH: (5)
R3 = OH: (6)

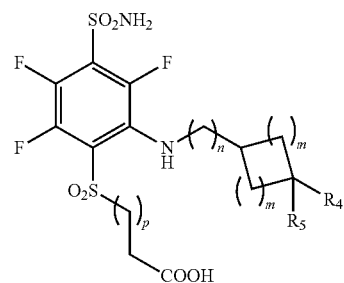

R4 = F, R5 = H: (7)a
R4, R5 = F: (7)b

-continued
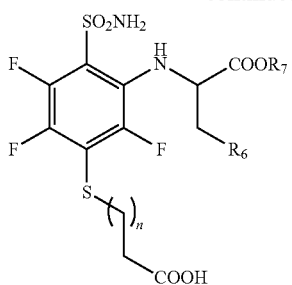
R6 = p-Ph, R7 = Bz: (9)
R6 = CH(CH3)2, R7 = Bz: (10a)
R6 = CH(CH3)2, R7 = H: (10b)
R6 = Imidazole, R7 = Bz: (11)
R6 = indole, R7 = Bz: (12)
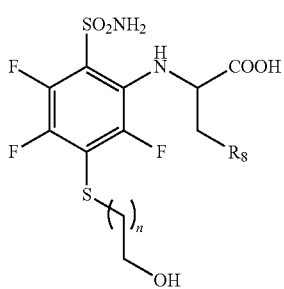
R8 = p-Ph: (13)
R8 = CH(CH3)2: (14)
R8 = Imidazole: (15)
R8 = indole: (16)
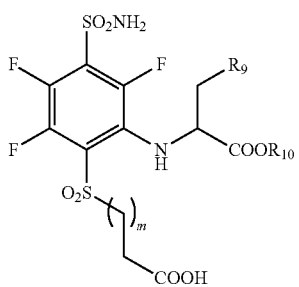
R9 = p-Ph, R10 = H: (17)
R9 = CH(CH3)2 R10 =H: (18a)
R9 = CH(CH3)2, R10 = Bz: (18b)
R9 = Imidazole, R10 = H: (19)
R9 = indole, R = H: (20)
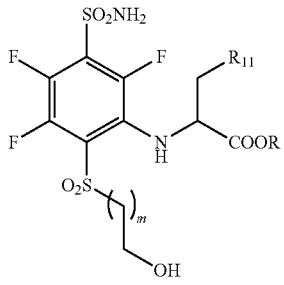
R11 = p-Ph: (21)
R11 = CH(CH3)2: (22)
R11 = Imidazole: (23)
R11 = indole: (24)
-continued
(46)
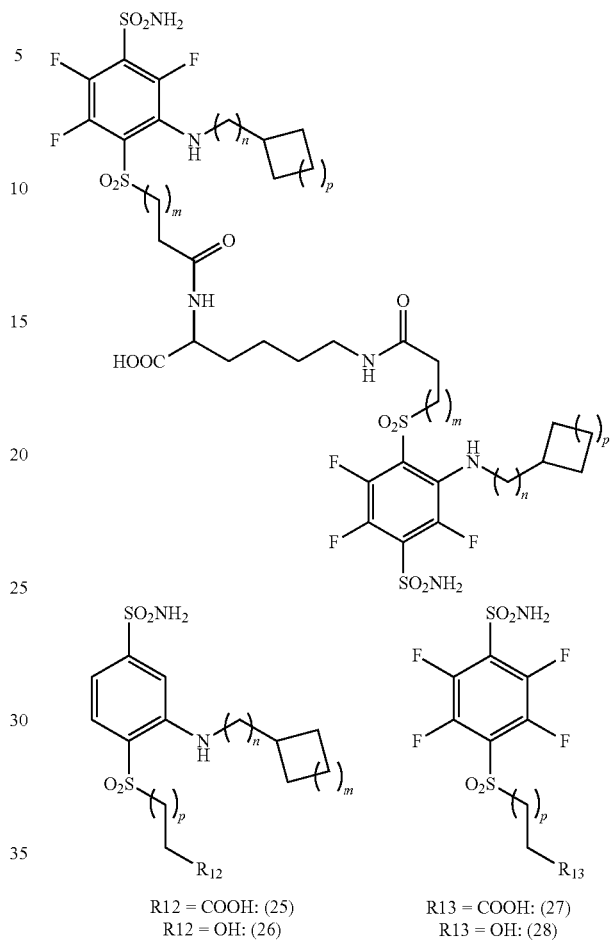
R12 = COOH: (25)    R13 = COOH: (27)
R12 = OH: (26)      R13 = OH: (28)
(29)
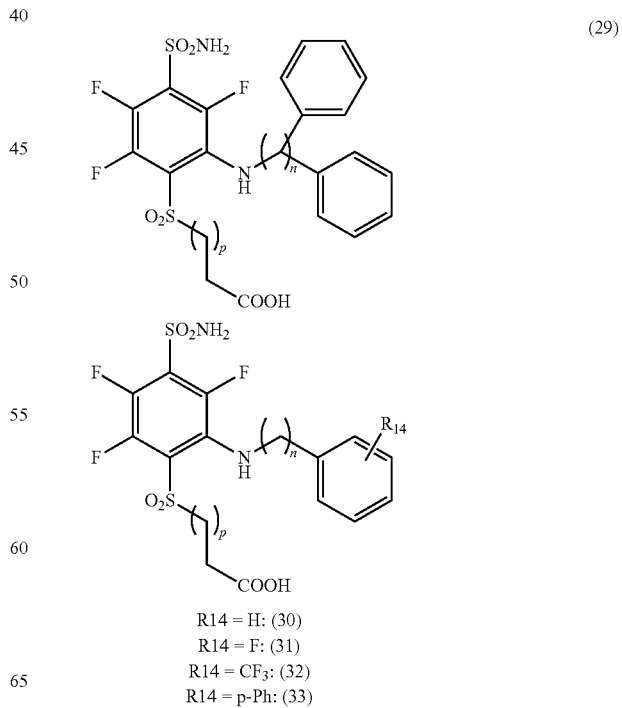
R14 = H: (30)
R14 = F: (31)
R14 = CF3: (32)
R14 = p-Ph: (33)

-continued

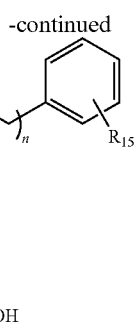

R15 = F: (34)
R15 = CF$_3$: (35)
R15 = p-Ph: (36)a
R15 = H: (37)

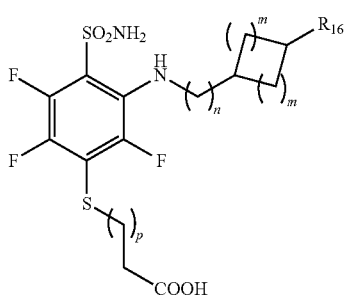

R16 = F: (37)
R16 = CF$_3$: (38)

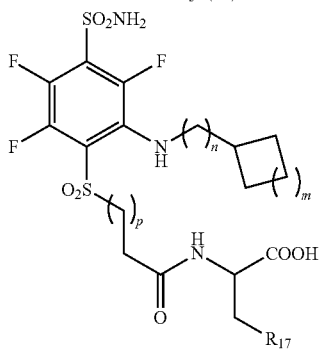

R17 = COOH: (39)
R17 = (CH$_2$)$_2$ Guanidinium: (40)
R17 = p-Ph: (41)
R17 = Imidazole: (42)
R17 = Indole: (43)
R17 = CH(CH$_3$)$_2$: (44)
R17 = CH(CH$_2$CH$_3$)CH$_3$: (45)

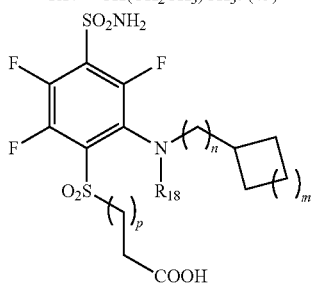

R18 = Guanidinium: (47)

In some embodiments compounds of the present invention have an absorption and emission maxima between about 500 nm and about 900 nm. In some embodiments compounds of the present invention have an absorption and emission maxima between about 600 nm and 800 nm.

In some embodiments compounds of the present invention are made to fluoresce after distribution thereof in tissue cells. In some embodiments compounds of the present invention are made to fluoresce by subjecting the compounds to excitation light of near infrared wavelength. In some embodiments compounds of the present invention have a binding affinity to CA IX that is similar to the binding affinity of AZM. In some embodiments compounds of the present invention are highly selective for targeting to a tumor cell.

In certain embodiments compounds of the present invention are administered to a subject in need thereof and in some embodiments the administered composition comprises, in addition to the compound, a pharmaceutically acceptable carrier, excipient or diluent.

Some embodiments of the present invention provide methods of optical imaging of CA IX-expressing biological tissue, said method comprising:
(a) contacting the biological tissue with a composition comprising a CA IX-targeted NIR dye compound,
(b) allowing time for the compound in the composition to distribute within the biological target;
(c) illuminating the tissue with an excitation light of a wavelength absorbable by the compound; and
(d) detecting the optical signal emitted by the compound.

In some embodiments, these methods are used in detection of diseases associated with high CA IX expression. In some embodiments, further comprising the step of constructing an image from the signal emitted in (d). In some embodiments, the invention provides the aforementioned method wherein step (a) includes two or more fluorescent compounds whose signal properties are distinguishable are contacted with the tissue, and optionally the tissue is in a subject. In some embodiments the present invention provides use of an endoscope, catheter, tomographic system, hand-held optical imaging system, surgical goggles, or intraoperative microscope for the illuminating and/or detecting method steps.

In some embodiments, compositions and methods of the present invention are used to treat cancer. In some embodiments, the cancer is selected from the group consisting of prostate cancer, bladder cancer, pancreatic cancer, liver cancer, lung cancer, kidney cancer, sarcoma, breast cancer, brain cancer, neuroendocrine carcinoma, colon cancer, testicular cancer or melanoma. In some embodiments, CA IX-targeted NIR dye compounds of the present invention are used for imaging of CA IX-expressing cells. In certain embodiments those cells are chosen from the group consisting of prostate cells, prostate cancer cells, bladder cancer cells, pancreatic cancer cells, liver cancer cells, lung cancer cells, kidney cancer cells, sarcoma cells, breast cancer cells, brain cancer cells, neuroendocrine carcinoma cells, colon cancer cells, testicular cancer cells or melanoma cells.

The present invention also provides methods of targeting a cell type in a biological sample comprising: a) contacting the biological sample with a CA IX-targeted NIR dye compound for a time and under conditions that allow for binding of the compound to at least one cell of the target cell type; and b) optically detecting the presence or absence of the compound of in the biological sample, wherein presence of the compound in detecting step c) indicates that the target cell type is present in the biological sample. In some embodiments the present invention provides methods for optical detection of CA IX-expressing cells comprising administering CA IX-targeting NIR dye compounds of the present invention and subjecting the compound to an excitation light source and detecting fluorescence from the compound. In some embodiments, the excitation light source is near-infrared wavelength light. In some embodiments the excitation light wavelength is within a range from about 600 to 1000 nanometers. In some embodiments the excitation light wavelength is within a range from about 670 to 850 nanometers.

In certain embodiments the present invention provides methods of performing image guided surgery on a subject comprising:
  a) administering a composition comprising a CA IX-targeting NIR dye compound under conditions and for a time sufficient for the compound to accumulate at a given surgical site;
  b) illuminating the compound to visualize the compound using infrared light; and
  c) performing surgical resection of the areas that fluoresce upon excitation by the infrared light.

In some embodiments methods of the present invention the infrared light wavelength is within a range from about 600 to about 1000 nanometers. In some embodiments methods of the present invention use an infrared light wavelength is within a range from about 670 to about 850 nanometers.

Some embodiments of the present invention provide a method of diagnosing a disease in a subject comprising:
  a) administering to a subject in need of diagnosis an amount of a CA IX-targeted NIR dye compound for a time and under conditions that allow for binding of the compound to at least one CA IX-expressing cell or tissues;
  b) measuring the signal from the compound of present in the biological sample;
  c) comparing the signal measured in b) with at least one control data set, wherein the at least one control data set comprises signals from the compound of claim 1 contacted with a biological sample that does not comprise the target cell type; and
  d) providing a diagnosis of disease wherein the comparison in step c) indicates the presence of the disease.

Some embodiments of the present invention provide a kit comprising a CA IX-targeting NIR dye compound. In some embodiments, the kit is used for the imaging of CA IX-expressing cells or tissues. In some embodiments the CA IX-expressing cells are tumor cells. In some embodiments the CA IX-expressing cells are non-prostate cancer cells. In certain embodiments the CA IX-expressing cells are prostate tumor cells. In certain embodiments the CA IX-expressing cells are cancer cells. In some embodiments the present invention is used for detection of metastatic disease. In some embodiments compounds of the present invention are used for improved surgical resection and/or improved prognosis. In some embodiments methods of the present invention provide cleaner surgical margins than non-NIR conjugated fluorescing dyes. In some embodiments CA IX-targeted NIR dye compounds of the present invention have an improved tumor-to-background ratio.

In other embodiments compounds of the present invention are used to image, diagnose, or detect non-prostate cancer cells chosen from the group consisting of bladder cancer cells, pancreatic cancer cells, liver cancer cells, lung cancer cells, kidney cancer cells, sarcoma cells, breast cancer cells, brain cancer cells, neuroendocrine carcinoma cells, colon cancer cells, testicular cancer cells or melanoma cells. In other embodiments, the cells being detected are more than 5 mm below the skin. In some embodiments, the tissue being detected is more than 5 mm below the skin. In other embodiments, the tumor being detected is more than 5 mm below the skin. In some embodiments, the cells being detected are more than 6 mm, 7 mm, 8 mm, 9 mm, or 10 mm below the subject's skin. In some embodiments of the present invention dye probes that are detectable outside of the visible light spectrum. In some embodiments dye probes greater than the visible light spectrum are used. In some embodiments compounds of the present invention comprise dye probes sensitive to wavelengths between 650 nm and 900 nm. In some embodiments the CA IX-targeted NIR dye compounds of the present invention have maximum light absorption wavelengths in the near infrared region of between about 650 nm and 1000 nm, for example and in one embodiment, at approximately 800 nm.

In still another embodiment of the methods provided, the non-prostate cancer is bladder cancer, pancreatic cancer, liver cancer, lung cancer, kidney cancer, sarcoma, breast cancer, brain cancer, neuroendocrine carcinoma, colon cancer, testicular cancer or melanoma.

In a further embodiment of the methods provided, the CA IX-expressing cancer cells are of a tumor. In still a further embodiment of the methods provided, the CA IX-expressing cancer is a tumor. In some embodiments, the volume of the tumor is at least 1000 mm$^3$. In some embodiments, the volume of the tumor is less than 1000 mm$^3$. In some embodiments, the volume of the tumor is less than 950 mm$^3$. In some embodiments, the volume of the tumor is less than 900 mm$^3$. In some embodiments, the volume of the tumor is less than 850 mm$^3$. In some embodiments, the volume of the tumor is less than 800 mm$^3$. In some embodiments, the volume of the tumor is less than 750 mm$^3$. In some embodiments, the volume of the tumor is less than 700 mm$^3$. In some embodiments, the volume of the tumor is less than 650 mm$^3$. In some embodiments, the volume of the tumor is less than 600 mm$^3$. In some embodiments, the volume of the tumor is less than 550 mm$^3$. In some embodiments, the volume of the tumor is less than 500 mm$^3$. In some embodiments, the volume of the tumor is less than 450 mm$^3$. In some embodiments, the volume of the tumor is less than 400 mm$^3$. In some embodiments, the volume of the tumor is less than 350 mm$^3$. In some embodiments, the volume of the tumor is less than 300 mm$^3$. In some embodiments, the volume of the tumor is less than 250 mm$^3$. In some embodiments, the volume of the tumor is less than 200 mm$^3$. In some embodiments, the volume of the tumor is less than 150 mm$^3$. In some embodiments, the volume of the tumor is less than 100 mm$^3$. In one embodiment, the volume of the tumor is at least 75 mm$^3$. In another embodiment, the volume of the tumor is less than 75 mm$^3$. In another embodiment, the volume of the tumor is less than 70 mm$^3$. In another embodiment, the volume of the tumor is less than 65 mm$^3$. In another embodiment, the volume of the tumor is less than 60 mm$^3$. In another embodiment, the volume of the tumor is less than 55 mm$^3$. In one embodiment, the volume of the tumor is at least 50 mm$^3$. In other embodiments, the tumor is less than 50 mm$^3$. In another embodiment, the volume of the tumor is less than 45 mm$^3$. In other embodiments, the volume of the tumor is less than 40 mm$^3$. In another embodiment, the volume of the tumor is less than 35 mm$^3$. In still another embodiment, the volume of the tumor is less than 30 mm$^3$. In another embodiment, the volume of the tumor is less than 25 mm$^3$. In still another embodiment, the volume of the tumor is less than 20 mm$^3$. In another embodiment, the volume of the tumor is less than 15 mm$^3$. In still another embodiment, the volume of the tumor is less than 10 mm$^3$. In still another embodiment, the volume of the tumor is less than 12 mm$^3$. In still another embodiment, the volume of the tumor is less than 9 mm³. In still another embodiment, the volume of the tumor is less than 8 mm³. In still another embodiment, the volume of the tumor is less than 7 mm³. In still another embodiment, the volume of the tumor is less than 6 mm³. In still another embodiment, the volume of the tumor is less than 5 mm³.

In one embodiment, the tumor has a length of at least 5 mm prior to surgical recision using a CA IX-targeted NIR dye compound of the present invention. In one embodiment, these methods detect tumors less than 5 mm. In other embodiments the methods herein detect tumors less than 4 mm. In some embodiments, the methods herein detect tumors less than 3 mm. In another embodiment, the tumor has a length of at least 6 mm. In still another embodiment, the tumor has a length of at least 7 mm. In yet another embodiment, the tumor has a length of at least 8 mm. In another embodiment, the tumor has a length of at least 9 mm. In still another embodiment, the tumor has a length of at least 10 mm. In yet another embodiment, the tumor has a length of at least 11 mm. In a further embodiment, the tumor has a length of at least 12 mm. In still a further embodiment, the tumor has a length of at least 13 mm. In still a further embodiment, the tumor has a length of at least 14 mm. In another embodiment, the tumor has a length of at least 15 mm. In yet another embodiment, the tumor has a length of at least 16 mm. In still another embodiment, the tumor has a length of at least 17 mm. In a further embodiment, the tumor has a length of at least 18 mm. In yet a further embodiment, the tumor has a length of at least 19 mm. In still a further embodiment, the tumor has a length of at least 20 mm. In another embodiment, the tumor has a length of at least 21 mm. In still another embodiment, the tumor has a length of at least 22 mm. In yet another embodiment, the tumor has a length of at least 23 mm. In a further embodiment, the tumor has a length of at least 24 mm. In still a further embodiment, the tumor has a length of at least 25 mm. In yet a further embodiment, the tumor has a length of at least 30 mm.

In some embodiments the present disclosure relates to carbonic anhydrase (CA)-targeted compounds conjugated to near-infra red (NIR) dyes and methods for their therapeutic and diagnostic use. More specifically, this disclosure provides compounds and methods for diagnosing and treating diseases associated with cells expressing carbonic anhydrase antigen (CA), such as cancer and related diseases. The disclosure further describes methods and compositions for making and using the compounds, methods incorporating the compounds, and kits incorporating the compounds. It has been discovered that a CA IX-targeted compound, such as AZM or conjugating CA IX-targeting ligand to an NIR dye via a linker (L=W-X-Y or X) may be useful in the imaging, diagnosis, and/or treatment of cancer, and related diseases that involve pathogenic cell populations expressing or overexpressing CA IX. CA is a cell surface protein that is internalized in a process analogous to endocytosis observed with cell surface receptors, such as vitamin receptors. CA also express in the neo-vasculature of most of solid tumors. Accordingly, it has been discovered that certain conjugates that include a linker having a predetermined length, and/or a predetermined diameter, and/or preselected functional groups along its length may be used to treat, image, and/or diagnose such diseases.

In one illustrative embodiment, the linker L may be a releasable or non-releasable linker. In one aspect, the linker L is at least about 6 atoms in length. In one variation, the linker L is at least about 10 atoms in length. In one variation, the linker L is at least about 14 atoms in length. In another variation, the linker L is between about 6 and about 22, between about 6 and about 24, or between about 6 and about 20 atoms in length. In another variation, the linker L is between about 14 and about 31, between about 14 and about 24, or between about 14 and about 20 atoms in length.

In an alternative aspect, the linker L (W-X-Y or X) is at least about 10 angstroms (A) in length.

In one variation, the linker L (W-X-Y) is at least about 15 A in length. In another variation, the linker L is at least about 20 A in length. In another variation, the linker L is in the range from about 10 A to about 30 A in length.

In an alternative aspect, at least a portion of the length of the linker L is about 5 A in diameter or less at the end connected to the binding ligand B. In one variation, at least a portion of the length of the linker L is about 4 A or less, or about 3 A or less in diameter at the end connected to the binding ligand B. It is appreciated that the illustrative embodiments that include a diameter requirement of about 5 A or less, about 4 A or less, or about 3 A or less may include that requirement for a predetermined length of the linker, thereby defining a cylindrical-like portion of the linker. Illustratively, in another variation, the linker includes a cylindrical portion at the end connected to the binding ligand that is at least about 7 A in length and about 5 A or less, about 4 A or less, or about 3 A or less in diameter.

In another embodiment, the linker L (W-X-Y or X) includes one or more hydrophilic linkers capable of interacting with one or more residues of CA, including amino acids that have hydrophilic side chains, such as Ser, Thr, Cys, Arg, Orn, Lys, Asp, Glu, Gln, and like residues. In another embodiment, the linker L includes one or more hydrophobic linkers capable of interacting with one or more residues of CA, including amino acids that have hydrophobic side chains, such as Val, Leu, Phe, Tyr, Met, and like residues. It is to be understood that the foregoing embodiments and aspects may be included in the linker L either alone or in combination with each other. For example, linkers L that are at least about 6 atoms in length and about 4 Å, or about 3 Å or less in diameter or less are contemplated and described herein, and also include one or more hydrophilic linkers capable of interacting with one or more residues of CA, including Val, Leu, Phe, Tyr, Met, and like residues are contemplated and described herein.

In another embodiment, one end of the linker is not branched and comprises a chain of carbon, oxygen, nitrogen, and sulfur atoms. In one embodiment, the linear chain of carbon, oxygen, nitrogen, and sulfur atoms is at least 5 atoms in length. In one variation, the linear chain is at least 7 atoms, or at least 10 atoms in length. In another embodiment, the chain of carbon, oxygen, nitrogen, and sulfur atoms are not substituted. In one variation, a portion of the chain of carbon, oxygen, nitrogen, and sulfur atoms is cyclized with a divalent fragment. For example, a linker (L) comprising the dipeptide Phe-Tyr may include a piperazin-1,4-diyl structure by cyclizing two nitrogens with an ethylene fragment, or substituted variation thereof.

In another embodiment, pharmaceutical compositions are described herein, where the pharmaceutical composition includes the conjugates described herein in amounts effective to treat diseases and disease states, diagnose diseases or disease states, and/or image tissues and/or cells that are associated with pathogenic populations of cells expressing or over expressing CA IX. Illustratively, the pharmaceutical compositions also include one or more carriers, diluents, and/or excipients.

In another embodiment, methods for treating diseases and disease states, diagnosing diseases or disease states, and/or imaging tissues and/or cells that are associated with pathogenic populations of cells expressing or over expressing CA IX are described herein. Such methods include the step of administering the conjugates described herein, and/or pharmaceutical compositions containing the conjugates described herein, in amounts effective to treat diseases and disease states, diagnose diseases or disease states, and/or image tissues and/or cells that are associated with pathogenic populations of cells expressing or over expressing CA IX.

In some embodiments, it is shown herein that such CA IX-targeted NIR dye conjugates bind to CA IX expressing tumor cells within a tissue. Moreover, the intensity of the fluorescence in greater than the intensity of previously observed with other near infrared dyes that are targeted with folate for folate receptor positive tumors. This increased intensity allows the targeting and clear identification of smaller areas of biological samples (e.g., smaller tumors) from a tissue being monitored. In addition, the increased intensity of the compounds of the present invention provides the added advantage that lower doses/quantities of the dye can be administered and still produces meaningful results. Thus, the compounds of the present invention lead to more economical imaging techniques. Moreover, there is an added advantaged that a lower dose of the compounds of the invention as compared to conventional imaging compounds minimizes the toxicity and other side effects that are attendant with administration of foreign materials to a body.

Furthermore, identification of small tumors will lead to a more accurate and more effective resection of the primary tumor to produce negative margins, as well as accurate identification and removal of the lymph nodes harboring metastatic cancer cells and identification of satellite disease. Each of these advantages positively correlates with a better clinical outcome for the patient being treated.

In specific embodiments, it is contemplated that in addition to tyrosine and tyrosine derivatives, a CA IX-targeted conjugate of a near infrared dye with cysteine or cysteine derivatives also may be useful. Furthermore, it is contemplated that a direct linkage of the CA IX-targeted moiety to the dye or linkage of the dye to AZM or a CA IX-targeted ligand through an amine linker also produces a loss of intensity of the fluorescence from the conjugate whereas the presence of the tyrosine or tyrosine derivative as the linking moiety between enhances the fluorescence of the conjugated compound as a result of the fact that the tyrosine-based compounds of the invention do not require an extra amine linker to conjugate the S0456 and further because conjugation through the phenol moiety of the tyrosine leads to enhanced fluorescence.

The compounds can be used with fluorescence-mediated molecular tomographic imaging systems, such as those designed to detect near-infrared fluorescence activation in deep tissues. The compounds provide molecular and tissue specificity, yield high fluorescence contrast, brighter fluorescence signal, and reduce background autofluorescence, allowing for improved early detection and molecular target assessment of diseased tissue in vivo (e.g., cancers). The compounds can be used for deep tissue three dimensional imaging, targeted surgery, and methods for quantifying the amount of a target cell type in a biological sample.

In specific embodiments, the linker is less than ten atoms. In other embodiments, the linker is less than twenty atoms. In some embodiments, the linker is less than 30 atoms. In some embodiments, the linker is defined by the number of atoms separating the CA IX-targeting compound and the NIR dye. In another embodiment, linkers have a chain length of at least 6 atoms. In some embodiments, linkers have a chain length of at least 14 atoms. In another embodiment, linkers have a chain length in the range from 7 atoms to 20 atoms. In another embodiment, linkers have a chain length in the range of 14 atoms to 24 atoms.

CA IX-targeting compounds suitable for use in the present invention can be selected, for example, based on the following criteria, which are not intended to be exclusive: binding to live cells expressing CA IX; binding to neovasculature expressing CA IX; high affinity of binding to CA IX; binding to a unique epitope on CA IX (to eliminate the possibility that antibodies with complimentary activities when used in combination would compete for binding to the same epitope); opsonization of cells expressing CA IX; mediation of growth inhibition, phagocytosis and/or killing of cells expressing CA IX in the presence of effector cells; modulation (inhibition or enhancement) of CA IX, growth inhibition, cell cycle arrest and/or cytotoxicity in the absence of effector cells; internalization of CA IX; binding to a conformational epitope on CA IX; minimal cross-reactivity with cells or tissues that do not express CA IX; and preferential binding to dimeric forms of CA IX rather than monomeric forms of CA IX.

CA IX-targeting compounds, CA IX antibodies and antigen-binding fragments thereof provided herein typically meet one or more, and in some instances, more than five of the foregoing criteria. In some embodiments, the CA IX-targeting compounds of the present invention meet six or more of the foregoing criteria. In some embodiments, the CA IX-targeting compounds of the present invention meet seven or more of the foregoing criteria. In some embodiments, the CA IX-targeting compounds of the present invention meet eight or more of the foregoing criteria. In some embodiments, the CA IX-targeting compounds of the present invention meet nine or more of the foregoing criteria. In some embodiments, the CA IX-targeting compounds of the present invention meet ten or more of the foregoing criteria. In some embodiments, the CA IX-targeting compounds of the present invention meet all of the foregoing criteria.

Examples of tumors that can be imaged with the CA IX-targeted compounds of the present invention (e.g., CA IX-targeted NIR dye conjugates) provided herein, include any tumor that expresses CA IX such as, e.g. bladder, pancreas, lung, colon, kidney, melanomas and sarcomas. A tumor that expresses CA IX includes tumors with tumor microenvironment expressing CA IX.

In some embodiments, a CA IX-targeted molecules bind to CA IX and are internalized with CA IX expressed on cells. Thus, a CA IX ligand conjugate comprising an internalized with CA IX expressed on cells. The mechanism by which this internalization occurs is not critical to the practice of the present invention.

In some embodiments, the CA IX targeting compounds bind to a conformational epitope within the extracellular domain of the CA IX molecule. In other embodiments, a CA IX-targeting compound binds to a dimer-specific epitope on CA IX. Generally, the compound that binds to a dimer-specific epitope preferentially binds the CA IX dimer rather than the CA IX monomer. In some embodiments of the present invention, the CA IX-targeting compound preferentially binds to the CA IX dimer. In some embodiments of the present invention, the CA IX-targeting compound has a low affinity for the monomeric CA IX protein.

In some embodiments, the CA IX-targeting compound is a ligand. In some embodiments, the CA IX-targeting compound is Fluorinated aromatic sulfonate with an extended hydrophobic residue or derivative thereof. In some embodiments, the CA IX-targeting compound is Fluorinated aromatic sulfonate with an extended hydrophobic residue or derivative of Fluorinated aromatic sulfonate with an extended hydrophobic residue, ligand, inhibitor, or agonist that binds to CA IX-expressing live cells.

The CA IX-targeting NIR dye of the present invention produces a tumor-to-background signal ratio that is higher than the tumor-to-background signal ratio of the CA IX-targeting compound conjugated to a non-NIR dye or non-targeted NIR dye. In some embodiments, the improvement is 10-fold. In some embodiments, the tumor-to-background signal ratio is at least a 4-fold improvement. In some embodiments, the tumor-to-background ratio is increased by at least 1.5-fold. In some embodiments, the CA IX-targeted NIR dye background signal is half the background signal of the CA IX-targeted compound conjugated to a fluorescent dye reactive to light less than 600 nm in wavelength. In some embodiments of the present invention, methods using the CA IX-targeted NIR dye on live cells produces a background signal less than half the background signal of the CA IX-targeted compound conjugated to a fluorescent dye reactive to light less than 600 nm in wavelength. In some embodiments of the present invention, methods using the CA IX-targeted NIR dye on live cells produces a background signal less than half the background signal of the CA IX-targeted compound conjugated to a fluorescent dye reactive to light less than 500 nm in wavelength. In some embodiments of the present invention, methods using the CA IX-targeted NIR dye on live cells produces a background signal less than one third of the background signal of the CA IX-targeted compound conjugated to a fluorescent dye reactive to light less than 600 nm in wavelength. In some embodiments of the present invention, methods using the CA IX-targeted NIR dye on live cells produces a background signal less than one third of the background signal of the CA IX-targeted compound conjugated to a fluorescent dye reactive to light less than 500 nm in wavelength. In some embodiments of the present invention, methods using the CA IX-targeted NIR dye on live cells produces a background signal less than one fourth the background signal of the CA IX-targeted compound conjugated to a fluorescent dye reactive to light less than 600 nm in wavelength. In some embodiments of the present invention, methods using the CA IX-targeted NIR dye on live cells produces a background signal less than one fourth the background signal of the CA IX-targeted compound conjugated to a fluorescent dye reactive to light less than 500 nm in wavelength. In some embodiments of the present invention, methods using the CA IX-targeted NIR dye on live cells produces a background signal less than one fifth the background signal of the CA IX-targeted compound conjugated to a fluorescent dye reactive to light less than 600 nm in wavelength. In some embodiments of the present invention, methods using the CA IX-targeted NIR dye on live cells produces a background signal less than one fifth the background signal of the CA IX-targeted compound conjugated to a fluorescent dye reactive to light less than 500 nm in wavelength. In some embodiments of the present invention, methods using the CA IX-targeted NIR dye on live cells produces a background signal less than one eighth the background signal of the CA IX-targeted compound conjugated to a fluorescent dye reactive to light less than 600 nm in wavelength. In some embodiments of the present invention, methods using the CA IX-targeted NIR dye on live cells produces a background signal less than one eighth the background signal of the CA Ix-targeted compound conjugated to a fluorescent dye reactive to light less than 500 nm in wavelength. In some embodiments of the present invention, methods using the CA IX-targeted NIR dye on live cells produces a background signal less than one tenth the background signal of the CA IX-targeted compound conjugated to a fluorescent dye reactive to light less than 600 nm in wavelength. In some embodiments of the present invention, methods using the CA IX-targeted NIR dye on live cells produces a background signal less than one tenth the background signal of the CA IX-targeted compound conjugated to a fluorescent dye reactive to light less than 500 nm in wavelength.

In some embodiments, the CA IX-targeting compound is a small molecule ligand that binds specifically CA IX. Such small molecule ligands may bind to the enzymatic site of PSMA in its native conformation. Also, such small molecule ligands may possess any one or more of the characteristics for CA IX antibody ligands.

This disclosure also provides methods for synthesizing amino acid linking groups that are conjugated to a PSMA-targeting compound used for the targeted imaging of CA IX-expressing cells, tissues, or tumors. In certain embodiments, this disclosure relates to a compound or a salt derivative thereof, that comprises a CA IX-targeting compound, a linking group, and an NIR dye. In certain embodiments, the linking group can be an amino acid, an isomer, a derivative, or a racemic mixture thereof. In some aspects, the dye is selected from the group consisting of LS288, IR800, SP054, S0121, KODAK, S2076, S0456 and/or the dyes selected from group consisting of:

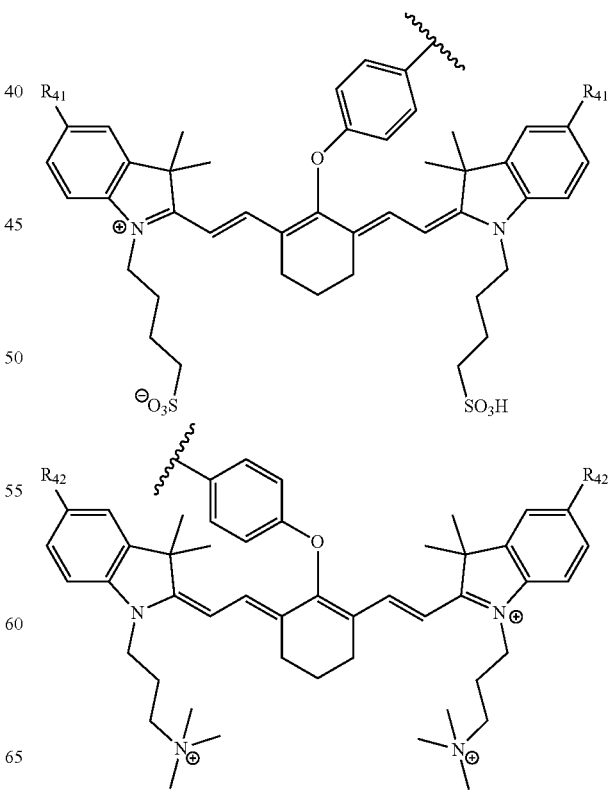

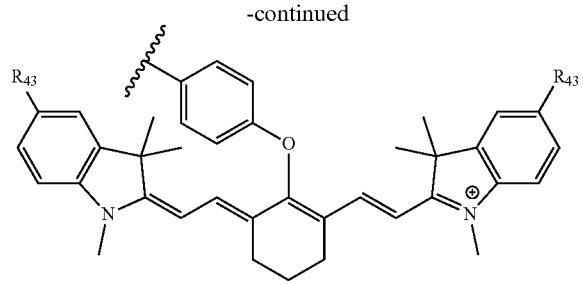

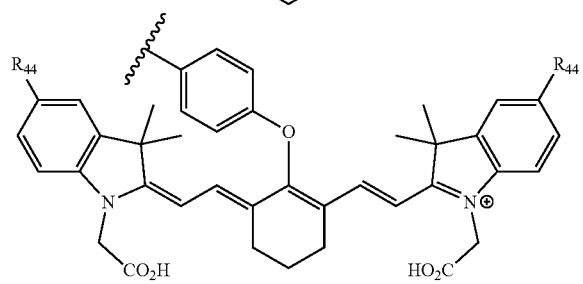

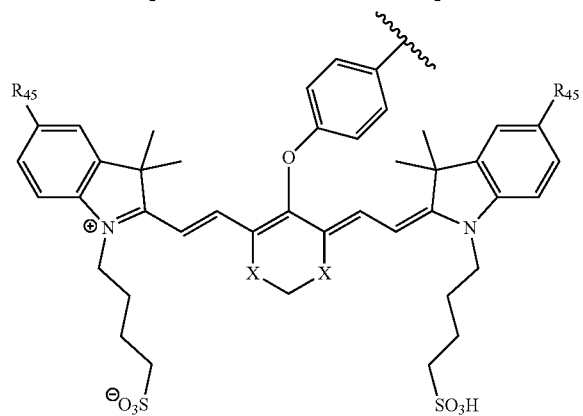

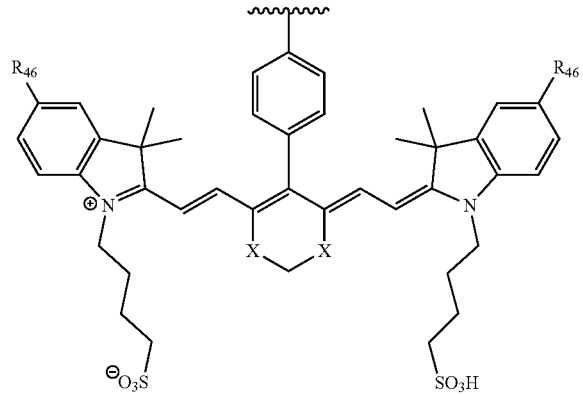

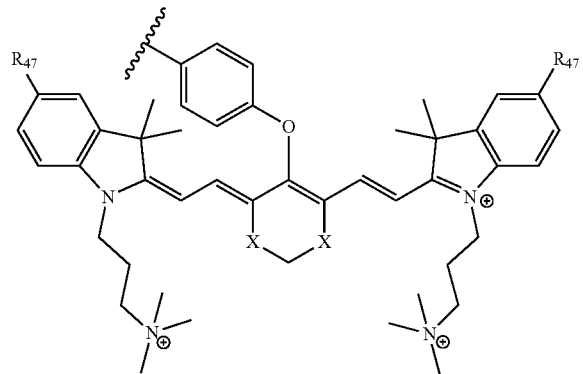

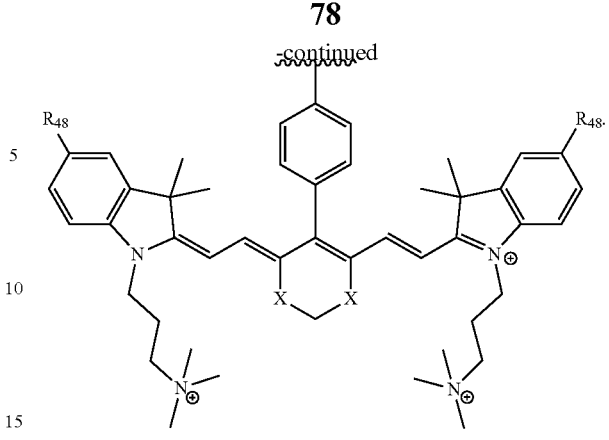

R41, R42, R43, R44, R45, R46, R47, R48 = H or SO₃H; X = O, S, N

In some aspects, this disclosure provides a method of conjugating an amino acid linking group to an NIR dye, wherein the amino acid can be tyrosine, serine, theronine, lysine, arginine, asparagine, glutamine, cysteine, selenocysteine, isomers, and the derivatives thereof. In certain embodiments, the amino acid, isomers, or the derivatives thereof, contain an —OH, —NH₂, or —SH functional group that upon addition of the fluorescent dye in slight molar excess produces the conjugation of fluorescent group with the amino acid, isomer, or the derivatives thereof. In other embodiments, the amino acid, isomers, or the derivatives thereof, contains an —OH functional group that upon synthesis generates an ether bond with the dye that increases the brightness and detection of the compound. In some embodiments, this disclosure relates to the conjugation of the amino acid linking group with the NIR dye, wherein the amino acid, isomers, or the derivatives thereof, contains an —SH, —SeH, —PoH, or —TeH functional group that upon synthesis generates a C—S, C—Se, C—Po, or C—Te bond with the dye. In some aspects, this disclosure relates to the conjugation of the amino acid linking group to a dye that has an absorption and emission maxima between about 500 nm and about 900 nm. In other aspects, the amino acid linking group is conjugated to a fluorescent dye that has an absorption and emission maxima between about 600 nm and about 800 nm.

In additional embodiments, this disclosure provides a method for conjugating the amino acid linking group to a CA IX ligand, wherein the amino acid linking group is tyrosine, serine, threonine, lysine, arginine, asparagine, glutamine, cysteine, selenocysteine, isomers or the derivatives thereof, and is conjugated to folate through a dipeptide bond. In additional aspects, this disclosure provides a method of conjugating the linking group with a folate ligand, wherein the linking group is tyrosine, serine, threonine, lysine, arginine, asparagine, glutamine, cysteine, selenocysteine, isomers, or the derivatives thereof. In other embodiments, this disclosure relates to a method of conjugating a pteroyl ligand to an amino acid linking group, wherein the linking group is tyrosine, serine, threonine, lysine, arginine, asparagine, glutamine, cysteine, selenocysteine, isomers or the derivatives thereof. In certain aspects, the carboxylic acid of the linking group is bound to the alpha carbon of any amino acid, hence increasing the specificity of the compound for targeted receptors. In some embodiments, the charge of the linker contributes specificity to the compound, wherein the observed binding affinity of the compound to targeted receptors is at least 15 nM.

In other embodiments, this disclosure relates to the use of a compound designated, Fluorinated aromatic sulfonate with an extended hydrophobic residue -SAHA-Tyr-S0456, wherein SAHA is six aminohexanoic acid, for image guided surgery, tumor imaging, prostate imaging, CA IX-expressing tissue imaging, CA IX-expressing tumor imaging, infection diseases, or forensic applications.

In some embodiments, the CA IX-targeted compound of the present invention is a small molecule ligand of CA IX.

The embodiments disclosed below are not intended to be exhaustive or limit the disclosure to the precise forms disclosed in the following detailed description. Rather, the embodiments are chosen and described so that others skilled in the art may utilize their teachings.

CA IC-Targeted NIR Dye Conjugates and their Synthesis

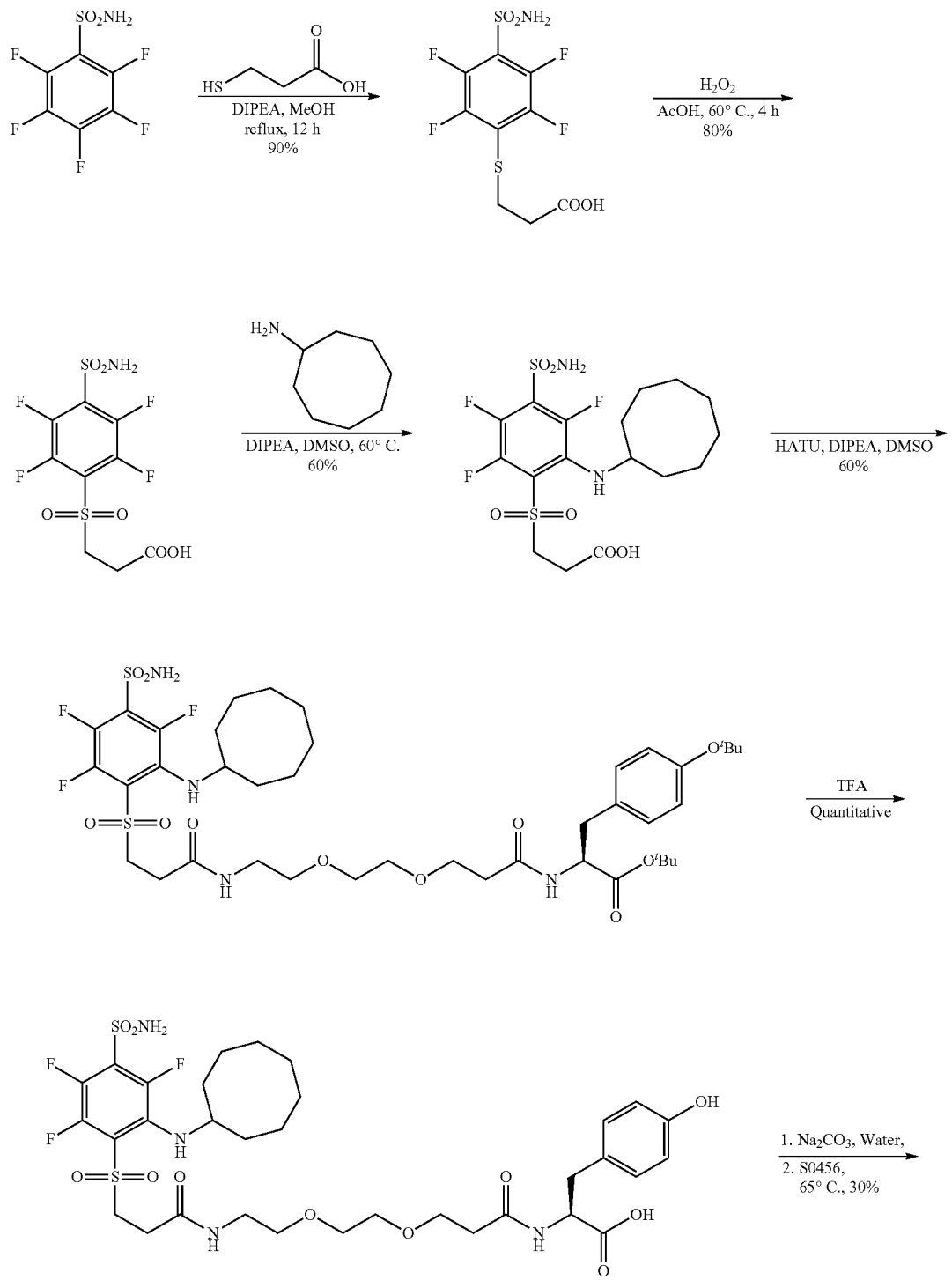

Scheme for the compound 61

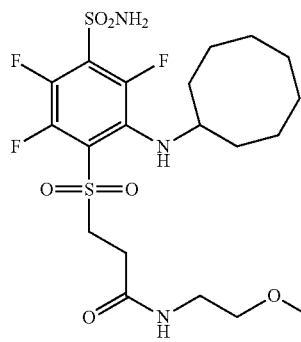
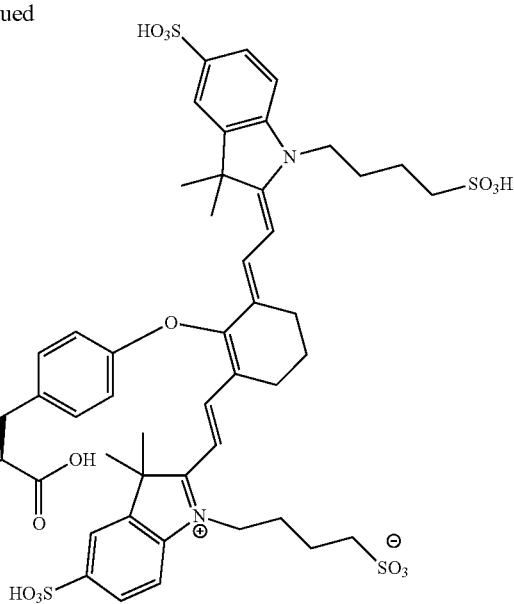

Experimental Procedures for the Compound 61

Synthesis of 3-((2,3,5,6-tetrafluoro-4-sulfamoylphenyl)thio)propanoic Acid

To a pentafluorobenzenesulfonamide (5.0 g, 20.23 mmol, 1.0 equiv) in MeOH (200 mL) was added DIPEA (4.2 mL, 24.24 mmol, 1.2 equiv), followed by 3-mercaptopropionic acid (2, 1.76 mL, 20.23 mmol, 1.0 equiv) under argon. The reaction mixture was refluxed for 6 h and reaction progress was monitored by thin layer chromatography. After completion of reaction, MeOH was evaporated using rotaevaporator and the resultant solid was filtered and washed with water and dried under lyophilization. The product was confirmed by LCMS and used for next step, yield, 90%.

Synthesis of 3-((2,3,5,6-tetrafluoro-4-sulfamoylphenyl)sulfonyl)propanoic Acid

To the 3-((2,3,5,6-tetrafluoro-4-sulfamoylphenyl)thio) propanoic acid (5.75 g, 17.25 mmol) in an acetic acid (34 mL) was added hydrogen peroxide (30% v/v, 15 mL) slowly at rt. The reaction mixture was stirred at 60° C. for 4 h. After completion of reaction confirmed by LCMS, reaction was quenched by addition of water. The reaction mixture was extracted with EtOAc (3×150 mL). The combined organics were washed with $H_2O$ (1×200 mL), brine (1×100 mL) and dried over anhy. $Na_2SO_4$ and concentrated. A white solid product was isolated in 80% yield and used for next step without further purification.

Synthesis of 3-((2-(cyclooctylamino)-3,5,6-trifluoro-4-sulfamoylphenyl)sulfonyl)propanoic Acid To a 3-((2,3,5,6-tetrafluoro-4-sulfamoylphenyl) sulfonyl) propanoic acid (1.0 g, 2.74 mmol, 1.0 equiv) in DMSO (5 mL), was added DIPEA (0.96 mL, 5.48 mmol, 2.0 equiv) followed by cyclooctylamine (0.413 mL, 3.01 mmol, 1.1 equiv) under argon. The reaction mixture was stirred at 60° C. for 6 h. The mixture was then diluted with $H_2O$ (30 mL) and extracted with EtOAc (3×50 mL). The combined organics were washed with brine (1×50 mL), dried over $Na_2SO_4$ and evaporated under reduced pressure. The crude mass was purified by silica-gel column chromatography using DCM:EtOAc. The desired product was isolated in 60% yield.

Synthesis of Meta-Substituted Ligands

The similar procedure as that of synthesis of 3-((2-(cyclooctylamino)-3,5,6-trifluoro-4-sulfamoylphenyl)sulfonyl)propanoic acid was used for the synthesis of the following ligands Compound 3: n=0, p=0, m=⅗
Compound 7: n=2, p=0, m=0
Compound 17: m=0
Compound 18: m=0
Compound 29: n=0, p=0
Compound 30: n=1, p=0
Compound 32: n=2, p=0

Also, Compound 25 (n=0, p=0, m=5) was prepared from 3-((2-fluoro-4-sulfamoylphenyl)sulfonyl)propanoic acid using similar procedure as that of synthesis of 3-((2-(cyclooctylamino)-3,5,6-trifluoro-4-sulfamoylphenyl)sulfonyl) propanoic acid Synthesis of tert-butyl (S)-2-(4-(tert-butoxy)benzyl)-16-((2-(cyclooctylamino)-3,5,6-trifluoro-4-sulfamoylphenyl) sulfonyl)-4,14-dioxo-7,10-dioxa-3,13-diazahexadecanoate:

A 50-mL round bottom flask was charged with a stirring bar, 3-((2-(cyclooctylamino)-3,5,6-trifluoro-4-sulfamoylphenyl) sulfonyl)propanoic acid (60 mg, 0.126 mmol, 1 equiv), tert-butyl (S)-2-(3-(2-(2-aminoethoxy)ethoxy)propanamido)-3-(4-(tert-butoxy)phenyl)propanoate (63.2 mg, 0.139 mmol, 1.1 equiv) and HATU (48.28 mg, 0.139 mmol, 1.1 equiv) then DMSO (1.3 mL) was added to give a clear solution. DIPEA (88 µL, 0.508 mmol, 4.0 equiv) was added slowly to the reaction mixture at 23° C. The reaction was stirred at 23° C. for 1.5 h and progress of the reaction was monitored by LC/MS. The reaction mixture was quenched by adding water (3 mL) dropwise and extracted with EtOAc (3×10 mL). The combined organics were washed with brine (10 mL), and dried over anhyd. $Na_2SO_4$ and concentrated. The crude mass was purified by silica-gel column chromatography using DCM-EtOAc to yield desired compound, 92 mg, 80% yield.

Synthesis of (3-(2-(2-(3-((2-(cyclooctylamino)-3,5,6-trifluoro-4-sulfamoylphenyl)sulfonyl) propanamido)ethoxy)ethoxy)propanoyl)-L-tyrosine A 5 mL round bottom flask was charged with a stirring bar and compound tert-butyl (S)-2-(4-(tert-butoxy)benzyl)-16-((2-(cyclooctylamino)-3,5,6-trifluoro-4-sulfamoylphenyl)sulfonyl)-4,14-dioxo-7,10-dioxa-3,13-diazahexadecanoate (52 mg, 0.057 mmol) and trifluoroacetic acid (TFA, 1 mL) was added to the reaction flask at rt. The reaction mixture was stirred at rt for 1 h and the progress of the reaction was monitored by LC/MS. The solvent was evaporated under vacuum (rotavapor) and the concentrated reaction mixture was added drop wise to stirred cold ether (5 mL) to give white precipitate which was centrifuged, washed with cold ether (2×5 mL), and dried under high vacuum to afford desired product as a white solid in quantitative yield.

Linker-Ligand Coupling

Various modified linkers were coupled to the CA-IX ligand using similar protocol as that of the synthesis of (3-(2-(2-(3-((2-(cyclooctylamino)-3,5,6-trifluoro-4-sulfamoylphenyl)sulfonyl) propanamido)ethoxy)ethoxy)propanoyl)-L-tyrosine as listed below Compound 39: n=0, m=5, p=0
Compound 40: n=0, m=5, p=0
Compound 41: n=0, m=5, p=0
Compound 42: n=0, m=5, p=0
Compound 43: n=0, m=5, p=0
Compound 44: n=0, m=5, p=0

Synthesis of 4-(2-((E)-2-((E)-2-(4-((S)-2-carboxy-16-((2-(cyclooctylamino)-3,5,6-trifluoro-4-sulfamoylphenyl)sulfonyl)-4,14-dioxo-7,10-dioxa-3,13-diazahexadecyl)phenoxy)-3-(2-((E)-3,3-dimethyl-5-sulfo-1-(4-sulfobutyl)indolin-2-ylidene)ethylidene)cyclohex-1-en-1-yl)vinyl)-3,3-dimethyl-5-sulfo-3H-indol-1-ium-1-yl)butane-1-sulfonate A 5-mL round bottom flask was charged with a stirring bar and Compound (3-(2-(2-(3-((2-(cyclooctylamino)-3,5,6-trifluoro-4-sulfamoylphenyl)sulfonyl)propanamido)ethoxy)ethoxy)propanoyl)-L-tyrosine (11 mg, 0.014 mmol, 1 equiv) and it was then dissolved in THF: water (1:2 ratio, 0.4 mL). The pH of the reaction mixture was adjusted to ~9.5-10 (utilizing wet pH paper) by using a solution of aqueous 1M $Na_2CO_3$ at room temperature. Then S0456 (13.2 mg, 0.014 mmol, 1 equiv) was added to give opaque green solution and stirred at 60° C. for 4 hours. The reaction progress was monitored by HRMS and usually reaction was completed in 4 hours. The reaction mixture was cooled to room temperature and purified by RP-HPLC. Pure fractions from the HPLC were combined, evaporated solvent and freeze samples are lyophilized to obtain desired product (8 mg) as a green solid.

Synthesis of CA-IX Dye Conjugates:

The similar procedure as that of synthesis of 4-(2-((E)-2-((E)-2-(4-((S)-2-carboxy-16-((2-(cyclooctylamino)-3,5,6-trifluoro-4-sulfamoylphenyl)sulfonyl)-4,14-dioxo-7,10-dioxa-3,13-diazahexadecyl)phenoxy)-3-(2-((E)-3,3-dimethyl-5-sulfo-1-(4-sulfobutyl)indolin-2-ylidene)ethylidene)cyclohex-1-en-1-yl)vinyl)-3,3-dimethyl-5-sulfo-3H-indol-1-ium-1-yl)butane-1-sulfonate was used for the preparation of all other CA-IX-dye conjugates.

Synthesis of $NH_2$-$PEG_2$-Tyr($^tBu$)- Linker

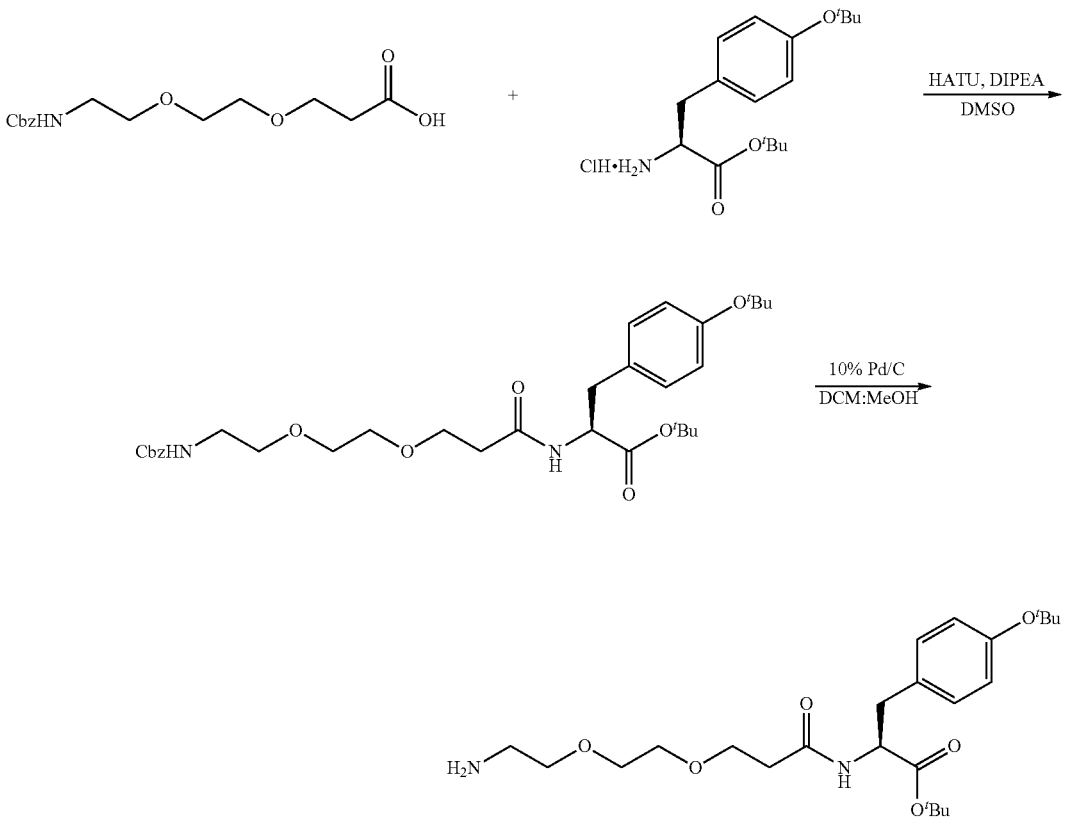

Synthesis of tert-butyl (S)-15-(4-(tert-butoxy)benzyl)-3,13-dioxo-1-phenyl-2,7,10-trioxa-4,14-diazahexadecan-16-oate A 50-mL round bottom flask was charged with a stirring bar, 12 (5.0 g, 16.05 mmol, 1 equiv), (L)-H-Tyr(-O'Bu)-O'Bu HCl (5.3 g, 16.05 mmol, 1.0 equiv) and HATU (6.41 g, 16.85 mmol, 1.05 equiv) then DMSO (29 mL) was added to give a clear solution. DIPEA (7.01 mL, 40.13 mmol, 2.5 equiv) was added slowly to the reaction mixture at 23° C., over 5 minutes. The reaction was stirred at 23° C. for 1.5 h and progress of the reaction was monitored by LC/MS. The reaction mixture was quenched by adding water (100 mL) dropwise and extracted with EtOAc (3×150 mL). The combined organics were washed with brine (100 mL), and dried over anhyd. Na$_2$SO$_4$ and filtered and concentrated. The crude mass was purified by silica-gel column chromatography using n-hexane-EtOAc to isolate desired compound in 95% yield.

Synthesis of Compound tert-butyl (S)-2-(3-(2-(2-aminoethoxy)ethoxy)propanamido)-3-(4-(tert-butoxy)phenyl)propanoate A 50 mL rb flask was charged with a stir bar, CbzNH-PEG$_2$-Tyr-(O'Bu)-O'Bu (1.10 g, 1.87 mmol), and DCM (10 mL). After dissolving the reaction mixture, Pd/C (10% Pd basis, 10% wt/wt, 110 mg) was added in portions to the rb flask followed by anhy. MeOH (10 mL). The reaction mixture was degassed (3×) and H$_2$ gas was bubbled through the reaction mixture for 3 h under stirring at room temperature. The reaction mixture was filtered through a Celite plug, washed with MeOH, and the filtrate was concentrated under vacuum to afford crude desired product (92%) which was analyzed by LC/MS and used for the next step without further purification.

Scheme for synthesis of 2,3,5,6-tetrafluoro-4-((2-hydroxyethyl)sulfonyl)benzenesulfonamide Synthesis of 2,3,5,6-tetrafluoro-4-((2-hydroxyethyl)sulfonyl)benzenesulfonamide To a pentafluorobenzenesulfonamide (2.0 g, 8.098 mmol, 1.0 equiv) in MeOH (81 mL) was added DIPEA (1.55 mL, 8.908 mmol, 1.1 equiv), followed by 2-mercaptoethane-1-ol (0.63 mL, 8.908 mmol, 1.1 equiv) under argon. The reaction mixture was refluxed for 16 h and reaction progress was monitored by thin layer chromatography. After completion of reaction, MeOH was evaporated using rotaevaporator and the resultant solid was filtered and washed with water and dried under lyophilization. The solid compound isolated (1.59 g, yield, 95%) was confirmed by LCMS and used for next step.

Oxidation of Sulfide to Sulfone:

To the alcohol compound (1.50 g, 4.913 mmol, 1.0 equiv) in an MeOH: H$_2$O (1:1, 50 mL) was added oxone (3.02 g, 9.826 mmol, 2.0 equiv) slowly at rt. The reaction mixture was stirred at 55° C. for 16 h. After completion of reaction confirmed by LCMS, reaction was filtered and was extracted with EtOAc (3×150 mL). The combined organics were washed with H$_2$O (1×100 mL), brine (1×100 mL) and dried over anhy. Na$_2$SO$_4$ and concentrated. A white solid compound isolated (1.65 g, quantitative yield), was used for next step without further purification.

The similar procedure as that of synthesis of 3-((3-(benzylamino)-2,5,6-trifluoro-4-sulfamoylphenyl)thio)propanoic acid was used to synthesize following ligands starting from 2,3,5,6-tetrafluoro-4-((2-hydroxyethyl)sulfonyl)benzenesulfonamide Compound 21: m=0
Compound 22: m=0

Synthesis of 3-((3-(benzylamino)-2,5,6-trifluoro-4-sulfamoylphenyl)thio)propanoic Acid

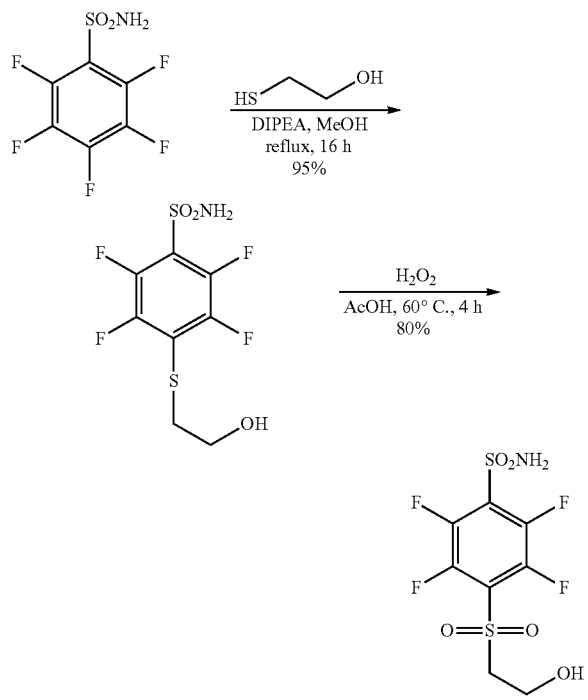

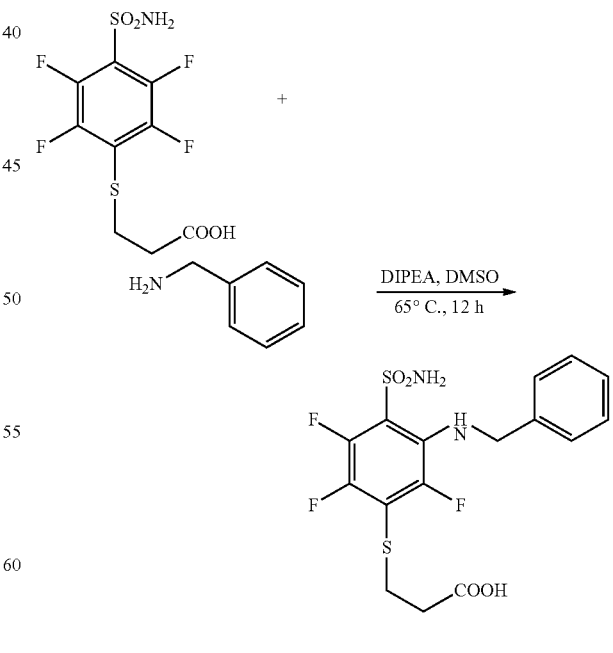

To a 3-((2,3,5,6-tetrafluoro-4-sulfamoylphenyl) thio) propanoic acid (50 mg, 0.15 mmol, 1.0 equiv) in DMSO (0.3 mL), was added DIPEA (53 µL, 0.3 mmol, 2.0 equiv) followed by benzylamine (16 µL, 0.15 mmol, 1.0 equiv)

under argon. The reaction mixture was stirred at 65° C. for 12 h. The mixture was then diluted with H₂O (2 mL) and extracted with EtOAc (3×10 mL). The combined organics were washed with brine (1×10 mL), dried over Na₂SO₄ and evaporated under reduced pressure. The crude mass was purified by silica-gel column chromatography using DCM: EtOAc. The desired amine coupling product was isolated (15 mg) in 24% yield.

Synthesis of Ortho Substituted Ligands

The similar procedure as that of synthesis of 3-((3-(benzylamino)-2,5,6-trifluoro-4-sulfamoylphenyl)thio)propanoic acid was used for the synthesis of following ligands Compound 1: n=0, p=0, m=⅗
Compound 34: n=2, p=0
Compound 36: n=2, p=0
Compound 36b: n=0, p=0

Scheme for 8-amino octanoic Acid_tyr(O$^t$Bu)-O$^t$Bu) Linker

O$^t$Bu)-O$^t$Bu HCl (100 mg, 0.303 mmol, 1.0 equiv) and HATU (138 mg, 0.364 mmol, 1.2 equiv) then DMSO (0.6 mL) was added to give a clear solution. DIPEA (133 µL, 0.756 mmol, 2.5 equiv) was added slowly to the reaction mixture at 23° C. The reaction was stirred at 23° C. for 1.5 h and progress of the reaction was monitored by LC/MS. The reaction mixture was quenched by adding water (3 mL) dropwise and extracted with EtOAc (3×5 mL). The combined organics were washed with brine (5 mL), and dried over anhyd. Na₂SO₄ and filtered and concentrated. The crude mass was purified by silica-gel column chromatography using n-hexane-EtOAc and product was isolated in 96% yield.

Synthesis of 8-amino octanoic Acid_tyr(O$^t$Bu)-O$^t$Bu

A 5 mL round bottom flask was charged with a stirring bar and Fmoc-8-amino octanoic acid_tyr(O$^t$Bu)-O$^t$Bu (200 mg,

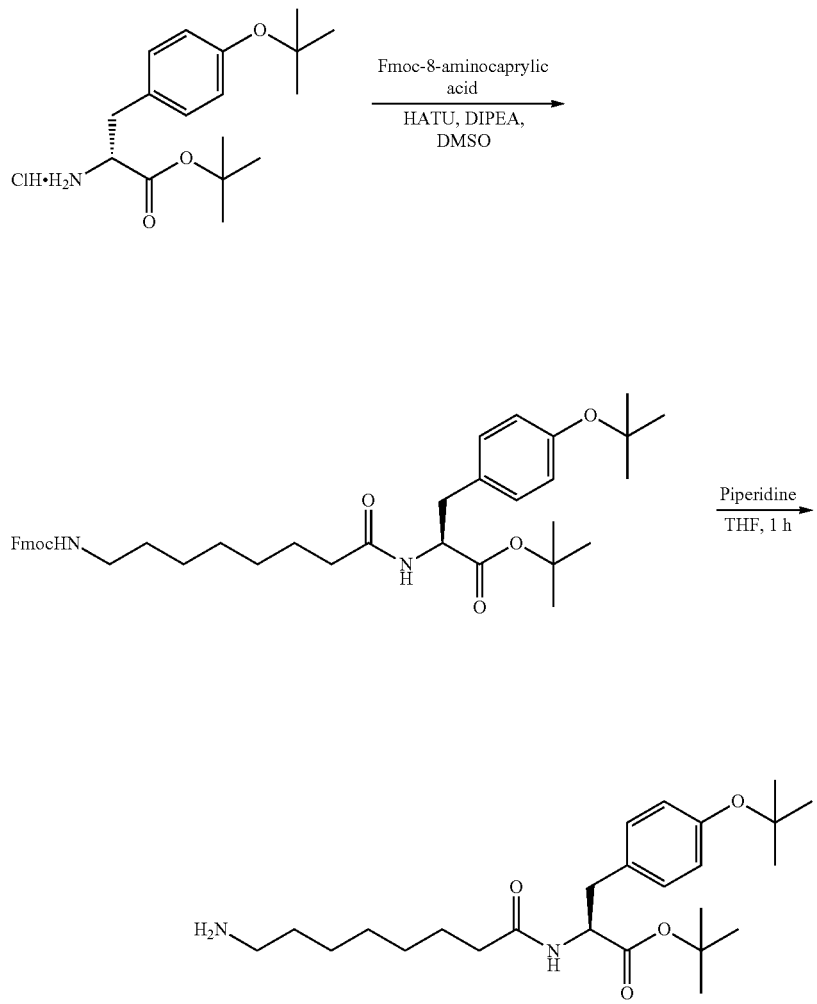

Synthesis of Fmoc-8-amino octanoic acid_tyr(O$^t$Bu)-O$^t$Bu

A 5-mL round bottom flask was charged with a stirring bar, 8-((((9H-fluoren-9-yl)methoxy)carbonyl)amino)octanoic acid (116 mg, 0.303 mmol, 1 equiv), (L)-H-Tyr(-

0.303 mmol) in tetrahydrofuran (THF, 2 mL) and piperidine (0.2 mL) was added to the reaction flask at rt. The reaction mixture was stirred at rt for 1 h and the progress of the reaction was monitored by LC/MS. The solvent was evaporated under vacuum (rotavapor) and the crude product was dried under high vacuum to afford 8-amino octanoic acid_tyr(O$^t$Bu)-O$^t$Bu as a white solid, 96% yield.

Scheme for synthesis of H-Leu_PEG$_2$_Tyr(O$^t$Bu)-O$^t$Bu Linker

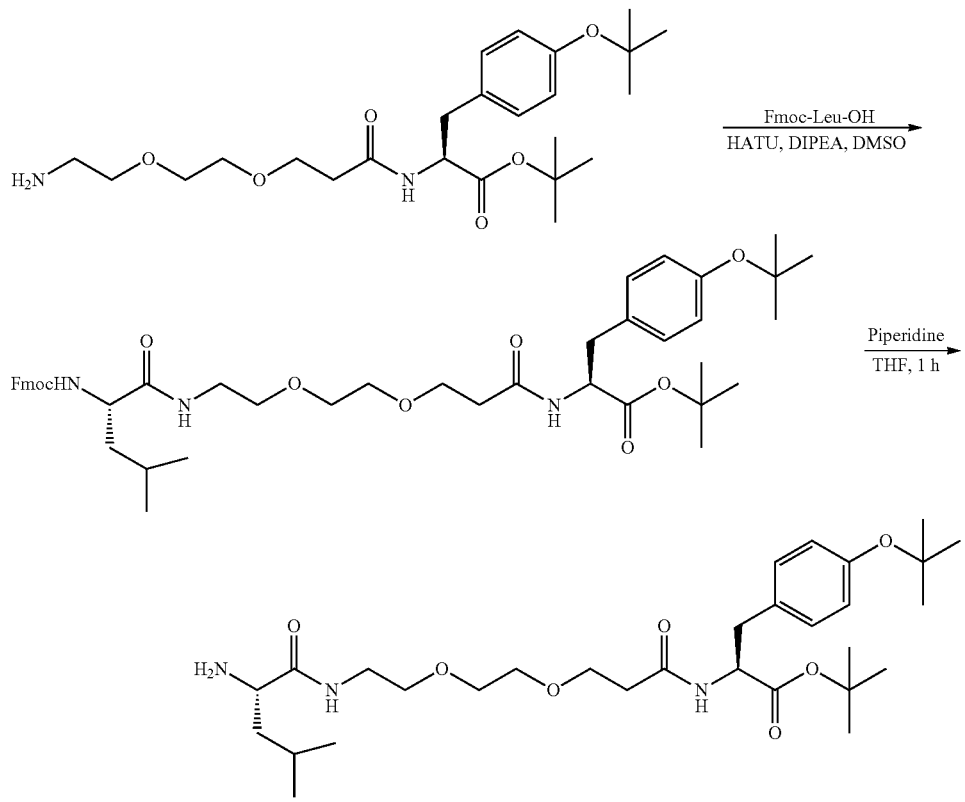

Synthesis of Fmoc-Leu_PEG$_2$_tyr(O$^t$Bu)-O$^t$Bu: A 5-mL round bottom flask was charged with a stirring bar, Fmoc-Leu-OH (16 mg, 0.044 mmol, 1 equiv), H$_2$N-PEG$_2$-Tyr(-O$^t$Bu)-O$^t$Bu (20 mg, 0.044 mmol, 1.0 equiv) and HATU (20 mg, 0.053 mmol, 1.2 equiv) then DMSO (0.15 mL) was added to give a clear solution. DIPEA (20 µL, 0.11 mmol, 2.5 equiv) was added slowly to the reaction mixture at 23° C. The reaction was stirred at 23° C. for 1.5 h and progress of the reaction was monitored by LC/MS. The reaction mixture was quenched by adding water (3 mL) dropwise and extracted with EtOAc (3×10 mL). The combined organics were washed with brine (5 mL), and dried over anhyd. Na$_2$SO$_4$ and filtered and concentrated. The crude mass was purified by silica-gel column chromatography using n-hexane-EtOAc and product was isolated, 32 mg, in 93% yield.

Synthesis of H-Leu_PEG$_2$_tyr(O$^t$Bu)-O$^t$Bu

A 5 mL round bottom flask was charged with a stirring bar and Fmoc-Leu_PEG$_2$_tyr(O$^t$Bu)-O$^t$Bu (32 mg, 0.041 mmol) in tetrahydrofuran (THF, 1 mL) and piperidine (0.2 mL) was added to the reaction flask at rt. The reaction mixture was stirred at rt for 1 h and the progress of the reaction was monitored by LC/MS. The solvent was evaporated under vacuum (rotavapor) and the crude product was dried under high vacuum to afford H-Leu_PEG$_2$_tyr(O$^t$Bu)-O$^t$Bu as a white solid, in quantitative yield.

Similar peptide bond forming coupling reaction followed by Fmoc-deprotection protocol was used for the preparation of various modified linkers.

EXAMPLES

Figure 2C:
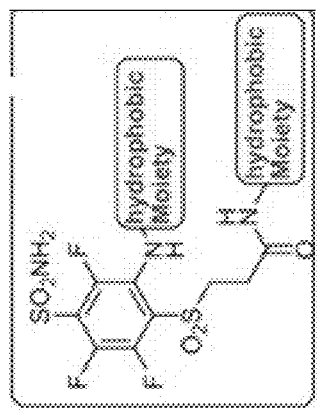
FIG. 2C shows general formula of newly designed CA IX ligand.
Figure 2B:
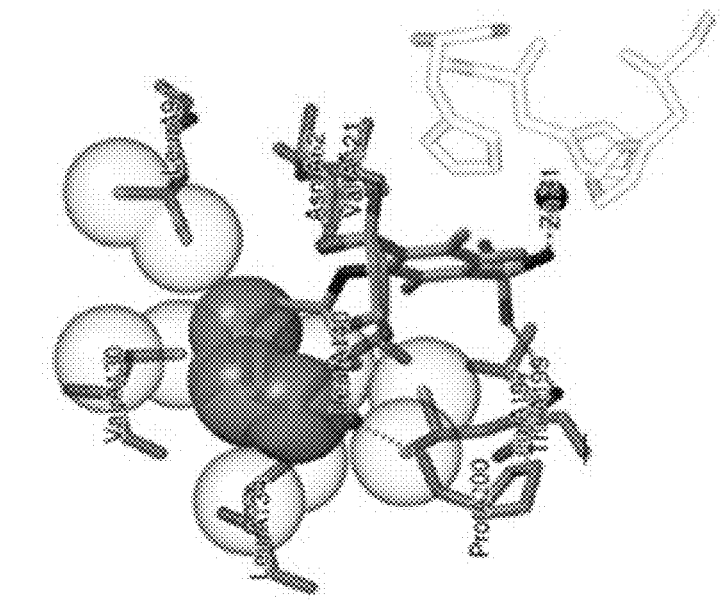
FIG. 2B shows CA IX ligand bound to CA IX protein as determined by crystal structure.
Figure 2A:
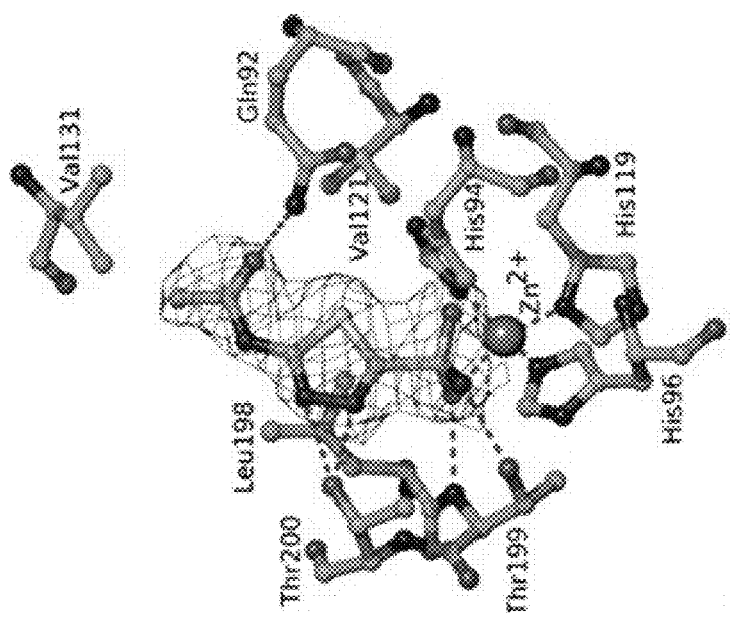
FIG. 2A shows (a) Stereoview of active site of human CA IX protein with in complex with azetazolamide.

Example: (1) Synthesis and Preclinical Evaluation of CA IX Ligands with Extended Binding Residue (FIG. 1-2)

Synthesis of Novel CA IX Ligands

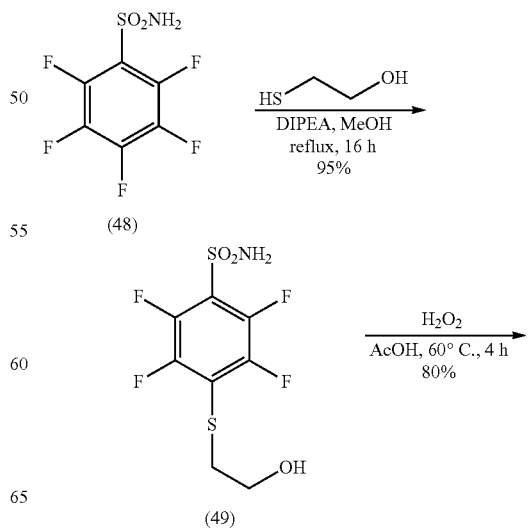

-continued

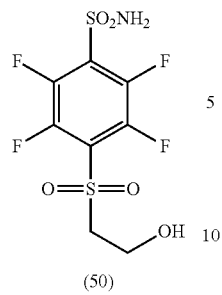

(50)

Scheme 1 Shows the Synthesis of 2,3,5,6-tetrafluoro-4-((2-hydroxyethyl)sulfonyl)benzenesulfonamide To a pentafluorobenzenesulfonamide (2.0 g, 8.098 mmol, 1.0 equiv) in MeOH (81 mL) was added DIPEA (1.55 mL, 8.908 mmol, 1.1 equiv), followed by 2-mercaptoethane-1-ol (0.63 mL, 8.908 mmol, 1.1 equiv) under argon. The reaction mixture was refluxed for 16 h and reaction progress was monitored by thin layer chromatography. After completion of reaction, MeOH was evaporated using rotaevaporator and the resultant solid was filtered and washed with water and dried under lyophilization. The solid compound isolated (1.59 g, yield, 95%) was confirmed by LCMS and used for next step.

Oxidation of sulfide to sulfone: To the alcohol compound (1.50 g, 4.913 mmol, 1.0 equiv) in an MeOH: $H_2O$ (1:1, 50 mL) was added oxone (3.02 g, 9.826 mmol, 2.0 equiv) slowly at rt. The reaction mixture was stirred at 55° C. for 16 h. After completion of reaction confirmed by LCMS, reaction was filtered and was extracted with EtOAc (3×150 mL). The combined organics were washed with $H_2O$ (1×100 mL), brine (1×100 mL) and dried over anhy. Na2SO4 and concentrated. A white solid compound isolated (1.65 g, quantitative yield), was used for next step without further purification.

The similar procedure as that of synthesis of 3-((3-(benzylamino)-2,5,6-trifluoro-4-sulfamoylphenyl)thio)propanoic acid was used to synthesize following ligands starting from 2,3,5,6-tetrafluoro-4-((2-hydroxyethyl)sulfonyl)benzenesulfonamide Compound 21: m=0; Compound 22: m=0

Synthesis of 3-((3-(benzylamino)-2,5,6-trifluoro-4-sulfamoylphenyl)thio)propanoic Acid

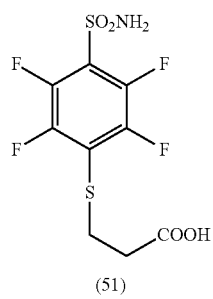

(51)

+

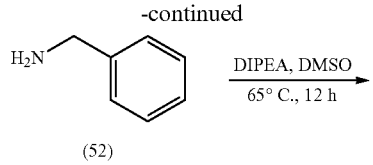

(52)

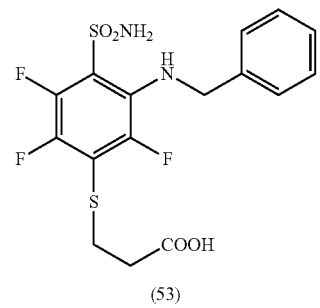

(53)

Scheme 2 shows the Synthesis of Synthesis of 3-((3-(benzylamino)-2,5,6-trifluoro-4-sulfamoylphenyl)thio)propanoic Acid To a 3-((2,3,5,6-tetrafluoro-4-sulfamoylphenyl) thio) propanoic acid (50 mg, 0.15 mmol, 1.0 equiv) in DMSO (0.3 mL), was added DIPEA (53 µL, 0.3 mmol, 2.0 equiv) followed by benzylamine (16 µL, 0.15 mmol, 1.0 equiv) under argon. The reaction mixture was stirred at 65° C. for 12 h. The mixture was then diluted with $H_2O$ (2 mL) and extracted with EtOAc (3×10 mL). The combined organics were washed with brine (1×10 mL), dried over Na2SO4 and evaporated under reduced pressure. The crude mass was purified by silica-gel column chromatography using DCM: EtOAc. The desired amine coupling product was isolated (15 mg) in 24% yield.

Synthesis of Ortho Substituted Ligands

The similar procedure as that of synthesis of 3-((3-(benzylamino)-2,5,6-trifluoro-4-sulfamoylphenyl)thio)propanoic acid was used for the synthesis of following ligands Compound 1: n=0, p=0, m=3/5; Compound 34: n=2, p=0; Compound 36: n=2, p=0; Compound 36b: n=0, p=0

Figure 3:
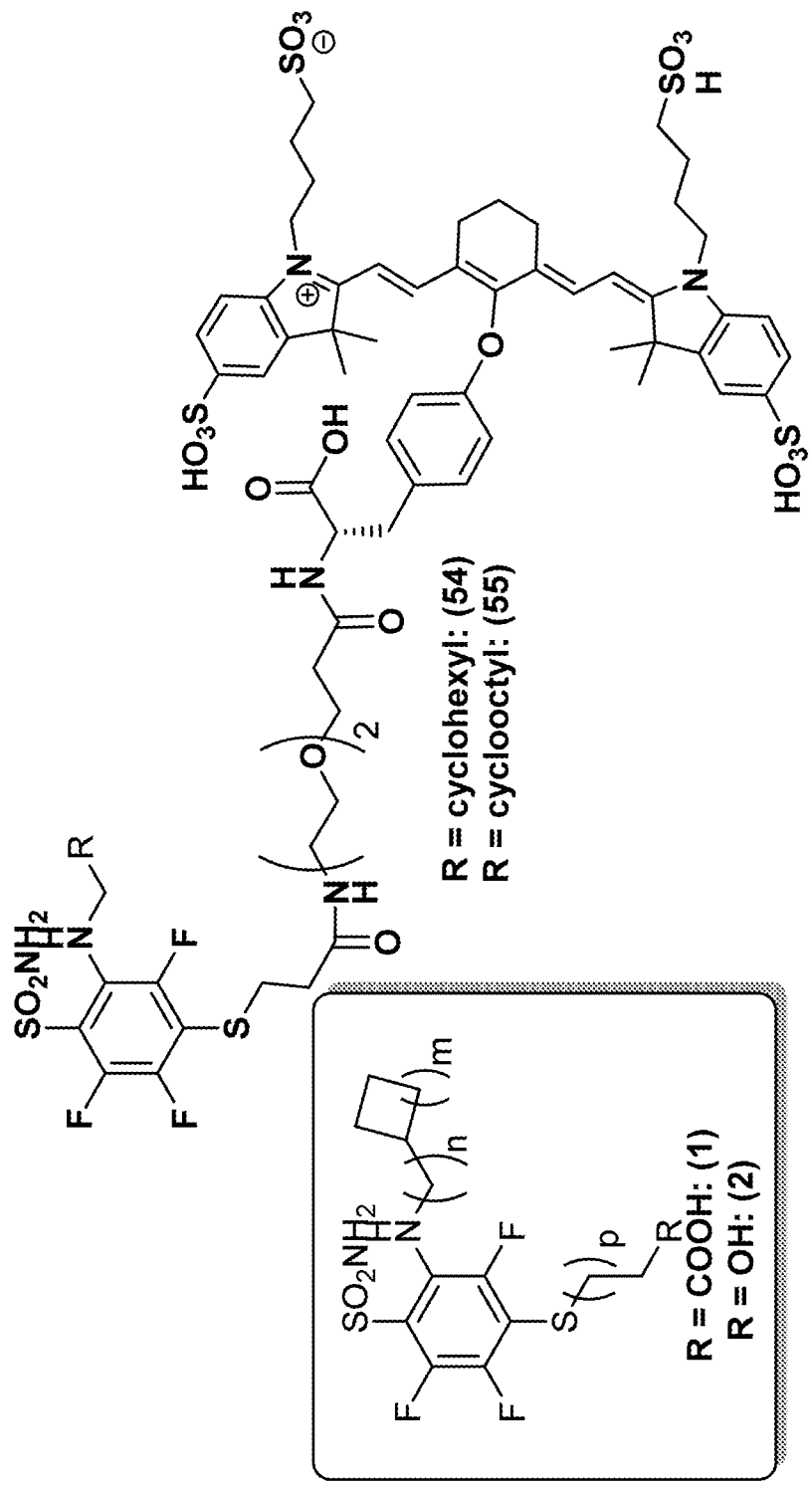
FIG. 3 shows the chemical structures of CA IX-Targeted NIR agents derived from the Ligands 1 & 2.

Example: (2) Preclinical Evaluation of Novel CA IX-Targeted NIR Agents Derived from the Ligands 1 & 2 (FIG. 3)

Synthesis

Synthesis of NH2-PEG2-Tyr($^t$Bu)- Linker

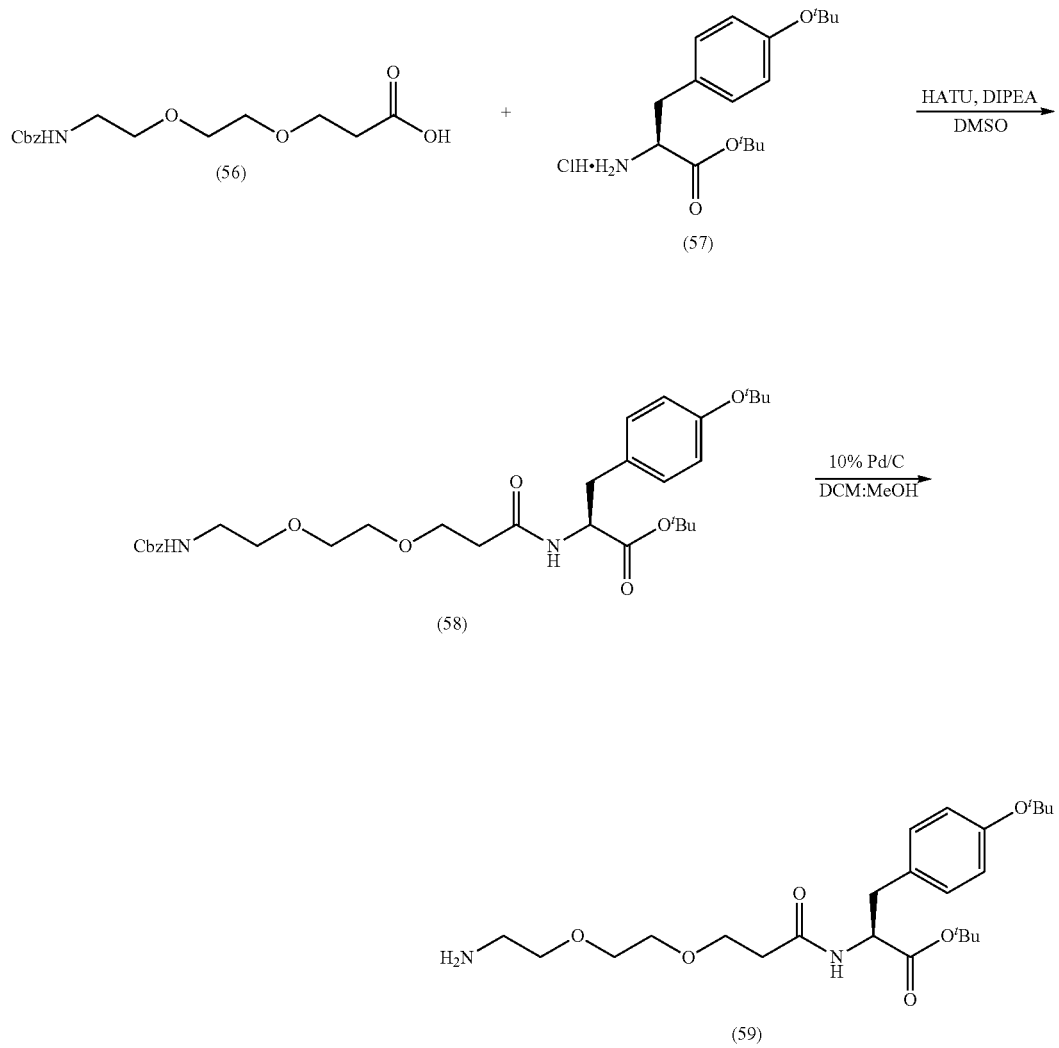

Synthesis of tert-butyl (S)-15-(4-(tert-butoxy)benzyl)-3,13-dioxo-1-phenyl-2,7,10-trioxa-4,14-diazahexadecan-16-oate: A 50-mL round bottom flask was charged with a stirring bar, 12 (5.0 g, 16.05 mmol, 1 equiv), (L)-H-Tyr(-O$^t$Bu)-O$^t$Bu.HCl (5.3 g, 16.05 mmol, 1.0 equiv) and HATU (6.41 g, 16.85 mmol, 1.05 equiv) then DMSO (29 mL) was added to give a clear solution. DIPEA (7.01 mL, 40.13 mmol, 2.5 equiv) was added slowly to the reaction mixture at 23° C., over 5 minutes. The reaction was stirred at 23° C. for 1.5 h and progress of the reaction was monitored by LC/MS. The reaction mixture was quenched by adding water (100 mL) dropwise and extracted with EtOAc (3×150 mL). The combined organics were washed with brine (100 mL), and dried over anhyd. Na2SO4 and filtered and concentrated. The crude mass was purified by silica-gel column chromatography using n-hexane-EtOAc to isolate desired compound in 95% yield.

Synthesis of Compound tert-butyl (S)-2-(3-(2-(2-aminoethoxy)ethoxy)propanamido)-3-(4-(tert-butoxy)phenyl)propanoate: A 50 mL rb flask was charged with a stir bar, CbzNH-PEG2-Tyr-(O$^t$Bu)-O$^t$Bu (1.10 g, 1.87 mmol), and DCM (10 mL). After dissolving the reaction mixture, Pd/C (10% Pd basis, 10% wt/wt, 110 mg) was added in portions to the rb flask followed by anhy. MeOH (10 mL). The reaction mixture was degassed (3×) and H2 gas was bubbled through the reaction mixture for 3 h under stirring at room temperature. The reaction mixture was filtered through a Celite plug, washed with MeOH, and the filtrate was concentrated under vacuum to afford crude desired product (92%) which was analyzed by LC/MS and used for the next step without further purification.

Figure 4:
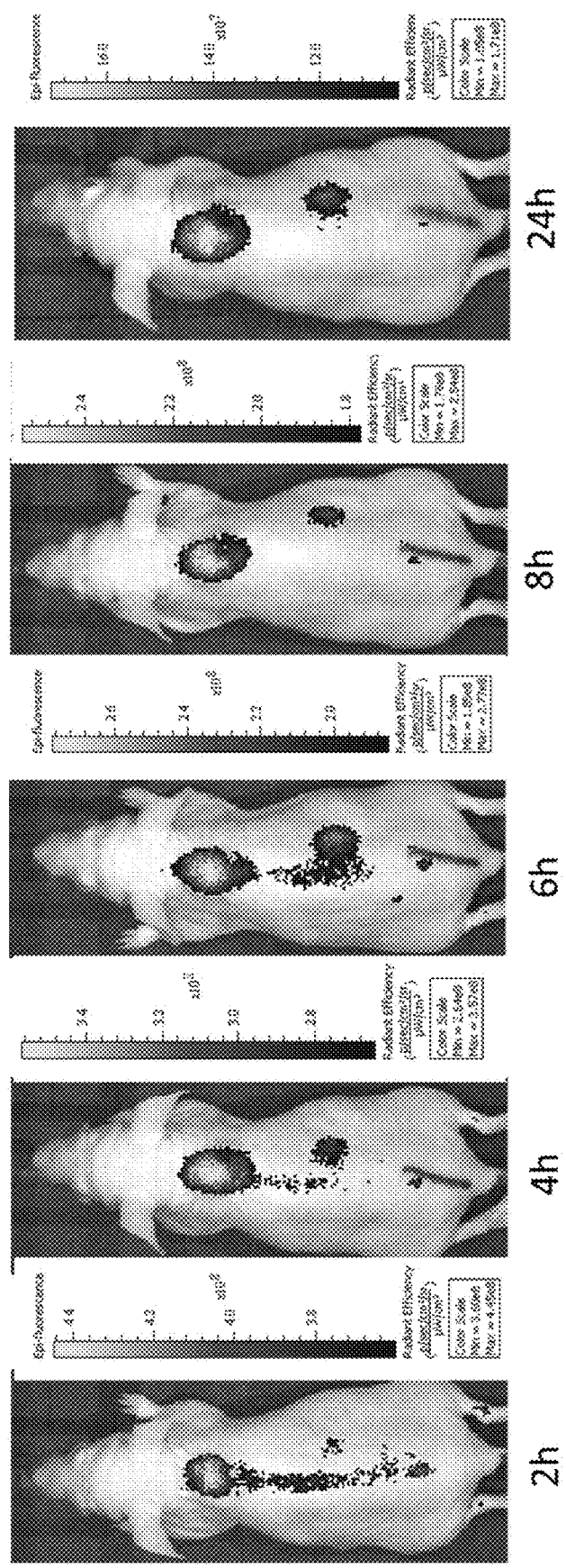
FIG. 4 shows an overlay of whole body fluorescence image over white light images after adjusting the threshold. SKRC52 human renal tumor xenograft bearing mouse was injected with 10 nmol of 54 and imaged with IVIS imager (ex=745 nm, em=ICG, exposure time=1 s) at different time intervals.
Figure 5:
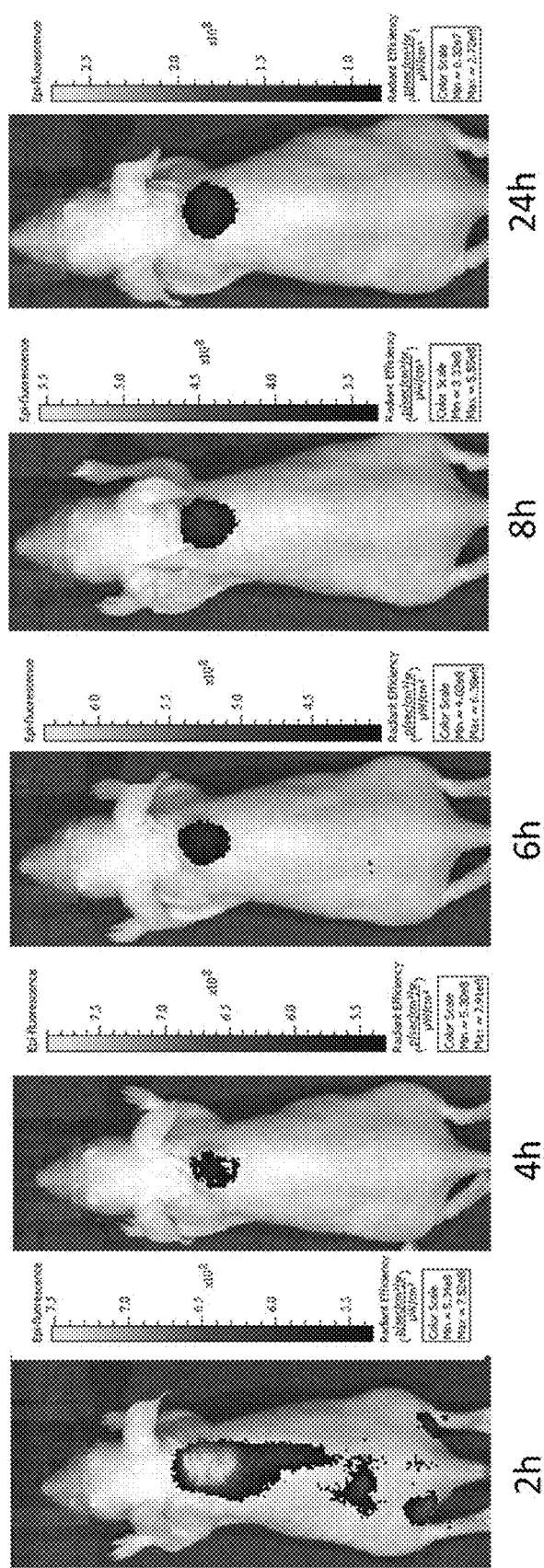
FIG. 5 shows an overlay of whole body fluorescence image over white light images after adjusting the threshold. SKRC52 human renal tumor xenograft bearing mouse was injected with 10 nmol of 55 and imaged with IVIS imager (ex=745 nm, em=ICG, exposure time=1 s) at different time intervals.

Conclusion: These in vivo studies demonstrate that compounds 54 and 55 accumulated and retained in the human renal cancer xenografts. (FIGS. 4 & 5)

Figure 6:
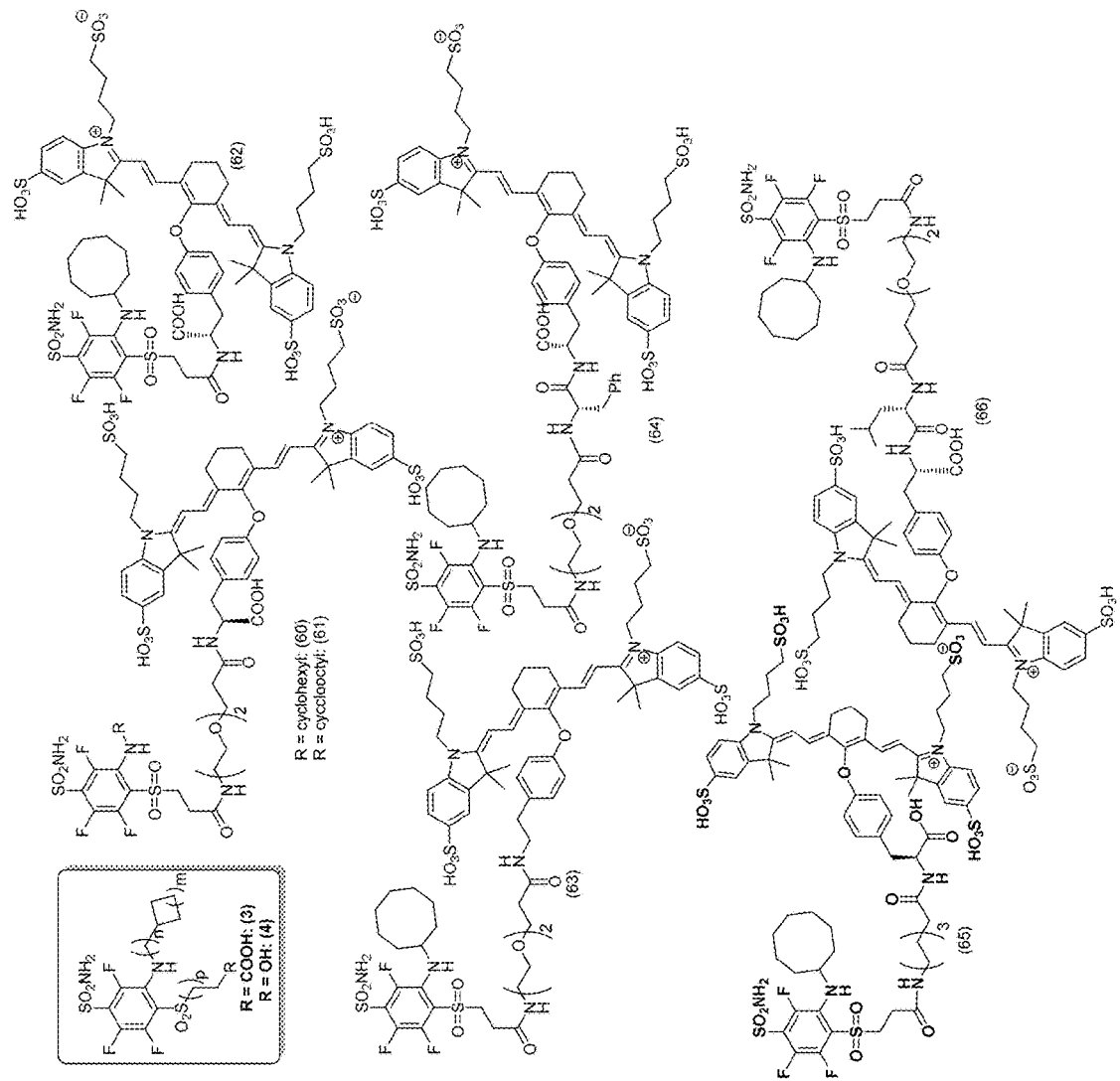
FIG. 6 shows the chemical structure of CA IX-Targeted NIR agents derived from the Ligands 3 & 4.

Example: (3) Preclinical Evaluation of Novel CA IX-Targeted NIR Agents Derived from the Ligands 3 & 4 (FIG. 6)
SYNTHESIS
Synthesis Scheme for the Compound 61:
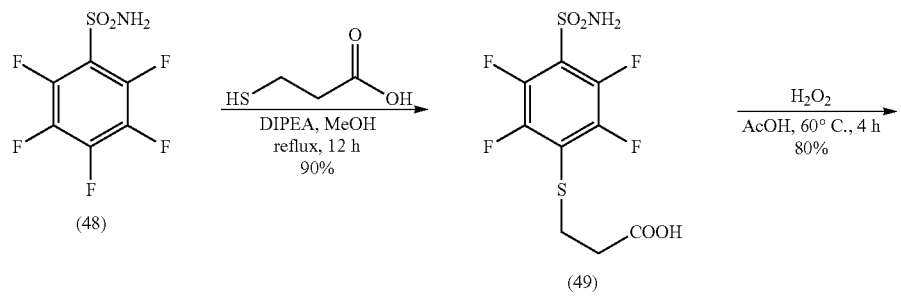
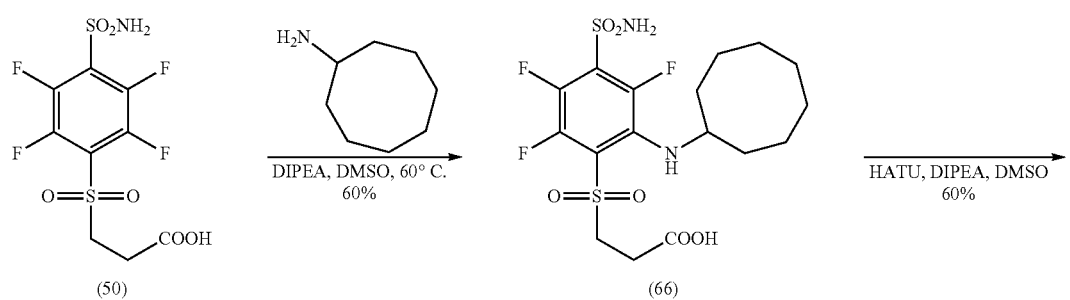
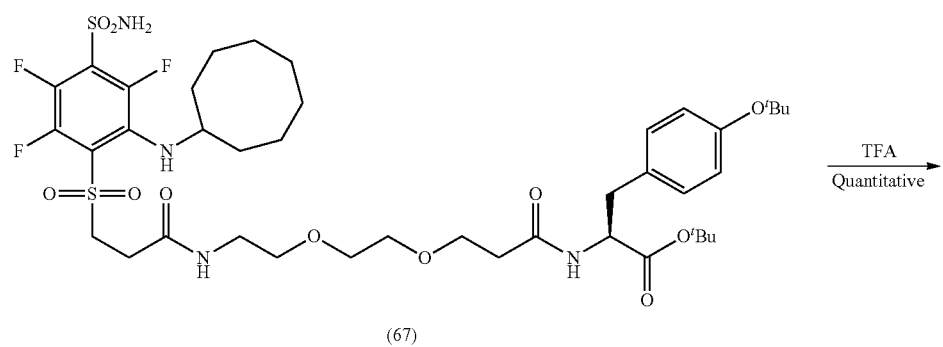
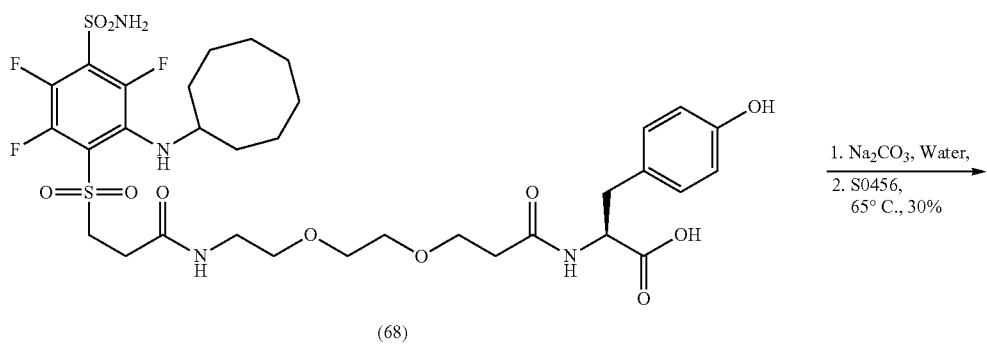

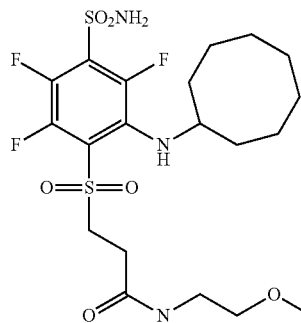
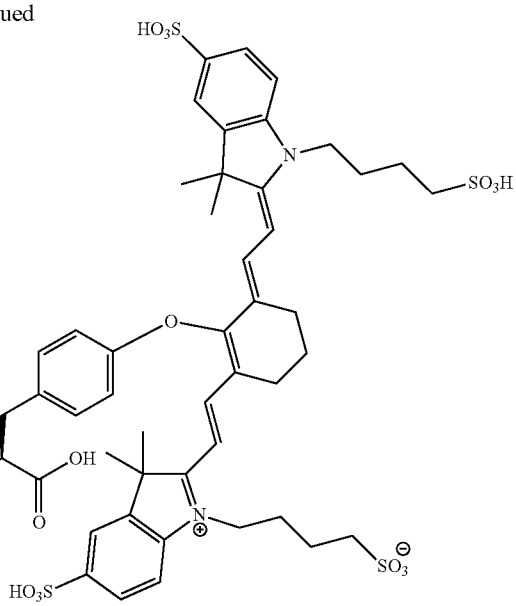

(61)

Experimental Procedures for the Compound 61

Synthesis of 3-((2,3,5,6-tetrafluoro-4-sulfamoylphenyl) thio)propanoic acid: To a pentafluorobenzenesulfonamide (5.0 g, 20.23 mmol, 1.0 equiv) in MeOH (200 mL) was added DIPEA (4.2 mL, 24.24 mmol, 1.2 equiv), followed by 3-mercaptopropionic acid (2, 1.76 mL, 20.23 mmol, 1.0 equiv) under argon. The reaction mixture was refluxed for 6 h and reaction progress was monitored by thin layer chromatography. After completion of reaction, MeOH was evaporated using rotaevaporator and the resultant solid was filtered and washed with water and dried under lyophilization. The product was confirmed by LCMS and used for next step, yield, 90%.

Synthesis of 3-((2,3,5,6-tetrafluoro-4-sulfamoylphenyl) sulfonyl)propanoic acid: To the 3-((2,3,5,6-tetrafluoro-4-sulfamoylphenyl)thio)propanoic acid (5.75 g, 17.25 mmol) in an acetic acid (34 mL) was added hydrogen peroxide (30% v/v, 15 mL) slowly at rt. The reaction mixture was stirred at 60° C. for 4 h. After completion of reaction confirmed by LCMS, reaction was quenched by addition of water. The reaction mixture was extracted with EtOAc (3×150 mL). The combined organics were washed with $H_2O$ (1×200 mL), brine (1×100 mL) and dried over anhy. Na2SO4 and concentrated. A white solid product was isolated in 80% yield and used for next step without further purification.

Synthesis of 3-((2-(cyclooctylamino)-3,5,6-trifluoro-4-sulfamoylphenyl)sulfonyl)propanoic acid: To a 3-((2,3,5,6-tetrafluoro-4-sulfamoylphenyl) sulfonyl) propanoic acid (1.0 g, 2.74 mmol, 1.0 equiv) in DMSO (5 mL), was added DIPEA (0.96 mL, 5.48 mmol, 2.0 equiv) followed by cyclooctylamine (0.413 mL, 3.01 mmol, 1.1 equiv) under argon. The reaction mixture was stirred at 60° C. for 6 h. The mixture was then diluted with $H_2O$ (30 mL) and extracted with EtOAc (3×50 mL). The combined organics were washed with brine (1×50 mL), dried over Na2SO4 and evaporated under reduced pressure. The crude mass was purified by silica-gel column chromatography using DCM:EtOAc. The desired product was isolated in 60% yield.

Synthesis of Meta-Substituted Ligands

The similar procedure as that of synthesis of 3-((2-(cyclooctylamino)-3,5,6-trifluoro-4-sulfamoylphenyl)sulfonyl)propanoic acid was used for the synthesis of the following ligands Compound 3: n=0, p=0, m=⅗

Compound 7: n=2, p=0, m=0

Compound 17: m=0

Compound 18: m=0

Compound 29: n=0, p=0

Compound 30: n=1, p=0

Compound 32: n=2, p=0

Also, Compound 25 (n=0, p=0, m=5) was prepared from 3-((2-fluoro-4-sulfamoylphenyl)sulfonyl)propanoic acid using similar procedure as that of synthesis of 3-((2-(cyclooctylamino)-3,5,6-trifluoro-4-sulfamoylphenyl)sulfonyl) propanoic acid Synthesis of tert-butyl (S)-2-(4-(tert-butoxy)benzyl)-16-((2-(cyclooctylamino)-3,5,6-trifluoro-4-sulfamoylphenyl) sulfonyl)-4,14-dioxo-7,10-dioxa-3,13-diazahexadecanoate: A 50-mL round bottom flask was charged with a stirring bar, 3-((2-(cyclooctylamino)-3,5,6-trifluoro-4-sulfamoylphenyl) sulfonyl)propanoic acid (60 mg, 0.126 mmol, 1 equiv), tert-butyl (S)-2-(3-(2-(2-aminoethoxy)ethoxy)propanamido)-3-(4-(tert-butoxy)phenyl)propanoate (63.2 mg, 0.139 mmol, 1.1 equiv) and HATU (48.28 mg, 0.139 mmol, 1.1 equiv) then DMSO (1.3 mL) was added to give a clear solution. DIPEA (88 µL, 0.508 mmol, 4.0 equiv) was added slowly to the reaction mixture at 23° C. The reaction was stirred at 23° C. for 1.5 h and progress of the reaction was monitored by LC/MS. The reaction mixture was quenched by adding water (3 mL) dropwise and extracted with EtOAc (3×10 mL). The combined organics were washed with brine (10 mL), and dried over anhyd. Na2SO4 and filtered and concentrated. The crude mass was purified by silica-gel column chromatography using DCM-EtOAc to yield desired compound, 92 mg, 80% yield.

Synthesis of (3-(2-(2-(3-((2-(cyclooctylamino)-3,5, 6-trifluoro-4-sulfamoylphenyl)sulfonyl)

propanamido)ethoxy)ethoxy)propanoyl)-L-tyrosine: A 5 mL round bottom flask was charged with a stirring bar and compound tert-butyl (S)-2-(4-(tert-butoxy)benzyl)-16-((2-(cyclooctylamino)-3,5,6-trifluoro-4-sulfamoylphenyl)sulfonyl)-4,14-dioxo-7,10-dioxa-3,13-diazahexadecanoate (52 mg, 0.057 mmol) and trifluoroacetic acid (TFA, 1 mL) was added to the reaction flask at rt. The reaction mixture was stirred at rt for 1 h and the progress of the reaction was monitored by LC/MS. The solvent was evaporated under vacuum (rotavapor) and the concentrated reaction mixture was added drop wise to stirred cold ether (5 mL) to give white precipitate which was centrifuged, washed with cold ether (2×5 mL), and dried under high vacuum to afford desired product as a white solid in quantitative yield.

Linker-Ligand Coupling

Various modified linkers were coupled to the CA-IX ligand using similar protocol as that of the synthesis of (3-(2-(2-(3-((2-(cyclooctylamino)-3,5,6-trifluoro-4-sulfamoylphenyl)sulfonyl) propanamido)ethoxy)ethoxy)propanoyl)-L-tyrosine as listed below Compound 39: n=0, m=5, p=0
Compound 40: n=0, m=5, p=0
Compound 41: n=0, m=5, p=0
Compound 42: n=0, m=5, p=0
Compound 43: n=0, m=5, p=0
Compound 44: n=0, m=5, p=0

Synthesis of 4-(2-((E)-2-((E)-2-(4-((S)-2-carboxy-16-((2-(cyclooctylamino)-3,5,6-trifluoro-4-sulfamoylphenyl) sulfonyl)-4,14-dioxo-7,10-dioxa-3,13-diazahexadecyl)phenoxy)-3-(2-((E)-3,3-dimethyl-5-sulfo-1-(4-sulfobutyl)indolin-2-ylidene)ethylidene)cyclohex-1-en-1-yl)vinyl)-3,3-dimethyl-5-sulfo-3H-indol-1-ium-1-yl)butane-1-sulfonate: A 5-mL round bottom flask was charged with a stirring bar and Compound (3-(2-(2-(3-((2-(cyclooctylamino)-3,5,6-trifluoro-4-sulfamoylphenyl)sulfonyl)propanamido)ethoxy) ethoxy)propanoyl)-L-tyrosine (11 mg, 0.014 mmol, 1 equiv) and it was then dissolved in THF: water (1:2 ratio, 0.4 mL). The pH of the reaction mixture was adjusted to ~9.5-10 (utilizing wet pH paper) by using a solution of aqueous 1M Na2CO3 at room temperature. Then S0456 (13.2 mg, 0.014 mmol, 1 equiv) was added to give opaque green solution and stirred at 60° C. for 4 hours. The reaction progress was monitored by HRMS and usually reaction was completed in 4 hours. The reaction mixture was cooled to room temperature and purified by RP-HPLC. Pure fractions from the HPLC were combined, evaporated solvent and freeze samples are lyophilized to obtain desired product (8 mg) as a green solid.

Synthesis of CA-IX Dye Conjugates

Figure 7:
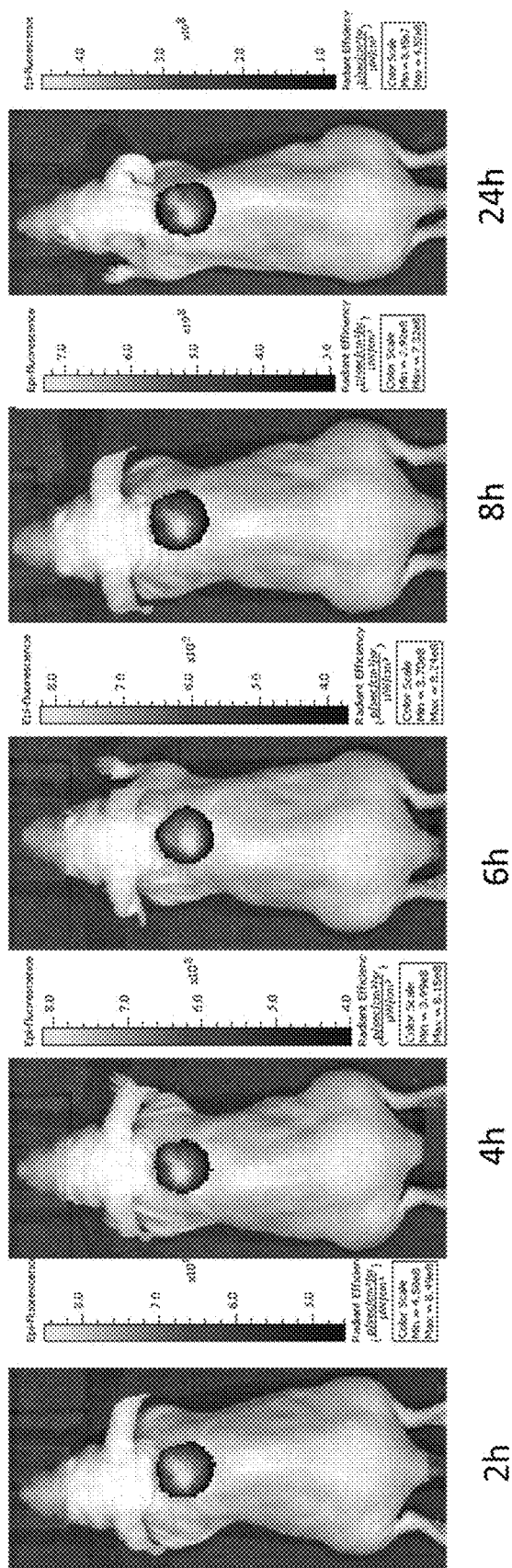
FIG. 7 shows an overlay of whole body fluorescence image over white light images after adjusting the threshold. SKRC52 human renal tumor xenograft bearing mouse was injected with 10 nmol of 60 and imaged with IVIS imager (ex=745 nm, em=ICG, exposure time=1 s) at different time intervals.

The similar procedure as that of synthesis of 4-(2-((E)-2-((E)-2-(4-((S)-2-carboxy-16-((2-(cyclooctylamino)-3,5,6-trifluoro-4-sulfamoylphenyl)sulfonyl)-4,14-dioxo-7,10-dioxa-3,13-diazahexadecyl)phenoxy)-3-(2-((E)-3,3-dimethyl-5-sulfo-1-(4-sulfobutyl)indolin-2-ylidene)ethylidene) cyclohex-1-en-1-yl)vinyl)-3,3-dimethyl-5-sulfo-3H-indol-1-ium-1-yl)butane-1-sulfonate was used for the preparation of all other CA-IX-dye conjugates FIG. 7 shows an overlay of whole body fluorescence image over white light images after adjusting the threshold. SKRC52 human renal tumor xenograft bearing mouse was injected with 10 nmol of 60 and imaged with IVIS imager (ex=745 nm, em=ICG, exposure time=is) at different time intervals.

Figure 8A:
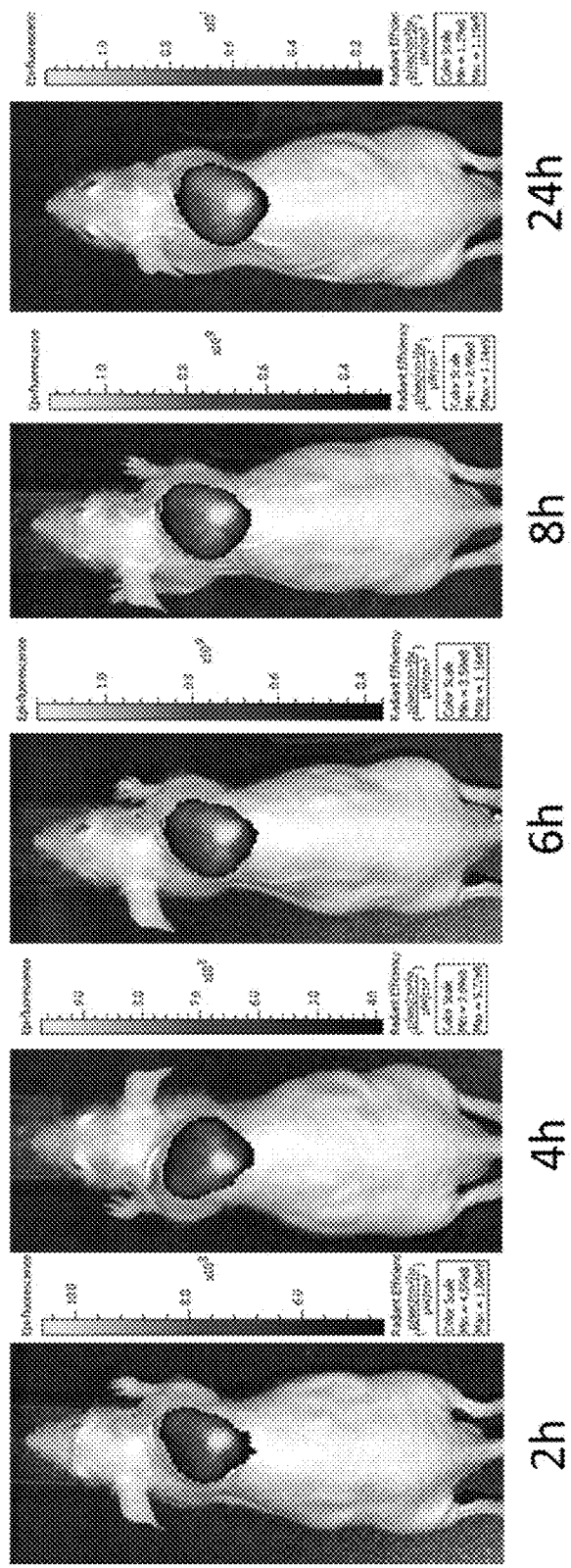
FIG. 8A shows a time dependent overlay of whole body fluorescence image over white light images after adjusting the threshold. SKRC52 human renal tumor xenograft bearing mouse was injected with 10 nmol of 61 and imaged with IVIS imager (ex=745 nm, em=ICG, exposure time=1 s) at different time intervals.
Figure 8B:
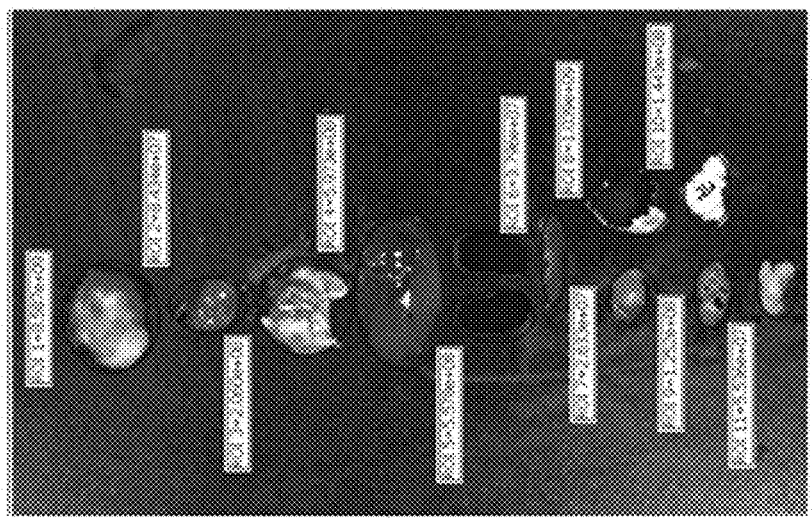
FIG. 8B shows a bio-distribution of SKRC52 human renal tumor xenograft bearing mouse was injected with 10 nmol of 61 and imaged with IVIS imager (ex=745 nm, em=ICG, exposure time=1 s)

FIG. 8 shows an overlay of whole body fluorescence image over white light images after adjusting the threshold. SKRC52 human renal tumor xenograft bearing mouse was injected with 10 nmol of 61 and imaged with IVIS imager (ex=745 nm, em=ICG, exposure time=is) at different time intervals.

Figure 9A:
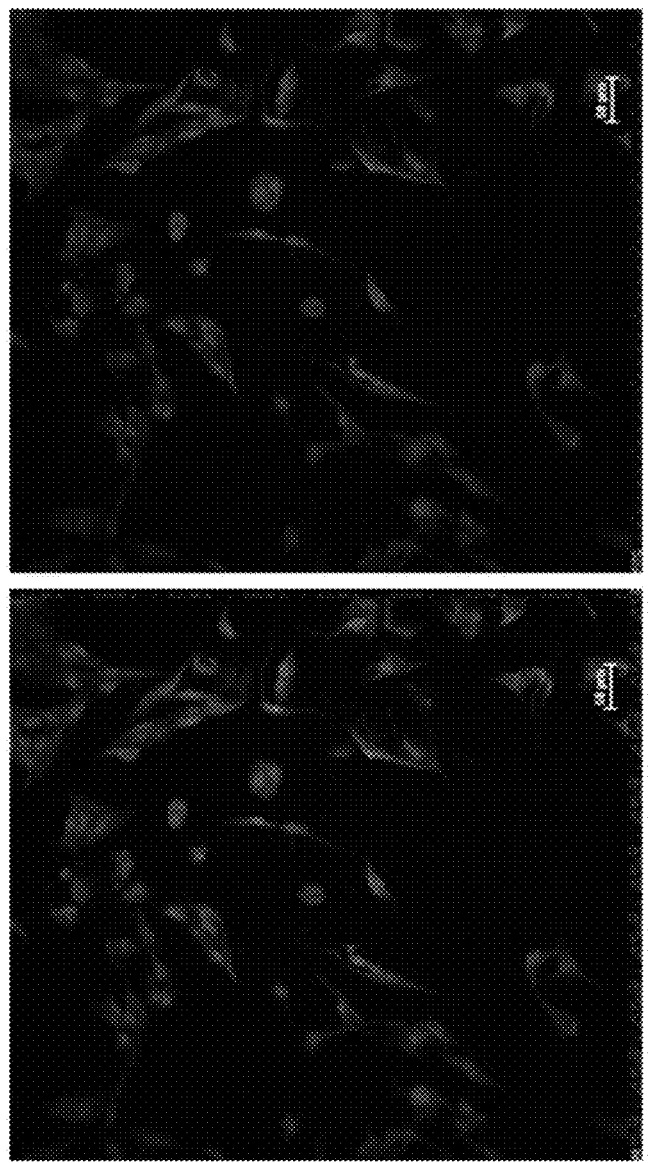
FIG. 9A shows the binding affinity of 61 to CA IX-positive SKRC52 cells using confocal microscopy. Tissue biodistribution of 61 in SKRC52 human renal tumor xenograft bearing mouse model. Mice were injected with 10 nmol of 61, harvested selected tissue and imaged with IVIS imager (ex=745 nm, em=ICG, exposure time=1 s) at different time intervals.
Figure 9B:
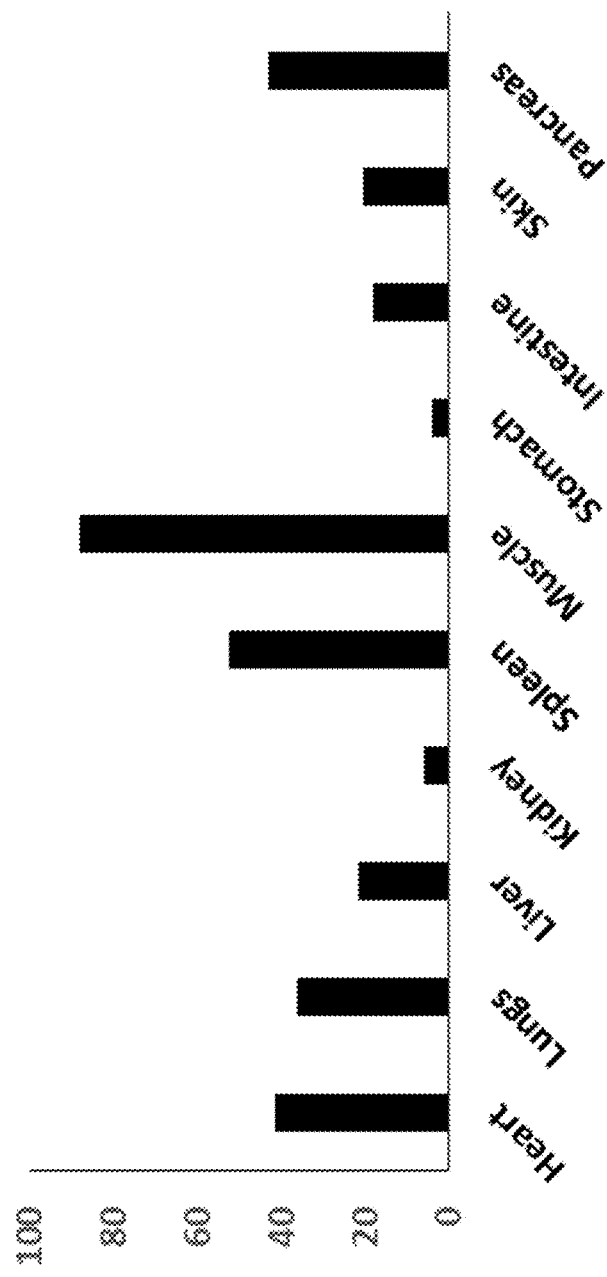
FIG. 9B shows tumor-to-background ratios in organs of 61 in SKRC52 human renal tumor xenograft bearing mouse model. Mice were injected with 10 nmol of 61, harvested selected tissue and imaged with IVIS imager (ex=745 nm, em=ICG, exposure time=1 s) at different time intervals.

FIG. 9 shows the binding affinity of 61 to CA IX-positive SKRC52 cells using confocal microscopy. Tissue biodistribution and tumor to the background of 61 in SKRC52 human renal tumor xenograft bearing mouse model. Mice were injected with 10 nmol of 61, harvested selected tissue and imaged with IVIS imager (ex=745 nm, em=ICG, exposure time=is) at different time intervals.

Figure 10A:
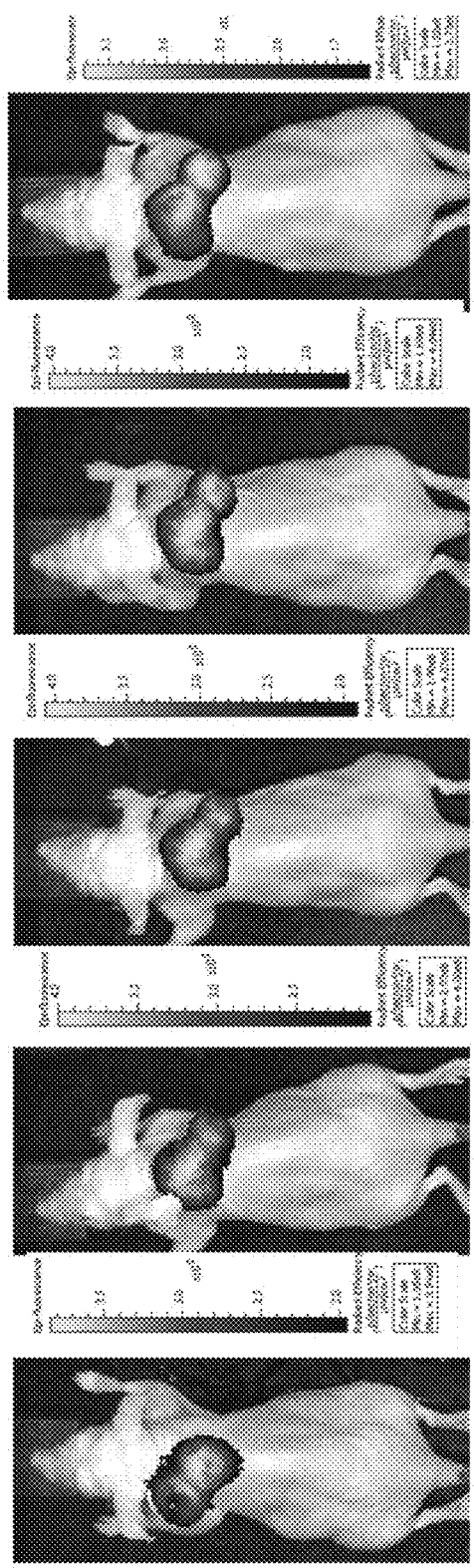
FIG. 10A shows an overlay of whole body fluorescence image over white light images after adjusting the threshold. HT29 (a human colon cancer cell line) tumor xenograft bearing mouse was injected with 10 nmol of 61 and imaged with IVIS imager (ex=745 nm, em=ICG, exposure time=1 s) at different time intervals.
Figure 10B:
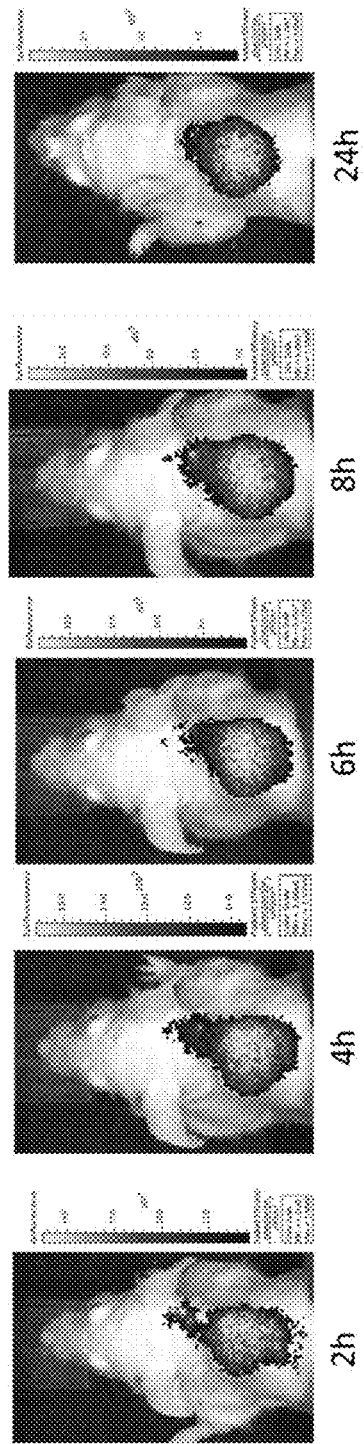
FIG. 10B shows an overlay of whole body fluorescence image over white light images after adjusting the threshold. HCC827 (a human lung cancer cell line) tumor xenograft bearing mouse was injected with 10 nmol of 61 and imaged with IVIS imager (ex=745 nm, em=ICG, exposure time=1 s) at different time intervals.

FIG. 10 shows an overlay of whole body fluorescence image over white light images after adjusting the threshold. HT29 (a human colon cancer cell line) and HCC827 (a human lung cancer cell line) tumor xenograft bearing mouse was injected with 10 nmol of 61 and imaged with IVIS imager (ex=745 nm, em=ICG, exposure time=1 s) at different time intervals.

Figure 11:
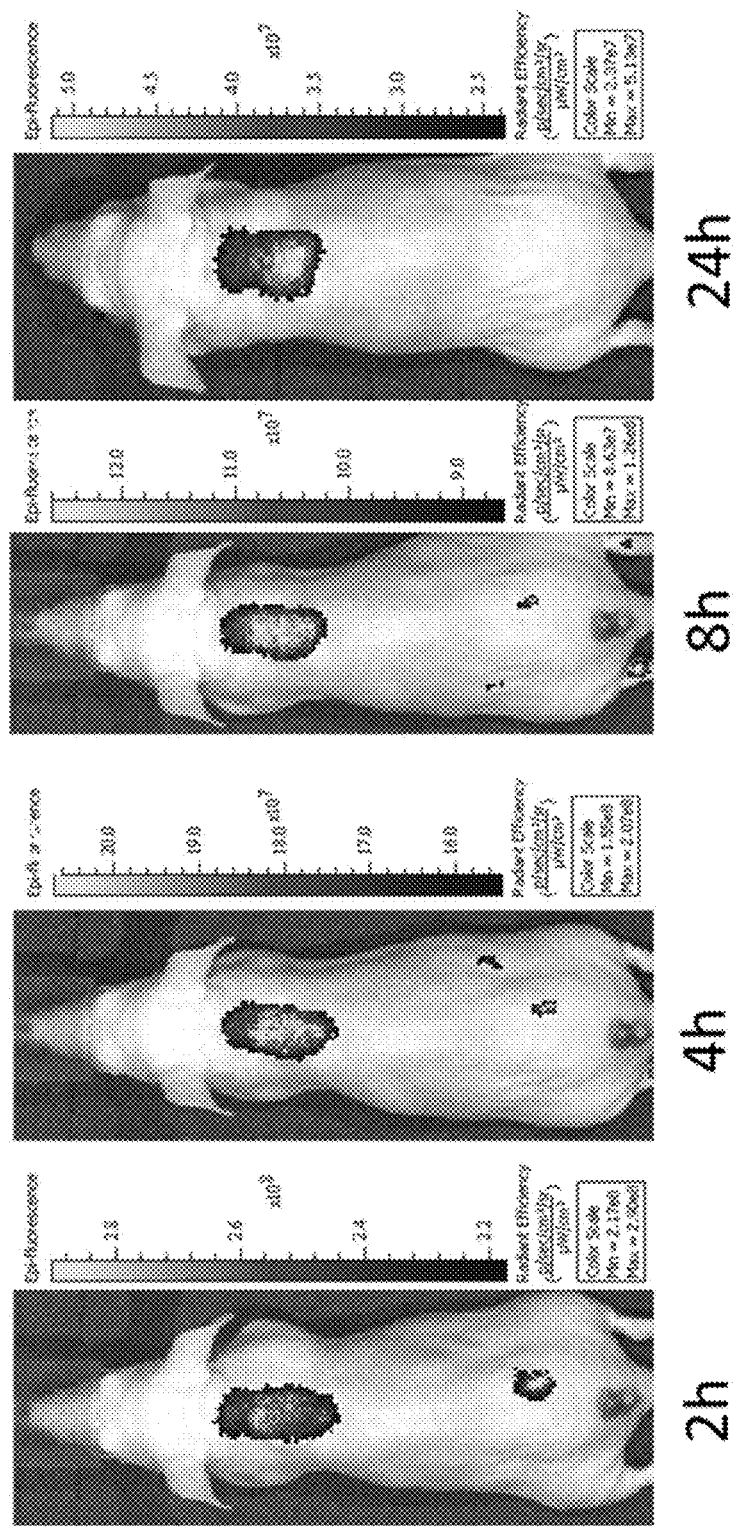
FIG. 11 shows an overlay of whole body fluorescence image over white light images after adjusting the threshold. SKRC52 human renal tumor xenograft bearing mouse was injected with 10 nmol of 62 and imaged with IVIS imager (ex=745 nm, em=ICG, exposure time=1 s) at different time intervals.

FIG. 11 shows an overlay of whole body fluorescence image over white light images after adjusting the threshold. SKRC52 human renal tumor xenograft bearing mouse was injected with 10 nmol of 62 and imaged with IVIS imager (ex=745 nm, em=ICG, exposure time=1 s) at different time intervals.

Figure 12:
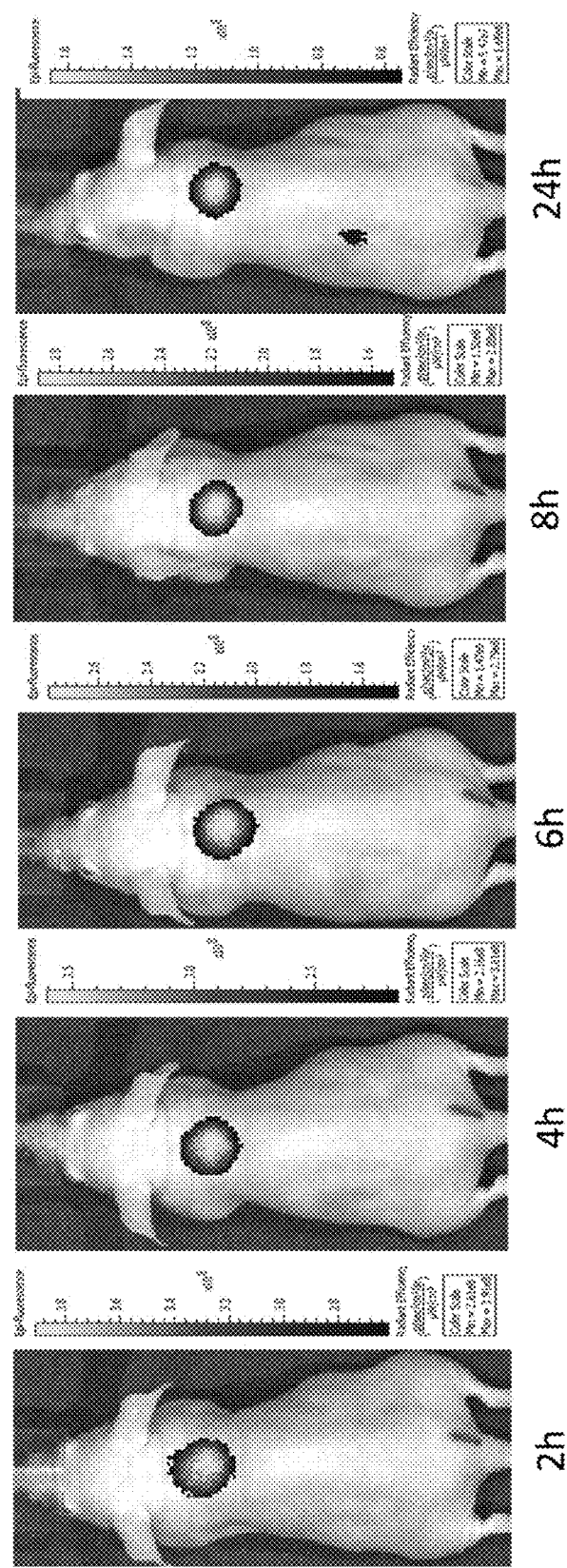
FIG. 12 shows an overlay of whole body fluorescence image over white light images after adjusting the threshold. SKRC52 human renal tumor xenograft bearing mouse was injected with 10 nmol of 65 and imaged with IVIS imager (ex=745 nm, em=ICG, exposure time=1 s) at different time intervals.

FIG. 12 shows an overlay of whole body fluorescence image over white light images after adjusting the threshold. SKRC52 human renal tumor xenograft bearing mouse was injected with 10 nmol of 65 and imaged with IVIS imager (ex=745 nm, em=ICG, exposure time=1 s) at different time intervals.

Conclusion: These in vivo tumor accumulation data demonstrated that compounds 60, 61, 62 and 65 showed very good whole-body imaging data within 2-24 hours after administering to the animal. In addition, compounds 60, 62 and 65 showed excellent tumor-to-background ratio (TBR) and tumor-to-skin ratio with very high accumulation. Moreover, compounds were remained in the tumor maintaining very high fluorescence over 24 hours. Moreover, the compound 61 selectively accumulated in CA IX-negative tumor xenografts of colon and lung cancer but not in the other healthy tissues. Although CA IX does not naturally express in NSCLC and colon cancer cells, uptake of 61 in those tumors is solely CA IX mediated indicating that induction of CA IX under tumor hypoxia conditions. After considering affinity and specificity for CA IX expressing prostate cancer cells and tumor tissues, fluorescence intensity in the tumor, tumor-to-background ratio, ease synthesis and availability of starting materials for low cost, compound 60, 61, and 65 can be considered as excellent clinical candidates, although the other compounds also may be useful both as clinical and/or experimental candidates. (FIGS. 7-12)

Figure 13:
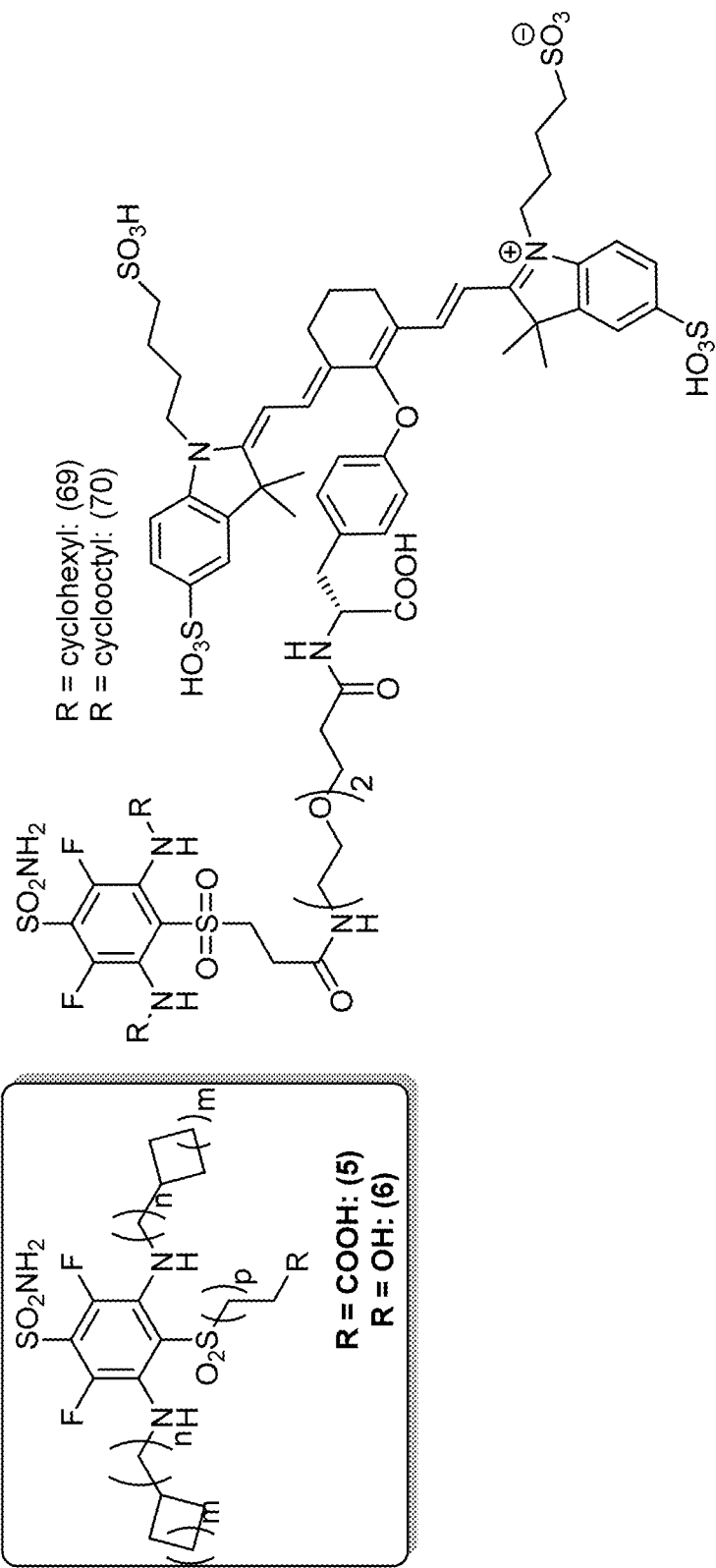
FIG. 13 shows The chemical structure of CA IX-Targeted NIR agents derived from the Ligands 5 & 6.

Example: (4) Preclinical Evaluation of Novel CA IX-Targeted NIR Agents Derived from Ligands 5 & 6 (FIG. 13)

Chemical Synthesis:
Both the compounds 69 and 70 were synthesized using similar methods as explain in the Example 1-3.

Figure 14:
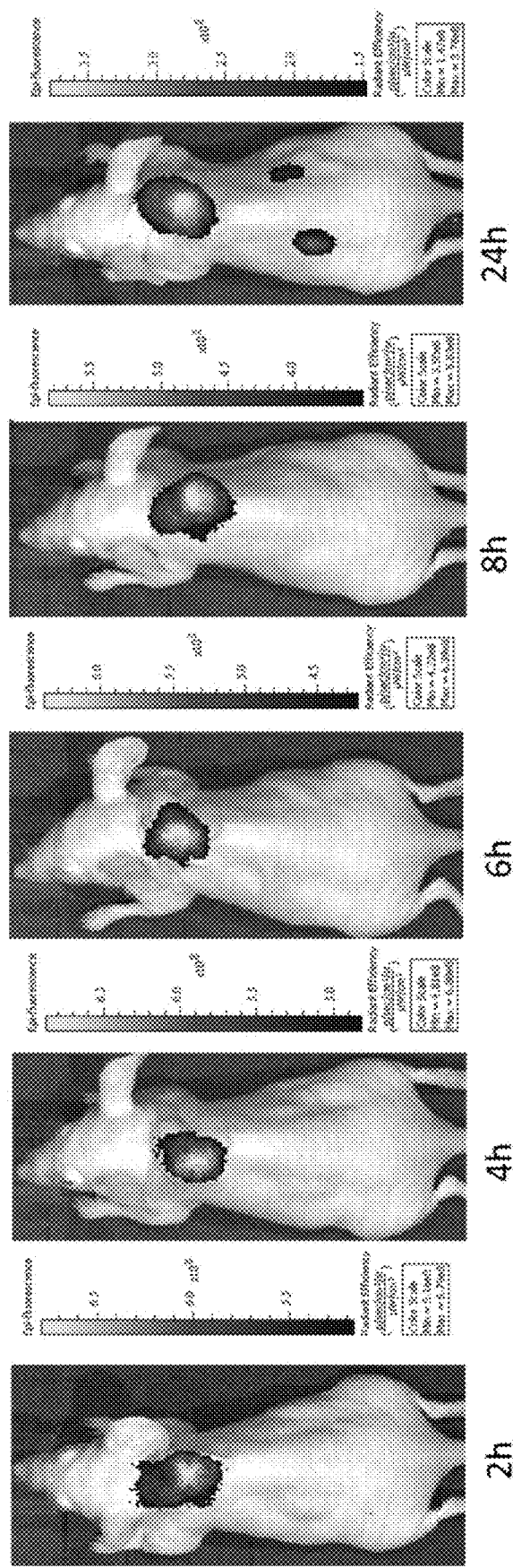
FIG. 14 shows an overlay of whole body fluorescence image over white light images after adjusting the threshold. SKRC52 human renal tumor xenograft bearing mouse was injected with 10 nmol of 69 and imaged with IVIS imager (ex=745 nm, em=ICG, exposure time=1 s) at different time intervals.

Animal Studies:
FIG. 14 shows an overlay of whole body fluorescence image over white light images after adjusting the threshold.

SKRC52 human renal tumor xenograft bearing mouse was injected with 10 nmol of 69 and imaged with IVIS imager (ex=745 nm, em=ICG, exposure time=1 s) at different time intervals.

Figure 15:
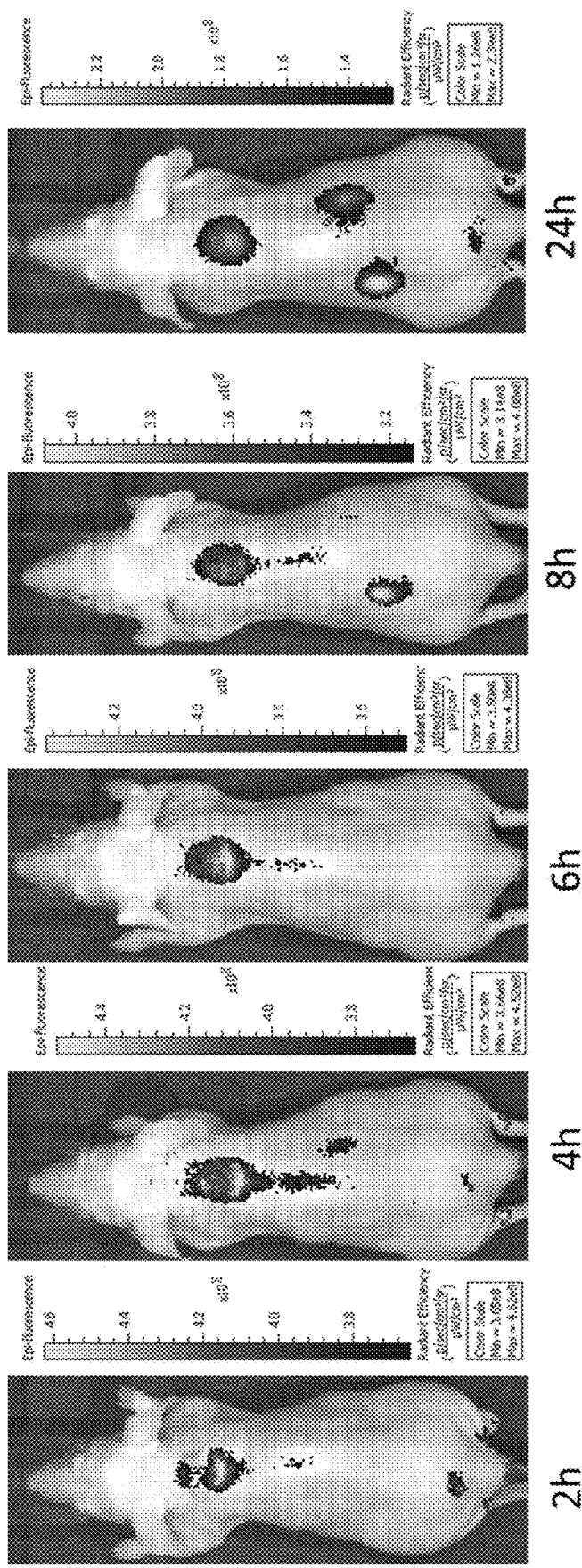
FIG. 15 shows an overlay of whole body fluorescence image over white light images after adjusting the threshold. SKRC52 human renal tumor xenograft bearing mouse was injected with 10 nmol of 70 and imaged with IVIS imager (ex=745 nm, em=ICG, exposure time=1 s) at different time intervals.

FIG. 15 shows an overlay of whole body fluorescence image over white light images after adjusting the threshold. SKRC52 human renal tumor xenograft bearing mouse was injected with 10 nmol of 70 and imaged with IVIS imager (ex=745 nm, em=ICG, exposure time=1 s) at different time intervals.

Conclusion: These in vivo tumor accumulation data demonstrated that both 69 and 70 showed very good whole-body imaging data within 2-24 hours after administering to the animal. In addition, the compound 69 showed excellent tumor-to-background ratio (TBR) and tumor-to-skin ratio with very high accumulation retained in the tumor maintaining very high fluorescence over 24 hours. These compounds also may be useful both as clinical and/or experimental candidates.

Figure 16:
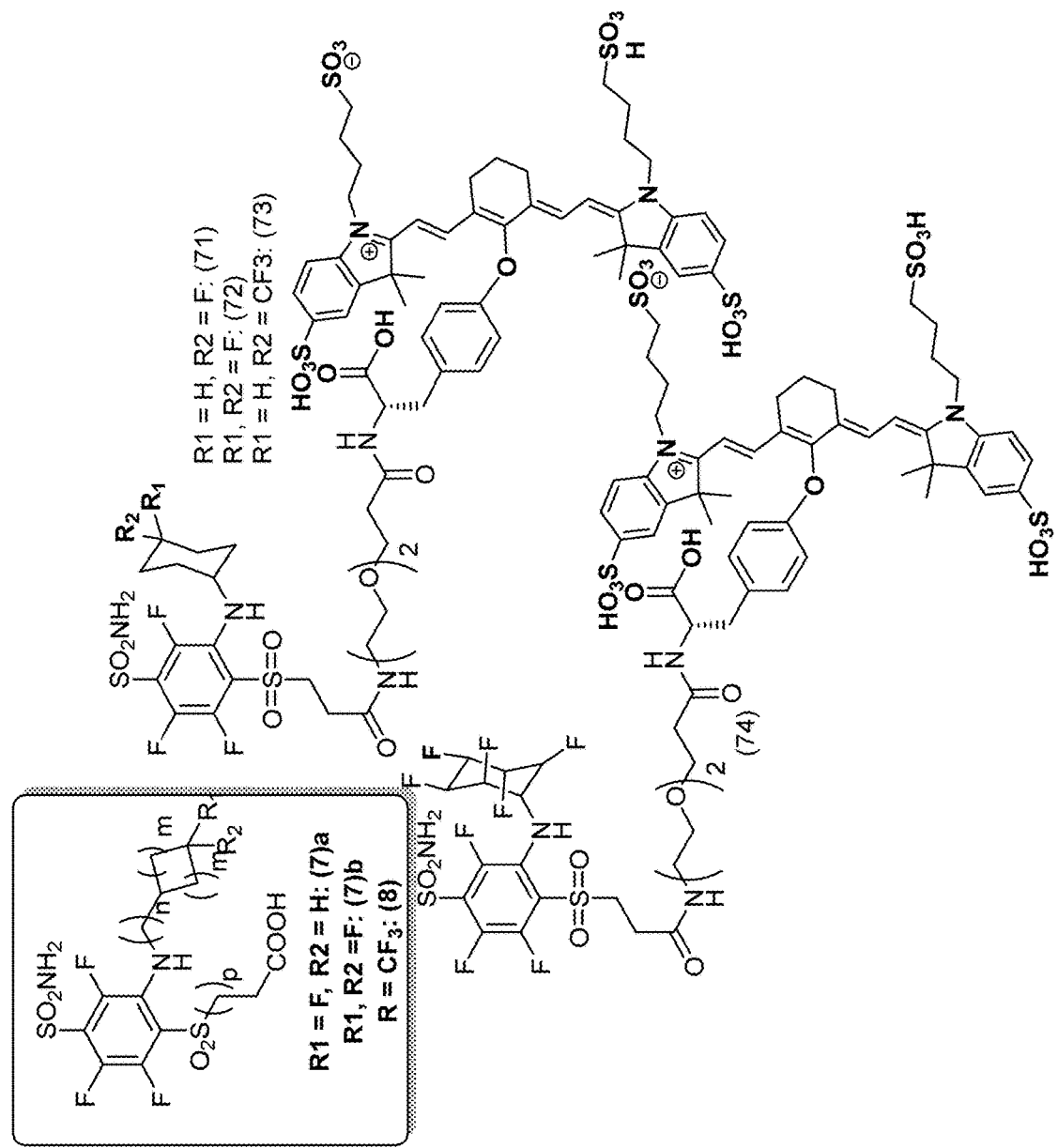
FIG. 16 shows the chemical structure of CA IX-Targeted NIR agents derived from the Ligands 7-8.

Example: (5) Preclinical Evaluation of Novel CA IX-Targeted NIR Agents Derived from Ligands 7-8 (FIG. 16)

Chemical Synthesis:
Both the compounds 71-74 were synthesized using similar methods as explain in the Example 1-3.

Figure 17:
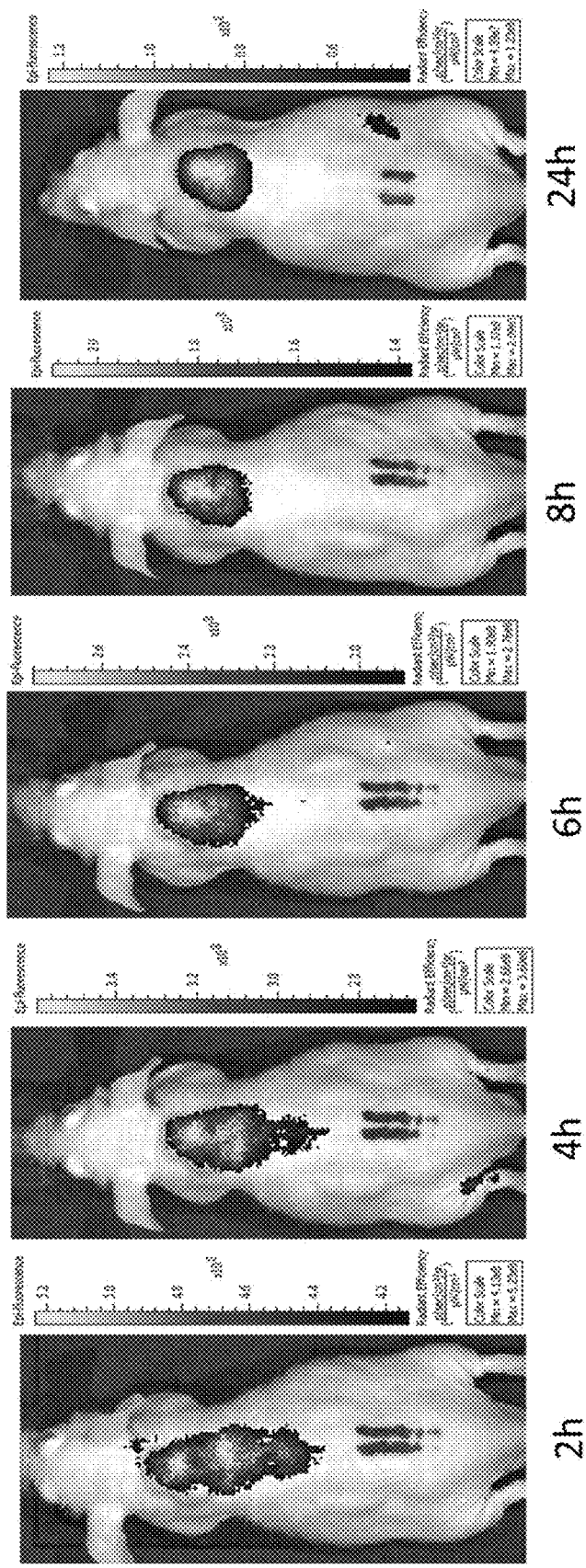
FIG. 17 shows an overlay of whole body fluorescence image over white light images after adjusting the threshold. SKRC52 human renal tumor xenograft bearing mouse was injected with 10 nmol 72 and imaged with IVIS imager (ex=745 nm, em=ICG, exposure time=1 s) at different time intervals.

FIG. 17 shows an overlay of whole body fluorescence image over white light images after adjusting the threshold. SKRC52 human renal tumor xenograft bearing mouse was injected with 10 nmol 72 and imaged with IVIS imager (ex=745 nm, em=ICG, exposure time=1 s) at different time intervals Conclusion: These in vivo tumor accumulation data demonstrated that both 72 showed very good whole-body imaging data within 2-24 hours after administering to the animal. In addition, the compound 72 showed excellent tumor-to-background ratio (TBR) and tumor-to-skin ratio with very high accumulation retained in the tumor maintaining very high fluorescence over 24 hours. These compounds also may be useful both as clinical and/or experimental candidates.

Example: (6) Preclinical Evaluation of Novel CA IX-Targeted NIR Agents Derived from Ligands 17-20 (FIG. 18)

Figure 18:
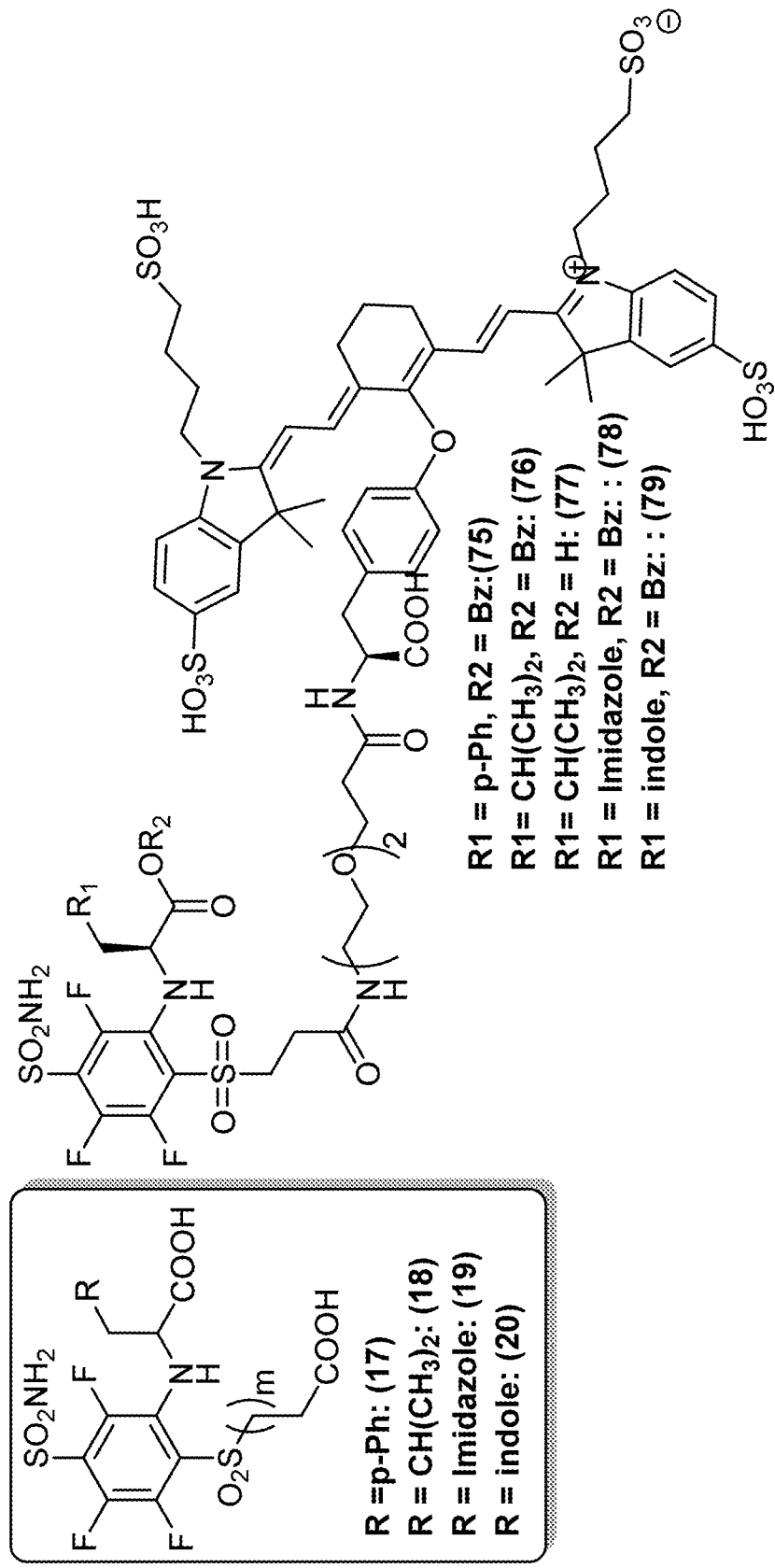
FIG. 18 shows the chemical structure of CA IX-Targeted NIR agents derived from the Ligands 17-20.

FIG. 18 shows The chemical structure of CA IX-Targeted NIR agents derived from the Ligands 17-20

Chemical Synthesis:
The compounds 75-79 were synthesized using similar methods as explain in the Example 1-3.

Figure 19:
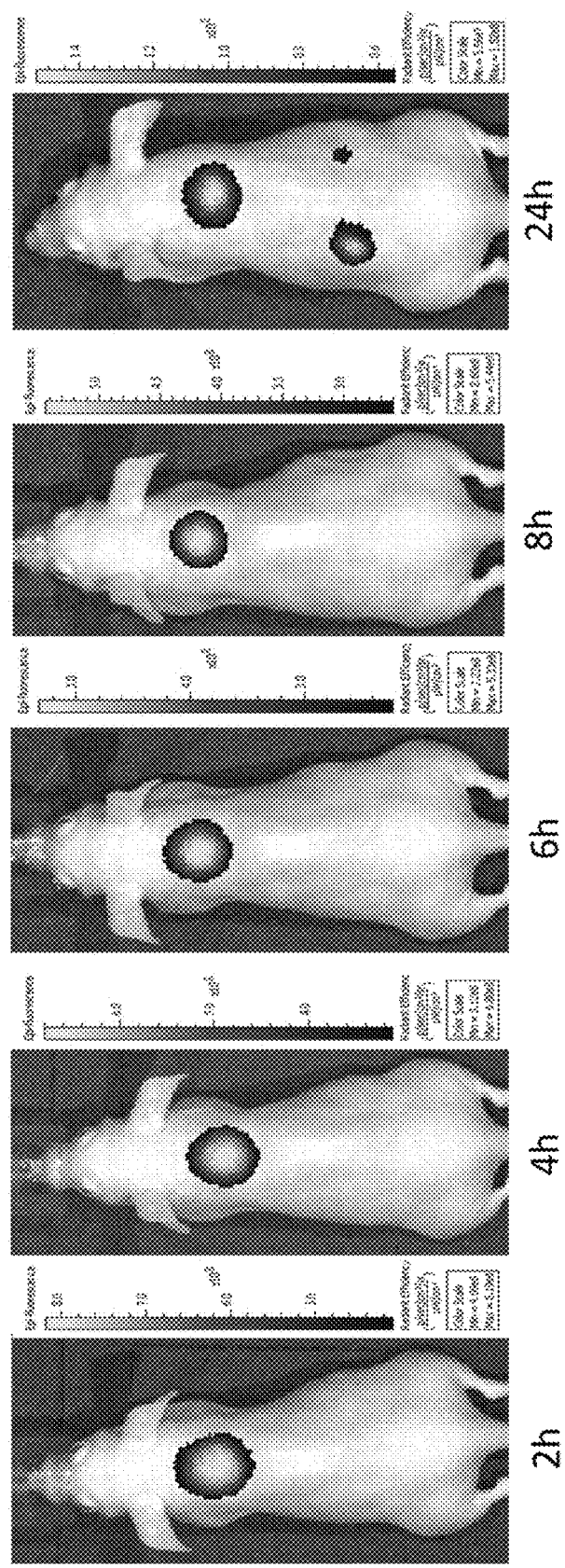
FIG. 19 shows an overlay of whole body fluorescence image over white light images after adjusting the threshold. SKRC52 human renal tumor xenograft bearing mouse was injected with 10 nmol of 76 and imaged with IVIS imager (ex=745 nm, em=ICG, exposure time=1 s) at different time intervals.
Figure 20:
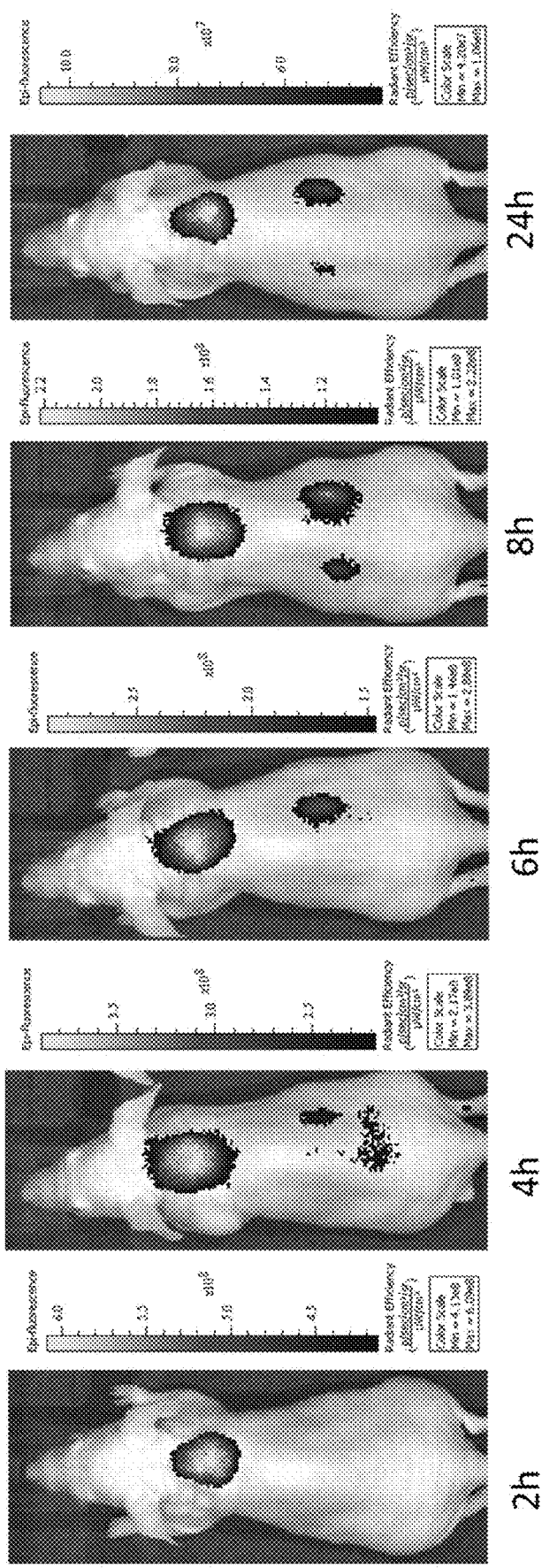
FIG. 20 shows an overlay of whole body fluorescence image over white light images after adjusting the threshold. SKRC52 human renal tumor xenograft bearing mouse was injected with 10 nmol of 77 and imaged with IVIS imager (ex=745 nm, em=ICG, exposure time=1 s) at different time intervals.

FIG. 19 shows an overlay of whole body fluorescence image over white light images after adjusting the threshold. SKRC52 human renal tumor xenograft bearing mouse was injected with 10 nmol of 76 and imaged with IVIS imager (ex=745 nm, em=ICG, exposure time=1 s) at different time intervals FIG. 20 shows an overlay of whole body fluorescence image over white light images after adjusting the threshold. SKRC52 human renal tumor xenograft bearing mouse was injected with 10 nmol of 77 and imaged with IVIS imager (ex=745 nm, em=ICG, exposure time=1 s) at different time intervals Conclusion: These in vivo tumor accumulation data demonstrated that both 76 and 77 showed very good whole-body imaging data within 2-24 hours after administering to the animal. In addition, both the compound showed excellent tumor-to-background ratio (TBR) and tumor-to-skin ratio with very high accumulation retained in the tumor maintaining very high fluorescence over 24 hours. These compounds also may be useful both as clinical and/or experimental candidates.

Figure 21:
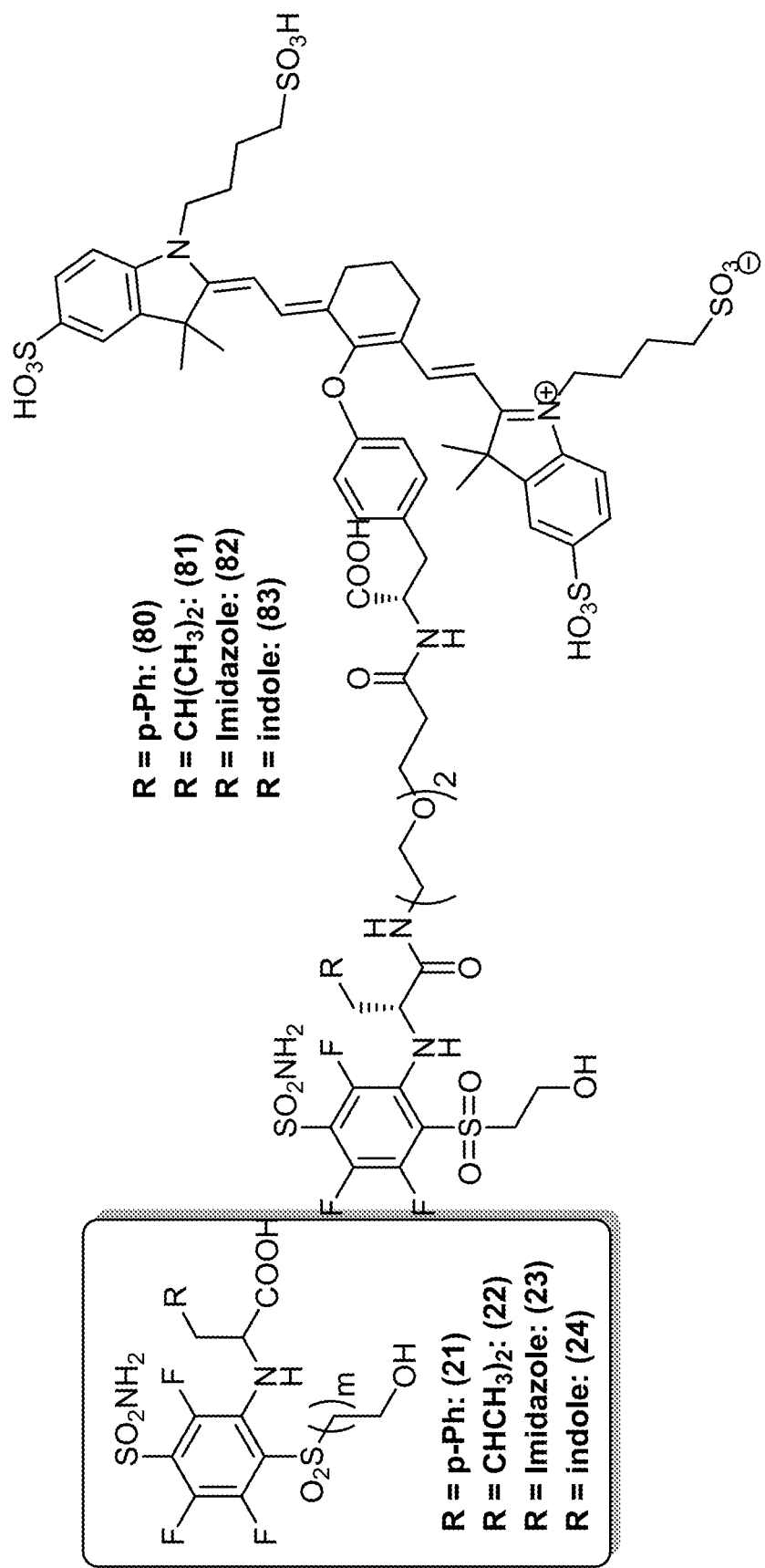
FIG. 21 shows the chemical structure of CA IX-Targeted NIR agents derived from the Ligands 21-24.

Example: (7) Preclinical Evaluation of Novel CA IX-Targeted NIR Agents Derived from Ligands 21-24 (FIG. 21)

Chemical Synthesis:
Both the compounds 80-83 were synthesized using similar methods as explain in the Example 1-3.

Figure 22:
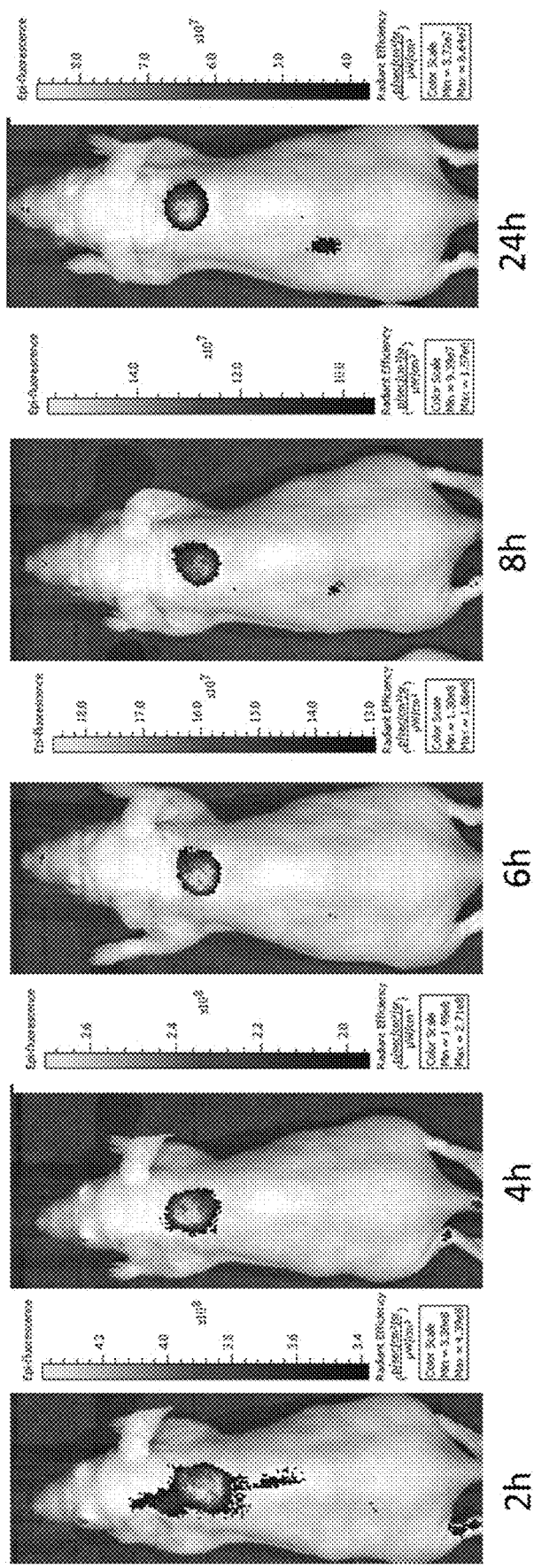
FIG. 22 shows an overlay of whole body fluorescence image over white light images after adjusting the threshold. SKRC52 human renal tumor xenograft bearing mouse was injected with 10 nmol of 80 and imaged with IVIS imager (ex=745 nm, em=ICG, exposure time=1 s) at different time intervals.
Figure 23:
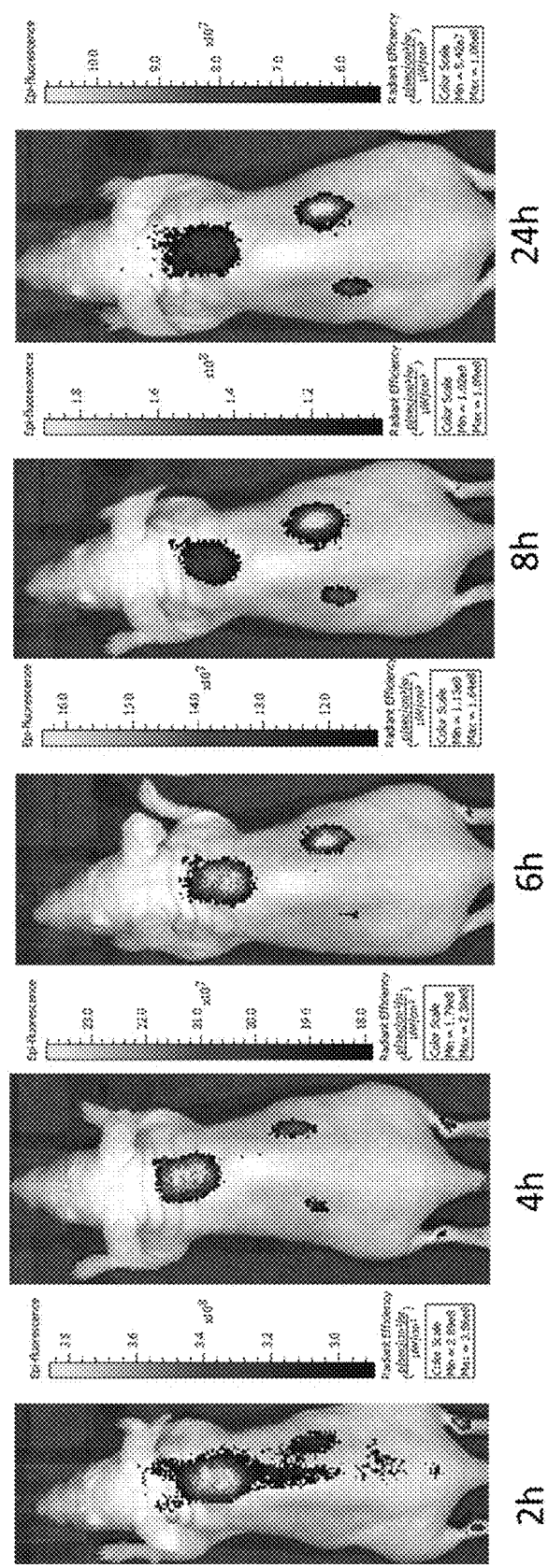
FIG. 23 shows an overlay of whole body fluorescence image over white light images after adjusting the threshold. SKRC52 human renal tumor xenograft bearing mouse was injected with 10 nmol of 81 and imaged with IVIS imager (ex=745 nm, em=ICG, exposure time=1 s) at different time intervals.

FIG. 22 shows an overlay of whole body fluorescence image over white light images after adjusting the threshold. SKRC52 human renal tumor xenograft bearing mouse was injected with 10 nmol of 80 and imaged with IVIS imager (ex=745 nm, em=ICG, exposure time=1 s) at different time intervals FIG. 23 shows an overlay of whole body fluorescence image over white light images after adjusting the threshold. SKRC52 human renal tumor xenograft bearing mouse was injected with 10 nmol of 81 and imaged with IVIS imager (ex=745 nm, em=ICG, exposure time=1 s) at different time intervals Conclusion: These in vivo tumor accumulation data demonstrated that both 80 and 81 showed very good whole-body imaging data within 2-24 hours after administering to the animal. In addition, the compound 80 showed excellent tumor-to-background ratio (TBR) and tumor-to-skin ratio with very high accumulation retained in the tumor maintaining very high fluorescence over 24 hours. These compounds also may be useful both as clinical and/or experimental candidates.

Figure 24:
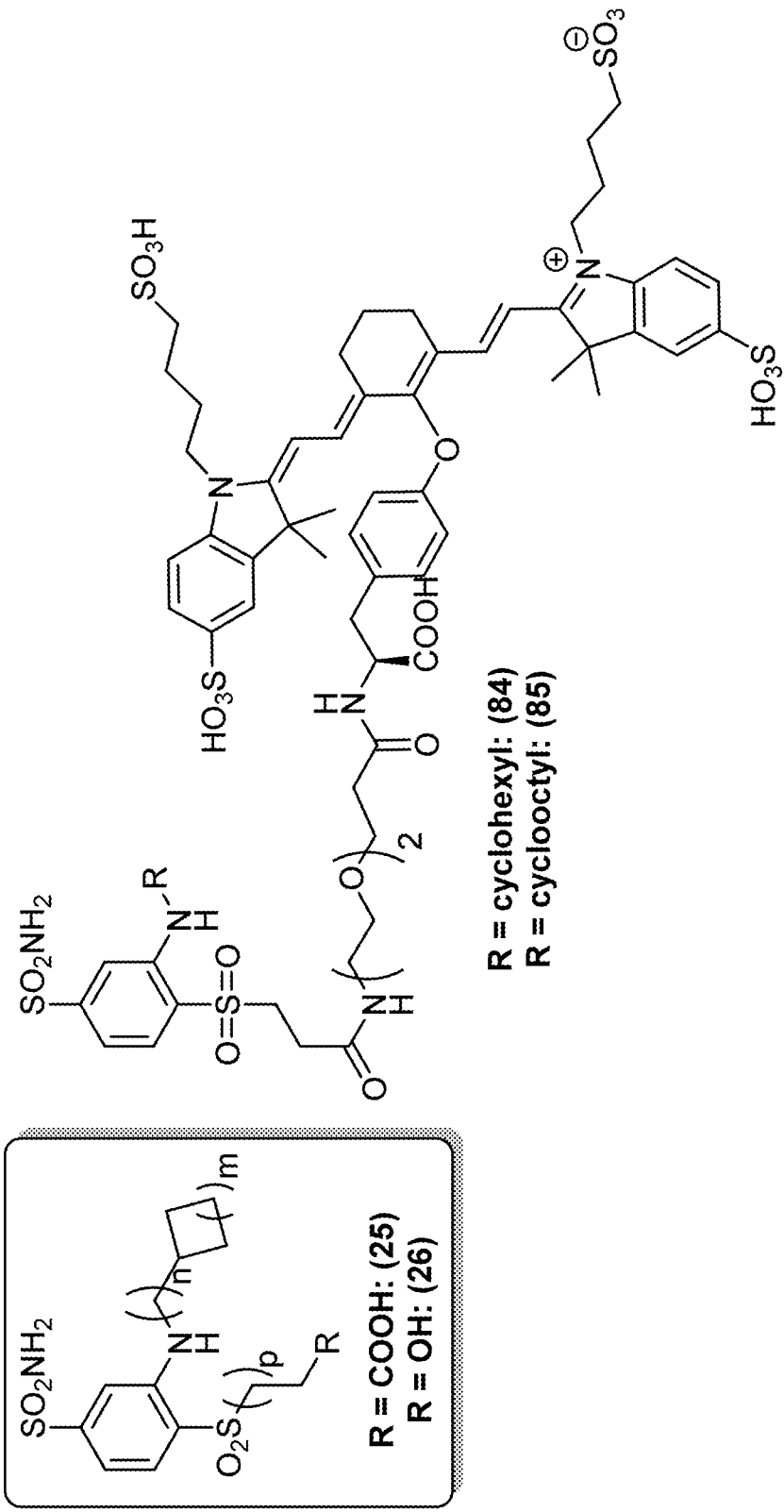
FIG. 24 shows the chemical structure of CA IX-Targeted NIR agents derived from the Ligands 25 &26.

Example: (8) Preclinical Evaluation of Novel CA IX-Targeted NIR Agents Derived from Ligands 25 & 26 (FIG. 24)

Chemical Synthesis:
Both the compounds 84-85 were synthesized using similar methods as explain in the Example 1-3.

Figure 25:
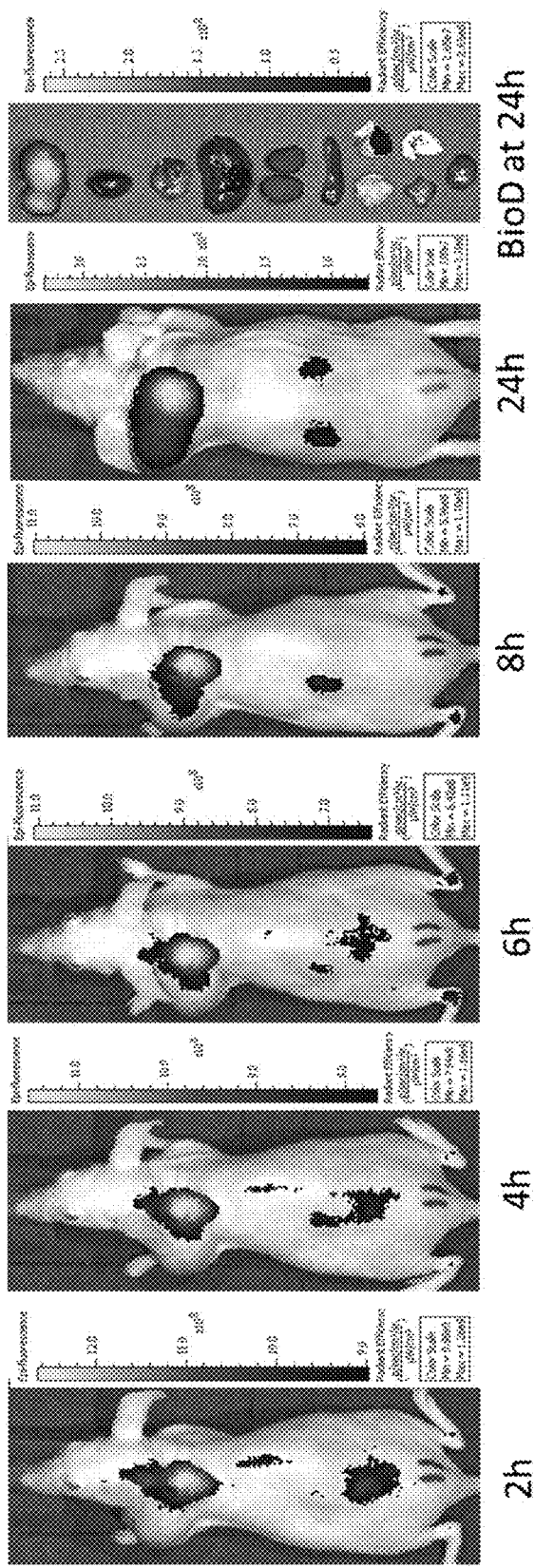
FIG. 25 shows an overlay of whole body fluorescence image over white light images after adjusting the threshold. SKRC52 human renal tumor xenograft bearing mouse was injected with 10 nmol of 85 and imaged with IVIS imager (ex=745 nm, em=ICG, exposure time=1 s) at different time intervals.

FIG. 25 shows an overlay of whole body fluorescence image over white light images after adjusting the threshold. SKRC52 human renal tumor xenograft bearing mouse was injected with 10 nmol of 85 and imaged with IVIS imager (ex=745 nm, em=ICG, exposure time=1 s) at different time intervals Conclusion: These in vivo tumor accumulation data demonstrated that the compound 85 showed very good whole-body imaging data within 2-24 hours after administering to the animal. In addition, the compound 85 showed excellent tumor-to-background ratio (TBR) and tumor-to-skin ratio with very high accumulation retained in the tumor maintaining very high fluorescence over 24 hours. However, the compound 85 showed less tumor fluorescence intensity and tumor-to-background ratio when compared to the compound 61. The difference between two compounds is the ligand of the 61 has three fluorine substitutions in the aromatic ring whereas 85 do not have that aromatic fluorine suggesting that importance of aromatic halogens for binding. The compound 85 also may be useful both as clinical and/or experimental candidates.

Example: (9) Preclinical Evaluation of Novel CA IX-Targeted NIR Agents Derived from Ligands 27 & 28 (FIG. 26)

Figure 26:
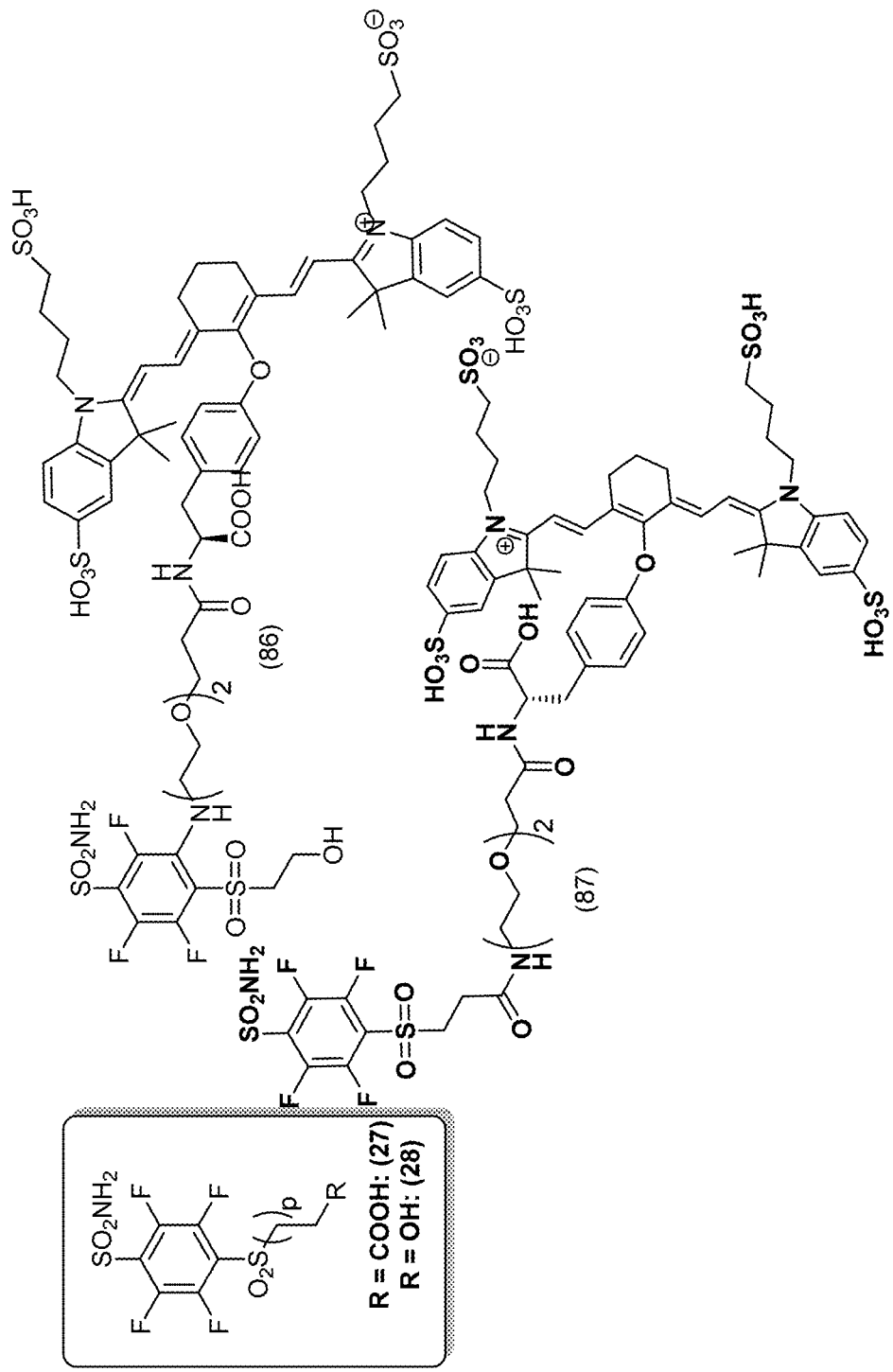
FIG. 26 shows the chemical structure of CA IX-Targeted NIR agents derived from the Ligands 27 & 28.

FIG. 26 shows The chemical structure of CA IX-Targeted NIR agents derived from the Ligands 27 & 28

Chemical Synthesis:

Both the compounds 86-87 were synthesized using similar methods as explain in the Example 1-3.

Figure 27:
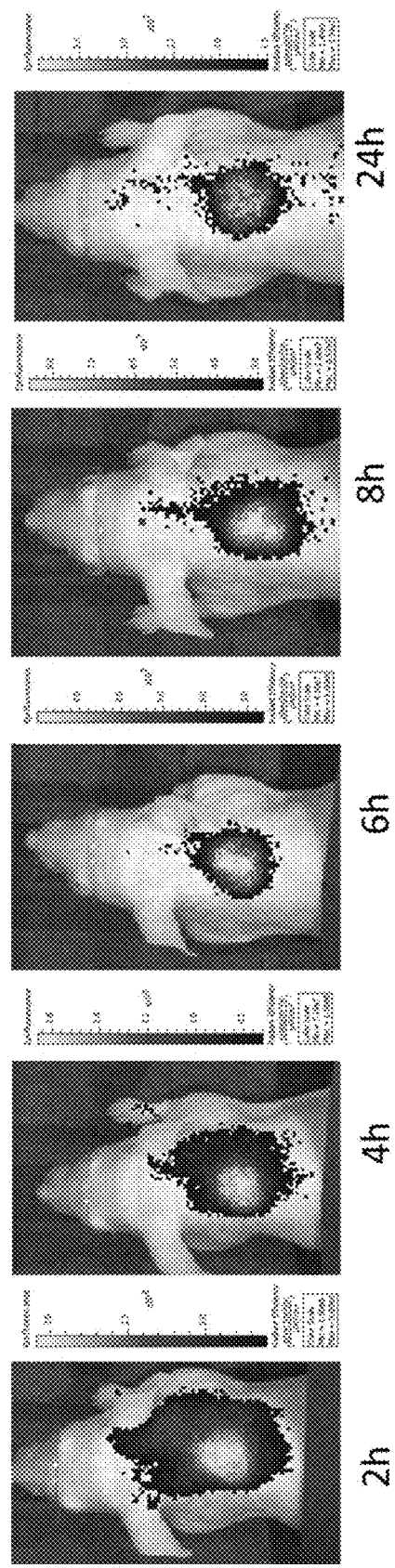
FIG. 27 shows an overlay of whole body fluorescence image over white light images after adjusting the threshold. SKRC52 human renal tumor xenograft bearing mouse was injected with 10 nmol of 86 and imaged with IVIS imager (ex=745 nm, em=ICG, exposure time=1 s) at different time intervals.
Figure 28:
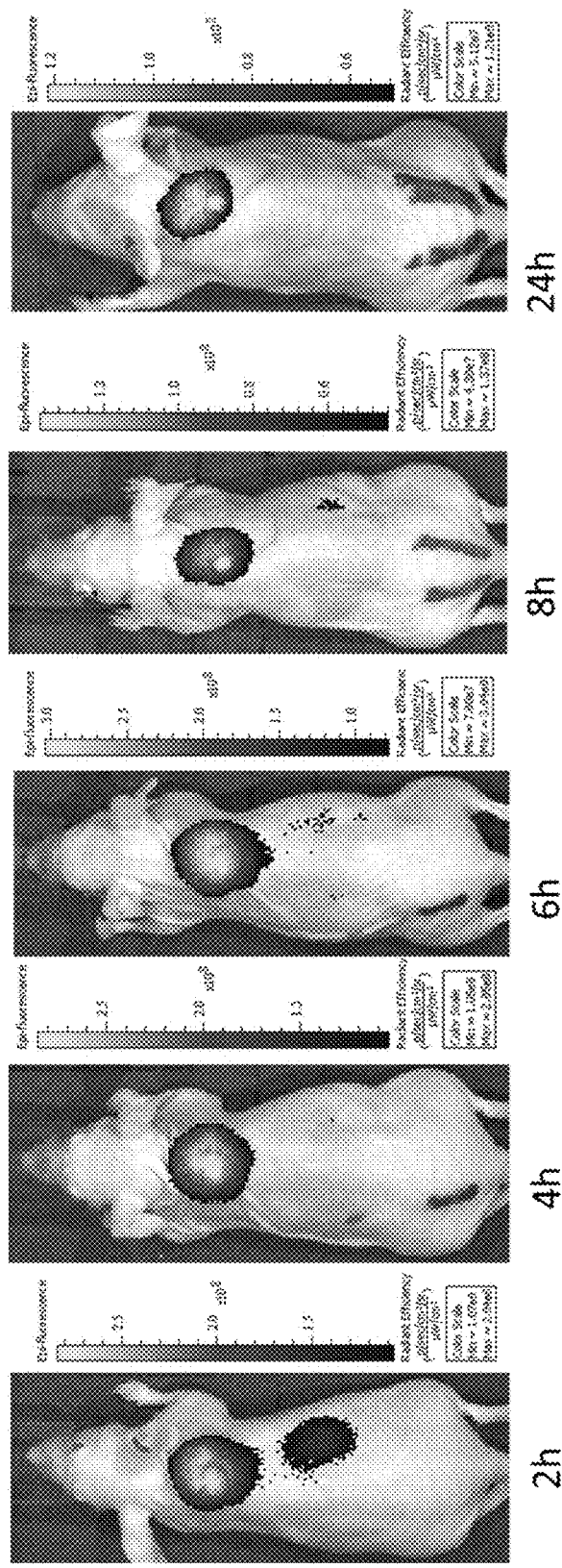
FIG. 28 shows an overlay of whole body fluorescence image over white light images after adjusting the threshold. SKRC52 human renal tumor xenograft bearing mouse was injected with 10 nmol of 87 and imaged with IVIS imager (ex=745 nm, em=ICG, exposure time=1 s) at different time intervals.

FIG. 27 shows an overlay of whole body fluorescence image over white light images after adjusting the threshold. SKRC52 human renal tumor xenograft bearing mouse was injected with 10 nmol of 86 and imaged with IVIS imager (ex=745 nm, em=ICG, exposure time=1 s) at different time intervals FIG. 28 shows an overlay of whole body fluorescence image over white light images after adjusting the threshold. SKRC52 human renal tumor xenograft bearing mouse was injected with 10 nmol of 87 and imaged with IVIS imager (ex=745 nm, em=ICG, exposure time=1 s) at different time intervals Conclusion: These in vivo tumor accumulation data demonstrated that both 86 and 87 showed very good whole-body imaging data within 2-24 hours after administering to the animal. However, the compound 87 showed excellent tumor-to-background ratio (TBR) and tumor-to-skin ratio with very high accumulation retained in the tumor maintaining very high fluorescence over 24 hours when compared to 86. This indicate that conjugation through meta-substitution loose the affinity for the CA XI and hydrophobic unit in the meta position of the aromatic ring is needed for binding. On the other hand 86 is less brighter than 60 and 61 indicating that having extra hydrophobic moiety increases the binding affinity and specificity to the receptor. These compounds also may be useful both as clinical and/or experimental candidates.

Figure 29:
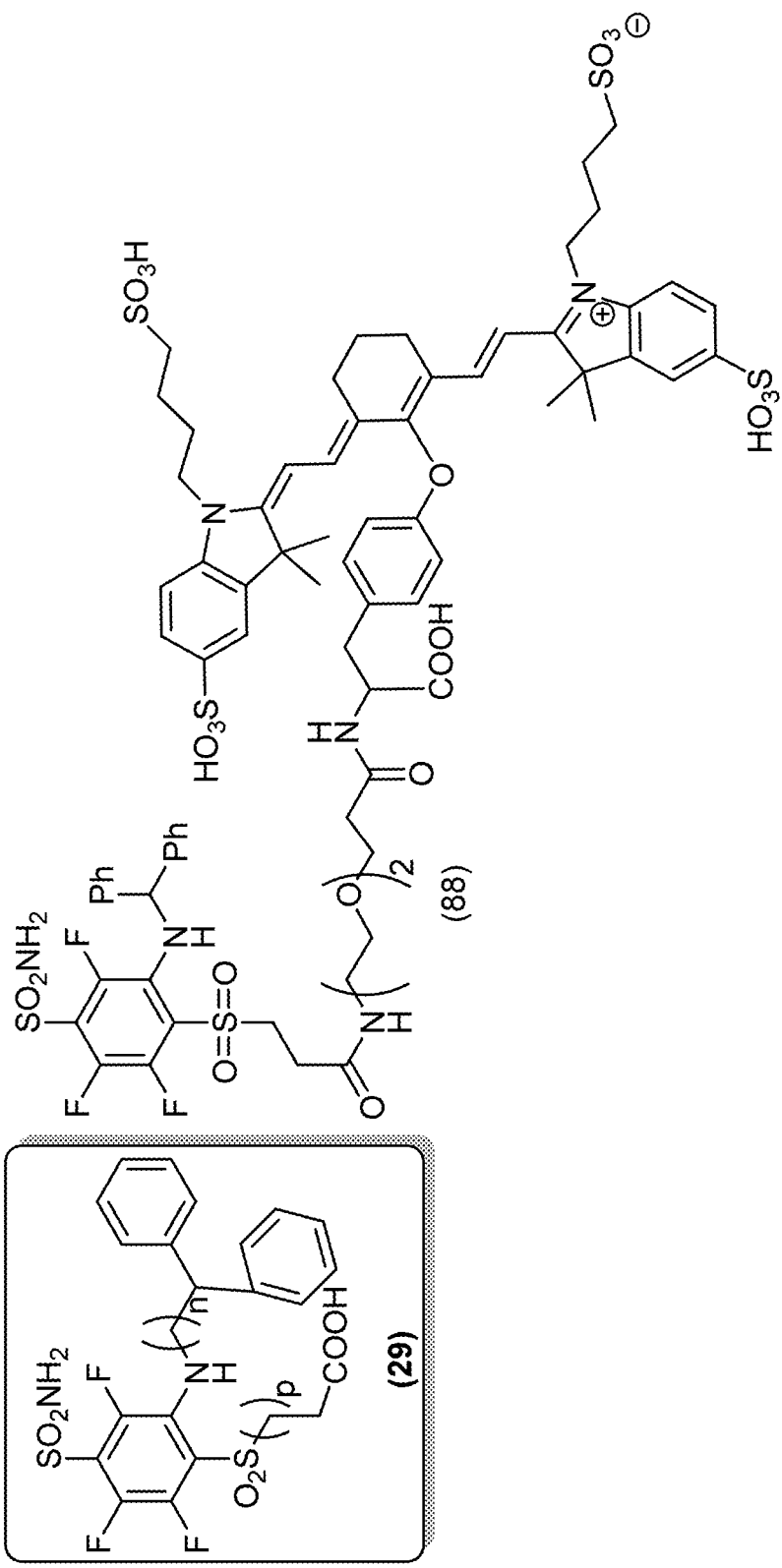
FIG. 29 shows the chemical structure of CA IX-Targeted NIR agents derived from the Ligands 29.

Example: (10) Preclinical Evaluation of Novel CA IX-Targeted NIR Agents Derived from Ligands 29 (FIG. 29)

Chemical Synthesis:

The compounds 88 was synthesized using similar methods as explain in the Example 1-3.

Figure 30:
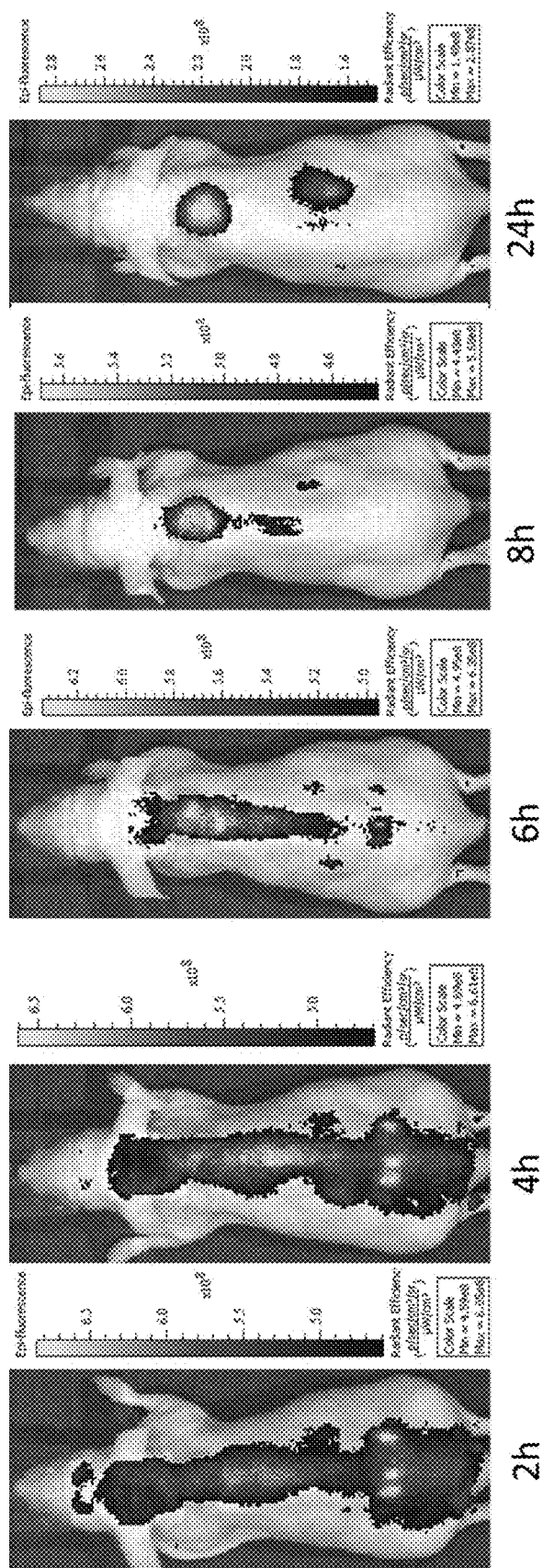
FIG. 30 shows an overlay of whole body fluorescence image over white light images after adjusting the threshold. SKRC52 human renal tumor xenograft bearing mouse was injected with 10 nmol of 88 and imaged with IVIS imager (ex=745 nm, em=ICG, exposure time=1 s) at different time intervals.

FIG. 30 shows an overlay of whole body fluorescence image over white light images after adjusting the threshold. SKRC52 human renal tumor xenograft bearing mouse was injected with 10 nmol of 88 and imaged with IVIS imager (ex=745 nm, em=ICG, exposure time=1 s) at different time intervals Conclusion: These in vivo tumor accumulation data demonstrated that the compound 88 showed good whole-body imaging data after 8 hours of administering to the animal. In addition, the compound 88 showed excellent tumor-to-background ratio (TBR) and tumor-to-skin ratio at 24 hour time point. The compound 88 also may be useful both as clinical and/or experimental candidates.

Figure 31:
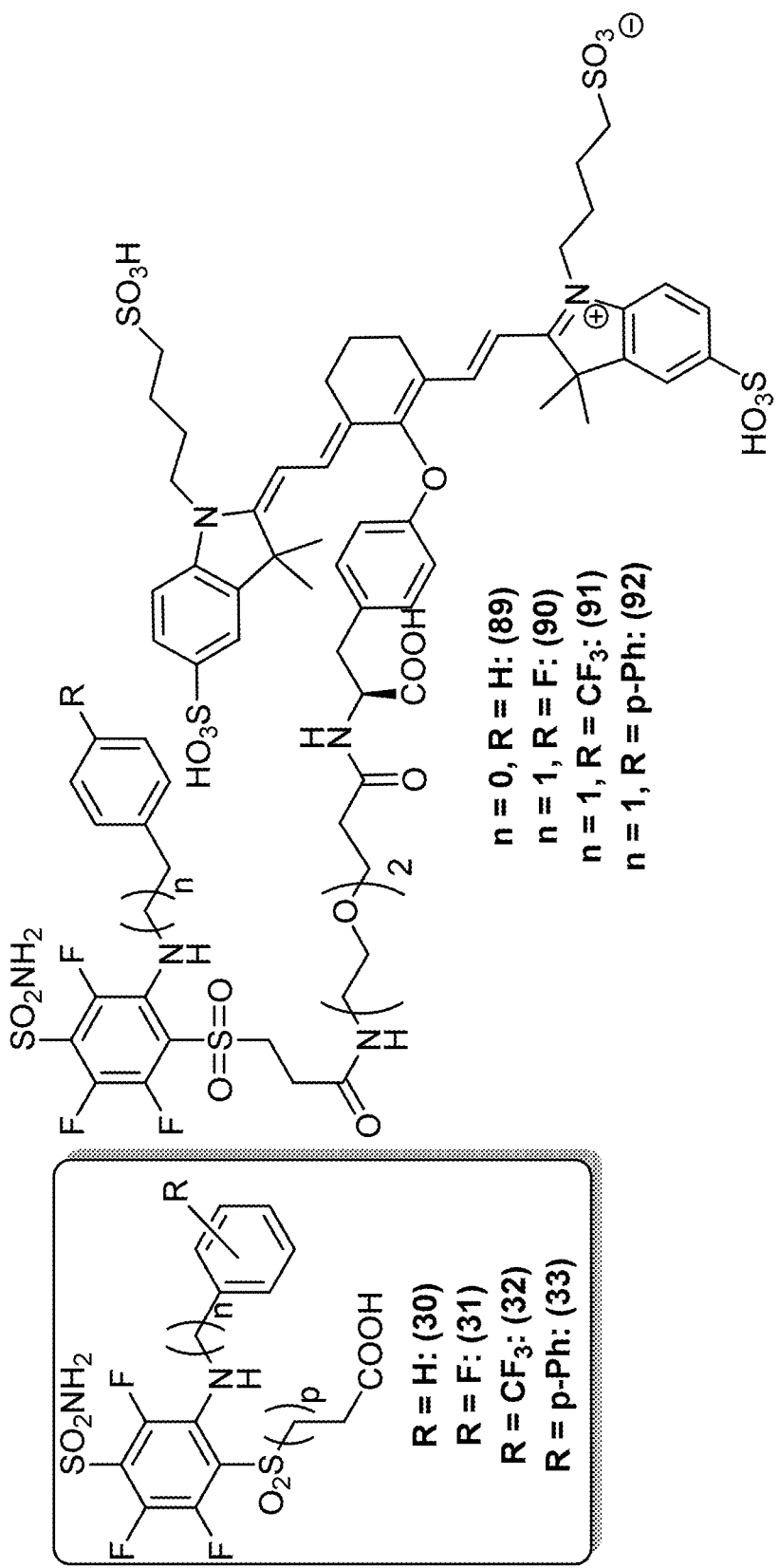
FIG. 31 shows the chemical structure of CA IX-Targeted NIR agents derived from the Ligands 30-33.

Example: (11) Preclinical Evaluation of Novel CA IX-Targeted NIR Agents Derived from Ligands 30-33 (FIG. 31)

Chemical Synthesis:

The compounds 89-92 were synthesized using similar methods as explain in the Example 1-3.

Figure 32:
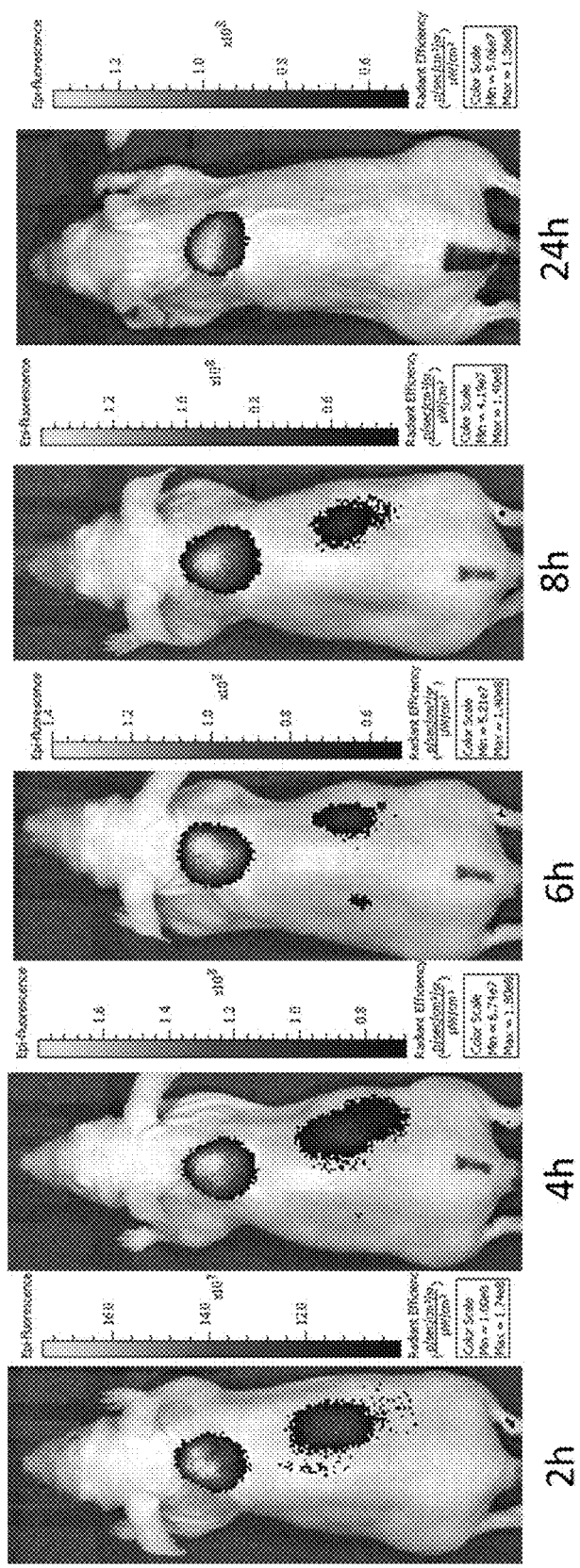
FIG. 32 shows an overlay of whole body fluorescence image over white light images after adjusting the threshold. SKRC52 human renal tumor xenograft bearing mouse was injected with 10 nmol of 89 and imaged with IVIS imager (ex=745 nm, em=ICG, exposure time=1 s) at different time intervals.
Figure 33:
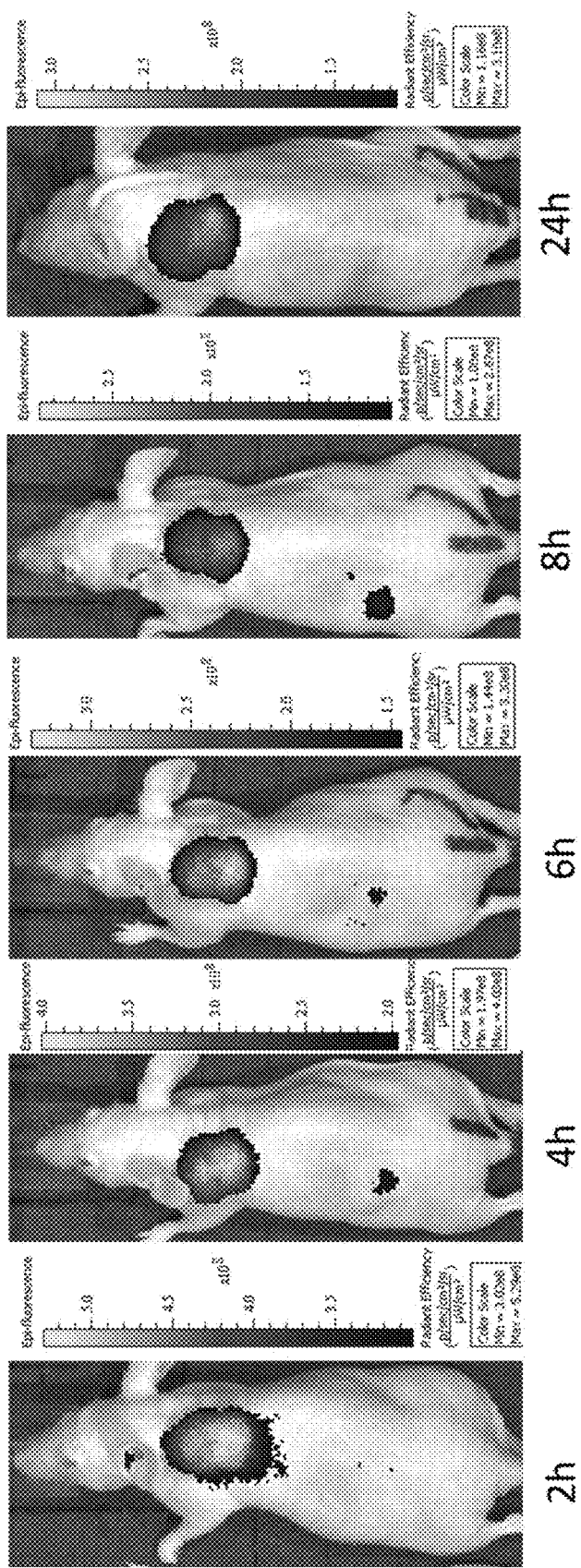
FIG. 33 shows an overlay of whole body fluorescence image over white light images after adjusting the threshold. SKRC52 human renal tumor xenograft bearing mouse was injected with 10 nmol of 90 and imaged with IVIS imager (ex=745 nm, em=ICG, exposure time=1 s) at different time intervals.

FIG. 32 shows an overlay of whole body fluorescence image over white light images after adjusting the threshold. SKRC52 human renal tumor xenograft bearing mouse was injected with 10 nmol of 89 and imaged with IVIS imager (ex=745 nm, em=ICG, exposure time=1 s) at different time intervals FIG. 33 shows an overlay of whole body fluorescence image over white light images after adjusting the threshold. SKRC52 human renal tumor xenograft bearing mouse was injected with 10 nmol of 90 and imaged with IVIS imager (ex=745 nm, em=ICG, exposure time=1 s) at different time intervals Conclusion: These in vivo tumor accumulation data demonstrated that both 89 and 90 showed very good whole-body imaging data within 2-24 hours after administering to the animal. In addition, the compounds showed excellent tumor-to-background ratio (TBR) and tumor-to-skin ratio with very high accumulation retained in the tumor maintaining very high fluorescence over 24 hours. These compounds also may be useful both as clinical and/or experimental candidates.

Figure 34:
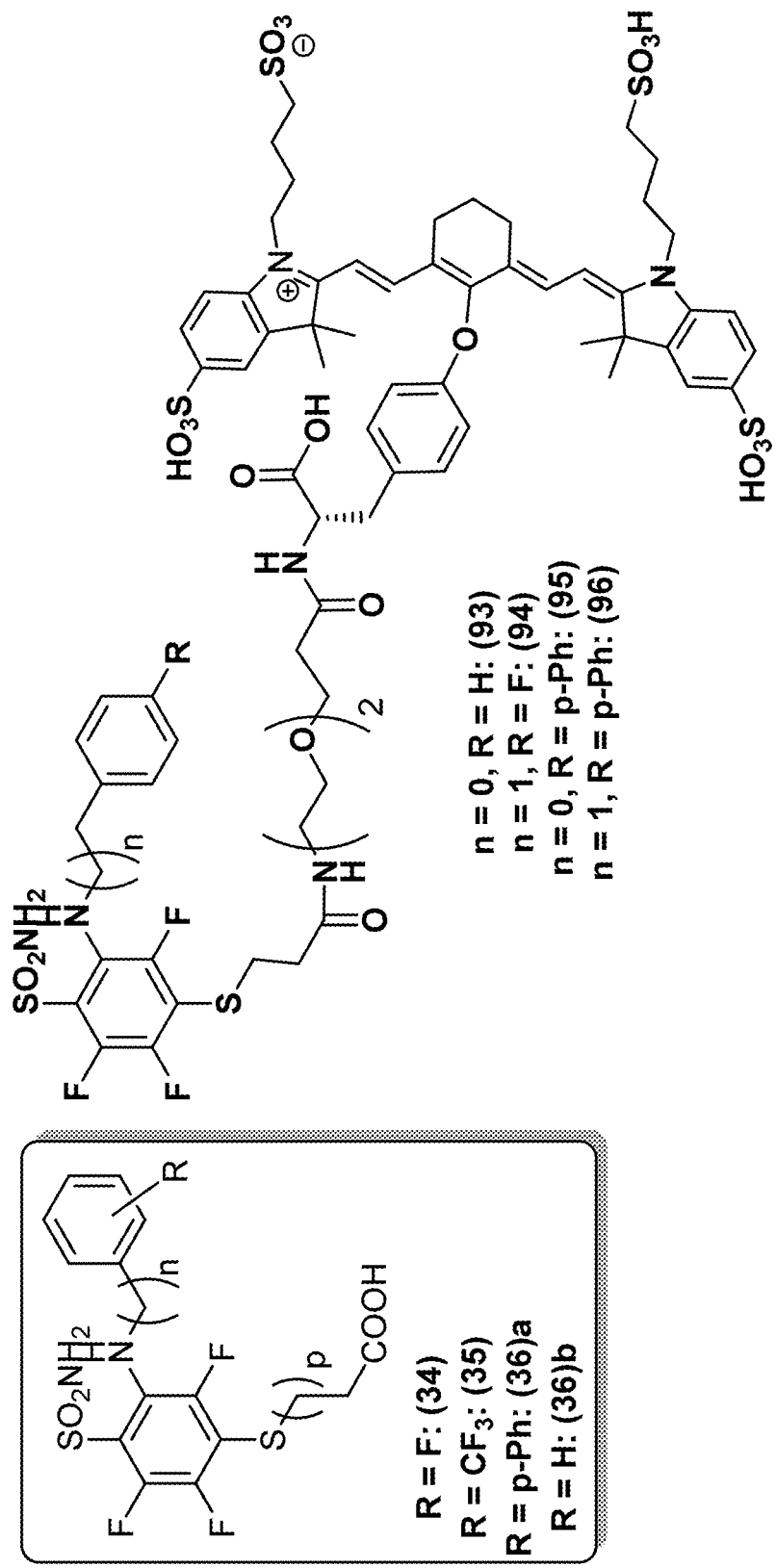
FIG. 34 shows the chemical structure of CA IX-Targeted NIR agents derived from the Ligands 34-36.

Example: (12) Preclinical Evaluation of Novel CA IX-Targeted NIR Agents Derived from Ligands 34-36 (FIG. 34)

Chemical Synthesis:

Both the compounds 93-96 were synthesized using similar methods as explain in the Example 1-3.

Figure 35:
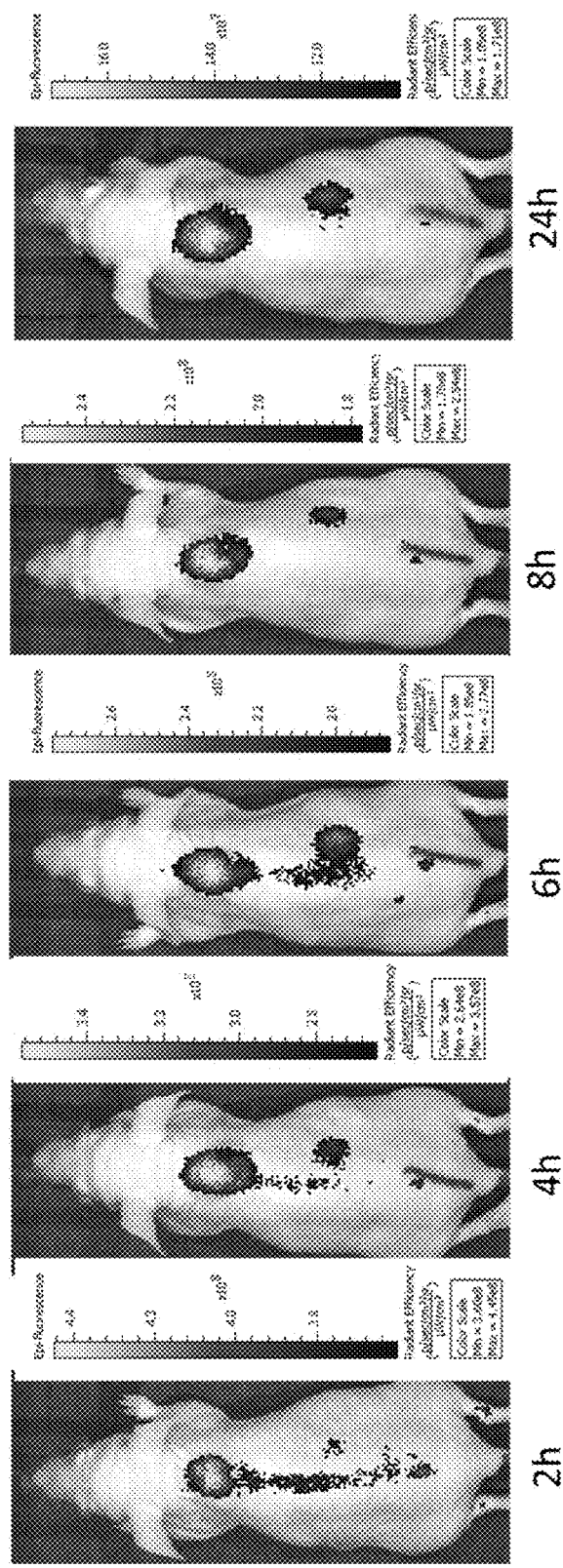
FIG. 35 shows an overlay of whole body fluorescence image over white light images after adjusting the threshold. SKRC52 human renal tumor xenograft bearing mouse was injected with 10 nmol of 93 and imaged with IVIS imager (ex=745 nm, em=ICG, exposure time=1 s) at different time intervals.
Figure 36:
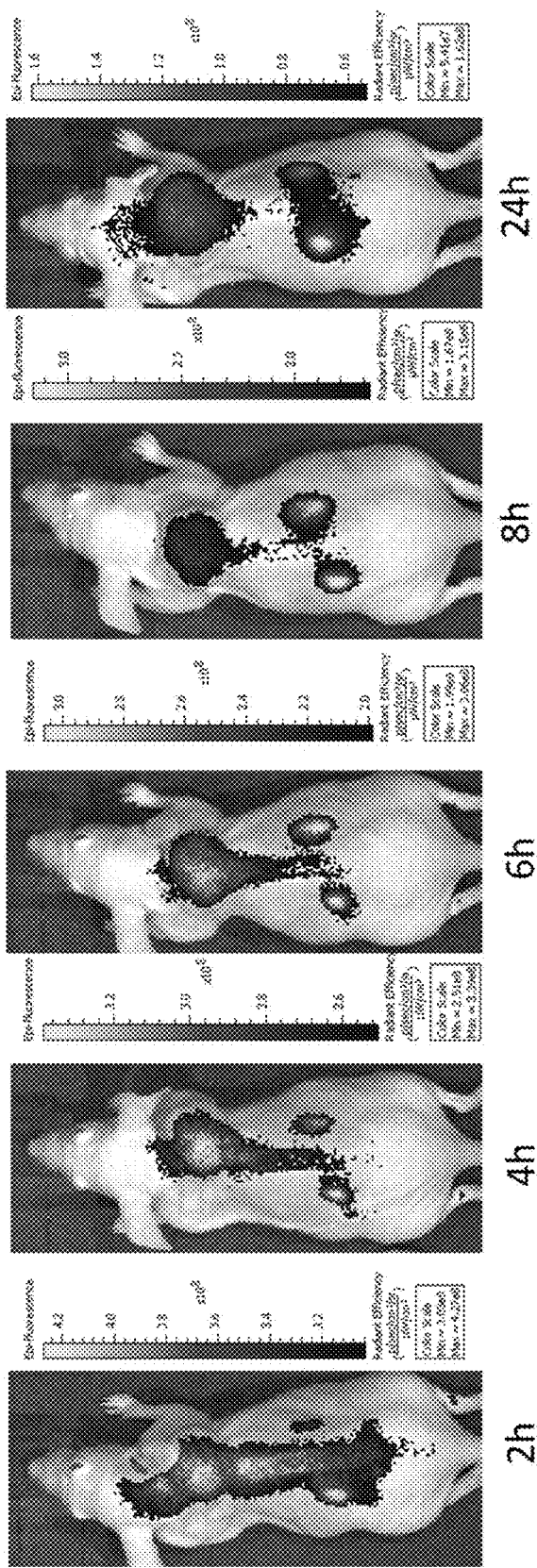
FIG. 36 shows an overlay of whole body fluorescence image over white light images after adjusting the threshold. SKRC52 human renal tumor xenograft bearing mouse was injected with 10 nmol of 94 and imaged with IVIS imager (ex=745 nm, em=ICG, exposure time=1 s) at different time intervals.
Figure 37:
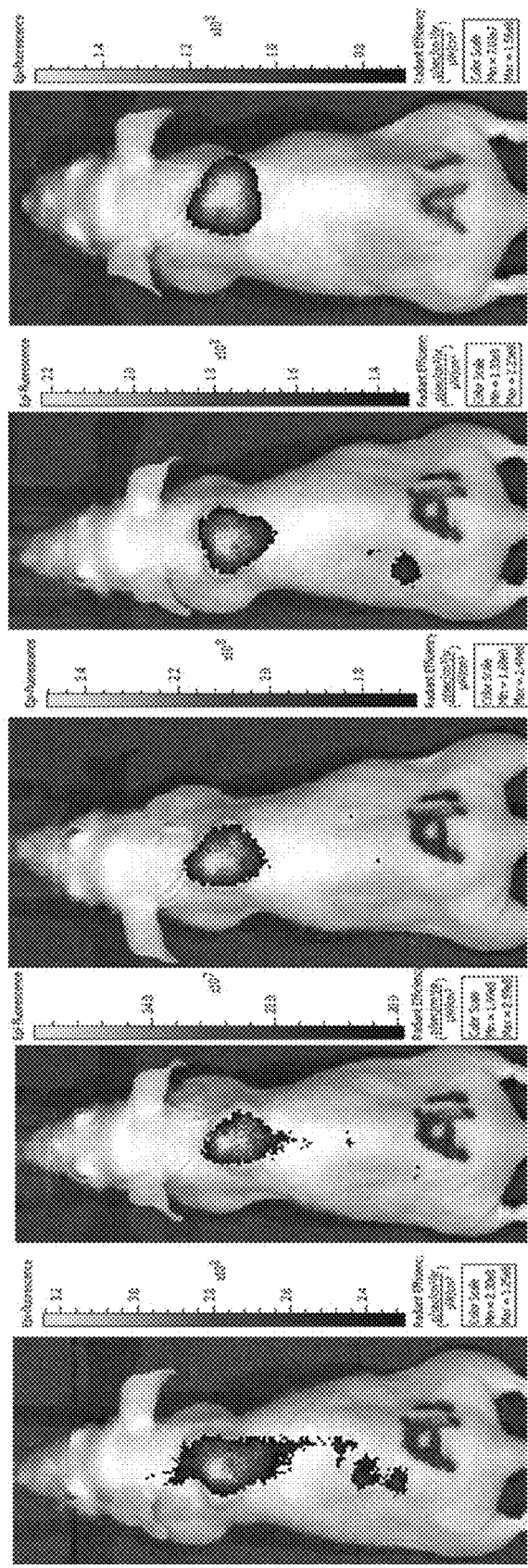
FIG. 37 shows an overlay of whole body fluorescence image over white light images after adjusting the threshold. SKRC52 human renal tumor xenograft bearing mouse was injected with 10 nmol of 95 and imaged with IVIS imager (ex=745 nm, em=ICG, exposure time=1 s) at different time intervals.
Figure 38:
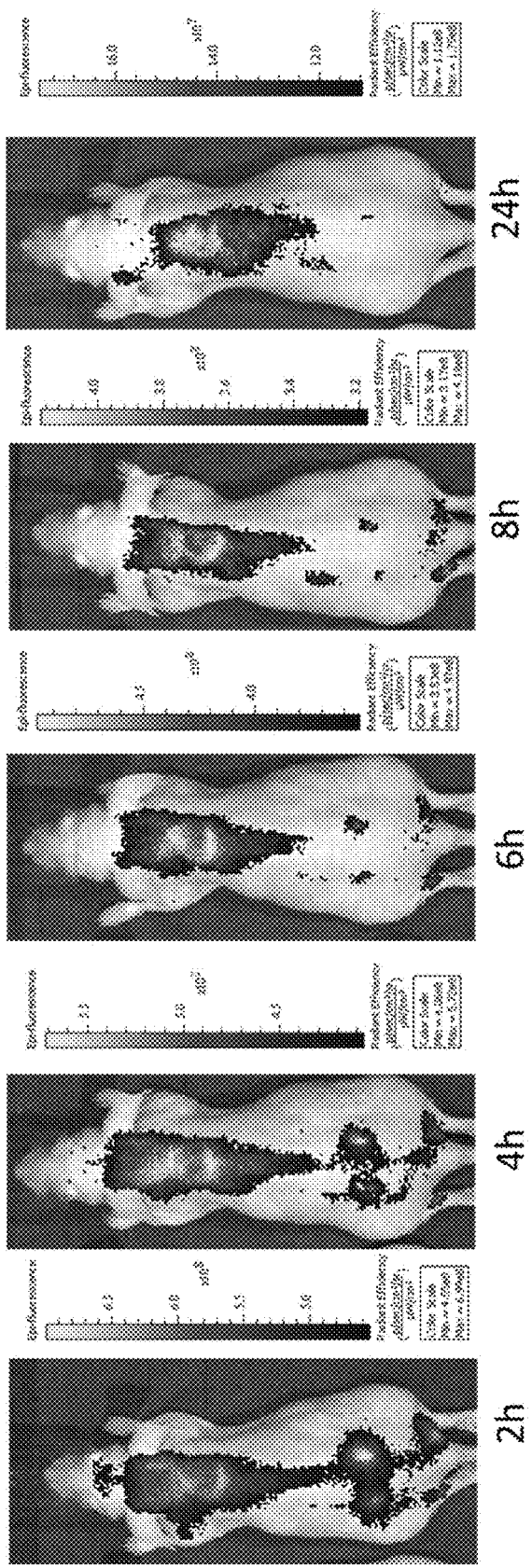
FIG. 38 shows an overlay of whole body fluorescence image over white light images after adjusting the threshold. SKRC52 human renal tumor xenograft bearing mouse was injected with 10 nmol of 96 and imaged with IVIS imager (ex=745 nm, em=ICG, exposure time=1 s) at different time intervals.

FIG. 35 shows an overlay of whole body fluorescence image over white light images after adjusting the threshold. SKRC52 human renal tumor xenograft bearing mouse was injected with 10 nmol of 93 and imaged with IVIS imager (ex=745 nm, em=ICG, exposure time=1 s) at different time intervals FIG. 36 shows an overlay of whole body fluorescence image over white light images after adjusting the threshold. SKRC52 human renal tumor xenograft bearing mouse was injected with 10 nmol of 94 and imaged with IVIS imager (ex=745 nm, em=ICG, exposure time=1 s) at different time intervals FIG. 37 shows an overlay of whole body fluorescence image over white light images after adjusting the threshold. SKRC52 human renal tumor xenograft bearing mouse was injected with 10 nmol of 95 and imaged with IVIS imager (ex=745 nm, em=ICG, exposure time=1 s) at different time intervals FIG. 38 shows an overlay of whole body fluorescence image over white light images after adjusting the threshold. SKRC52 human renal tumor xenograft bearing mouse was injected with 10 nmol of 96 and imaged with IVIS imager (ex=745 nm, em=ICG, exposure time=1 s) at different time intervals Conclusion: These in vivo tumor accumulation data demonstrated that the compounds 93 and 95 showed very good whole-body imaging data within 2-24 hours after administering to the animal. In addition, the compound 95 showed excellent tumor-to-background ratio (TBR) and tumor-to-skin ratio with very high accumulation retained in the tumor maintaining very high fluorescence over 24 hours. These compounds also may be useful both as clinical and/or experimental candidates.

Figure 39:
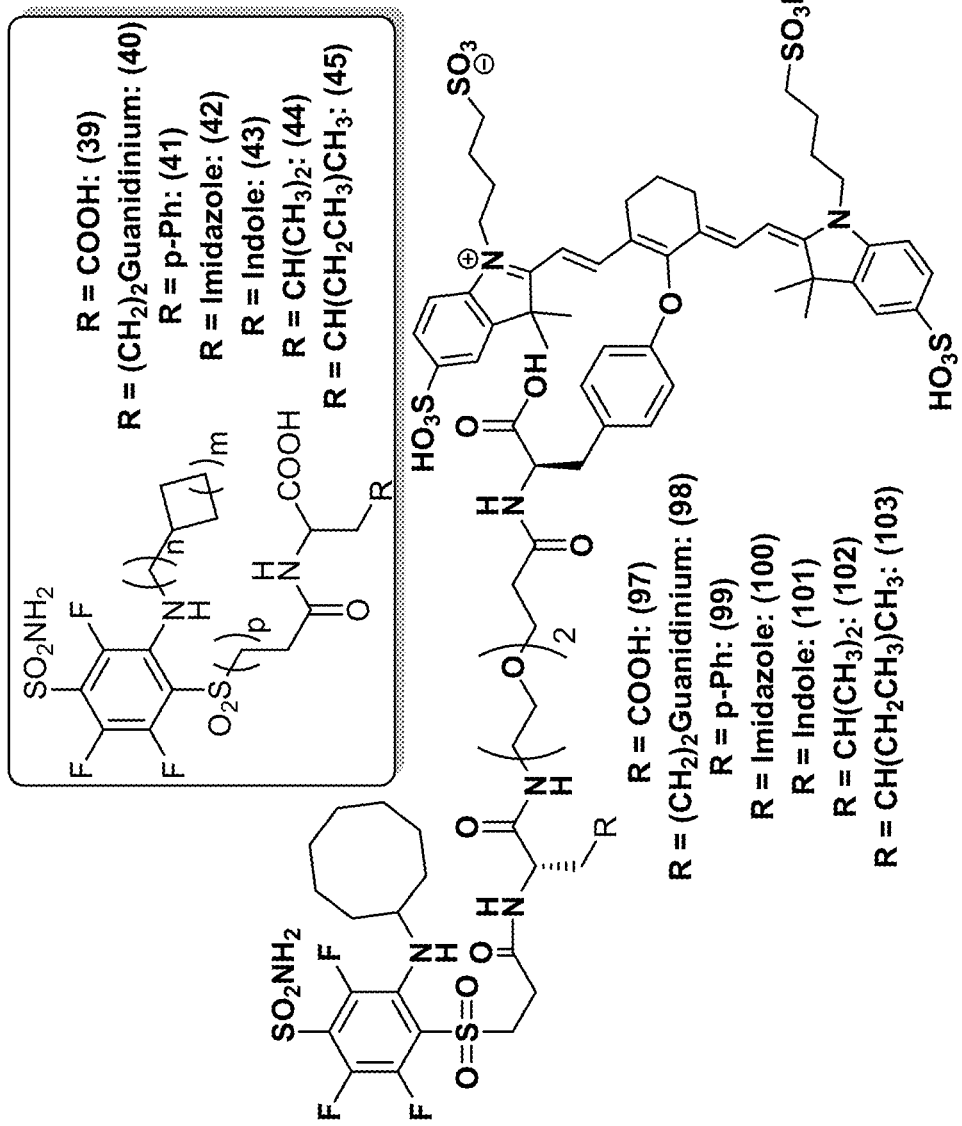
FIG. 39 shows the chemical structure of CA IX-Targeted NIR agents derived from the Ligands 39-45.

Example: (13) Preclinical Evaluation of Novel CA IX-Targeted NIR Agents Derived from Ligands 39-45 (FIG. 39)

Chemical Synthesis:

Both the compounds 97-103 were synthesized using similar methods as explain in the Example 1-3.

Figure 40:
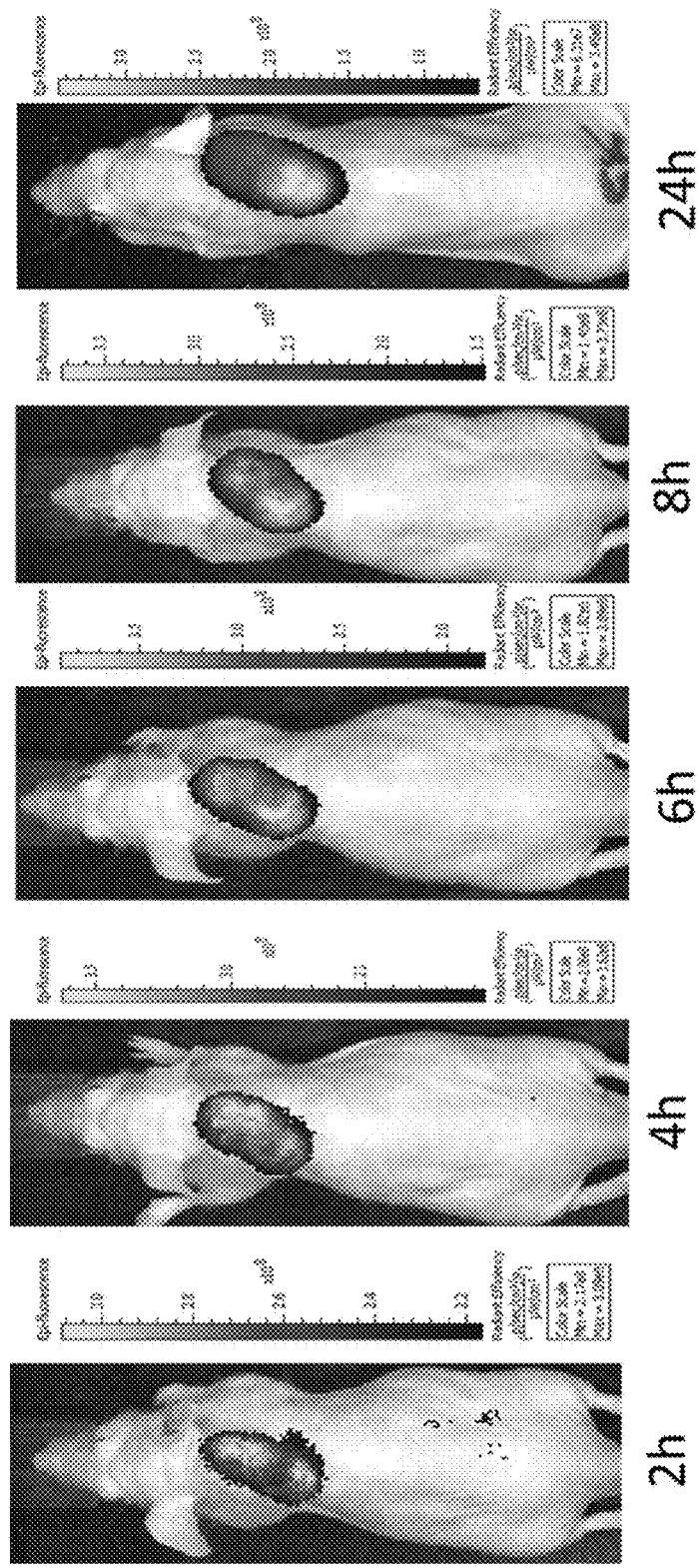
FIG. 40 shows an overlay of whole body fluorescence image over white light images after adjusting the threshold. SKRC52 human renal tumor xenograft bearing mouse was injected with 10 nmol of 99 and imaged with IVIS imager (ex=745 nm, em=ICG, exposure time=1 s) at different time intervals.
Figure 41:
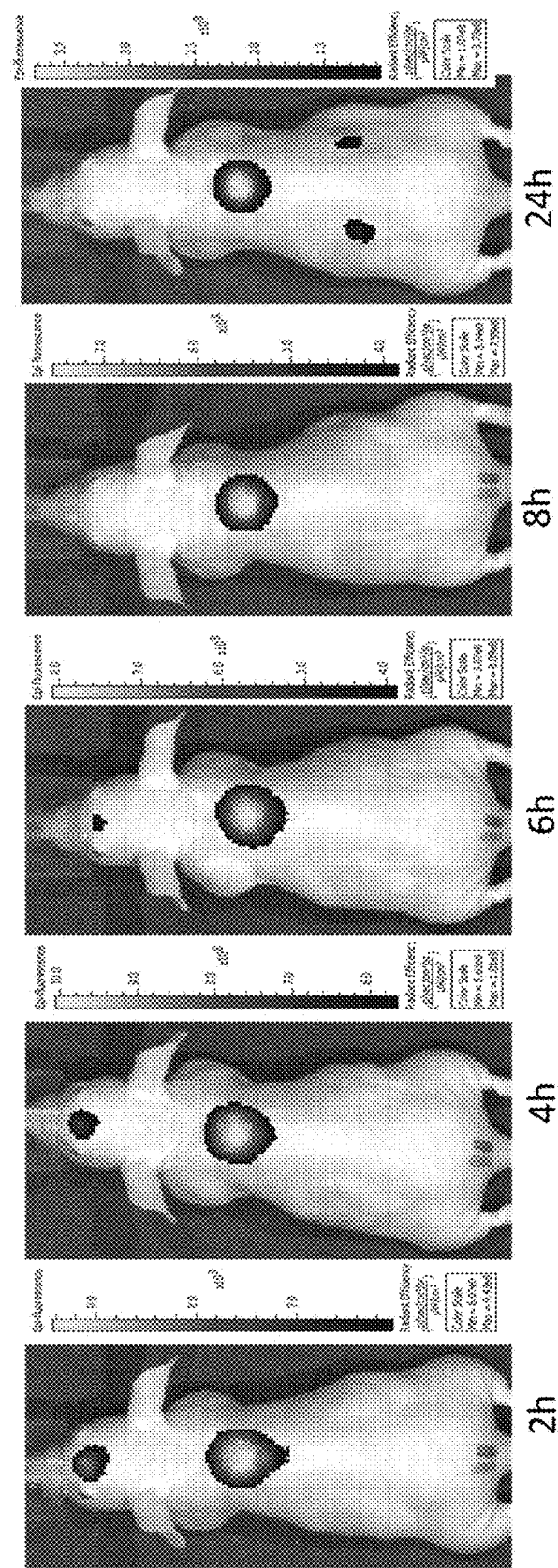
FIG. 41 shows an overlay of whole body fluorescence image over white light images after adjusting the threshold. SKRC52 human renal tumor xenograft bearing mouse was injected with 10 nmol of 102 and imaged with IVIS imager (ex=745 nm, em=ICG, exposure time=1 s) at different time intervals.

FIG. 40 shows an overlay of whole body fluorescence image over white light images after adjusting the threshold. SKRC52 human renal tumor xenograft bearing mouse was injected with 10 nmol of 99 and imaged with IVIS imager (ex=745 nm, em=ICG, exposure time=1 s) at different time intervals FIG. 41 shows an overlay of whole body fluorescence image over white light images after adjusting the threshold. SKRC52 human renal tumor xenograft bearing mouse was injected with 10 nmol of 102 and imaged with IVIS imager (ex=745 nm, em=ICG, exposure time=1 s) at different time intervals Conclusion: These in vivo tumor accumulation data demonstrated that both 99 and 102 showed very good whole-body imaging data within 2-24 hours after administering to the animal. In addition, the both compounds showed excellent tumor-to-background ratio (TBR) and tumor-to-skin ratio with very high accumulation retained in the tumor maintaining very high fluorescence over 24 hours. These compounds also may be useful both as clinical and/or experimental candidates.

Figure 42:
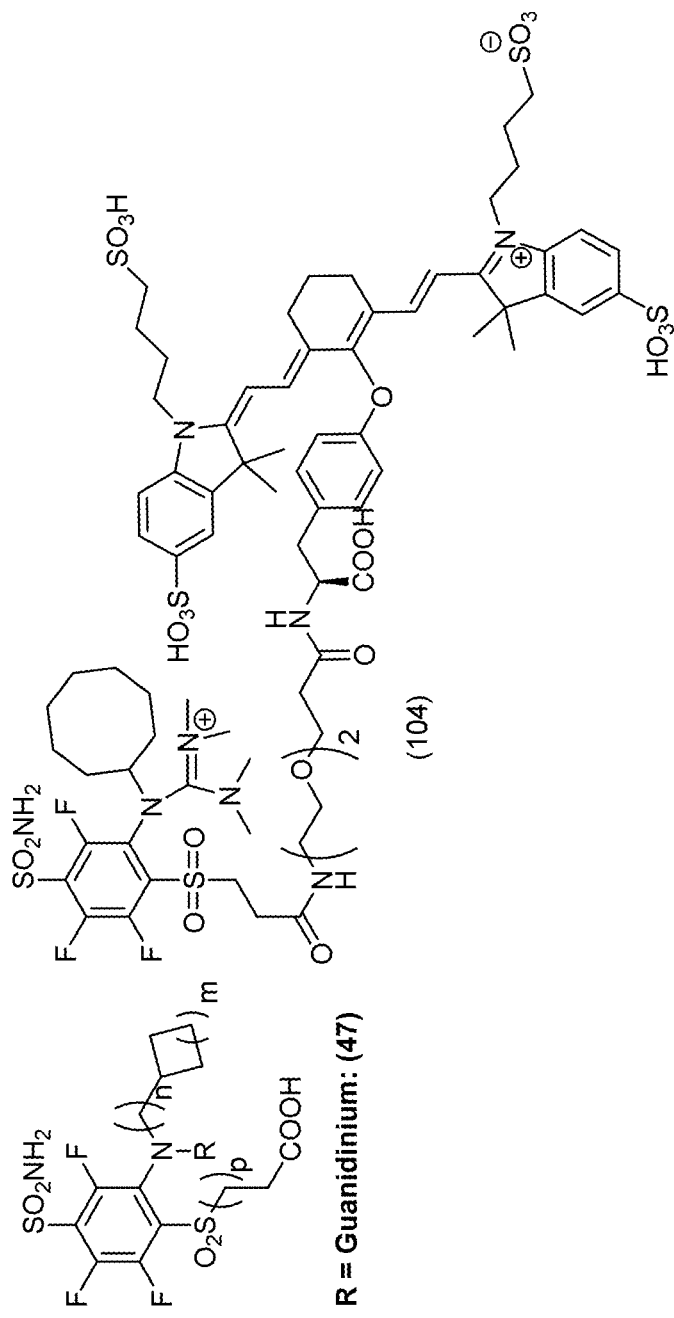
FIG. 42 shows the chemical structure of CA IX-Targeted NIR agents derived from the Ligands 47.

Example: (14) Preclinical Evaluation of Novel CA IX-Targeted NIR Agents Derived from Ligand 47 (FIG. 42)

Chemical Synthesis:

Both the compounds 104 were synthesized using similar methods as explain in the Example 1-3.

Figure 43:
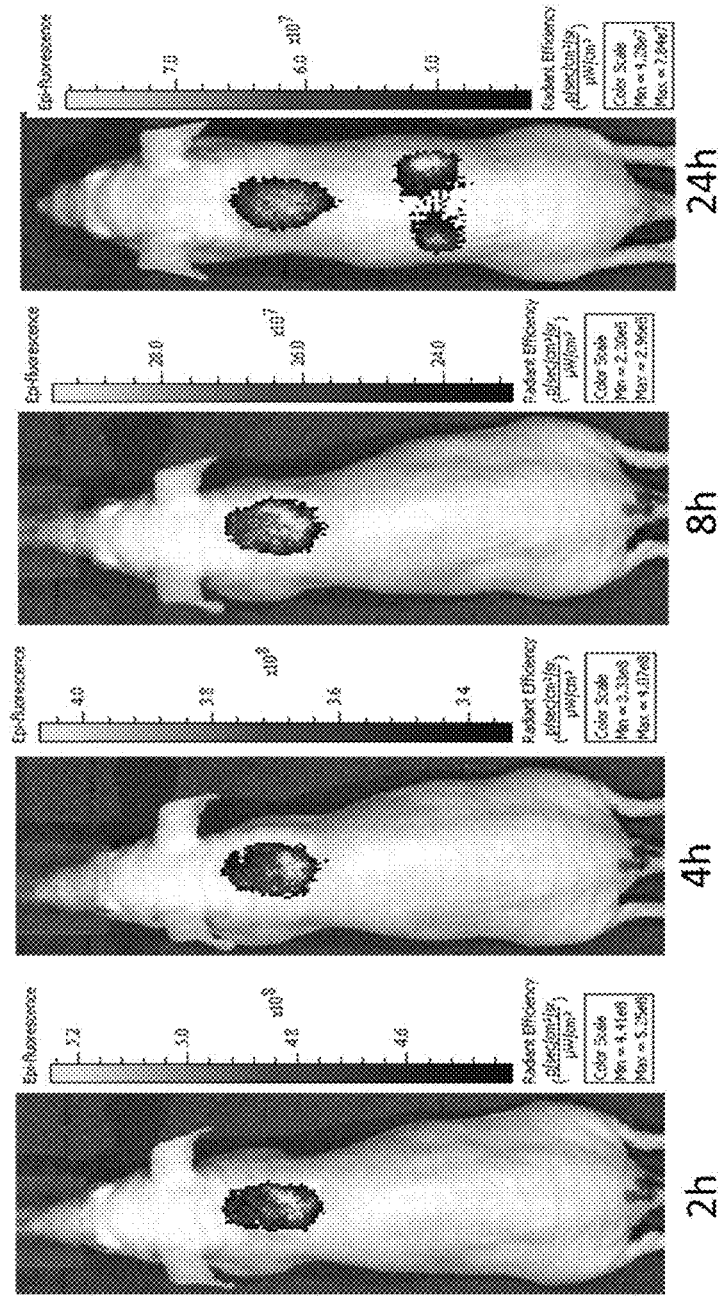
FIG. 43 shows an overlay of whole body fluorescence image over white light images after adjusting the threshold. SKRC52 human renal tumor xenograft bearing mouse was injected with 10 nmol of 104 and imaged with IVIS imager (ex=745 nm, em=ICG, exposure time=1 s) at different time intervals.

FIG. 43 shows an overlay of whole body fluorescence image over white light images after adjusting the threshold. SKRC52 human renal tumor xenograft bearing mouse was injected with 10 nmol of 104 and imaged with IVIS imager (ex=745 nm, em=ICG, exposure time=1 s) at different time intervals Conclusion: These in vivo tumor accumulation data demonstrated that the compound 104 showed good whole-body imaging data within 2-24 hours after administering to the animal. In addition, the compound 104 showed excellent tumor-to-background ratio (TBR) and tumor-to-skin ratio with very high accumulation retained in the tumor maintaining very high fluorescence over 24 hours. The compound also may be useful both as clinical and/or experimental candidates.

Figure 44:
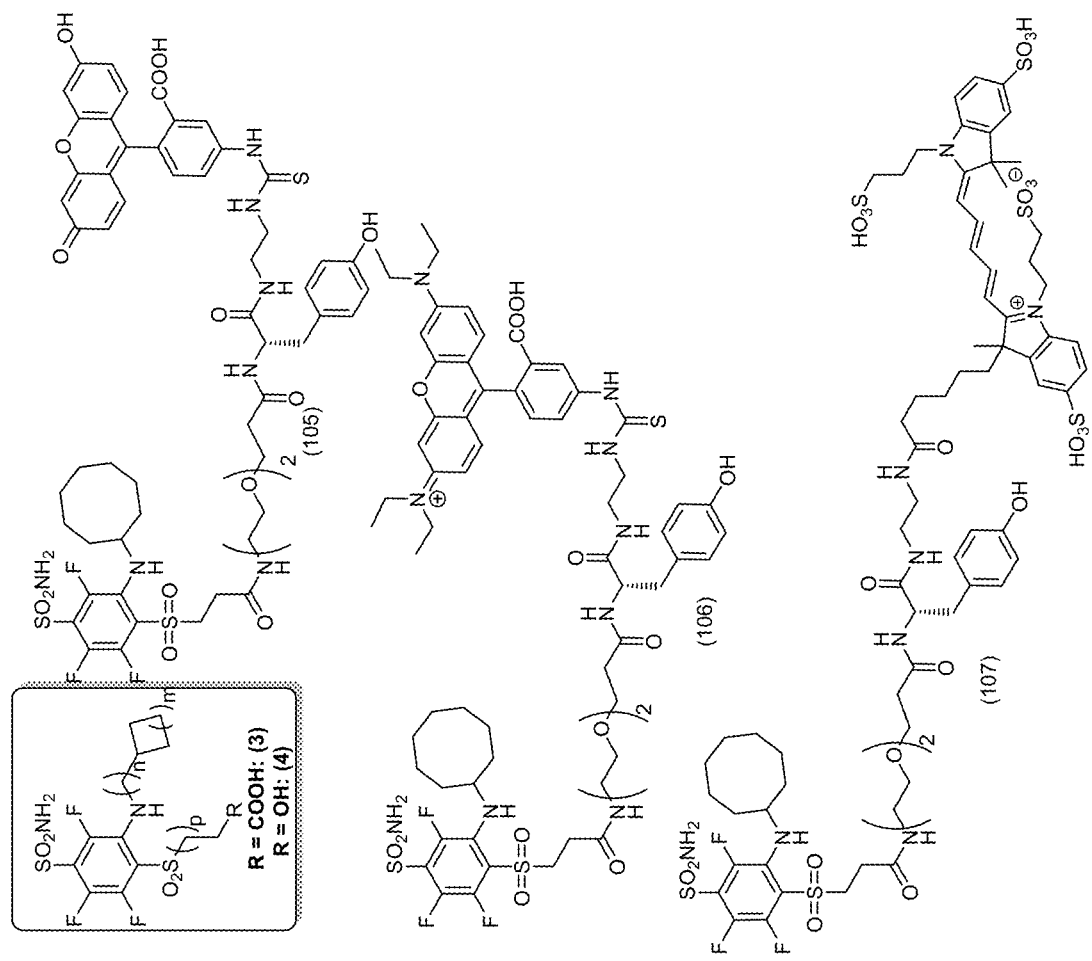
FIG. 44 shows the chemical structure of CA IX-Targeted NIR agents derived from the Ligands 3-4.

Example: (15) Preclinical Evaluation of Novel CA IX-Optical Imaging Agents Derived from Ligand 4 (FIG. 44)

Figure 45:
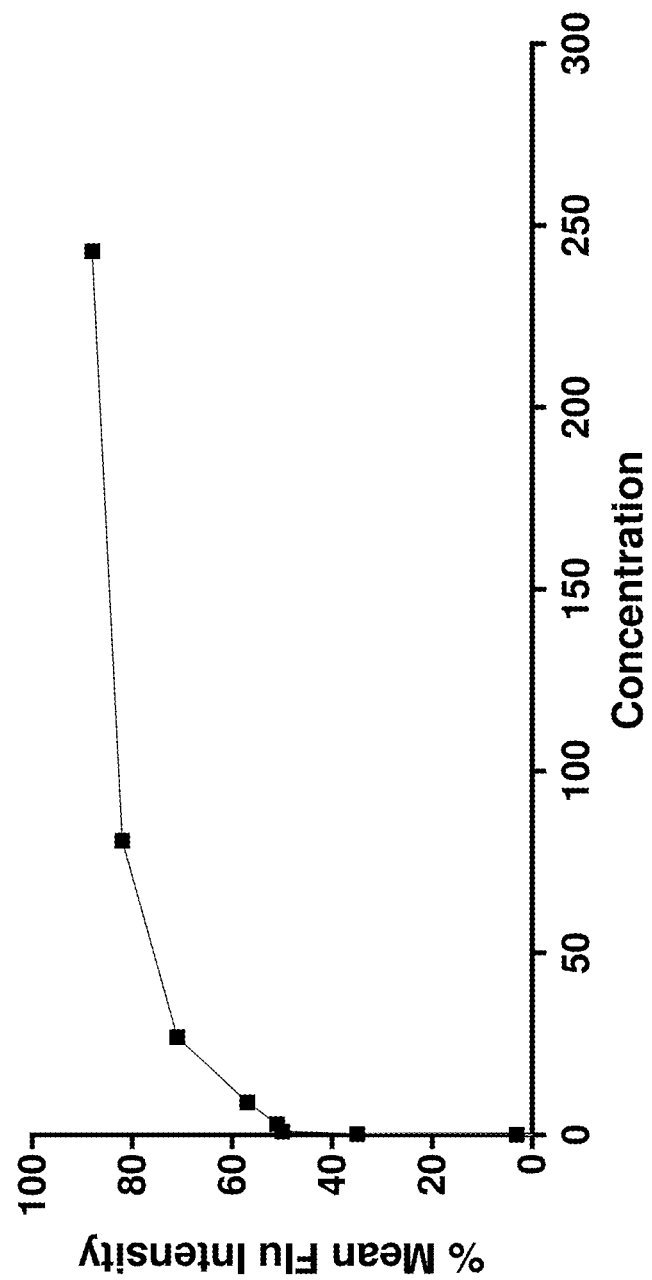
FIG. 45 shows the binding affinity of 105 to CA IX-positive SCRC52 cells using flow cytometry analysis.
Figure 46:
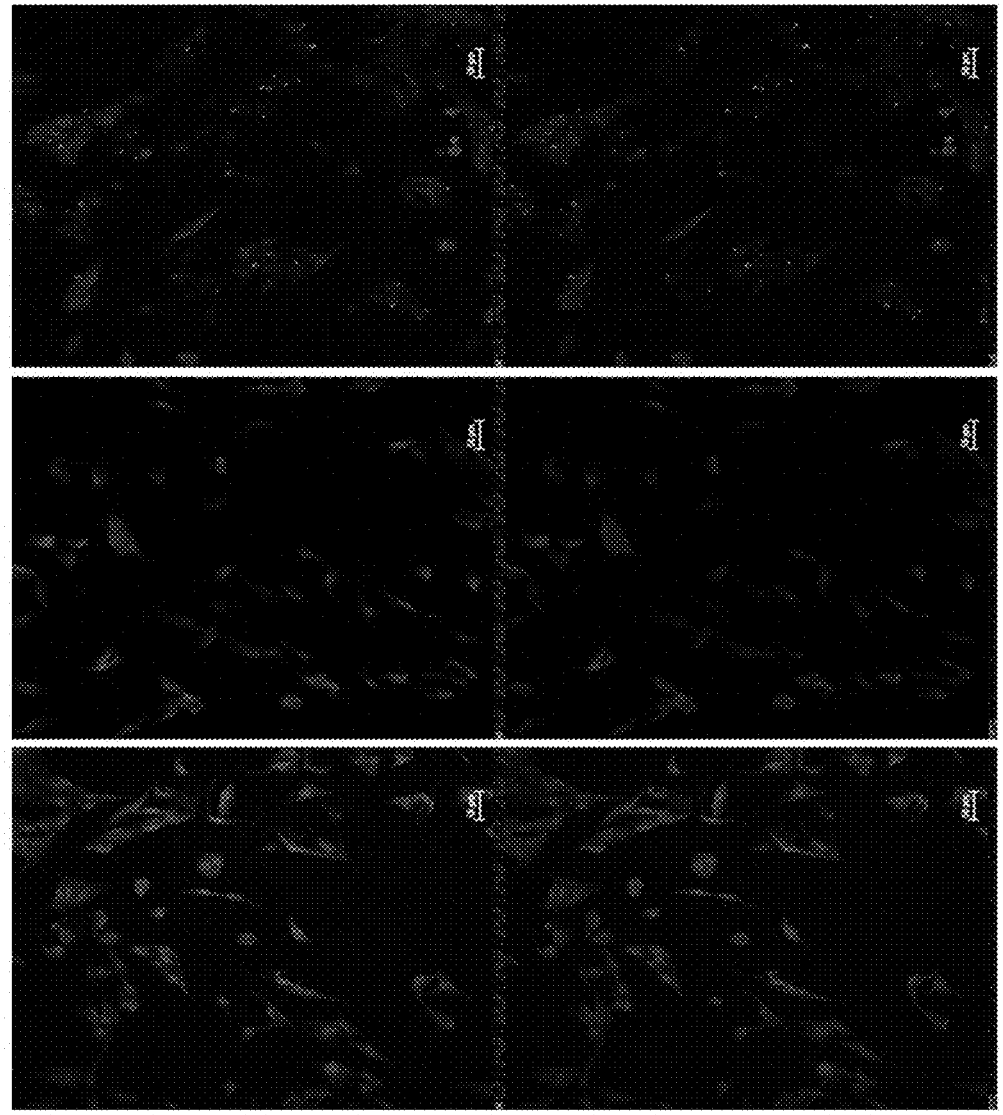
FIG. 46 shows the binding affinity of 105-107 to CA IX-positive SCRC52 cells using confocal microscopy.
Figure 47A:
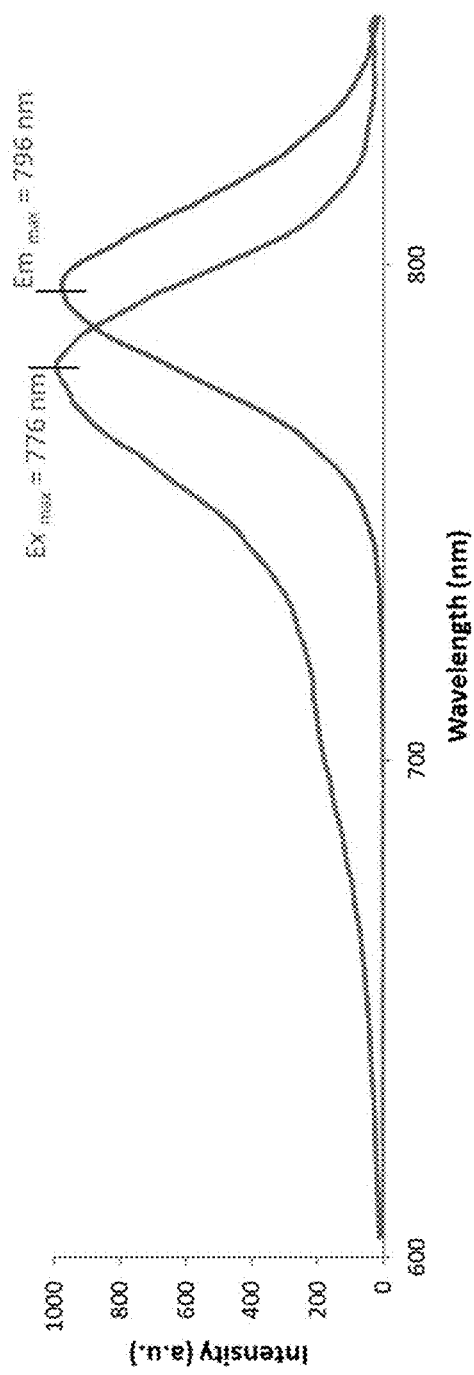
FIG. 47A illustrates the excitation and emission spectra of OTL410.
Figure 47B:
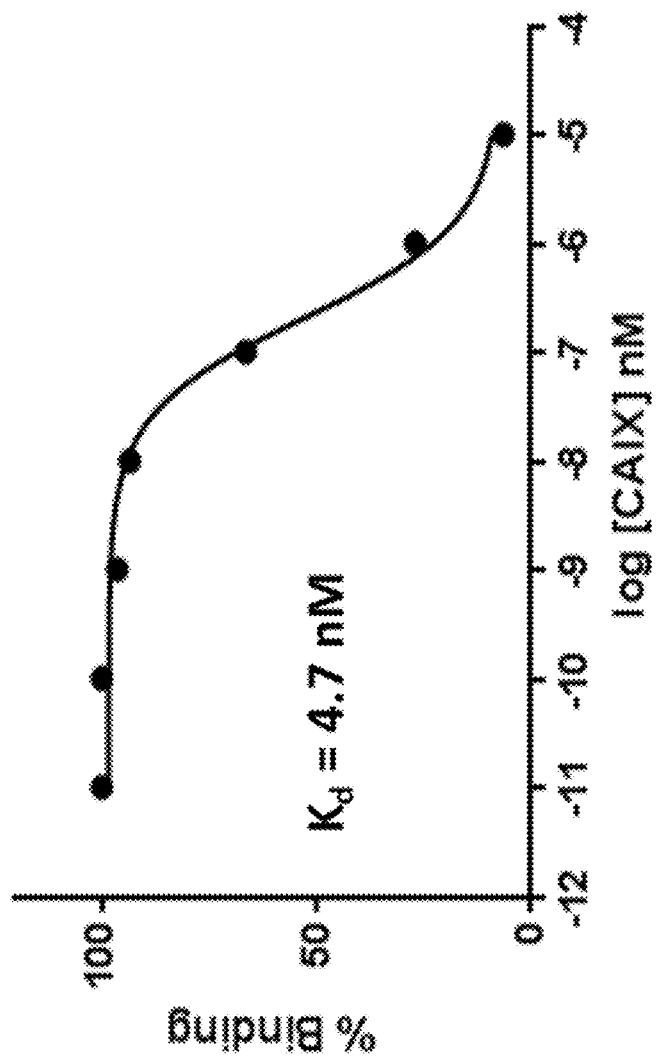
FIG. 47B illustrates competitive binding of OTL410 to SKRC52 cells in presence of 100 nM FITC-conjugated ligand monitored by FLOW cytometry.
Figure 47C:
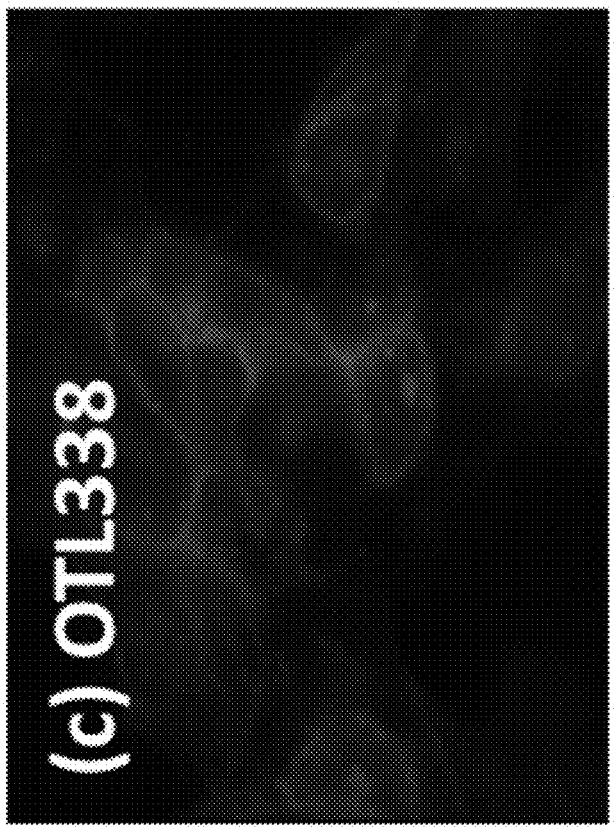
FIG. 47C illustrates uptake of OTL410 by SKRC cells in vitro demonstrated by fluorescence microscopy. SKRC52 cells were incubated with 100 nmols of OTL410 for 2 h, and fluorescence images were acquired after removing unbound conjugate, and washing cells 2× with media.
Figure 47D:
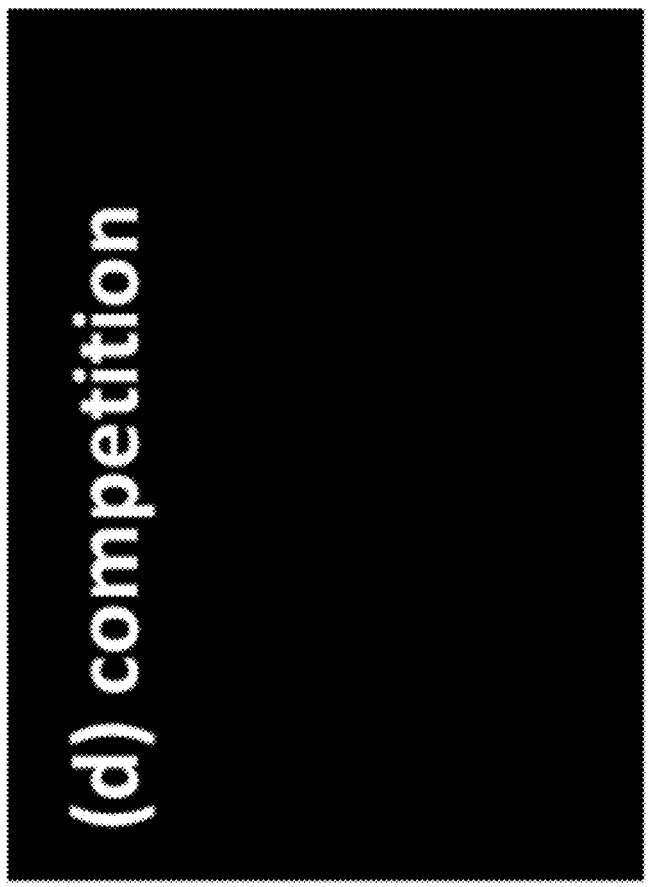
FIG. 47D illustrates in vitro competition of OTL410 by non-fluorescent ligand for binding of SKRC cells. Prior to acquisition of the image, cells were treated as described above except for the inclusion of 200× ligand in the media.
Figure 48A:
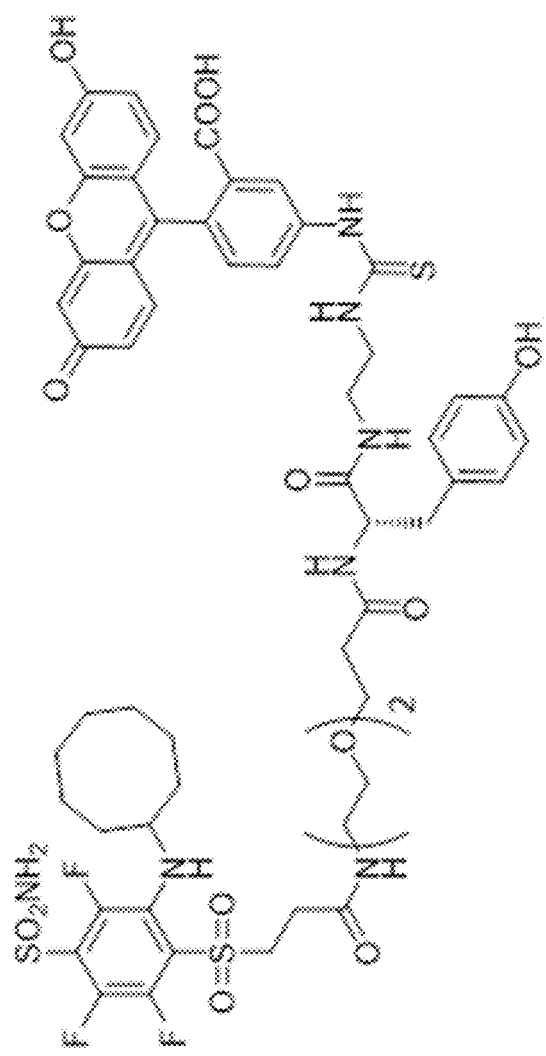
FIG. 48A illustrates the chemical structure of CA IX-ligand-Linker-FITC conjugate to SKRC52 cells.
Figure 48B:
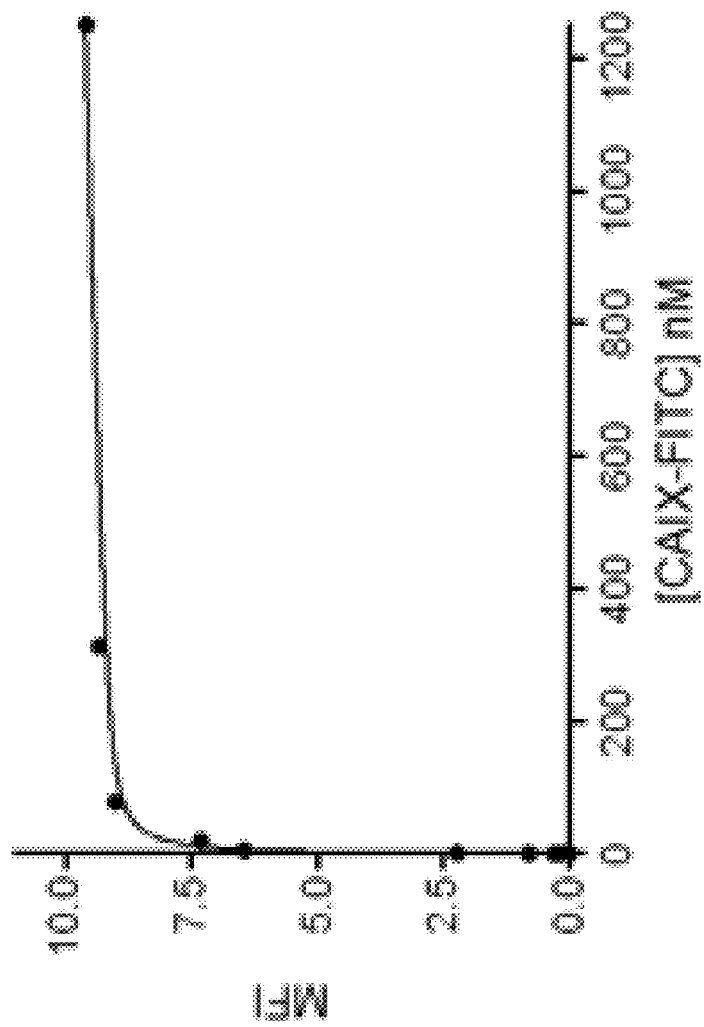
FIG. 48B illustrates the binding affinity of CA IX-ligand-Linker-FITC conjugate to SKRC52 cells.
Figure 49:
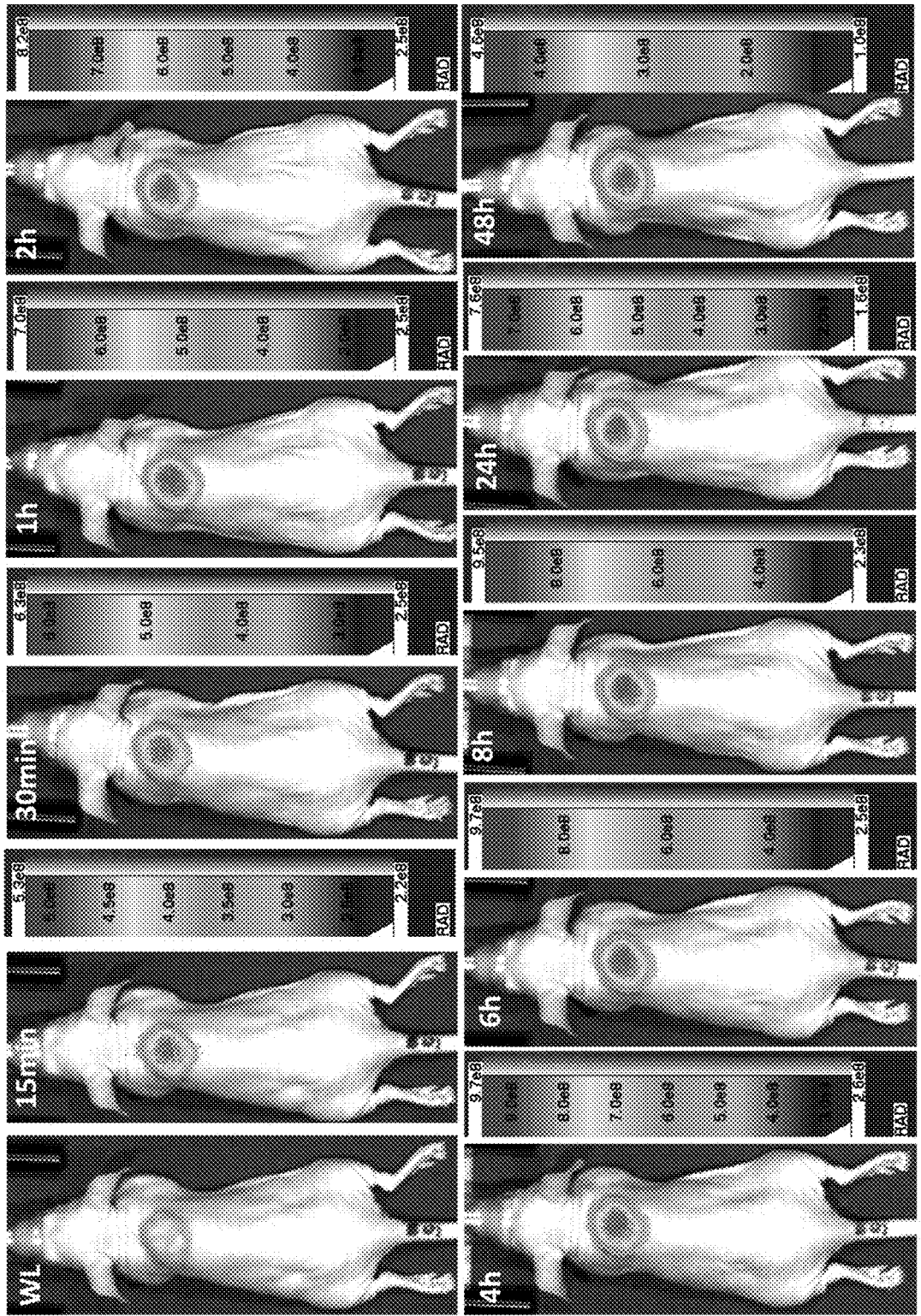
FIG. 49 illustrates the time course of tumor accumulation by OTL410 by fluorescence imaging of nude mice bearing SKRC52 xenografts. After intravenous administration of 1 nmol of the conjugate in 100 µl of 5% aqueous dextrose, mice were anesthetized by isoflurane right before collecting each image. Tumor accumulation is evident as early as 15 min after injection of the conjugate, reaching peak intensity by 4 h. No loss in fluorescence intensity is seen at 8 h, and ca 80% of peak intensity is maintained even after 24 h.
Figure 50:
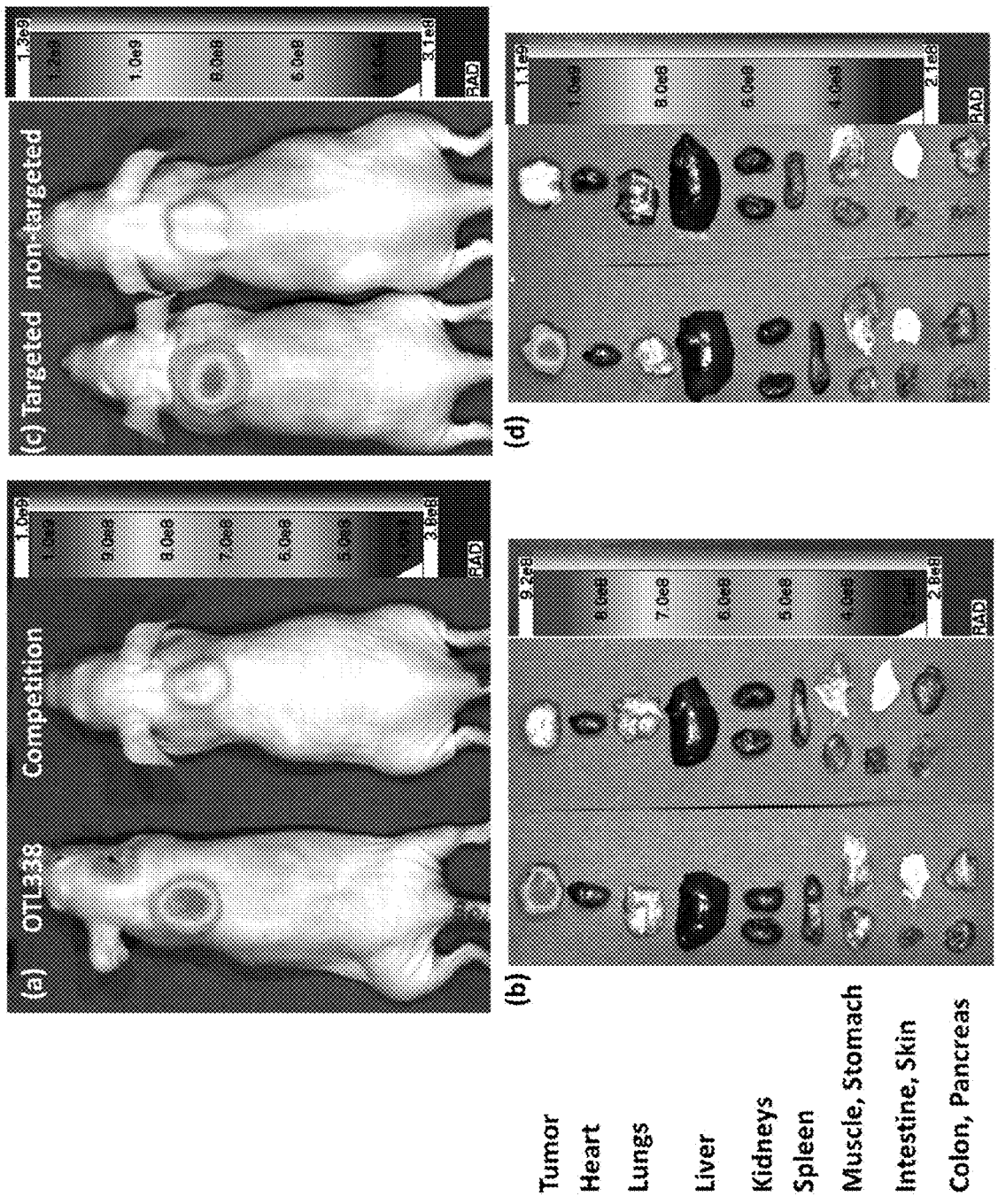
FIG. 50 illustrates the evaluation of in vivo specificity of OTL410 by fluorescence imaging. (a) Comparison of tumor accumulation of 1 nmol of OTL410 in the absence (left) and presence (right) of competing non-fluorescent ligand; (b) Biodistribution of OTL410 in the absence (left) and presence (right) of excess competing ligand; (c) Comparison of tumor uptake of 1 nmol of OTL410 (left) with 1 nmol of untargeted dye (right); (d) Biodistribution of OTL410 (left) and untargeted dye (right). The conjugate either alone or along with competing ligand was administered in 100 µl of 5% aqueous dextrose by tail vein injection, and the mice were euthanized by $CO_2$ inhalation 3 h post injection and the images were collected ex vivo (Ex=745 nm, Em=810 nm, FOV=25, binning 2, lamp power=55%).
Figure 51A:
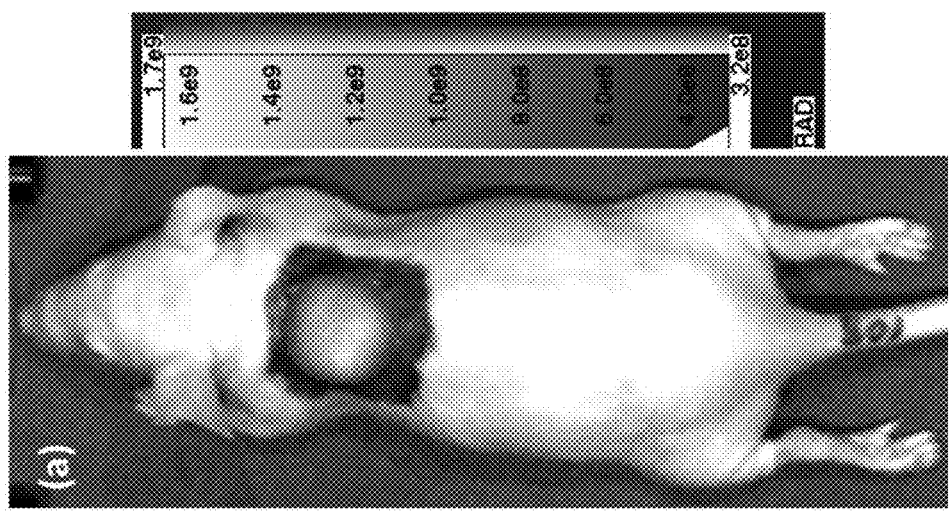
FIGS. 51A-51D illustrate the evaluation of TBR ratio from AMI fluorescence imaging and Image J analysis.
Figure 51B:
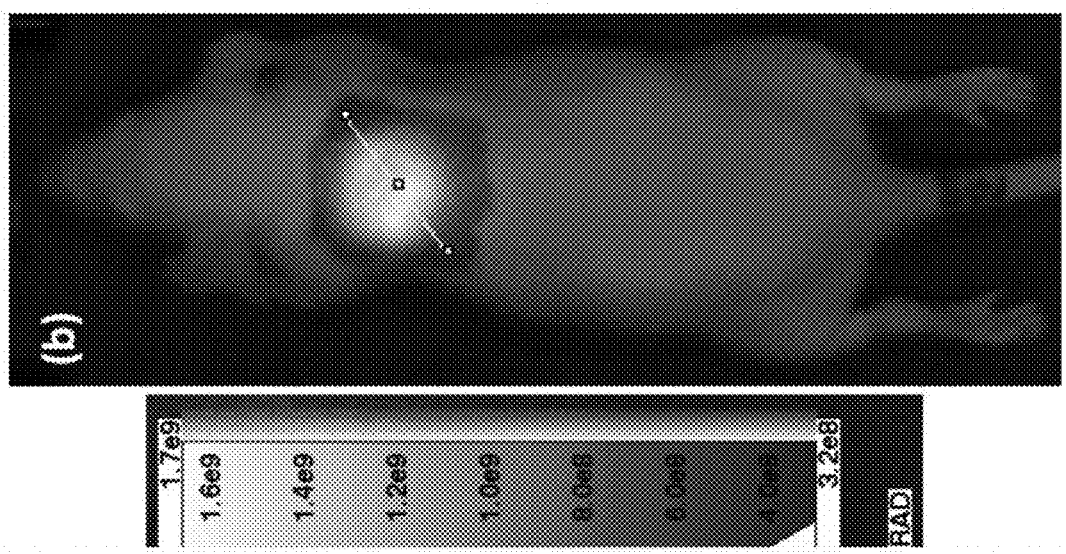
Figure 51C:
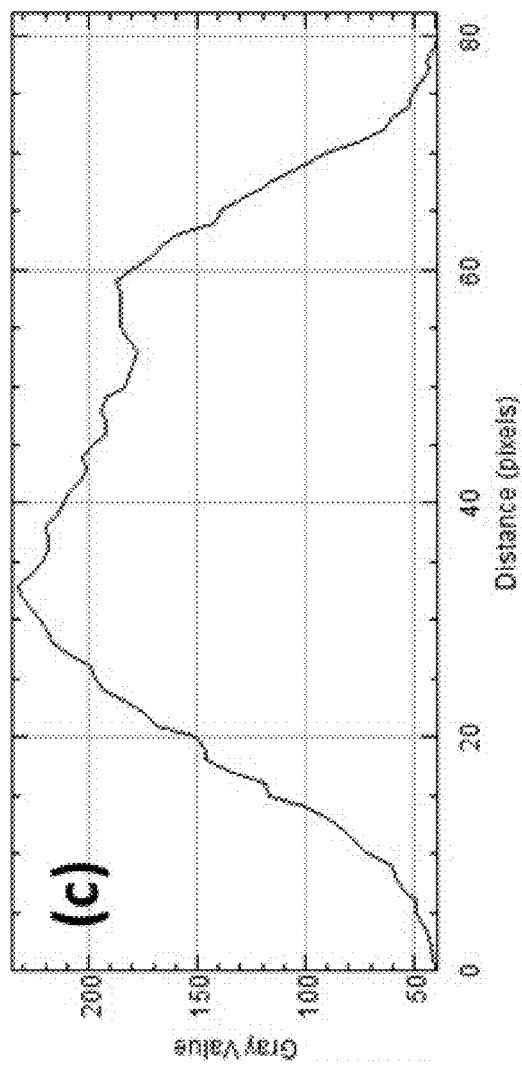
Figure 51D:
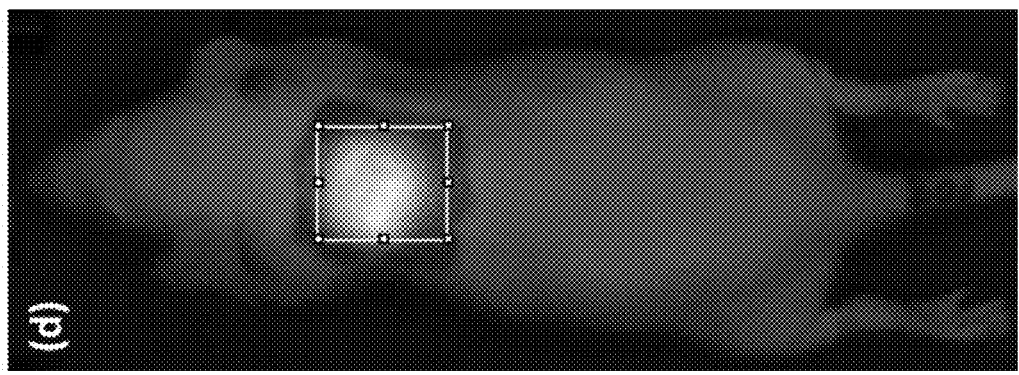
Figure 51E:
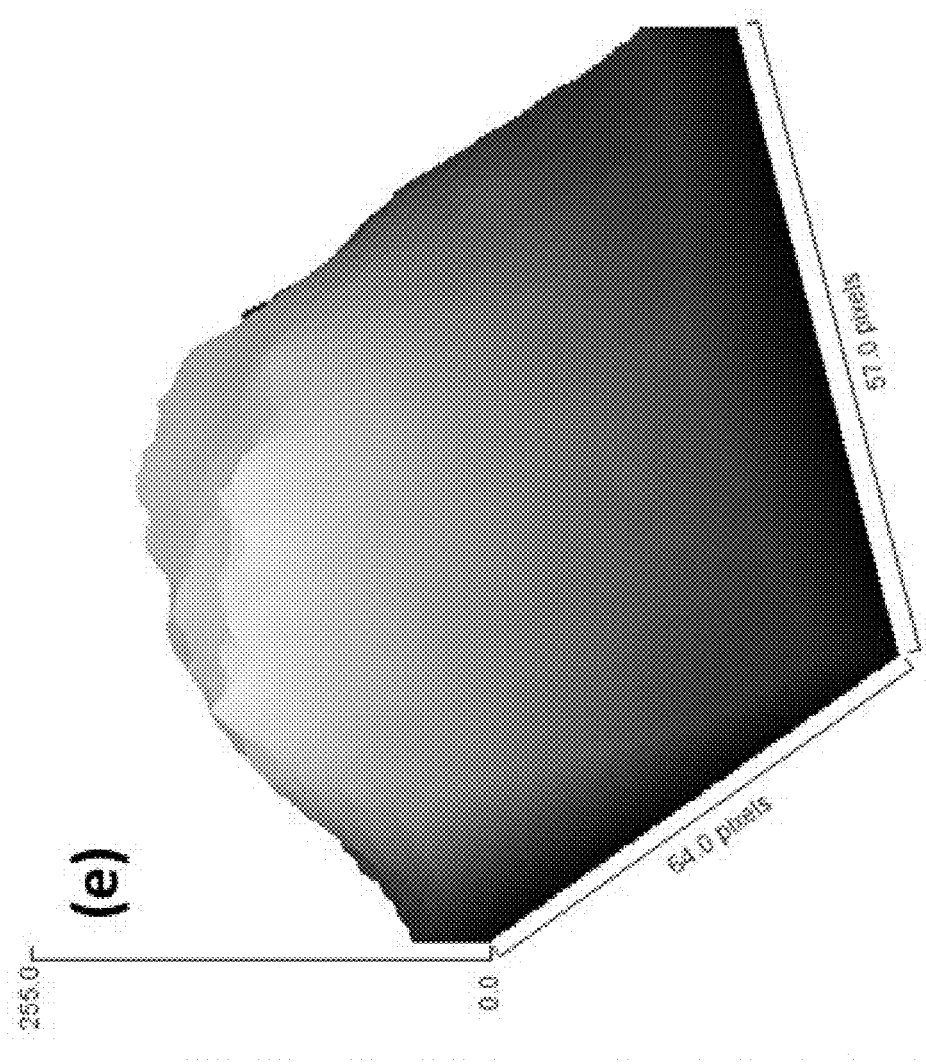
FIG. 51E shows surface plot generated from the tumor.
Figure 52A:
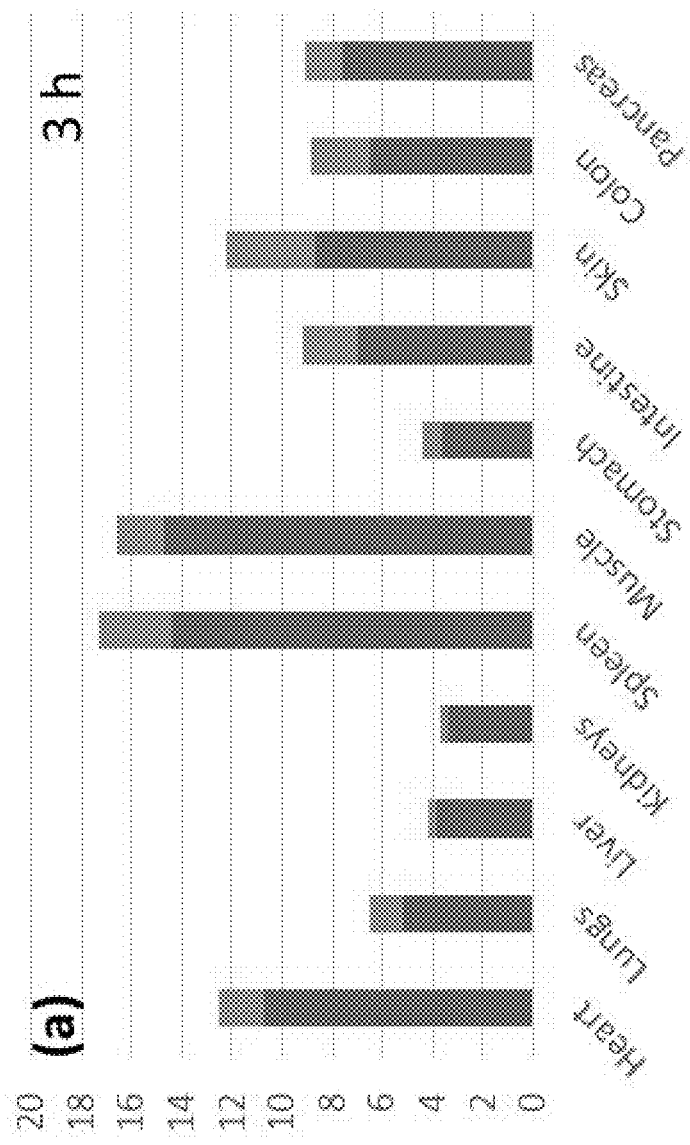
FIGS. 52A-52D illustrate the TBR obtained from biodistribution studies of OTL410 in female nude mice bearing SKRC52 tumor xenografts at a dose of 1 nmol per mouse at various time points.
Figure 52B:
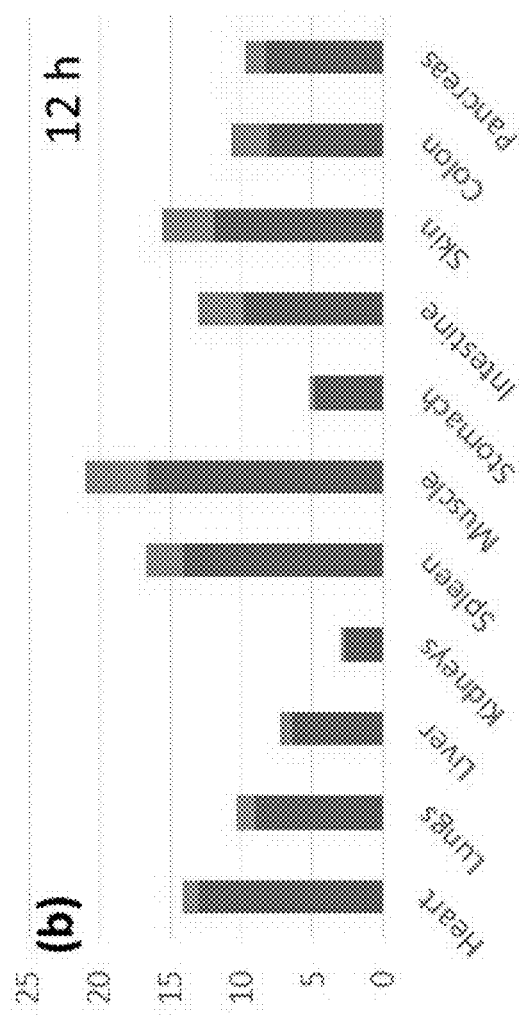
Figure 52C:
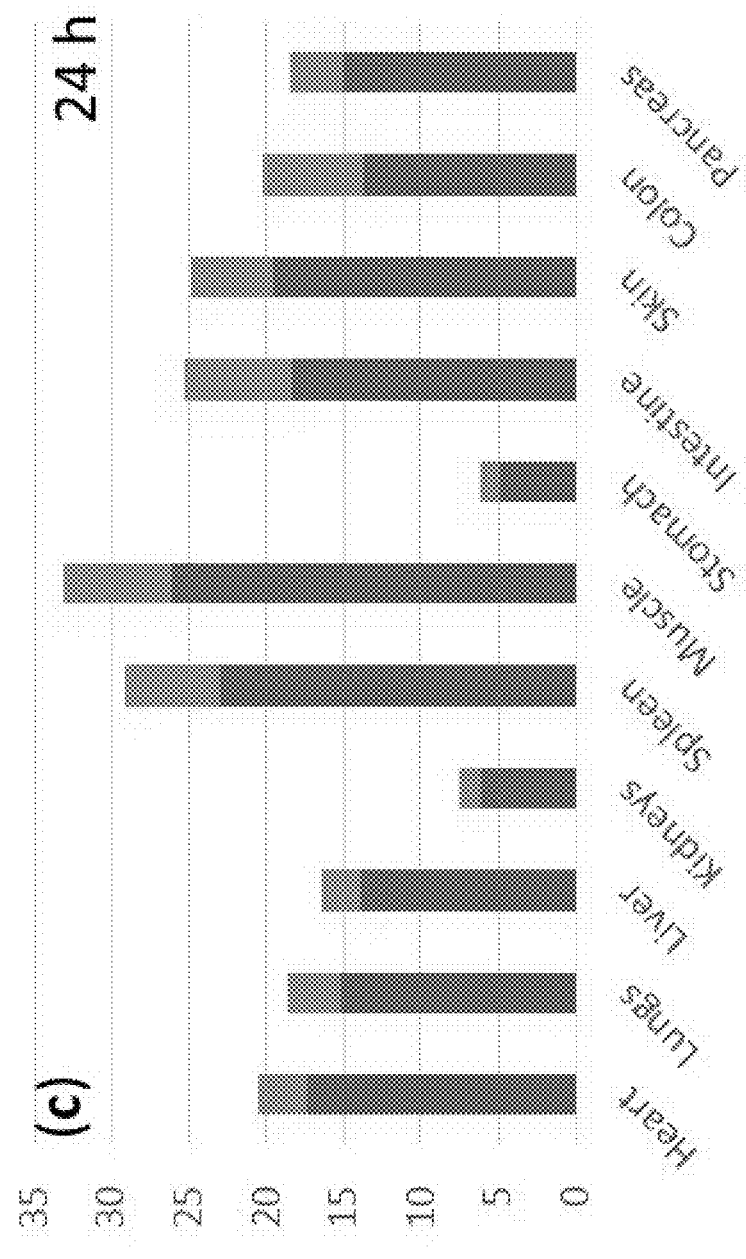
Figure 52D:
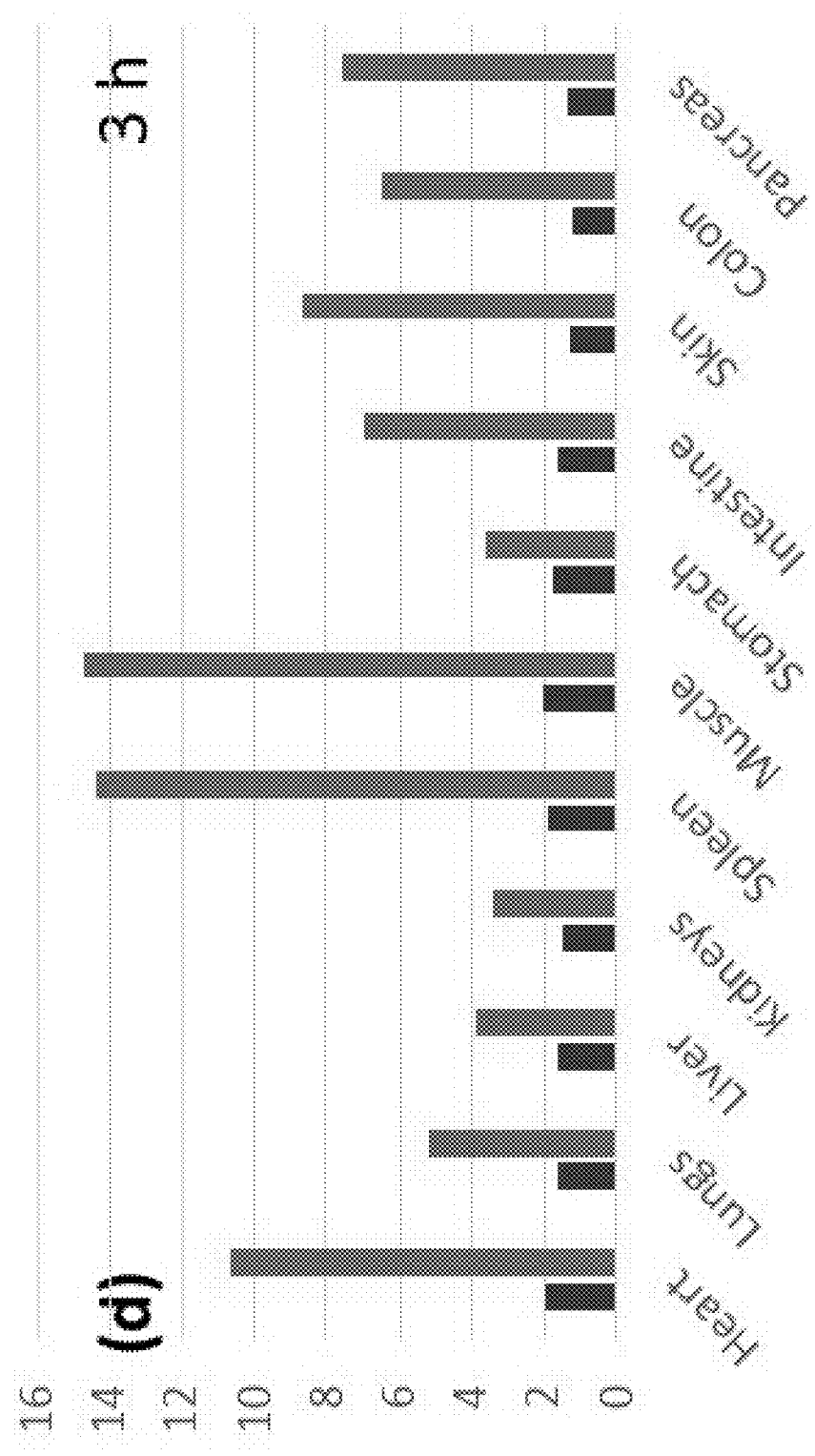
Figure 53A:
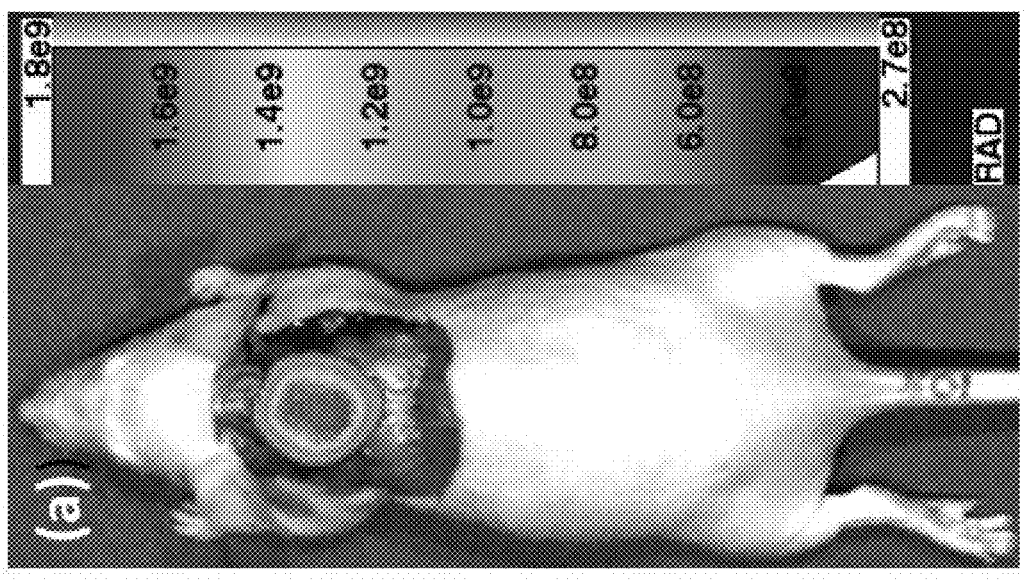
FIGS. 53A and 53B illustrate a demonstration of OTL410 fluorescence-guided resection of CAIX expressing SKRC52 tumor from nude mice. OTL410 was administered at a dose of 1 nmol/mouse in 100 µl of 5% aqueous dextrose, and the mouse was euthanized 24 h later.
Figure 53B:
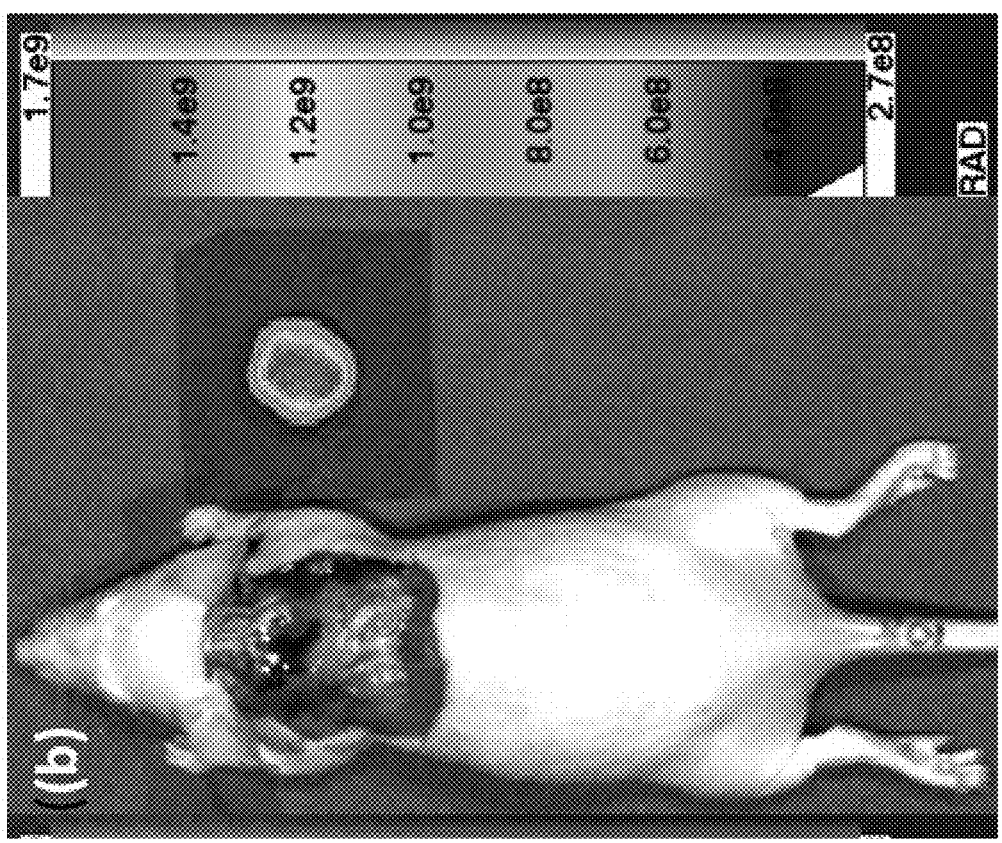
Figures 54A, 54B:
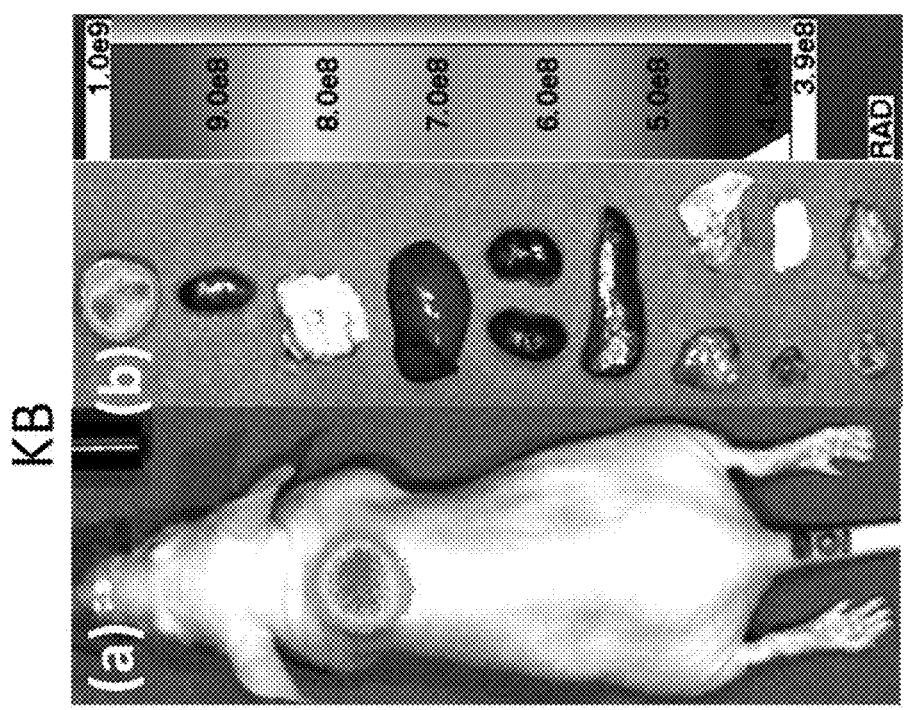
FIGS. 54A-54H illustrate tumor-specific accumulation of OTL410 in tumor xenografts derived from cell lines representing several major human cancers.
Figures 54C, 54D:
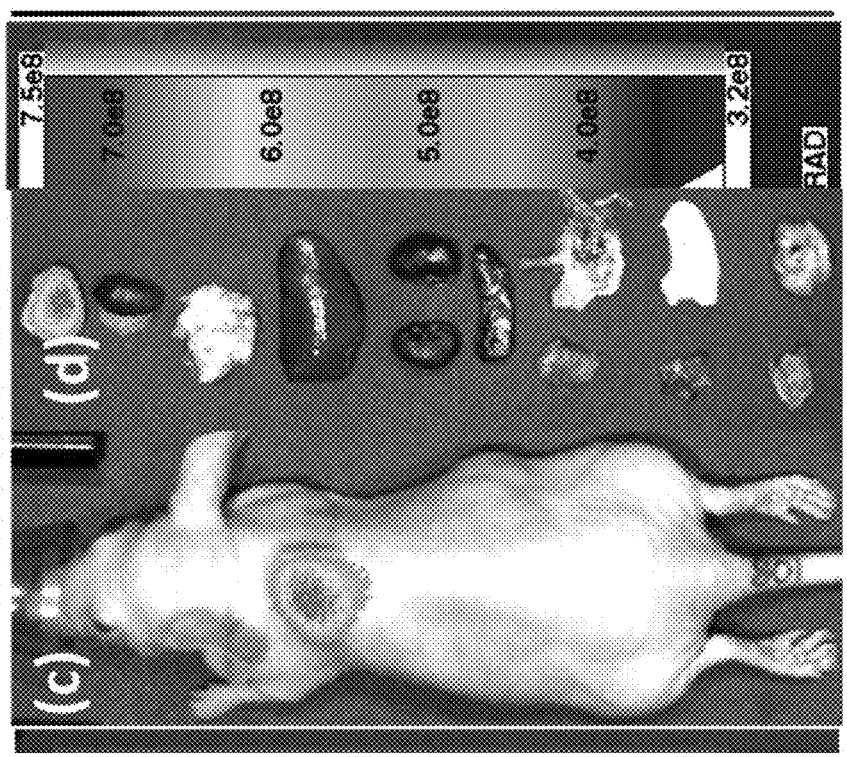
Figures 54E, 54F:
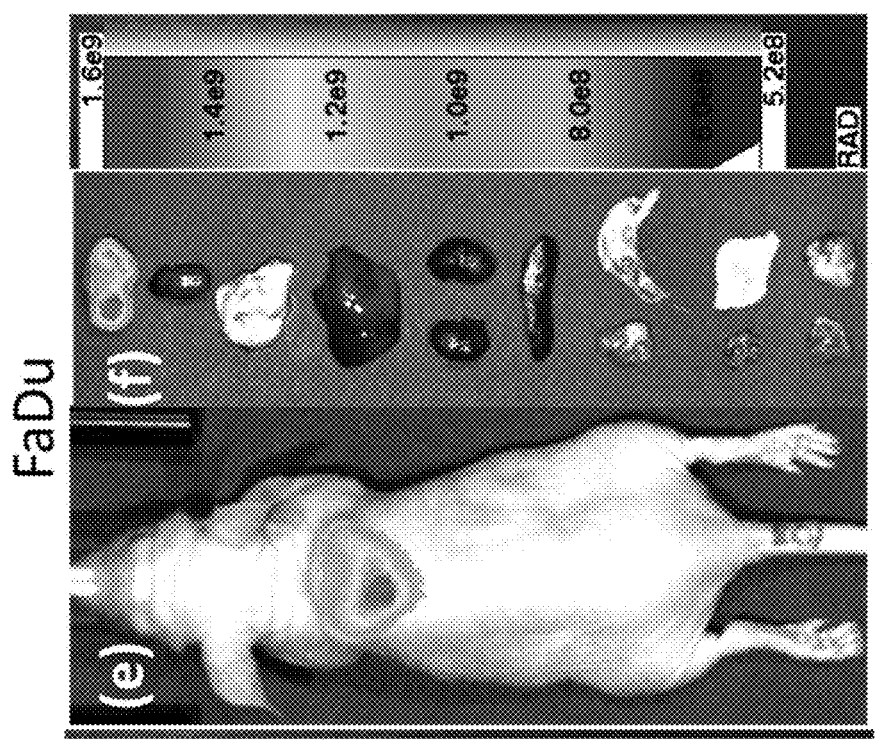
Figures 54G, 54H:
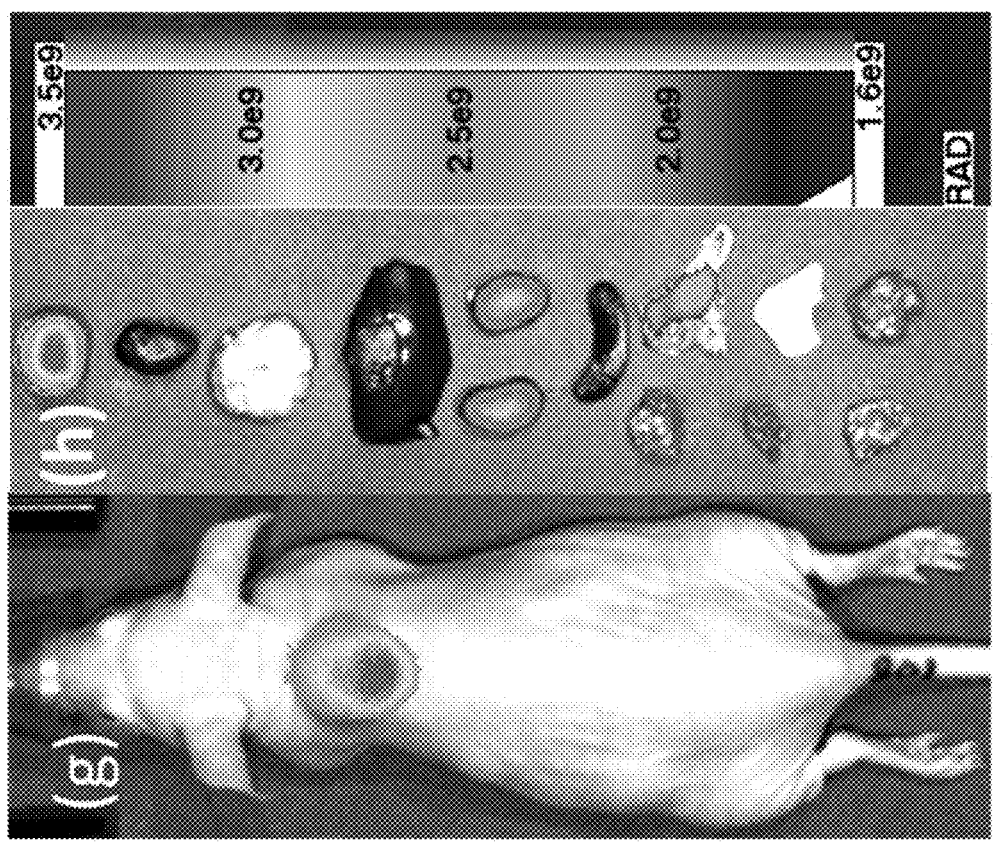
Figure 55:
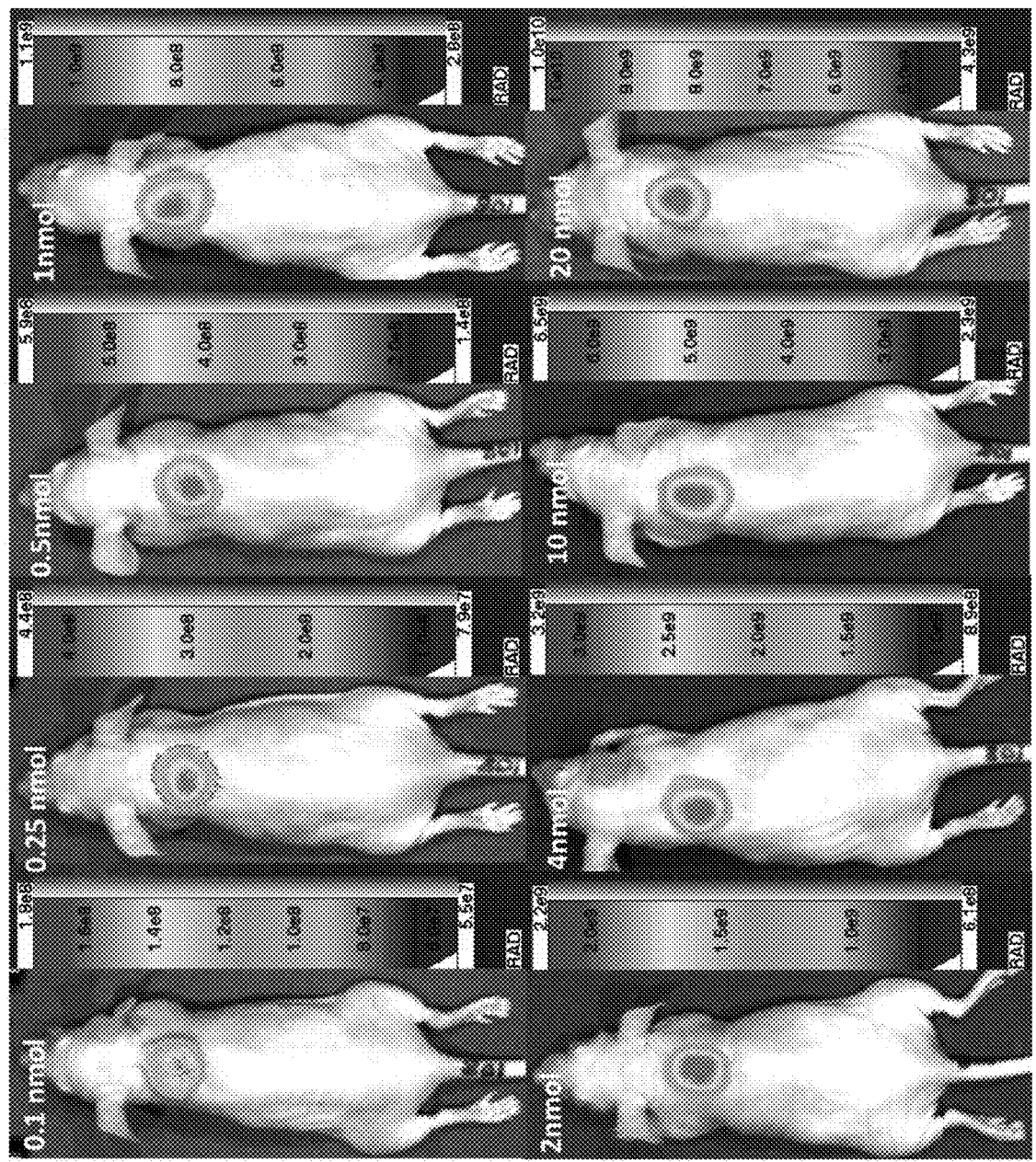
FIG. 55 illustrates dose dependent accumulation of OTL410 in SKRC52 tumor xenografts in nude mice by fluorescence imaging. Mice were euthanized by $CO_2$ inhalation 3 h after intravenous administration of indicated concentrations of the conjugate, and epifluorescence images were collected ex vivo (Ex=745 nm, Em=810 nm FOV=25, binning 2, lamp power=55%). Five mice/per group were used for doses 0.25 nmol to 20 nmol, and image of 1 mouse representing each dose is presented.
Figure 56:
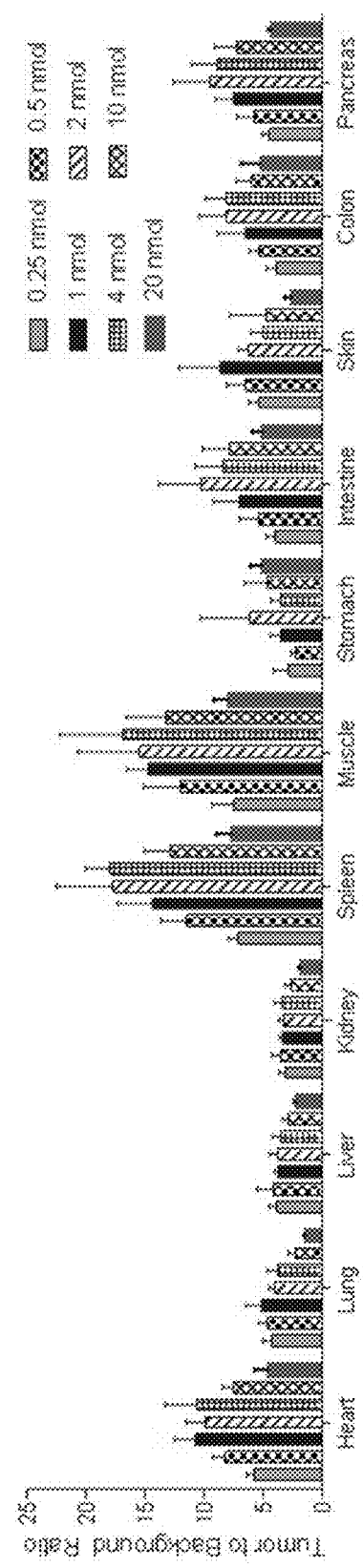
FIG. 56 illustrates TBR from biodistribution studies of OTL410 in female nude mice bearing SKRC52 tumor xenografts at various doses. The dose was escalated from 0.25 nmol/mouse to 20 nmol/mouse, with n=5 mice per each experimental group. The conjugate was administered by tail vein injection in 100 µl of 5% aqueous dextrose, and the mice were euthanized by $CO_2$ inhalation 3 h post injection. Whole body fluorescence images were collected ex vivo, and subsequently, indicated tissues and organs were isolated and imaged using an AMI small animal imager (Ex=745 nm, Em=810 nm, FOV=25, binning 2, lamp power=55%).
Figure 57:
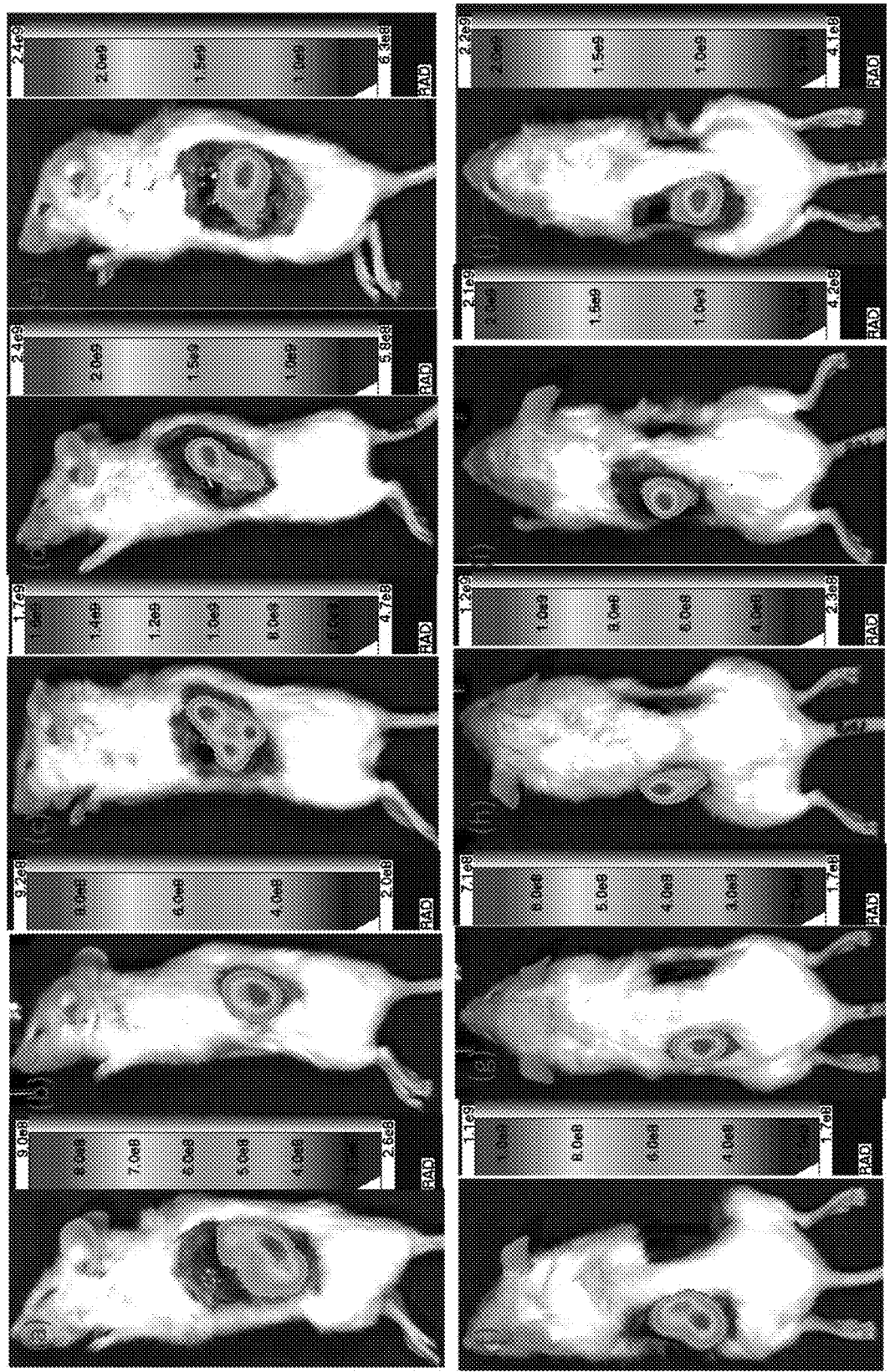
FIG. 57 illustrates In vivo efficacy and specificity of OTL410 in orthotopic tumor model using AMI image system. Representative fluorescence images from AMI image system showing mice bearing SKRC52 orthotopic (n=5 mice/group) tumors 2 h after administering 2 nmol of OTL410. (a-e) side view and (f-j).
Figure 58:
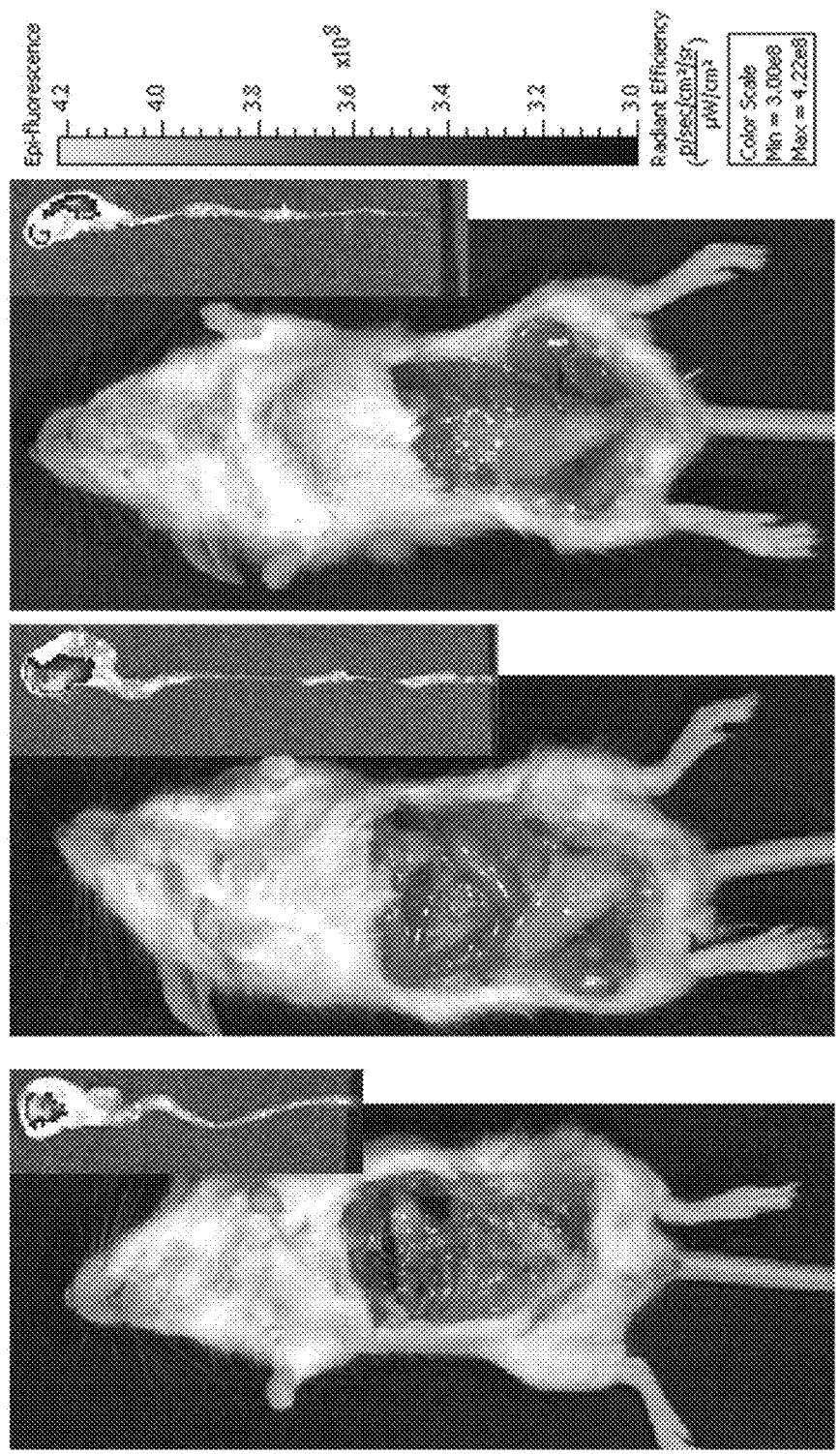
FIG. 58 illustrates imaging of ulcerative colitis with OTL410.
Figure 59:
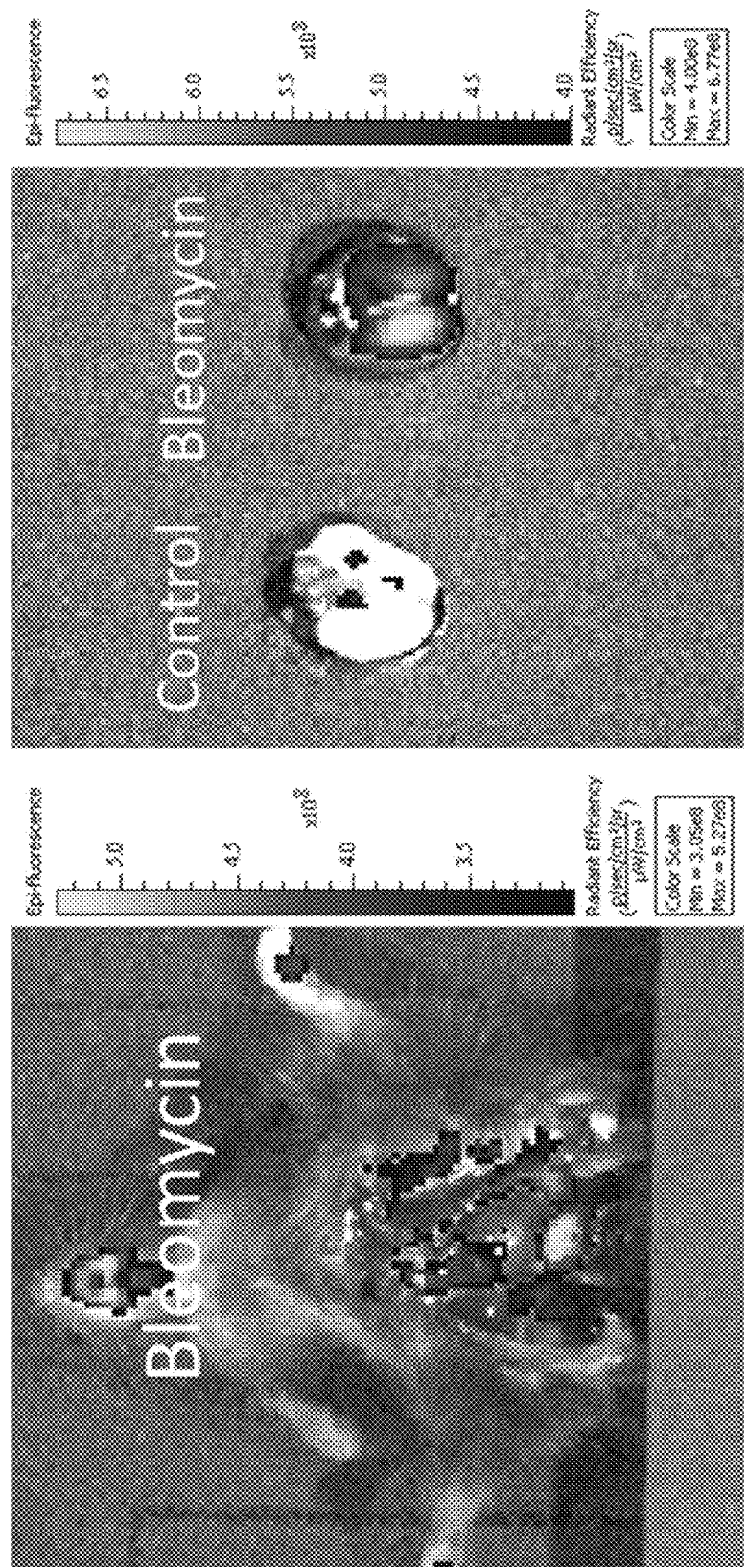
FIG. 59 illustrates imaging of pulmonary fibrosis with OTL410.
Figure 60:
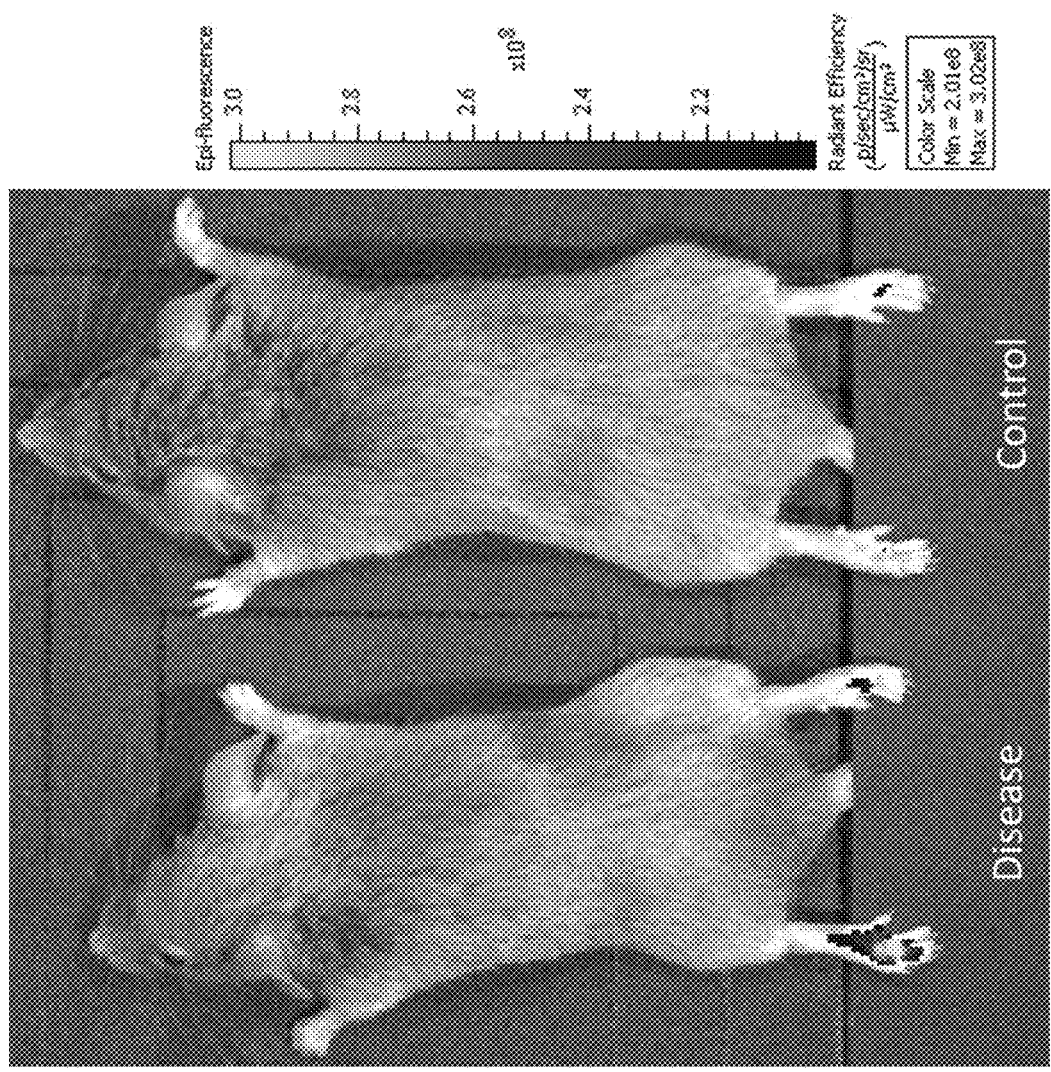
FIG. 60 illustrates imaging of Collagen Induced Arthritis (CIA) with OTL410.
Figure 61:
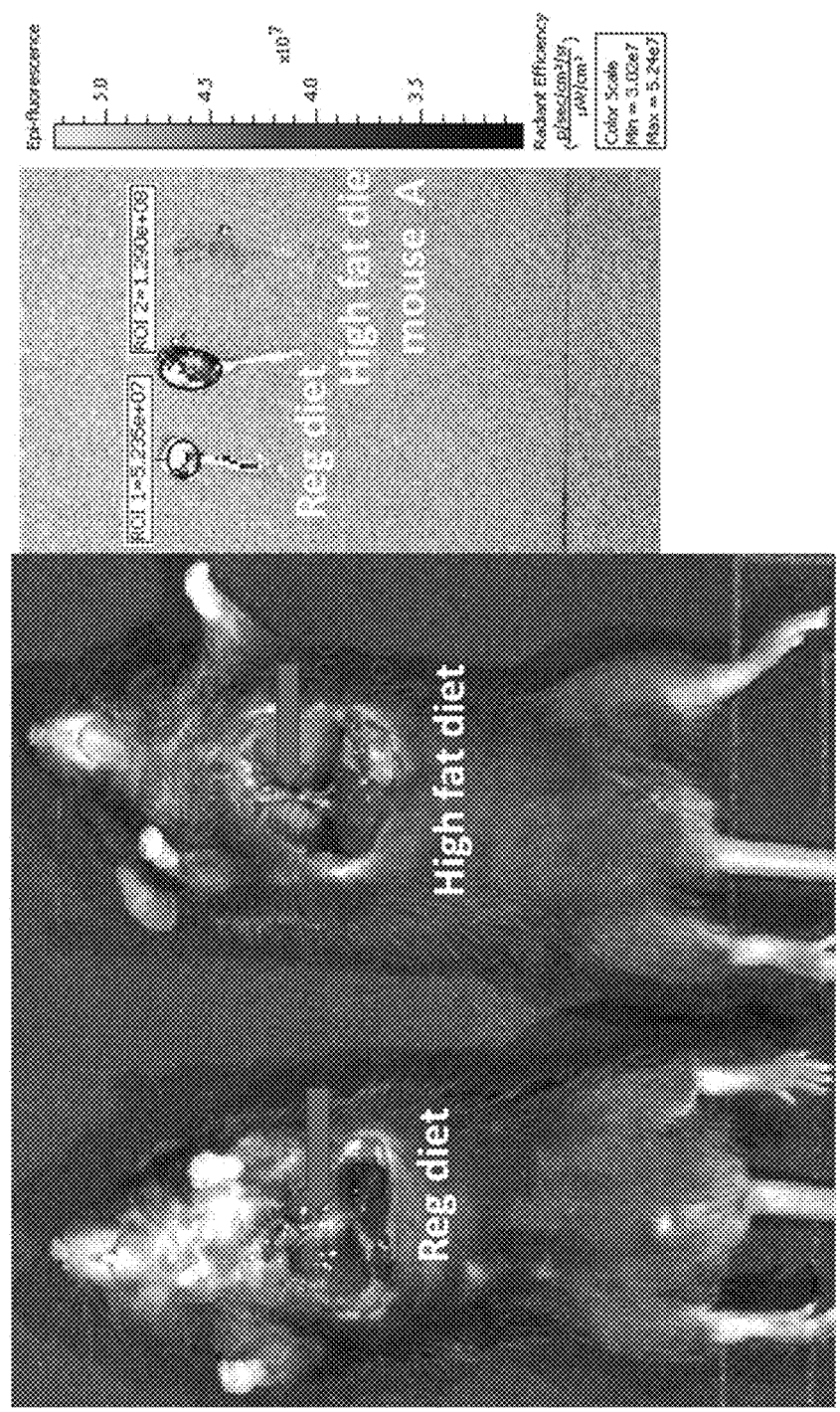
FIG. 61 illustrates imaging of Atherosclerosis with OTL410.

FIG. 45 shows the binding affinity of 105 to CA IX-positive SCRC52 cells using flow cytometry analysis FIG. 46 shows the binding affinity of 105-107 to CA IX-positive SCRC52 cells using confocal microscopy Conclusion: Both confocal microscopy and flow cytometry analysis demonstrated that compound 105-107 binds to CA IX-positive SKRC52 cells (a human renal cancer cell line) with very high affinity. The compound also may be useful both as clinical and/or experimental candidates.

Imaging cancer and inflammatory diseases with OTL410

General Methods for Cancer Imaging:

Cell culture and animals: FBS (US origin), HC Matrigel, Trypsin-EDTA, 75 cm2 and 150 cm2 cell culture treated flasks, monoject 28G×½" 1 ml insulin syringe, BD 1 mL Tuberculin slip tip syringe, Lab-Tek 8 chambered borosilicate cover glass system, Gibco Trypsin-EDTA (0.25%), Gibco phosphate buffered saline, Gibco penicillin streptomycin (10,000 units/ml), RPMI 1640 media with glutamine, and folate deficient RPMI 1640 media were purchased from Fisher Scientific. DMSO for cell culture, and BD precision glide needle (22G×1½") were bought from Sigma Aldrich. SKRC52 cells, a clear cell kidney cancer cell line, were purchased from Memorial Sloan Kettering. KB cells, MDA-MB-231 breast cancer cell line, A549 lung cancer cell line, and HT29 colon cancer cell line were purchased from ATCC. Six-to-eight-week old female or male nude mice were bought from Envio (Indianapolis, Ind.).

All cells cultured were cultured in a humidified atmosphere in presence of 5% $CO_2$:95% air in a cell culture incubator at 37° C. KB cells were cultured in folate deficient RPMI 1640 media, and SKRC-52, MDA-MB-231, 22RV1 and HT29 cells were cultured in RPMI 1640 media. All media were supplemented with FBS (10%), penicillin (50 units/mL), and streptomycin (50 μg/mL). Media for 22RV1 were additionally supplemented with 1% sodium pyruvate. Trypsin-EDTA (1×) solution was used for cell detachment during cell splitting.

All animal procedures were approved by the Purdue Animal Care and Use Committee in accordance with National Institutes of Health guidelines. Six to eight-week-old athymic female nu/nu mice were purchased from Envigo, and housed in a sterile environment on a standard 12 h light-dark cycle and maintained on normal rodent chow.

Binding studies: For estimation of binding constant, clear cell kidney cancer SKRC52 cells were harvested using trypsin-EDTA, and was washed with complete media and counted. 150,000 cells each were placed in Eppendorf tubes and treated with 900 μl of media containing varying concentrations of a fluorescein conjugated version OTL338 for 1 h at 37° C. in a cell culture incubator. After 1 h, the cells were spun down and the supernatant was removed, and resuspended in fresh media. This process was repeated twice, and after the second centrifugation, cells were resuspended in 900 μl of serum free media, and were filtered using Falcon 5 ml round bottom polystyrene tubes with cell strainer cap and placed in ice until analysis using a flow cytometer (BC FC500 Cell Analyzer). Binding constant of the fluorescein version of OTL410 was calculated using the Graph Pad Prism software. For estimation of binding constant of OTL410, 150,000 SKRC52 cells were incubated with varying concentrations of OTL410 in presence of 100 nmols of the fluorescein conjugated version of OTL410 in 900 μl of media for 1 h at 37° C. in a cell culture incubator. Cells were processed as described above, and the florescence intensity from cell-bound FITC-ligand conjugate was measured using the aforementioned flow cytometer. Relative binding constant of OTL410 was estimated using the Graph Pad Prism software using concentrations of OTL410, ligand-FITC conjugate, and binding constant of the FITC-conjugate.

For competition studies, 50,000 SKRC cells were grown on 8 well glass bottom slides for 48 h. Spent media was removed, and the cells were incubated with 100 nmols of OTL410 in 500 μl of fresh media alone or in presence of 200× non-fluorescent ligand (i.e. OTL410 without the dye) in a cell culture incubator for 2 h. Cells were then washed 2× with 500 μl of media, and after the second step of washing, 500 μl of serum free media was added to the cells. These cells were then imaged using a Nikon wide-field microscope.

Tumor Implantation and imaging: For establishing subcutaneous tumors from SKRC52, HT29 and 22RV1 cells, female nude mice were inoculated subcutaneously with 5×10⁶ cells in 150 μl of 50% matrigel on the flank. KB tumors were established by inoculating female nude mice subcutaneously with 1×10⁶ KB cells in 100 μl of folate deficient RPMI 1640 media. MDA MB-231 tumors were established by inoculating female nude mice subcutaneously with 2×10⁶ cells in 100 μl of RPMI 1640 media. Tumor sizes were measured using a digital calipers and tumor volumes were calculated using the formula (L/2)×W2 where L and W represent the length and width of the tumor. When the tumors reached desired size (500-700 mm3), mice were randomly assigned to groups of 4-5. Each mouse was injected with varying concentrations of OTL410 in 100 μl of 5% aqueous dextrose. For the time course study, mice were imaged under anesthesia at varying time points starting at 15 minutes and up to 24 h using a Spectral AMI imaging system (Spectral Instruments Imaging) using the imaging parameters t=1 sec, f stop=2, FOV=25, binning=2, and lamp power=55%. For the biodistribution studies, mice were euthanized at 3 h, 12 h or 24 h after injection of OTL410, and fluorescence images were collected ex vivo using the same instrument and imaging parameters described above. For quantification of tumor to background ratios, region of interest (ROI) was drawn for tumor and each tissue of interest and the total and mean fluorescence intensity were calculated using the proprietary software from Spectral Instruments. TBR for each organ and respective standard deviations were calculated using Excel software.

For ImageJ analysis, the whole-body imaging was acquired in gray scale and processed in ImageJ software. Either a line across the tumor or box around the tumor was drawn to define the fluorescence to be quantitated. The tumor-to-muscle ratio was analyzed using a plot of the fluorescence gray value versus distance.

For orthotopic tumors, 2×105 SKRC52 cells/mouse in 10% high concentrated (HC) matrigel with RPMI1640 medium were surgically implanted in a kidney of seven-week-old male SCID mice. Briefly, seven-week-old male SCID mice were given 1-5% isoflurane for anesthesia and subcutaneous injection of 5 mg/kg meloxicam preoperatively for analgesia. The mice were placed ventral side up and washed above a kidney with a chlorhexidine scrub to ensure a sterile area for incision. After an insertion was made using scalpel through the skin, 1.5-cm flank incision was carried down to the kidney. ventral lobes were exteriorized and gently stabilized with a wet (PBS) cotton swab. SKRC52 cells (in 10 μL of 10% HC-matrigel) were injected a kidney using a 28-gage needle. After placing the kidney back into the peritoneum, the abdominal wall was sutured, the body wall was closed using 3-0 or 4-0 vicryl and the skin was closed using staples. Animals were monitored until use them for the studies. After one month, the animals were administered with OTL410 (10 nmol in 100 μL saline per mouse), euthanized after 2 h by CO2 asphyxiation, and imaged using AMI image system.

Inflammatory Models

In vivo studies of ulcerative colitis with OTL410: Seven weeks old Balb/c mice (Harlan Laboratories) maintained on a folate-deficient diet were administered 5% dextran sodium sulfate (DSS) in their drinking water to induce ulcerative colitis. Healthy control mice received normal drinking water. After 8 days, mice were intraperitoneally injected with 2 nmol OTL410. After 4 hours, the mice were euthanized and imaged using an IVIS lumina II.

In vivo studies of collagen-induced arthritis (CIA) (as a model for rheumatoid arthritis) with OTL410: 6-7 weeks old female DBA/1 mice (Jackson Laboratories) were maintained on folate-deficient diet (Harlan-Teklad). Mice were immunized at the base of the tail with 100 μg bovine type II collagen emulsified in complete Freund's adjuvant (Chondrex, Inc., Redmond, Wash., USA). Mice were then boosted 21 days later with a similar injection of 100 μg bovine type II collagen emulsified in incomplete Freund's adjuvant. After four days (Day 25), onset of arthritis was synchronized in all mice with an intraperitoneal injection of 25 μg lipopolysaccharide (LPS) dissolved in saline. Healthy control mice did not undergo arthritis induction. On Day 39, mice received an intraperitoneal injection of 10 nmol OTL410. After 4 hours, mice were euthanized and imaged on an IVIS lumina II.

In vivo studies of atherosclerosis with OTL410: Five weeks old male ApoE−/− mice were purchased from Jackson Laboratories and placed on an adjusted calorie diet (42% from fat, Harlan Laboratories). Healthy control mice were maintained on normal chow. After 20 weeks, mice received an i.p. injection of 10 nmol OTL410. After 4 hours, mice were euthanized and imaged on an IVIS lumina II.

In vivo studies of pulmonary fibrosis with OTL410: 6 weeks old female C57BL/6 mice (Harlan Laboratories), maintained on a folate-deficient diet were anaesthetized with isoflurane, and 50 μL of bleomycin (2 U/kg body weight) dissolved in saline was intratracheally instilled into each mouse. Healthy control mice were similarly intratracheally instilled with 50 μL saline. On Day 15, mice received an i.p. injection of 10 nmol OTL410. After 4 hours, mice were euthanized and imaged on an IVIS lumina II.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

The invention claimed is:

1. A method of imaging cancer or inflammatory diseases, the method comprising contracting tissue with a compound, or salt thereof, the compound having the formula:

B-W-X-Y-Z wherein B is a CA IX-targeted molecule is selected from the group consisting of

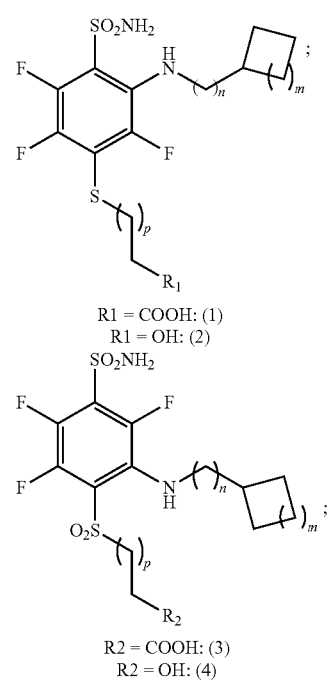

R1 = COOH: (1)
R1 = OH: (2)

R2 = COOH: (3)
R2 = OH: (4)

-continued
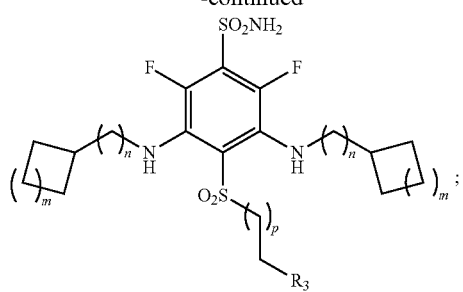
R3 = COOH: (5)
R3 = OH: (6)
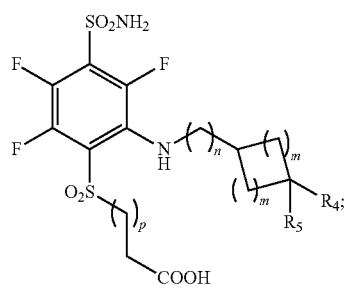
R4 = F, R5 = H: (7)a
R4, R5 = F: (7)b
R4 = CF3, R5 = H: (8)
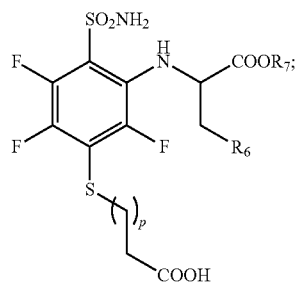
R6 = p-Ph, R7 = Bz: (9)
R6 = CH(CH3)2, R7 = Bz: (10a)
R6 = CH(CH3)2, R7 = H: (10b)
R6 = Imidazole, R7 = Bz: (11)
R6 = indole, R7 = Bz: (12)
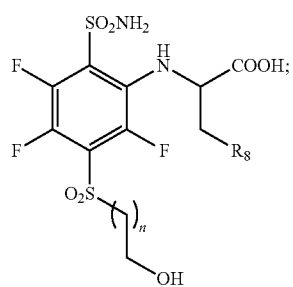
R8 = p-Ph: (13)
R8 = CH(CH3)2: (14)
R8 = Imidazole: (15)
R8 = indole: (16)
-continued
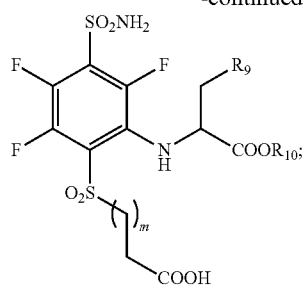
R9 = p-Ph, R10 = H: (17)
R9 = CH(CH3)2, R10 = H: (18a)
R9 = CH(CH3)2, R10 = Bz: (18b)
R9 = Imidazole, R10 = H: (19)
R9 = indole, R = H: (20)
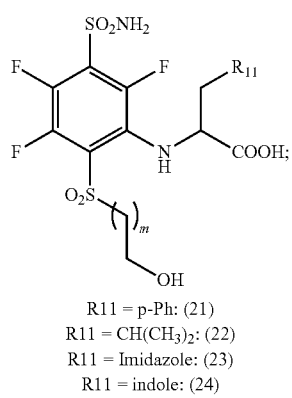
R11 = p-Ph: (21)
R11 = CH(CH3)2: (22)
R11 = Imidazole: (23)
R11 = indole: (24)
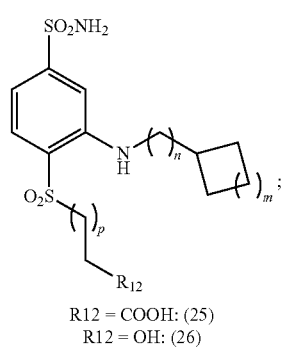
R12 = COOH: (25)
R12 = OH: (26)
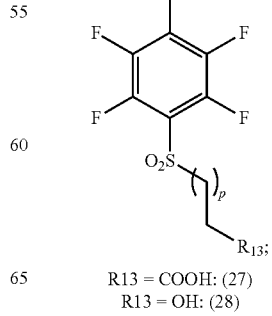
R13 = COOH: (27)
R13 = OH: (28)

-continued
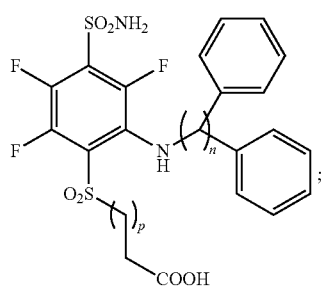
(29)
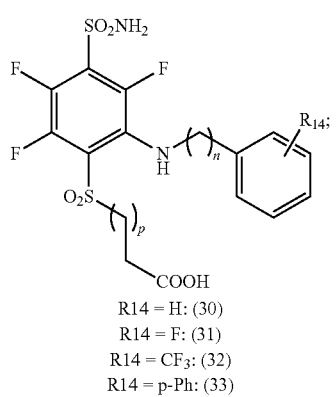
R14 = H: (30)
R14 = F: (31)
R14 = CF₃: (32)
R14 = p-Ph: (33)
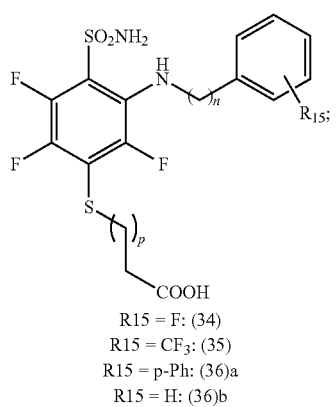
R15 = F: (34)
R15 = CF₃: (35)
R15 = p-Ph: (36)a
R15 = H: (36)b
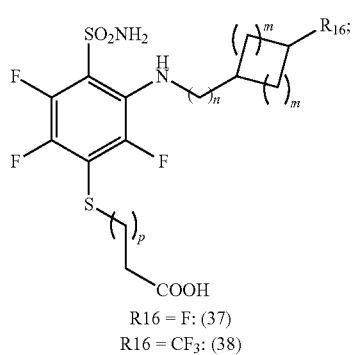
R16 = F: (37)
R16 = CF₃: (38)
-continued
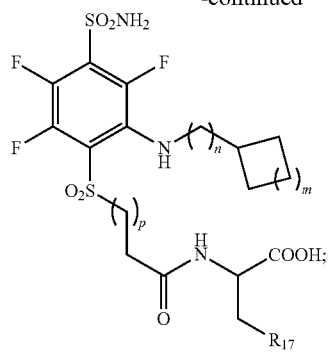
R17 = COOH: (39)
R17 = (CH₂)₂Guanidinium: (40)
R17 = p-Ph: (41)
R17 = Imidazole: (42)
R17 = Indole: (43)
R17 = CH(CH₃)₂: (44)
R17 = CH(CH₂CH₃)CH₃: (45)
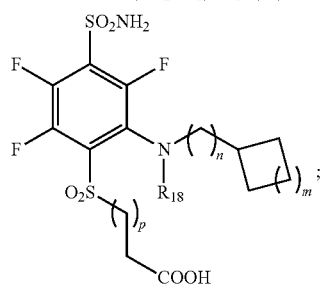
R18 = Guanidinium: (47)
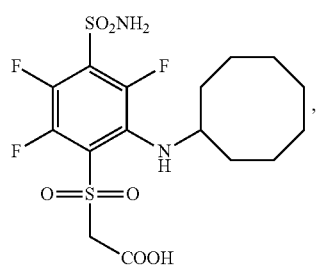
(3a)
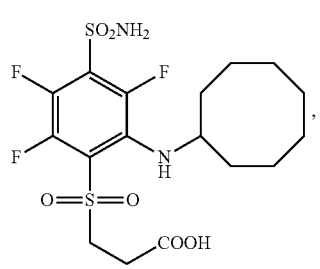
(3b)-C-SPA
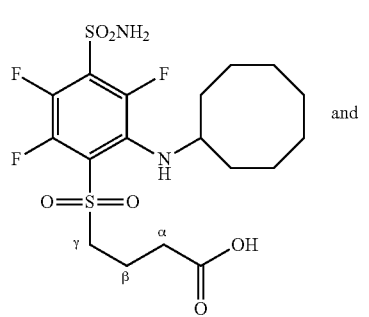
(3c) C-SBA
and -continued

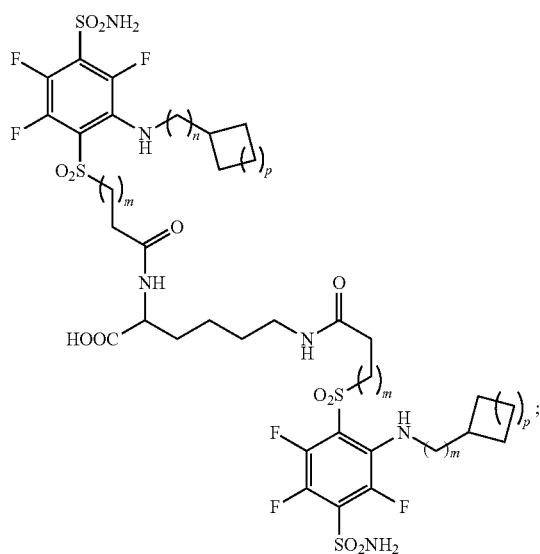

(46)

wherein n is 0, 1, 2, or 3; m is 0, 1, 2, 3, 4, or 5, and p is 0, 1, 2, or 3;

W comprises an extended hydrophobic residue;
X comprises a hydrophobic spacer;
Y comprises an amino acid spacer; and
Z comprises a NIR dye,
illuminating the tissue with an excitation light of a wavelength absorbed by the compound; and
detecting the optical signal emitted by the compound in the tissue.

2. The method of claim 1, wherein W is a hydrophobic amino acid, aromatic amino acid or derivative thereof.

3. The method of claim 1, wherein W is selected from the group consisting of: alanine, leucine, isoleucine, valine, proline, phenylalanine, tryptophan, methionine, tyrosine, arginine, histidine, lysine, glycine, serine, threonine, cysteine, tyrosine, asparagine, aspartic acid, glutamic acid, and glutamine and derivatives thereof.

4. The method of claim 1, wherein X is a length from 7 atoms to 14 atoms.

5. The method of claim 1, wherein X is selected from the group consisting of eight aminooctonoic acid (EAOA), polyethylene glycol (PEG), polyethylene amine (PEA), N-amino-dPEG$_2$ acid, a chain of 6 atoms, a spacer 6 atoms in length, a chain from 6 to 20 atoms in length, and a peptide comprising aryl or aryl alkyl groups, each of which is optionally substituted, and wherein one aryl or aryl alkyl group is about 6 to about 10, or about 6 to about 14 atoms, and the other aryl or aryl alkyl group is about 10 to about 14, or about 10 to about 15 atoms, or about 1 to about 20 atoms.

6. The method of claim 1, wherein X, Y, and Z, are independently selected from the group consisting of a variable charge, negative charge, and positive charge.

7. The method of claim 1, wherein X is a peptide compromising positively charged amino acids or quaternary amine containing amino acid.

8. The method of claim 1, wherein Y is selected from the group consisting of an aromatic amino acid, an amino acid spacer with a chalcogen-containing side chain group, an amino acid spacer with a sulfur-containing side chain group, an amino acid spacer with a sulfur-containing thiophenol moiety, a tyrosine with a carbon isotope on the aromatic ring of tyrosine, a an amino acid with an aromatic ring with a hydrogen isotope aspartic acid, glutamic acid, arginine, histidine, lysine, glycine, serine, threonine, cysteine, tyrosine, asparagine, aspartic acid, glutamic acid, glutamine, alanine, leucine, isoleucine, valine, proline, phenylalanine, tryptophan, methionine, and derivatives thereof.

9. The method of claim 1, wherein the near-infrared dye is selected from the group consisting of, IR800, SP054, S0121, S2076, S0456,

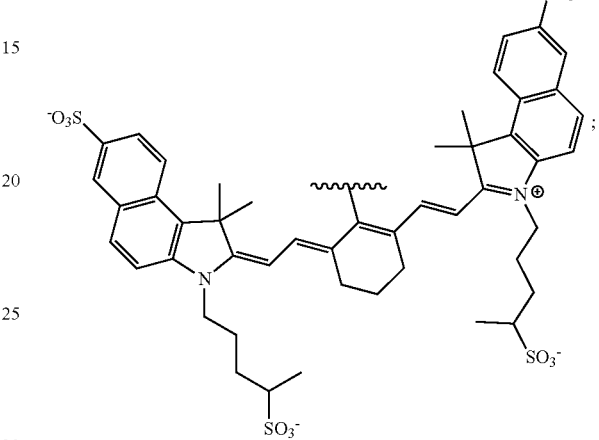

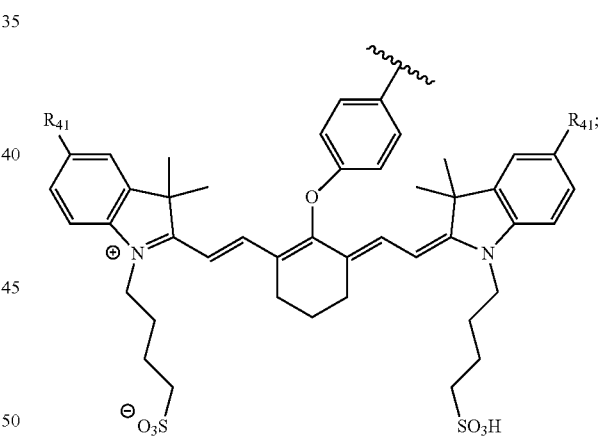

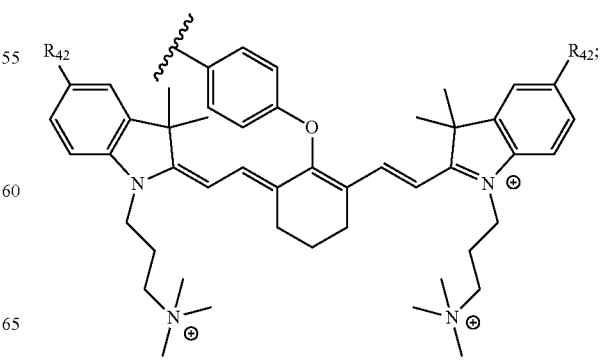

-continued

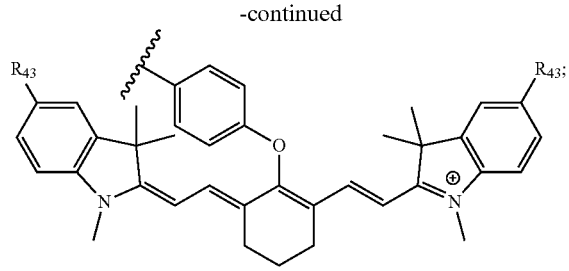

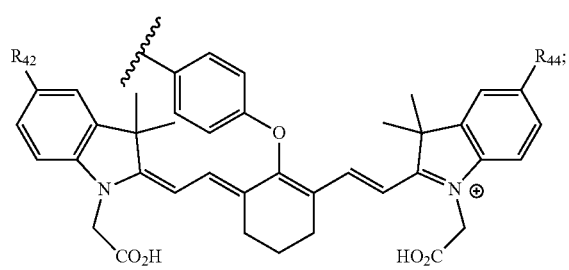

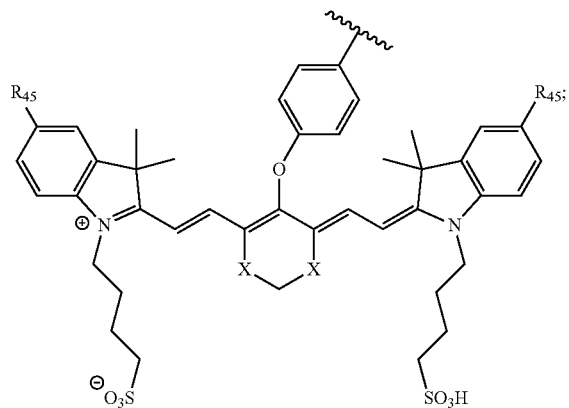

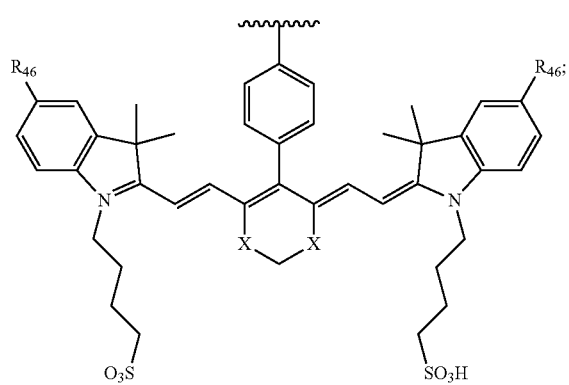

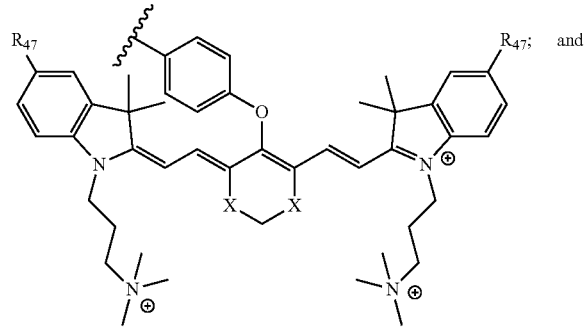

-continued

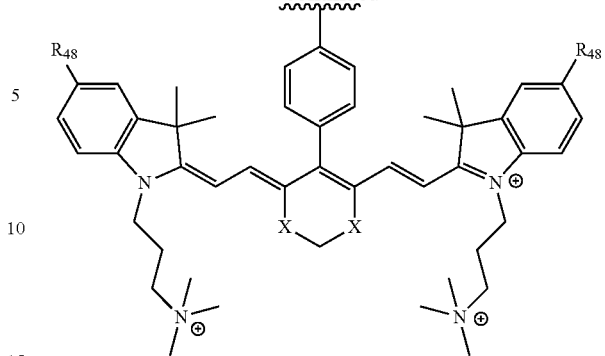

wherein R41, R42, R43, R44, R45, R46, R47, R48, =H or SO₃H; X=O, S, or NH.

10. The method of claim 1, wherein B is

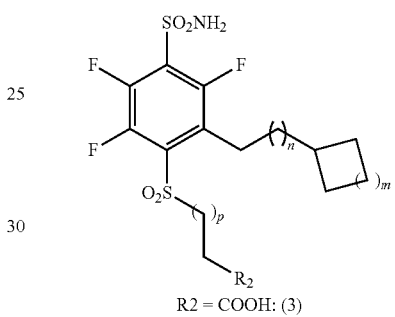

R2 = COOH: (3)
R2 = OH: (4)

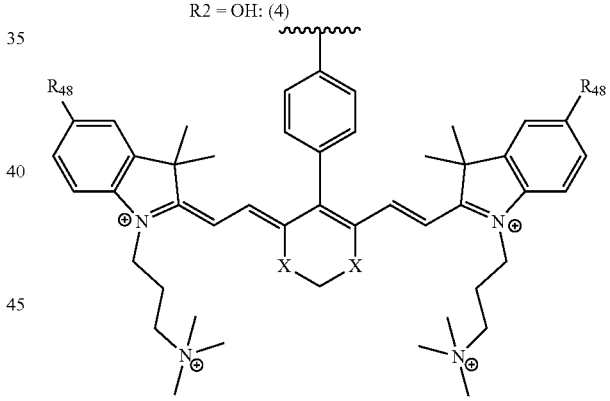

wherein n is 0, m is 5 and p is 2;

W is PEG or PEA;

X is PEG or PEA;

Y is selected from the group consisting of tyrosine, phenylalanine-tyrosine, phenylalanine-arginine-tyrosine, and histidine-tyrosine;

and Z comprises S0456.

11. The method of claim 1, wherein the compound has an absorption and emission maxima between about 500 nm and about 900 nm.

12. The method of claim 1, wherein the tissue is biological tissue.

13. The method of claim 1, wherein the compound may be formulated in a pharmaceutically or therapeutically acceptable composition.

14. The method of claim 1, wherein the signal emitted by the compound is used to construct an image.

15. The method of claim 1, wherein the tissue is in a subject and the subject is an animal or human.

16. The method of claim 1, wherein the method further comprises contacting the biological tissue with at least one additional fluorescent compound.

17. The method of claim 16, wherein the at least one additional fluorescent compound comprises a pteroyl ligand conjugated to an amino acid linking group or a PSMA-targeting compound conjugated to an amino acid linking group.

18. The method of claim 1, wherein the compound has a formula selected from the group consisting of

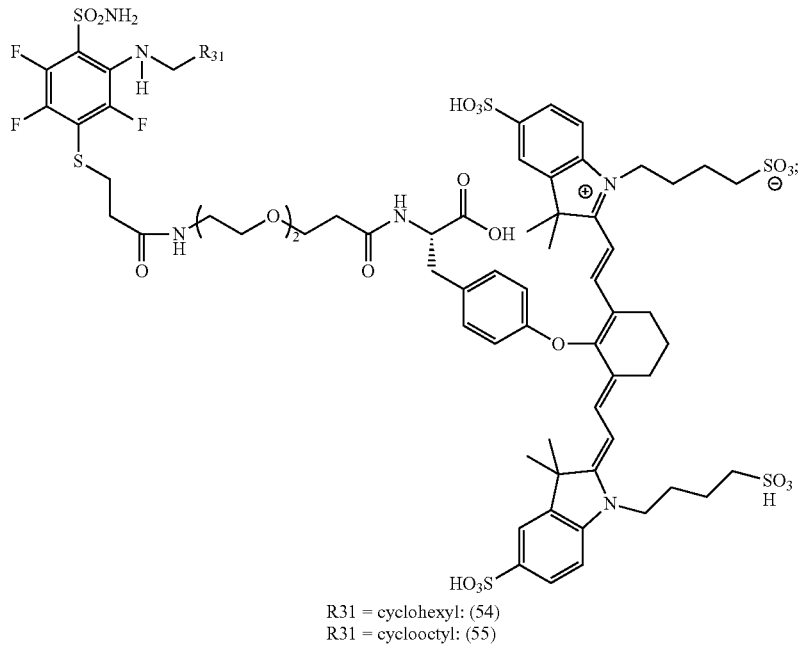

R31 = cyclohexyl: (54)
R31 = cyclooctyl: (55)

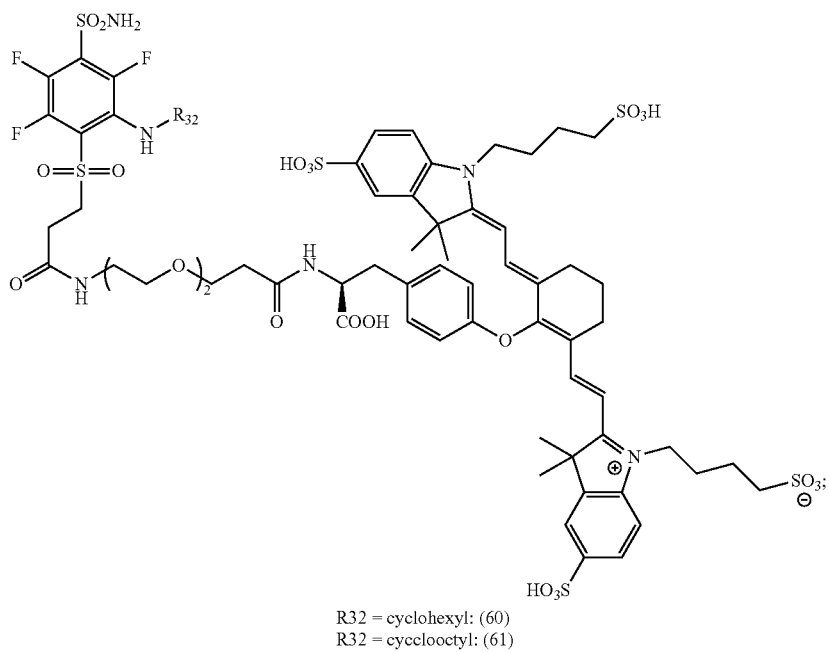

R32 = cyclohexyl: (60)
R32 = cyclooctyl: (61)

(62)
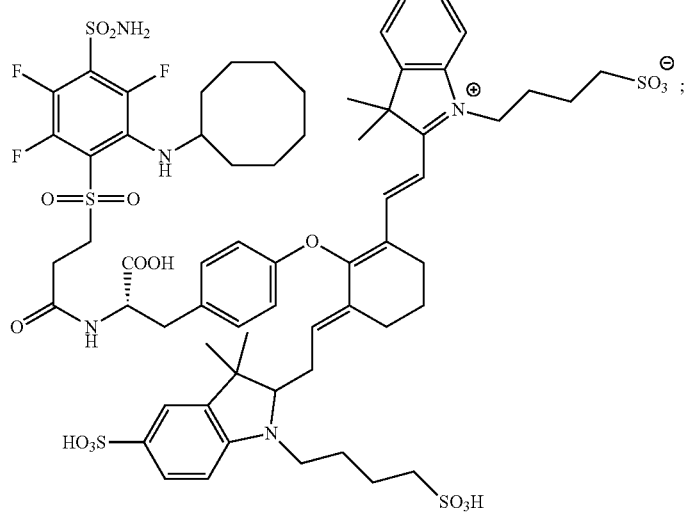
(63)
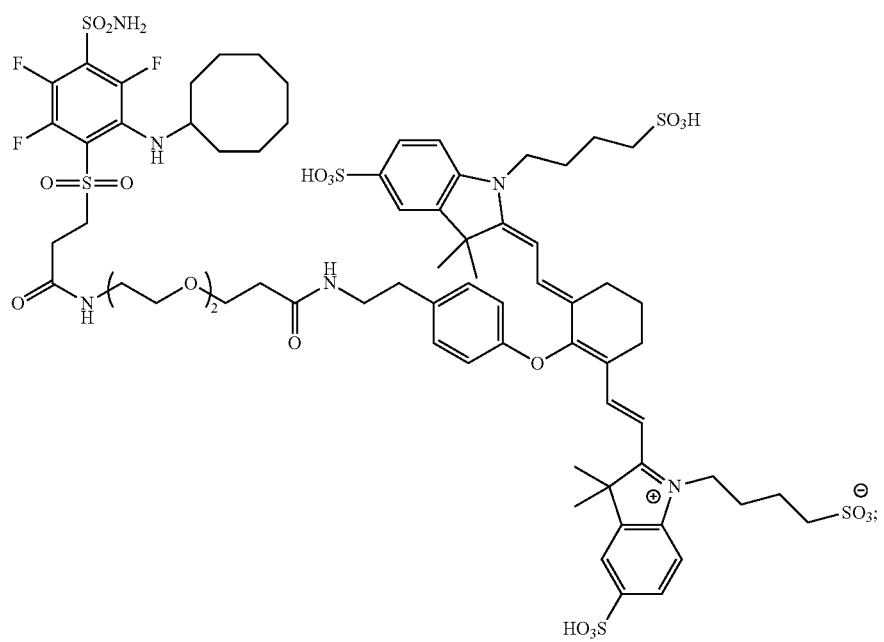

(64)
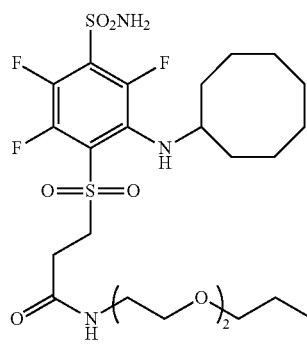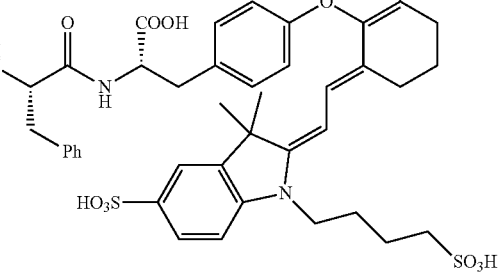
(65)
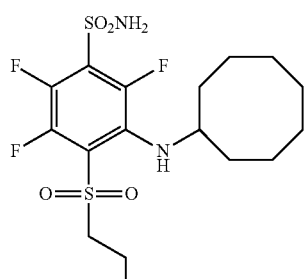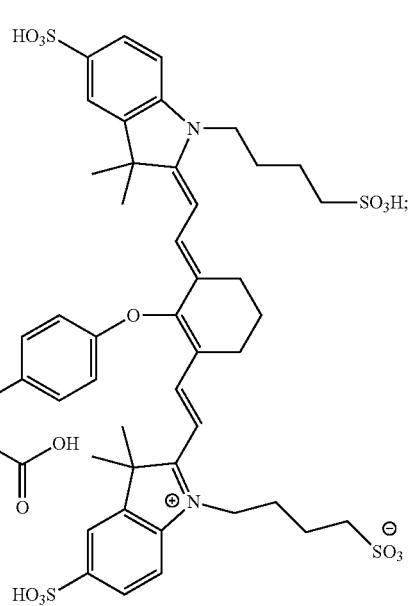

-continued
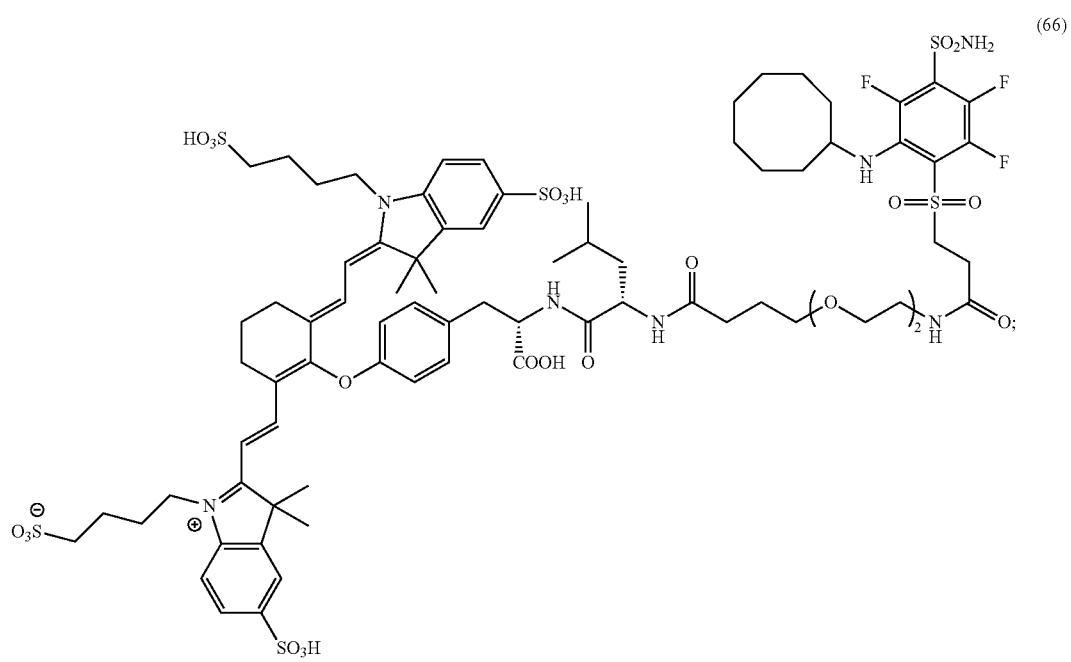
(66)
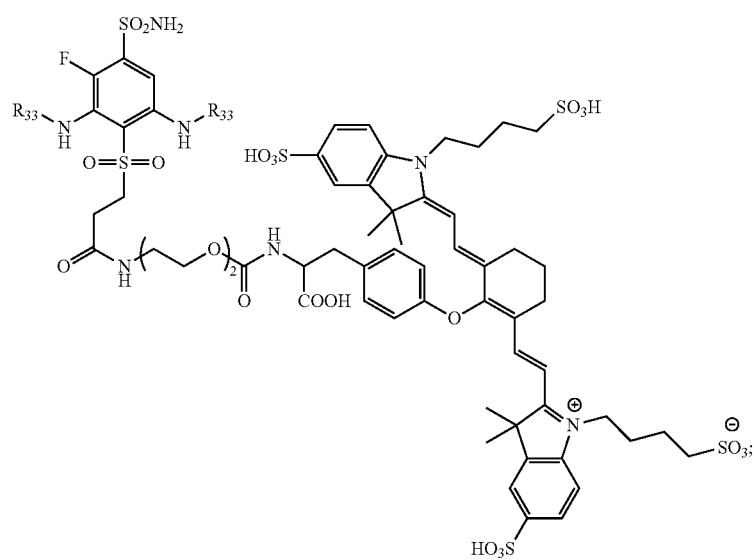
R33 = cyclohexyl: (69)
R33 = cyclooctyl: (70)

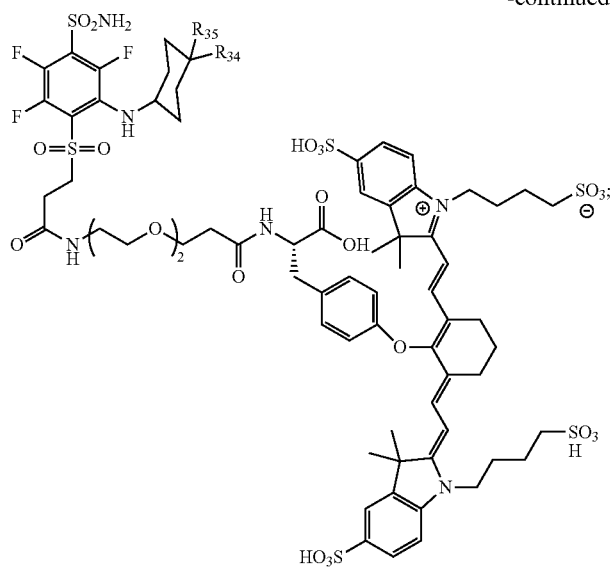
R34 = H, R35 = F: (71)
R34, R35 = F: (72)
R34 = H, R35 = CF3: (73)
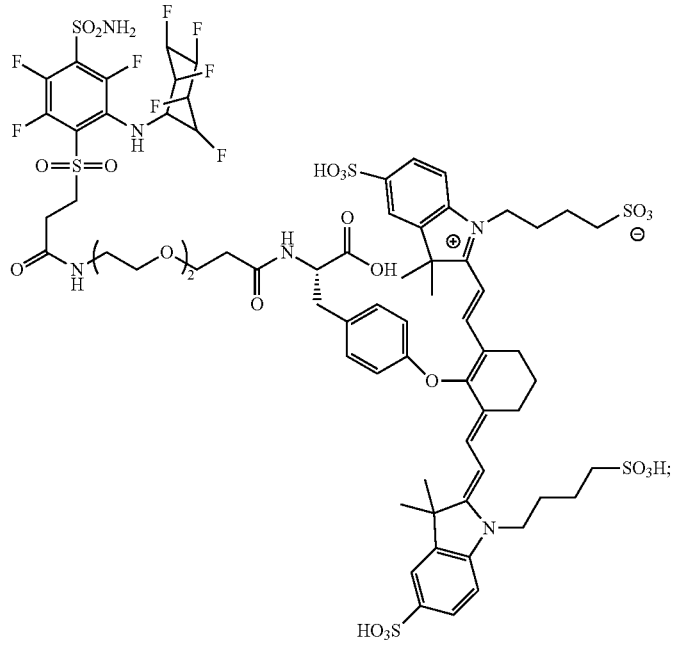
(74)

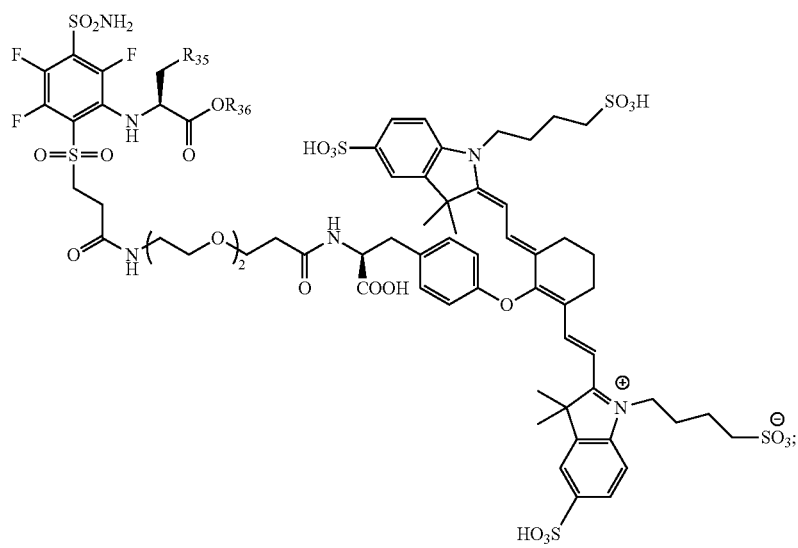
R35 = p-Ph, R36 = Bz: (75)
R35 = CH(CH₃)₂, R36 = Bz: (76)
R35 = CH(CH₃)₂, R36 = H: (77)
R35 = Imidazole, R36 = Bz: (78)
R35 = indole, R36 = Bz: (79)
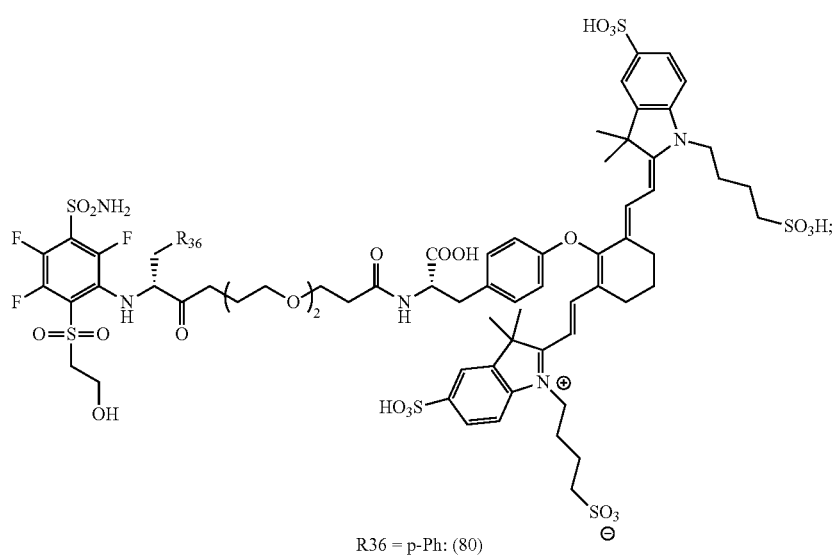
R36 = p-Ph: (80)
R36 = CH(CH₃)₂: (81)
R36 = Imidazole: (82)
R36 = indole: (83)

-continued
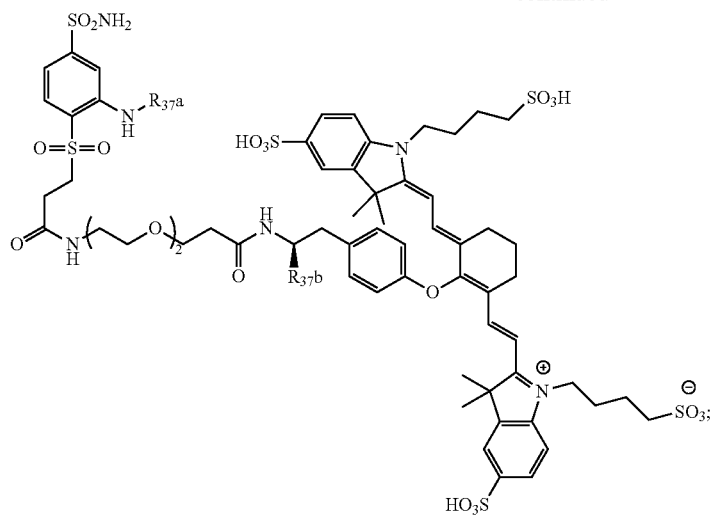
R37 = cyclohexyl: (84)
R37a = cyclooctyl, R37b = COOH: (85a)
R37a = cyclooctyl, R37b = H: (85b)
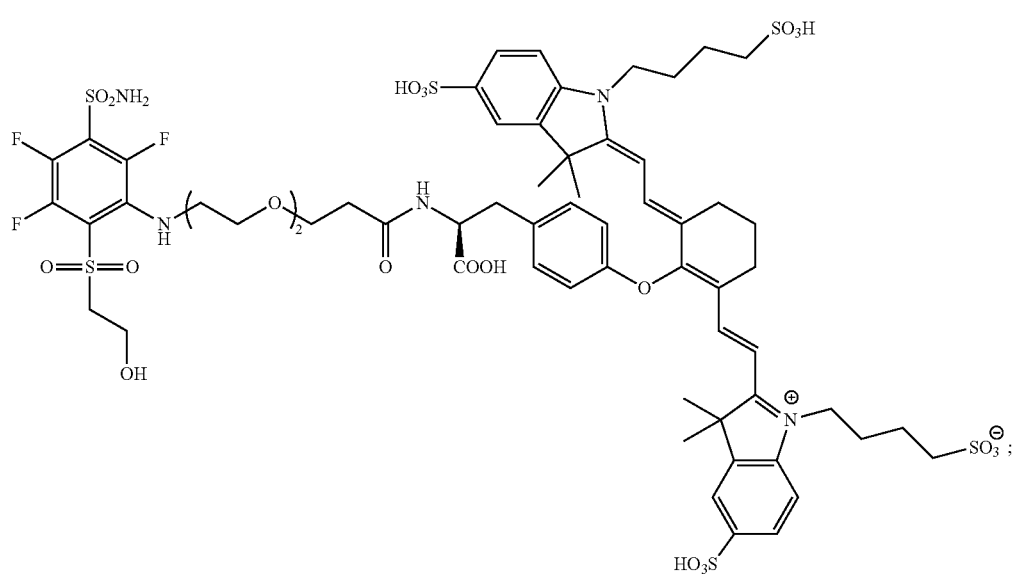
(86)

(87)
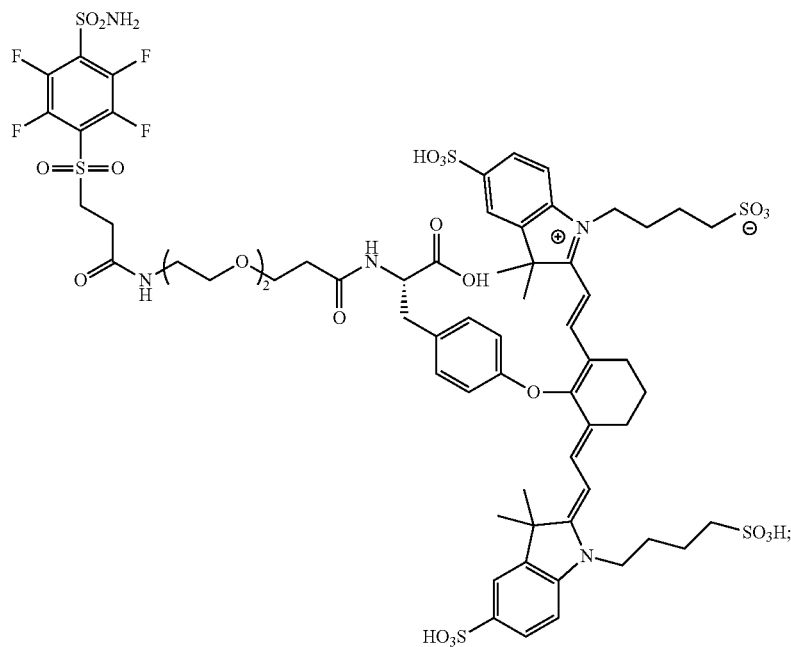
(88)
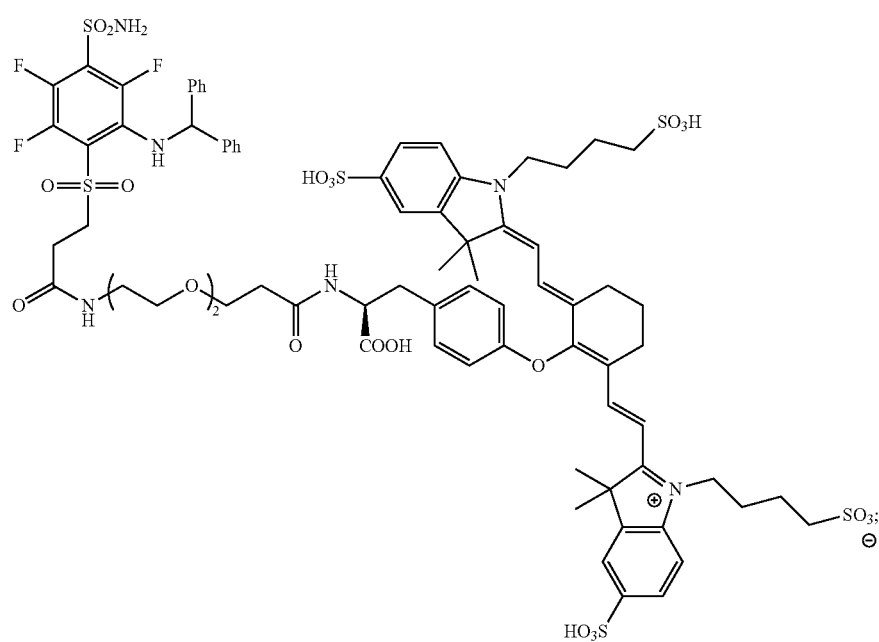

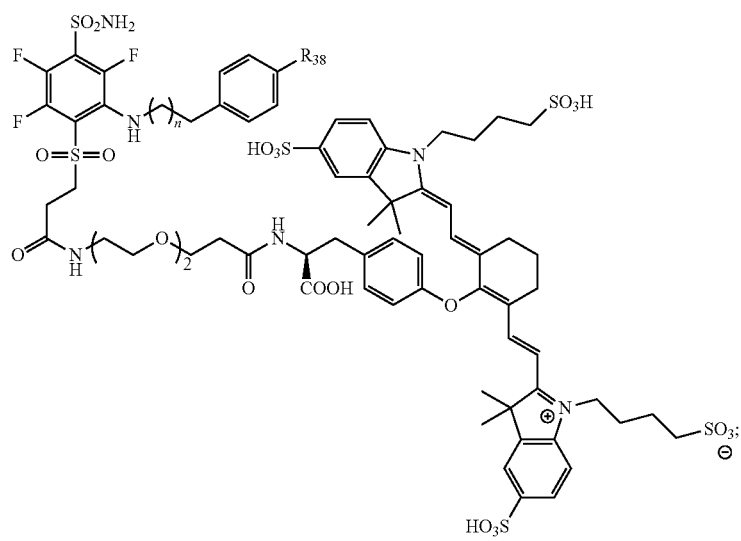
n = 0, R38 = H: (89)
n = 1, R38 = F: (90)
n = 1, R38 = CF₃: (91)
n = 1, R38 = p-Ph: (92)
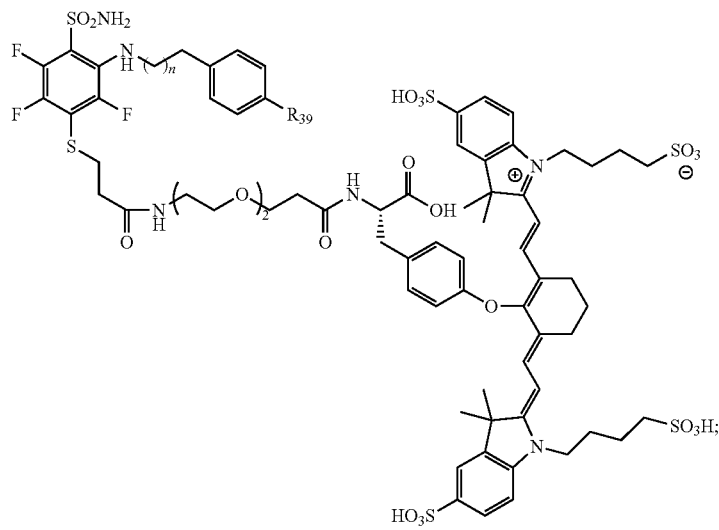
n = 0, R39 = H: (93)
n = 1, R39 = F: (94)
n = 0, R39 = p-Ph: (95)
n = 1, R39 = p-Ph: (96)

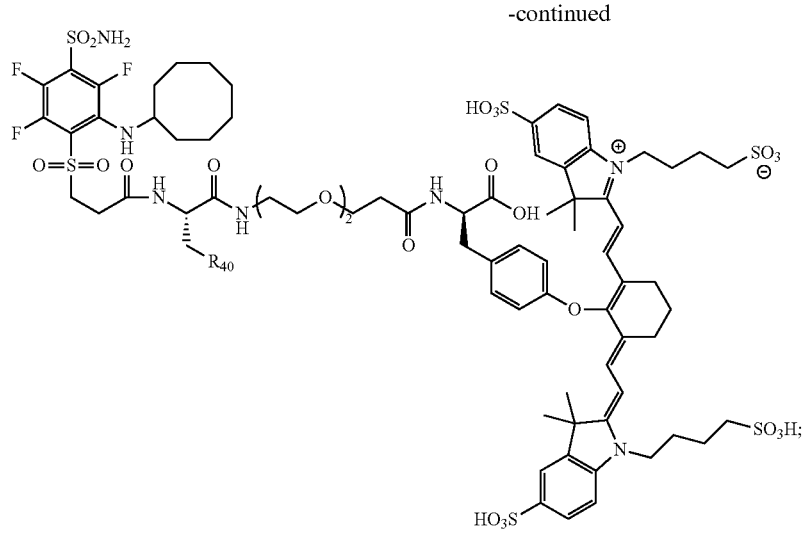
R40 = COOH: (97)
R40 = (CH₂)₂Guanidinium: (98)
R40 = p-Ph: (99)
R40 = Imidazole: (100)
R40 = Indole: R41 = COOH: (101a)
R40 = Indole, R41 = H: (101b)
R40 = CH(CH₃)₂, R41 = COOH: (102a)
R40 = CH(CH₃)₂, R41 = H: (102b)
R40 = CH(CH₂CH₃)CH₃: (103)
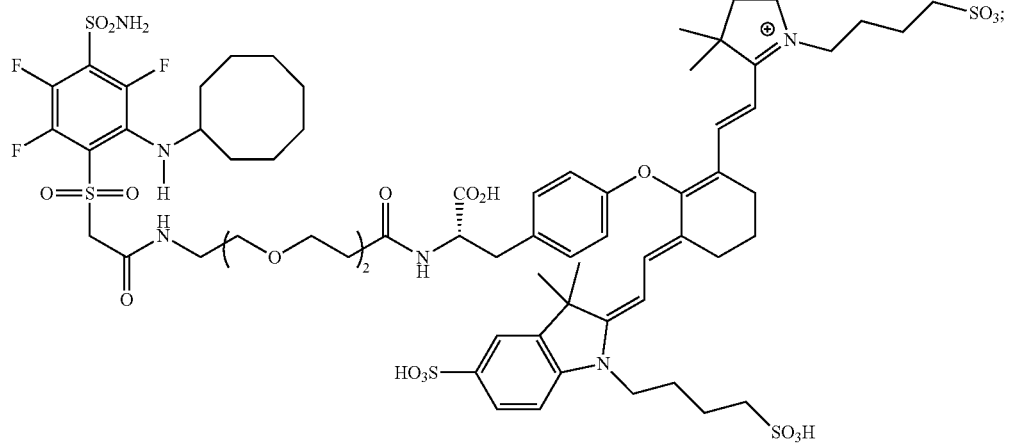
(104)

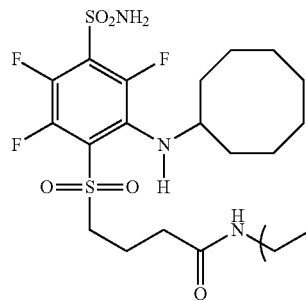
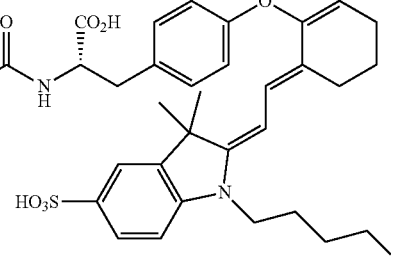
(105) = OTL410
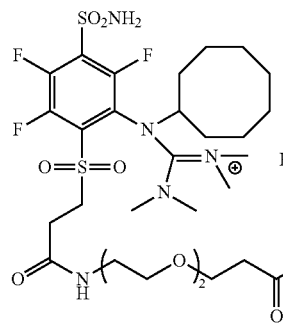
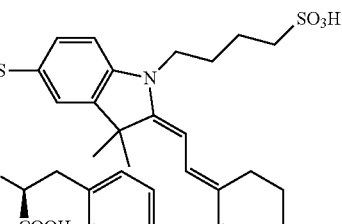
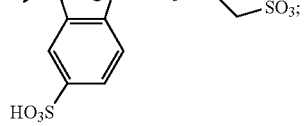
(106)
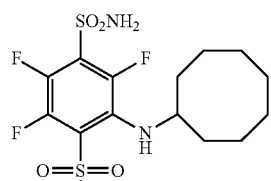
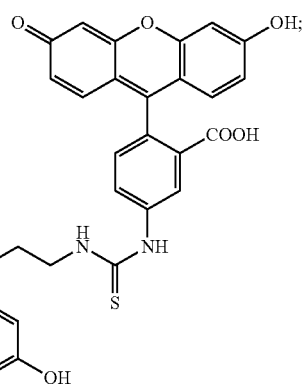
(107)

-continued
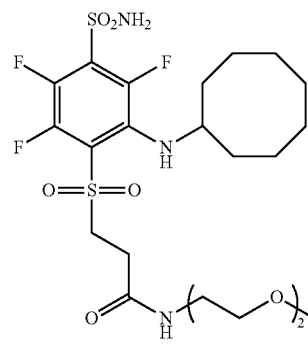 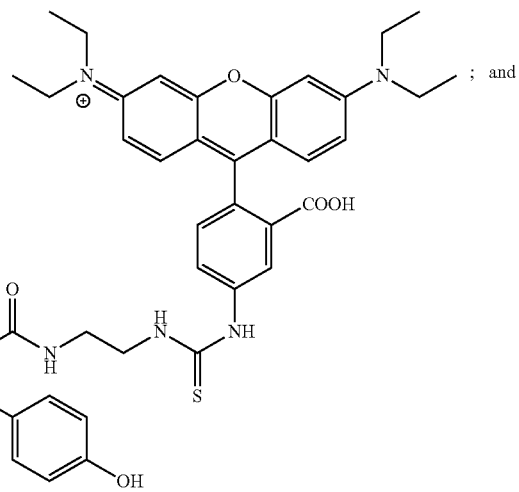
(108)
; and
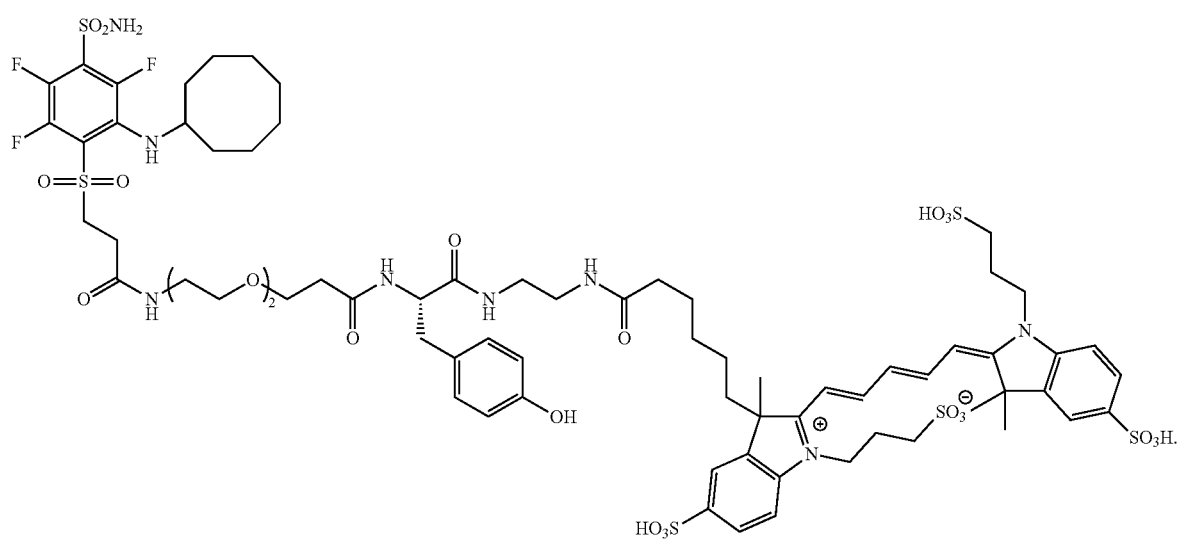
(109)

19. A composition comprising a compound selected from the group consisting of:
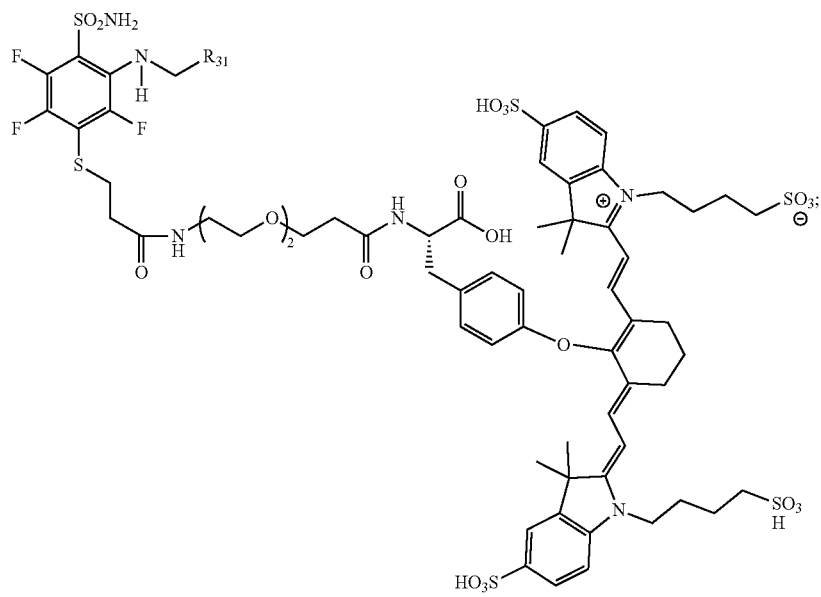
R31 = cyclohexyl: (54)
R31 = cyclooctyl: (55)
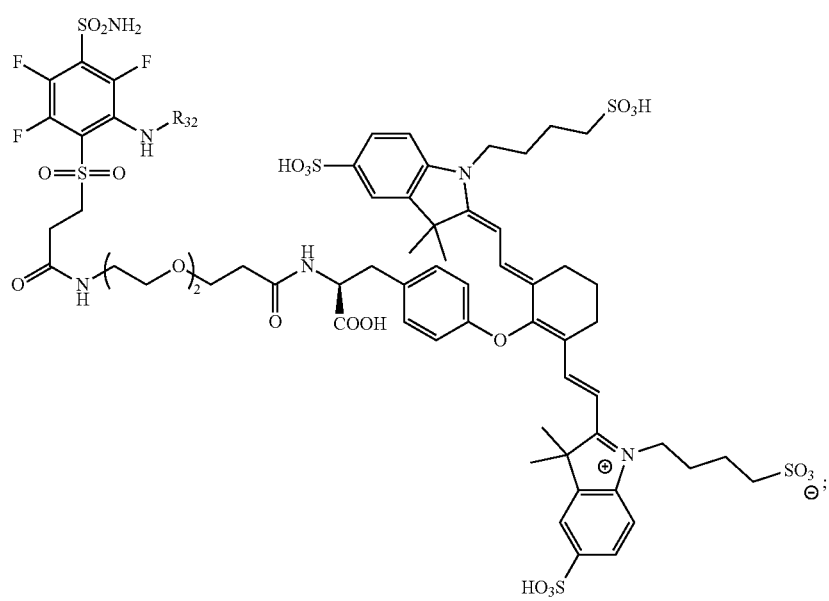
R32 = cyclohexyl: (60)
R32 = cyclooctyl: (61)

(62)
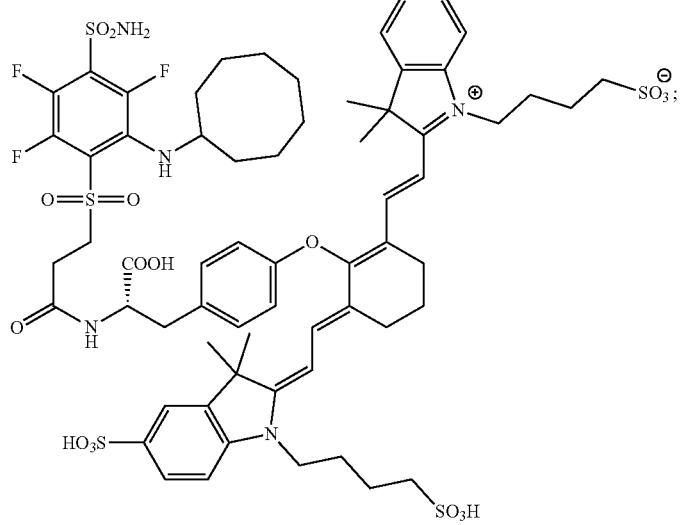
(63)
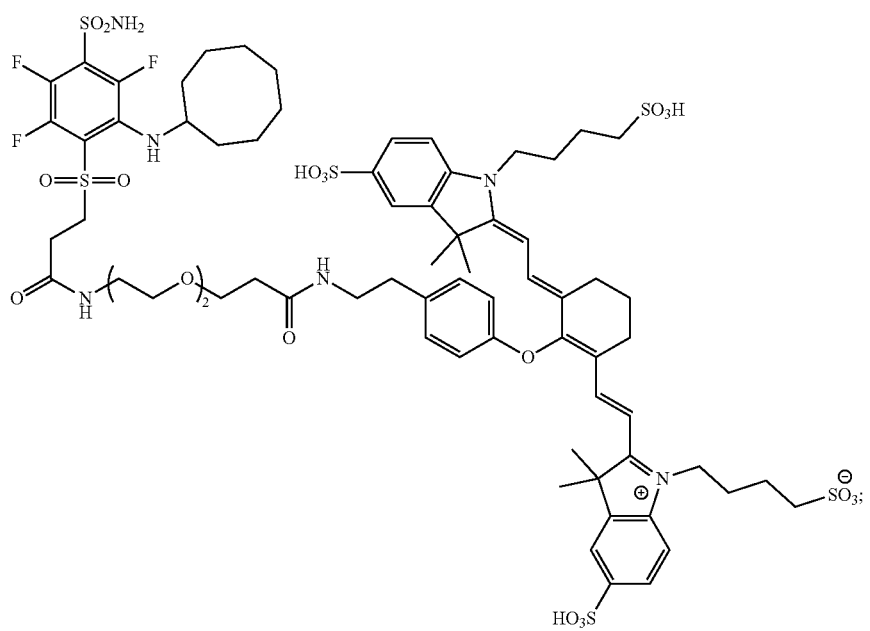

(64)
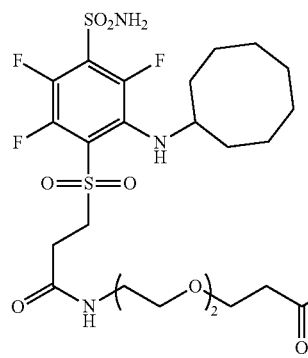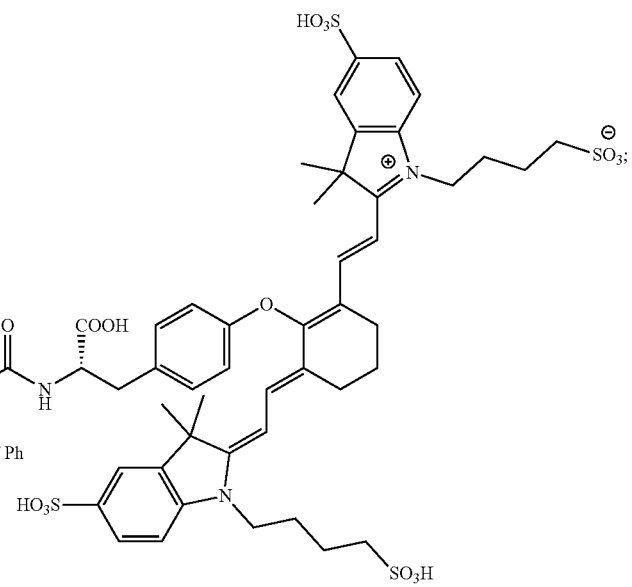
(65)
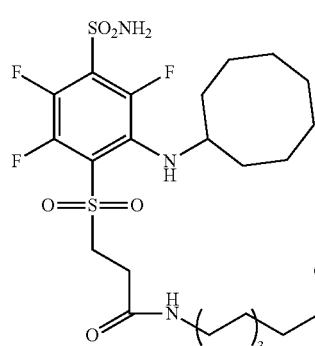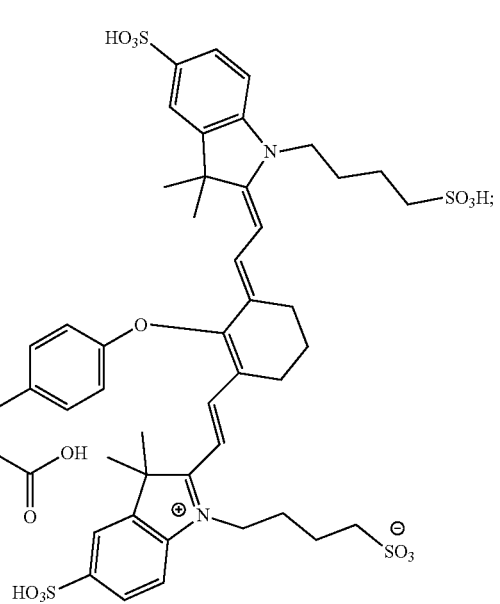

-continued
(66)
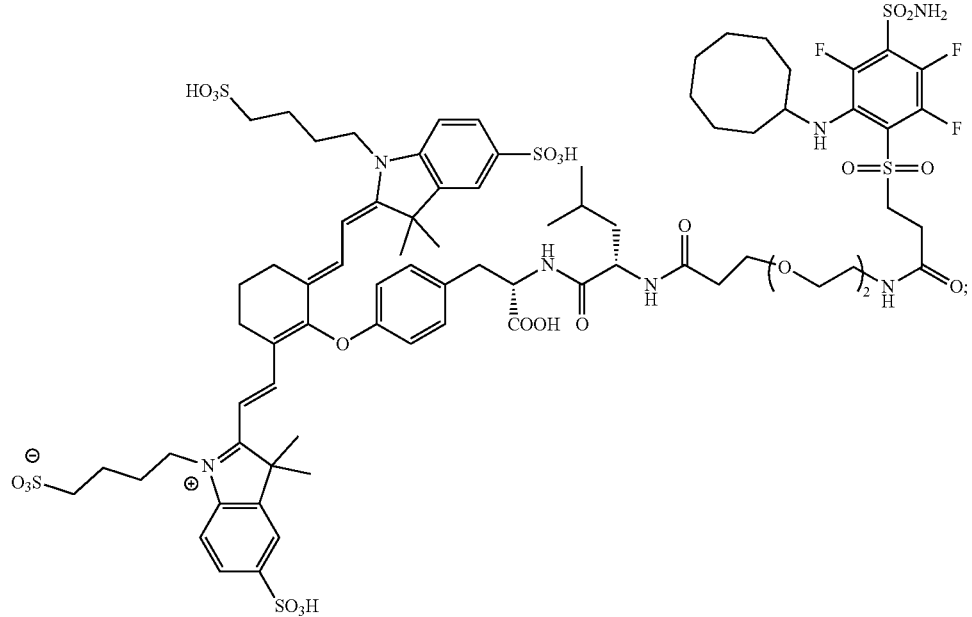
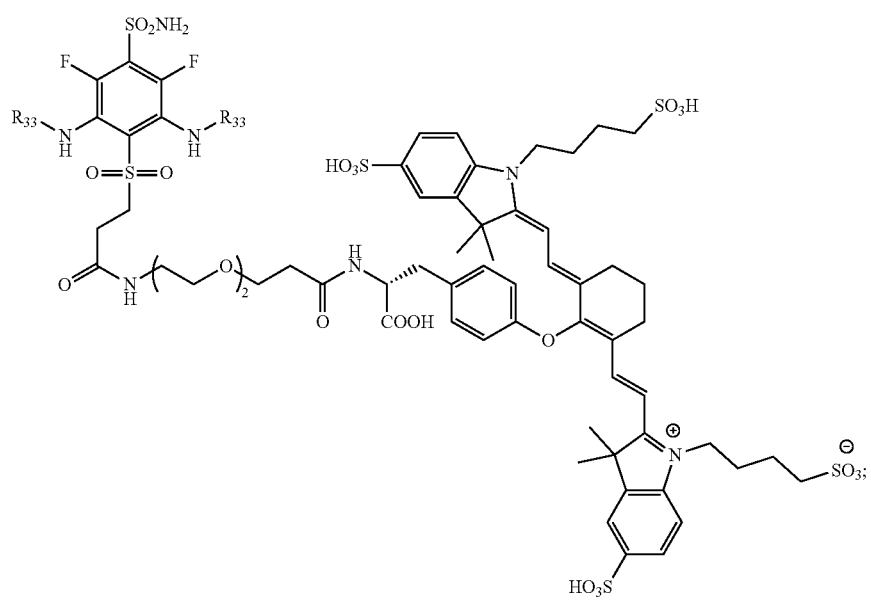
R33 = cyclohexyl: (69)
R33 = cyclooctyl: (70)

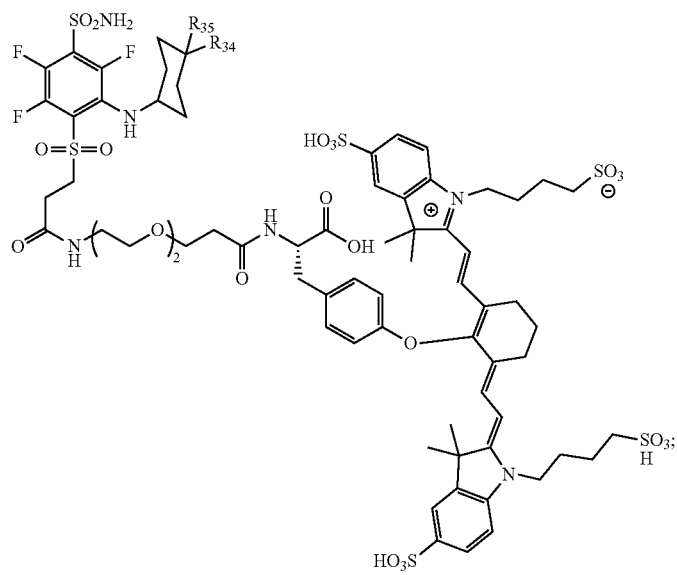
R34 = H, R35 = F: (71)
R34, R35 = F: (72)
R34 = H, R35 = CF3: (73)
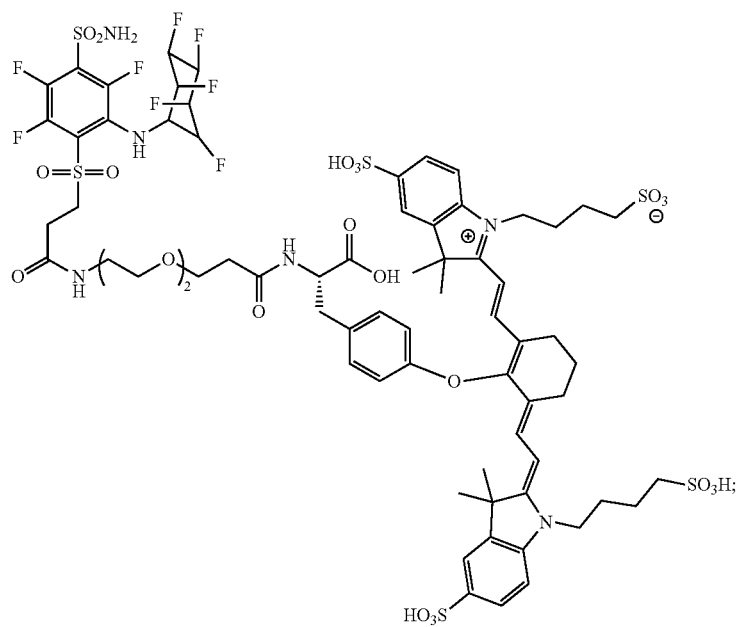
(74)

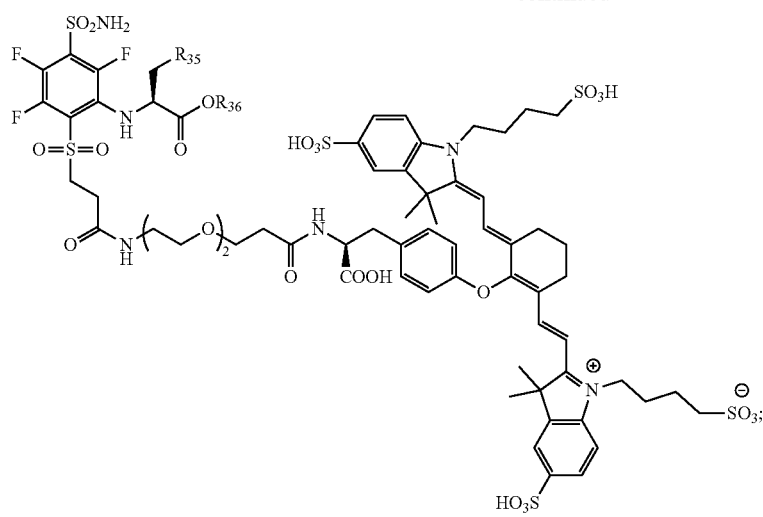
R35 = p-Ph, R36 = Bz: (75)
R35 = CH(CH₃)₂, R36 = Bz: (76)
R35 = CH(CH₃)₂, R36 = H: (77)
R35 = Imidazole, R36 = Bz: (78)
R35 = indole, R36 = Bz: (79)
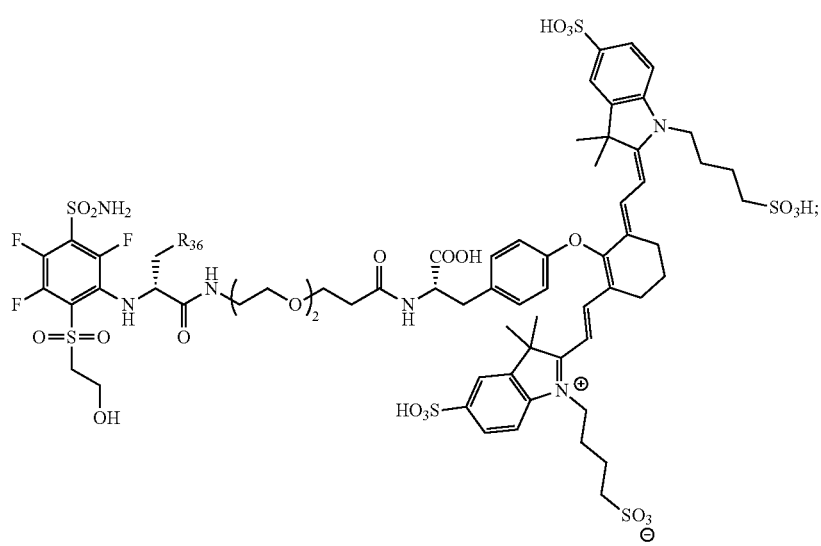
R36 = p-Ph: (80)
R36 = CH(CH₃)₂: (81)
R36 = Imidazole: (82)
R36 = indole: (83)

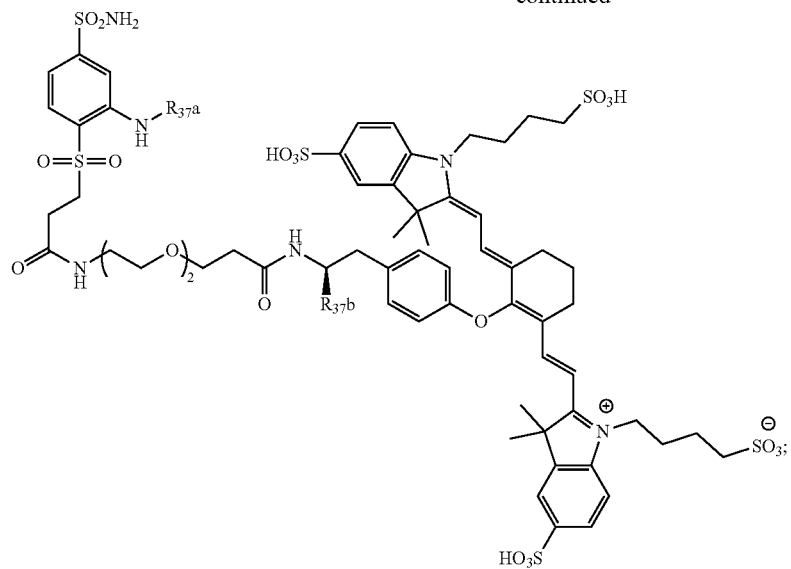
R37 = cyclohexyl: (84)
R37a = cyclohexyl, R37b = COOH: (85a)
R37a = cyclooctyl, R37b = H: (85b)
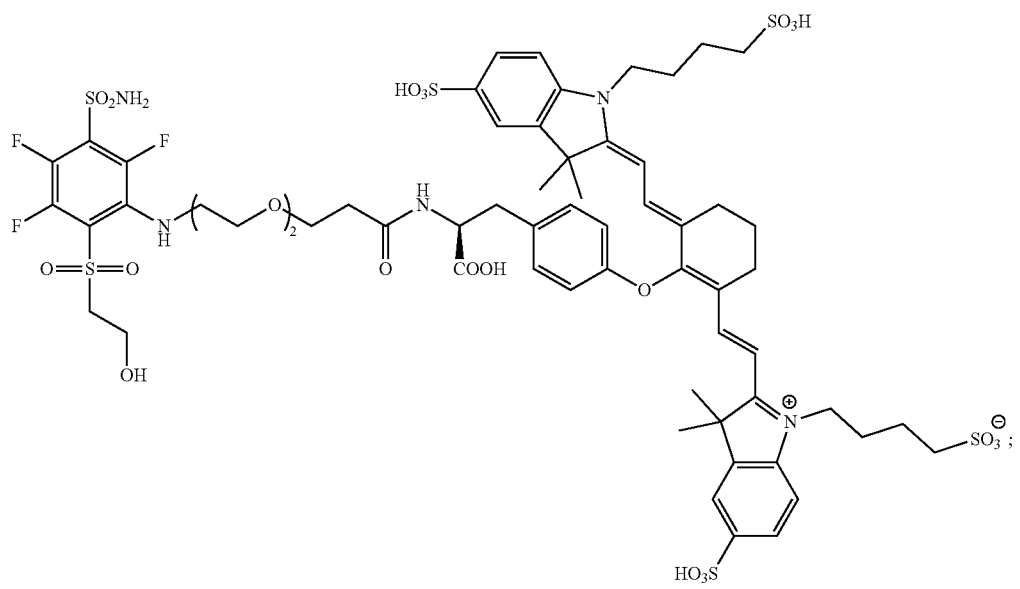
(86)

-continued
(87)
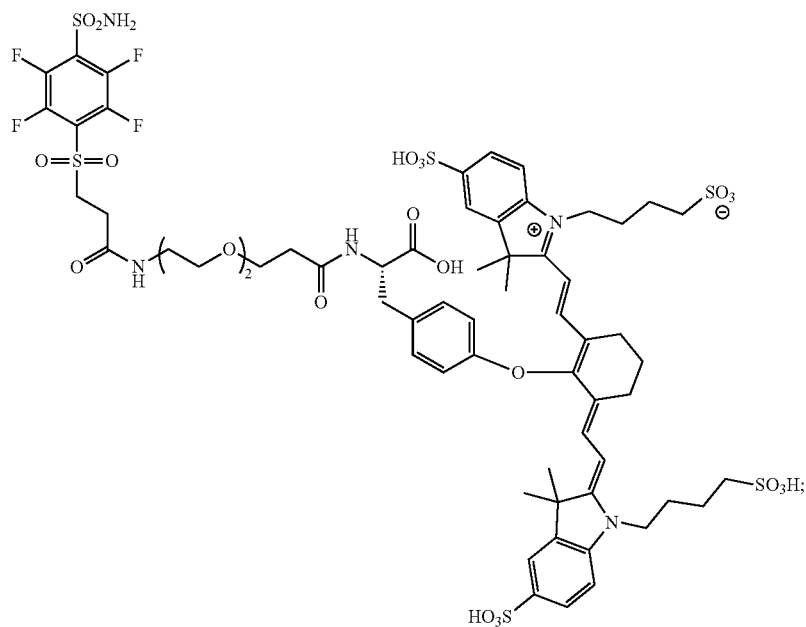
(88)
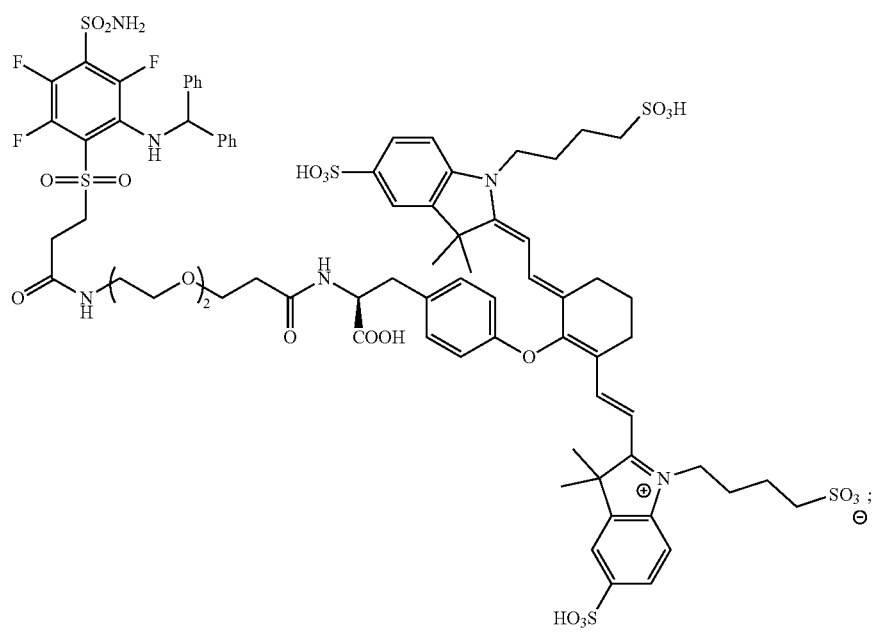

-continued
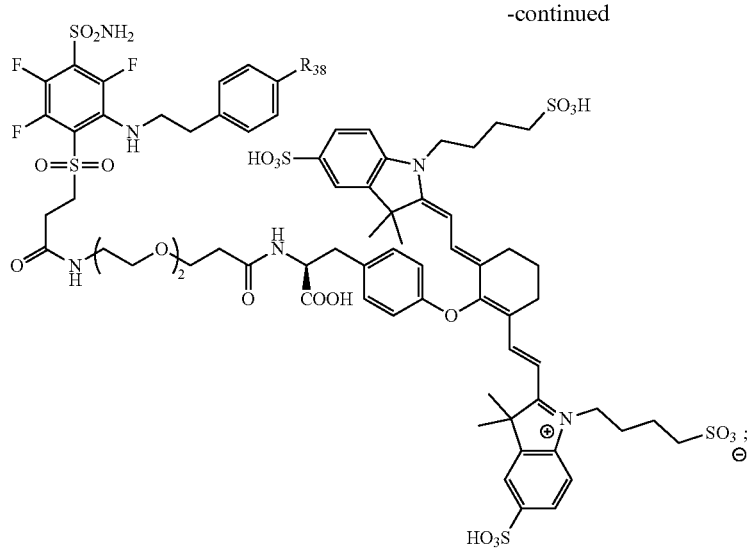
n = 0, R38 = H: (89)
n = 1, R38 = F: (90)
n = 1, R38 = CF3: (91)
n = 1, R38 = p-Ph: (92)
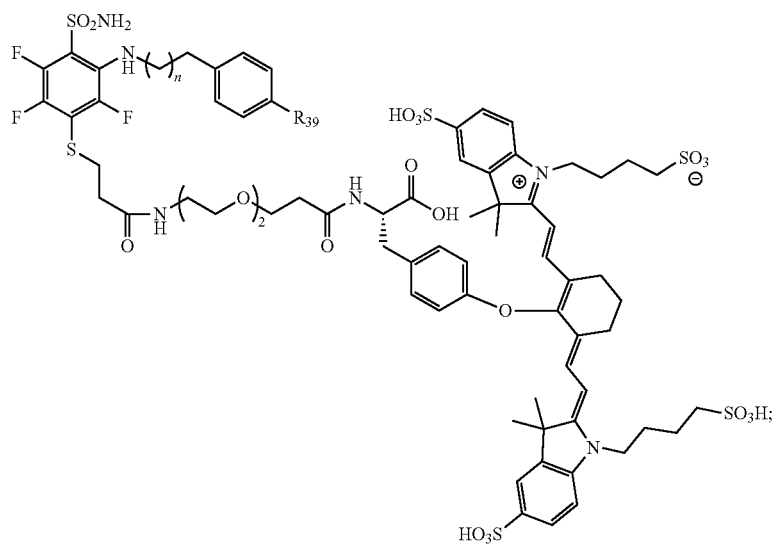
n = 0, R39 = H: (93)
n = 1, R39 = F: (94)
n = 0, R39 = p-Ph: (95)
n = 1, R39 = p-Ph: (96)

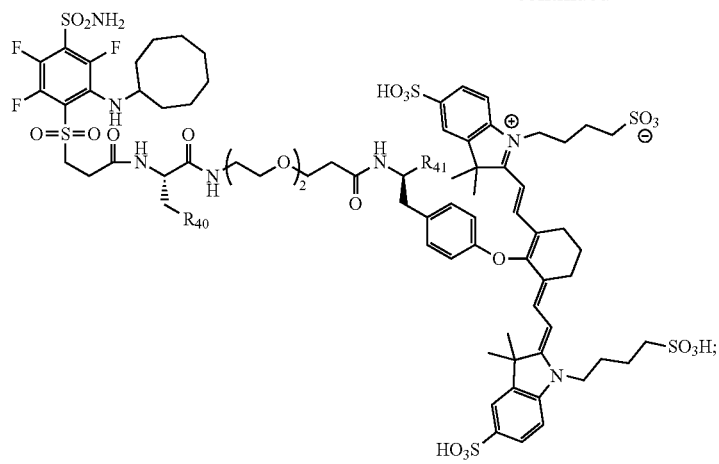
R40 = COOH: (97)
R40 = (CH₂)₂Guanidinium: (98)
R40 = p-Ph: (99)
R40 = Imidazole: (100)
R40 = Indole, R41 = COOH: (101a) R40 = Indole, R41 = H: (101b)
R40 = CH(CH₃)₂, R41 = COOH: (102a) R40 = CH(CH₃)₂, R41 = H: (102b)
R40 = CH(CH₂CH₃)CH₃: (103)
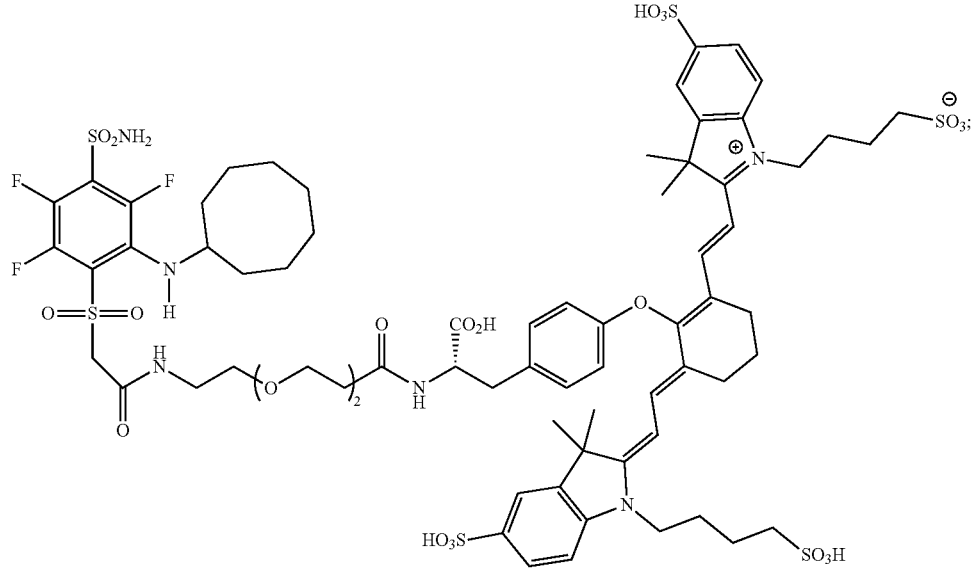
(104)

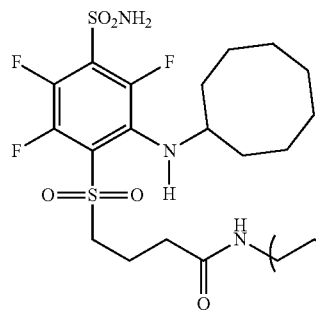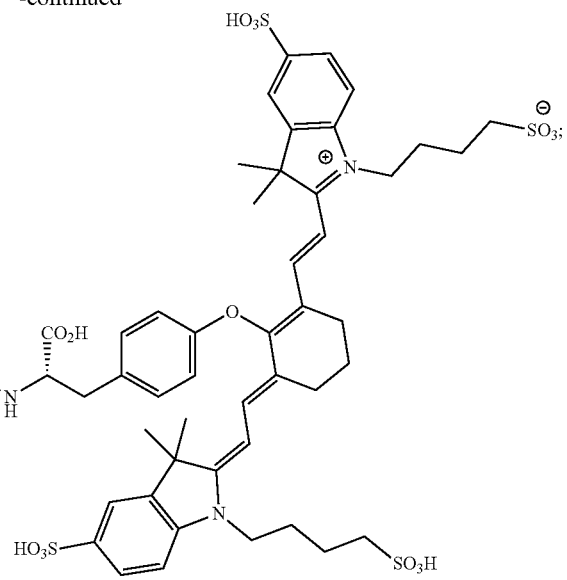
(105) = OTL410
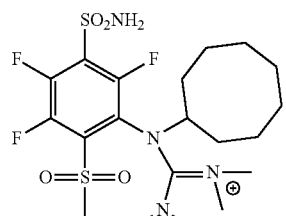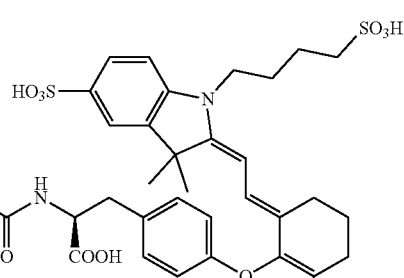
(106)
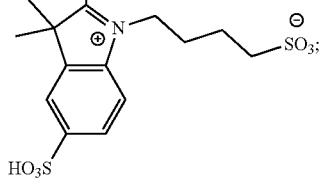
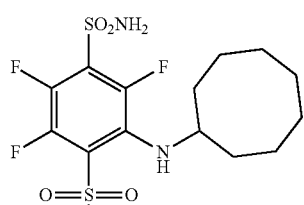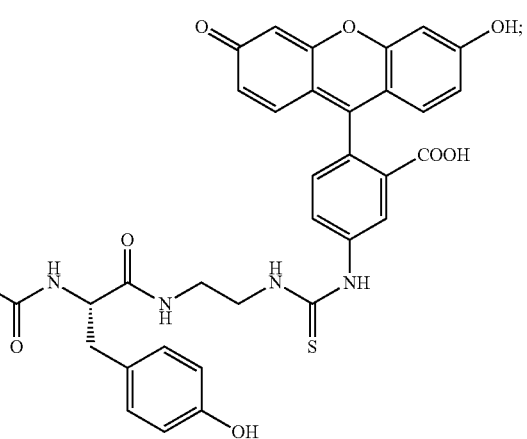
(107)

-continued
(108)
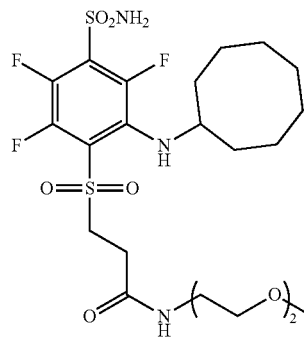
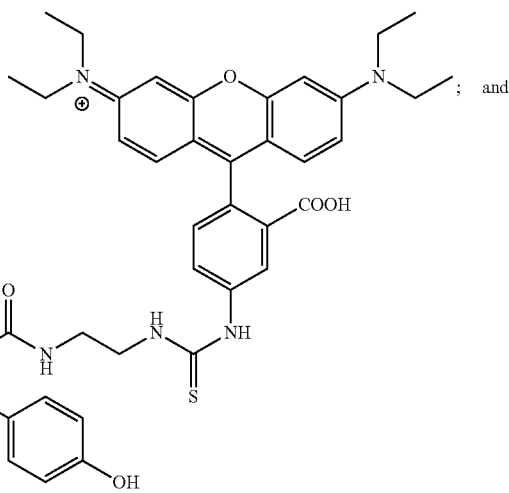
(109)
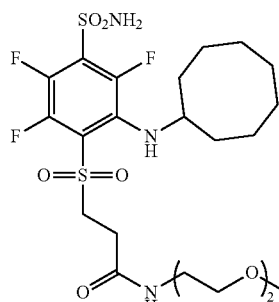
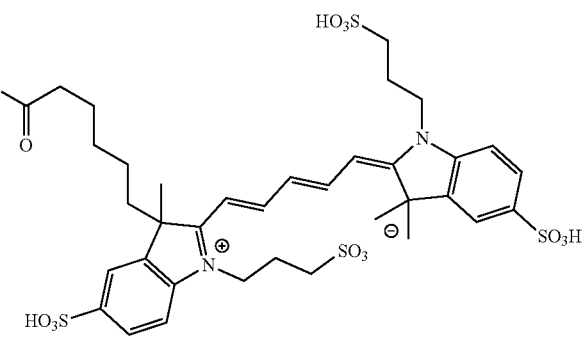
and at least one additional fluorescent compound.
20. The composition of claim 19, wherein the at least one additional fluorescent compound comprises a pteroyl ligand conjugated to an amino acid linking group or a PSMA-targeting compound conjugated to an amino acid linking group.
\* \* \* \* \*